(12) United States Patent
Ip et al.

(10) Patent No.: US 9,150,608 B2
(45) Date of Patent: Oct. 6, 2015

(54) NEURO-PROTECTIVE COMPOUNDS AND THEIR USE

(75) Inventors: Nancy Yuk-Yu Ip, Hong Kong (CN); Fanny Chui-Fun Ip, Hong Kong (CN); Shengjun Guo, Hong Kong (CN)

(73) Assignee: Biotechnology Research Corp. Ltd., Hong Kong (CN)

( * ) Notice: Subject to any disclaimer, the term of this patent is extended or adjusted under 35 U.S.C. 154(b) by 30 days.

(21) Appl. No.: 13/635,603

(22) PCT Filed: Mar. 18, 2011

(86) PCT No.: PCT/IB2011/000567
§ 371 (c)(1),
(2), (4) Date: Dec. 3, 2012

(87) PCT Pub. No.: WO2011/114220
PCT Pub. Date: Sep. 22, 2011

(65) Prior Publication Data
US 2013/0079293 A1    Mar. 28, 2013

Related U.S. Application Data

(60) Provisional application No. 61/315,254, filed on Mar. 18, 2010.

(51) Int. Cl.
| | |
|---|---|
| *A01N 51/00* | (2006.01) |
| *A61K 31/655* | (2006.01) |
| *C07J 17/00* | (2006.01) |
| *A61K 31/015* | (2006.01) |
| *A61K 31/045* | (2006.01) |
| *A61K 36/906* | (2006.01) |
| *A61K 31/05* | (2006.01) |
| *A61K 31/01* | (2006.01) |
| *A61K 36/896* | (2006.01) |
| *A61K 36/27* | (2006.01) |
| *C07C 43/23* | (2006.01) |
| *C07C 49/83* | (2006.01) |
| *C07D 307/79* | (2006.01) |
| *C07D 307/80* | (2006.01) |
| *C07D 319/20* | (2006.01) |
| *C07J 63/00* | (2006.01) |
| *C07C 59/90* | (2006.01) |
| *C07C 62/32* | (2006.01) |
| *C07H 7/04* | (2006.01) |
| *C07H 7/06* | (2006.01) |

(52) U.S. Cl.
CPC ............... *C07J 17/005* (2013.01); *A61K 31/01* (2013.01); *A61K 31/015* (2013.01); *A61K 31/045* (2013.01); *A61K 31/05* (2013.01); *A61K 36/27* (2013.01); *A61K 36/896* (2013.01); *A61K 36/906* (2013.01); *C07C 43/23* (2013.01); *C07C 49/83* (2013.01); *C07C 59/90* (2013.01); *C07C 62/32* (2013.01); *C07D 307/79* (2013.01); *C07D 307/80* (2013.01); *C07D 319/20* (2013.01); *C07H 7/04* (2013.01); *C07H 7/06* (2013.01); *C07J 63/008* (2013.01); *C07C 2102/10* (2013.01)

(58) Field of Classification Search
None
See application file for complete search history.

(56) References Cited

FOREIGN PATENT DOCUMENTS

CN         1091372 C       9/2002

OTHER PUBLICATIONS

Tsai et al. Phytochemistry (1996), vol. 43, pp. 1261-1263.*
Shiba et al. Journal of Molecular Catalysis B: Enzymatic (2000), vol. 10, pp. 605-615.*
Hattori et al. Chem. Pharm. Bull. (1987), vol. 35, pp. 668-674.*
Aquino et al., "New polyoxypregnane ester derivatives from *Leptadenia hastate*," J. Nat. Prod., 1996, vol. 59, No. 6, pp. 555-564.
Gao et al., Gracillosides A-F, six new 8,14-seco-pregnane glycosides from *Adelostemma gracillimum*, Sterioids, 2009, 74, 694-700.
Hattori et al., "New Acyclic Bis-phenylpropanoids from the Aril of *Myristica fragrans*," Chem. Pharm. Bull., 1987, vol. 35, No. 2, pp. 668-674.
Oh et al., "Cardiovascular effects of lignans isolated from *Saururus chinensis*," Planta Medica, 2008, vol. 74, No. 3, pp. 233-238.
Mu et al., Studies on the Constituents of *Adelostemma gracillimum*, Plant Med. 1992, 58, 200-204.
PCT/IB2011/000567, International Search Report, mailed Aug. 11, 2011, 3 pages.
Achenbach et al., "Lignans, Neolignans and Norneolignans from *Krameria Cystisoides*," Phytochemistry, 1987, vol. 26(4), pp. 1159-1166.
Shimomura et al., "Lignans from *Machilus Thunbergii*," Phytochemistry, 1987, vol. 26(5), pp. 1513-1515.

* cited by examiner

*Primary Examiner* — Patrick Lewis
(74) *Attorney, Agent, or Firm* — Kilpatrick Townsend & Stockton

(57) ABSTRACT

Isolated compounds from *Adelostemma gracillimum* refined fractions and compositions containing the compounds are provided by the present invention. *Adelostemma gracillimum* refined fractions and the extraction process thereof are also provided by the present invention. The uses of the compounds and the *Adelostemma gracillimum* refined fractions for inhibiting the activities of NMDA receptor or amyloid-beta peptide, for improving memory, and for treating neurodegenerative diseases, neuropathological conditions or epilepsy are further provided by the present invention.

14 Claims, 41 Drawing Sheets

A.

B.

C.

NEURO-PROTECTIVE COMPOUNDS AND THEIR USE

CROSS-REFERENCES TO RELATED APPLICATIONS

This application is a U.S. National phase application under 35 U.S.C. §371 of PCT Application No. PCT/IB2011/000567 filed Mar. 18, 2011. which claims priority to U.S. Patent Application Ser. No. 61/315,254, filed Mar. 18, 2010, the contents of each of which are herein incorporated by reference in their entirety.

REFERENCE TO A "SEQUENCE LISTING," A TABLE, OR A COMPUTER PROGRAM LISTING APPENDIX SUBMITTED AS AN ASCII TEXT FILE

The Sequence Listing written in file -5-1.TXT, created on Oct. 10, 2012, 4,096 bytes, machine format IBM-PC, MS-Windows operating system, is hereby incorporated by reference in its entirety for all purposes.

BACKGROUND OF THE INVENTION

*Adelostemma gracillimum* (Asclepiadaceae) is an herb found in Southwest of China and Burma. Extracts from the plant have been used for thousands of years in folk medicine for therapeutic purposes. The roots of the herb are used as a nourishing and roborant tonic and in treating convulsions in children. Extracts of *Adelostemma gracillimum* have been found to contain pregnane glycosides (Mu et al., 1992; Gao et al., 2009).

The central nervous system (CNS) is regulated by many complex pathways which monitor crucial cellular events such as proliferation, differentiation, and apoptosis (or cell death). While apoptosis is an integral part of neuronal development, defects in the mechanisms of apoptosis are thought to contribute to the disease pathology of stroke, epilepsy, and a host of neurodegenerative diseases (Raff et al., 1993). Thus, one area of drug development is to understand the processes that underlie neuronal survival and apoptosis.

Studies have shown that many, growth factors and neurotrophins, including insulin, insulin-like growth factor-1, brain-derived neurotrophic factor (BDNF), nerve-growth factor (NGF), and neurotropins 3 and 4/5, can promote neuronal survival by mediating specific signaling cascades such as the ERK and the PI 3-kinase pathways (Segal and Greenberg, 1996). Thus, it is desirable to identify and/or to develop compounds that can promote neuronal survival against apoptosis induced by nutrient withdrawal.

NMDA receptors are ligand-gated ion channels located primarily within the CNS. They belong to the family of ionotropic glutamate receptors and exist as multiple subtypes due to the different combinations of subunits—NR1, NR2 (NR2A, NR2B, NR2C, NR2D) and NR3—that can be expressed. In addition to the agonist binding site, NMDA receptors have multiple distinct binding sites for various compounds that enhance, modulate and inhibit the activation of the receptors.

It is known that NMDA receptors are involved in neuronal communication and play important roles in synaptic plasticity and mechanisms that underlie learning and memory. Under normal conditions, NMDA receptors engage in synaptic transmission via the neurotransmitter glutamate, which regulates and refines synaptic growth and plasticity. However, when there are abnormally high levels of glutamate (i.e. under pathological conditions), NMDA receptors become over-activated, resulting in an excess of $Ca^{2+}$ influx into neuronal cells, which in turn causes excitotoxicity and the activation of several signaling pathways that trigger neuronal apoptosis. Glutamate-induced apoptosis in brain tissue also accompanies oxidative stress resulting in loss of ATP, loss of mitochondrial membrane potential, and the release of reactive oxygen species and reactive nitrogen species (e.g. $H_2O_2$, NO, $OONO^-$, $O_2^-$) causing associated cell damage and death. Decreased nerve cell function and neuronal cell death eventually occur. Excitotoxicity also occurs if the cell's energy metabolism is compromised.

Over-activation of the NMDA receptors is implicated in neurodegenerative diseases and other neuro-related conditions as it causes neuronal loss and cognitive impairment, and also plays a part in the final common pathway leading to neuronal injury in a variety of neurodegenerative disorders such as amyotrophic lateral sclerosis, Parkinson's disease, Alzheimer's disease and Huntington's disease, as well as conditions such as stroke. NMDA receptors are also implicated in many other neurological disorders, such as multiple sclerosis, cerebral palsy (periventricular leukomalacia), and spinal cord injury, as well as in chronic and severe mood disorders (Mathew SJ et al., *Rev Bras Psiquiatr*, 27:243-248 (2005)).

NMDA receptors have played crucial roles in both regulating and promoting normal nervous system functions as well as causing cell death, which leads to lethal conditions. There has been increasing evidence to show that the type of signal given to a cell depends on the location of the activated NMDA receptor. Growth and survival-promoting signals result from activated synaptic NMDA receptors, while cell death causing signals result from extrasynaptic NMDA receptors. Recent studies also indicate that activated synaptic NMDA receptors lead to robust phosphorylation of the transcription factor CREB on the transcriptional regulatory residue Ser133 and promote CREB-dependent gene expression and neuronal survival. However, activated extrasynaptic NMDA receptors transiently phosphorylate CREB and do not activate CREB-dependent gene expression, resulting in neuronal cell death (Hardingham et al., 2002).

Yet, there are few effective therapeutic agents for excitotoxicity to alleviate symptoms of its associated neuronal disorders. One complication for the development of effective NMDA antagonists as neurotherapeutic drugs is that many NMDA antagonists also exhibit psychotogenic and neurotoxic properties. For example, MK-801 (dizocilpine maleate) is capable of providing certain degree of neuroprotection in ischemic stroke, but is associated with psychotropic and adverse motor effects. Thus, it is desirable to identify and/or to develop compounds that can potentiate NMDA synaptic activity resulting in neuroprotection.

Amyloid beta (Aβ) is a cleavage product derived from the amyloid precursor protein (APP), which accumulates as extracellular or senile plaques, the characteristic hallmark of the neurodegenerative disease Alzheimer's disease (AD). While the actual cause of AD remains elusive, Aβ has been implicated in many reports to play a part in the initiation and progression of the disease (Hock et al., 2003). Furthermore, studies have shown that Aβ is neurotoxic (Hartman et al., 2005), resulting in neuronal loss and subsequent memory loss and cognitive impairment. Upon the addition of Aβ to primary neuronal cultures, apoptosis is triggered which leads to cell death (Estus et al., 1997). Caspases are a family of cysteine-aspartic acid proteases that are involved in cell apoptosis through sequential activation by proteolytic processing of inactive proenzymes to form the active enzyme. Caspase-3 is considered to be the executioner of the apoptotic pathway and is the predominant caspase involved in the cleavage of the amyloid precursor protein as well as in the production of Aβ, which is associated with neuronal death in Alzheimer's disease. Exogenous addition of Aβ into neuronal cultures initiates caspase-3 dependent apoptosis. Therefore, developing inhibitors against caspase-3 activation is one therapeutic approach in AD treatment.

Dendritic spines, or spines, are small membranous protrusions from a neuron's dendrite that typically receive input from a single synapse of an axon. Dendritic spines serve as a storage site for synaptic strength and help transmit electrical signals to the neuron's cell body. Spines, however, require maturation after formation. Immature spines have impaired signaling capabilities, and typically only have necks and lack, or have very small, "heads". Matured spines maintain both heads and necks. Spines with strong synaptic contacts typically have a large spine head, which connect to the dendrite via a membranous neck (mushroom shape) (Yuste and Denk, 1995). Decreased spine density has been reported in aged neurons of the CA1 area of hippocampus as well as the layer III pyramidal layer (Duan et al., 2003; von Bohlen und Halbach et al., 2006). In stressed animals, an overall shift in the population of spines is observed with a reduction in large spines and an increase in small spines in the prefrontal cortex (Radley et al., 2008). Spine reduction is also associated with major depression as well as in schizophrenia (Law et al., 2004). Cognitive disorders such as autism, mental retardation, Fragile X Syndrome, stroke, and chronic alcoholism may be resultant from abnormalities in dendritic spines, especially in regards to the number of spines and their maturity (Bhatt et al., 2009; von Bohlen und Halbach et al., 2009).

Epilepsy is a clinical phenomenon consisting of excessive neuronal activities in the brain which are manifested by seizures (Fisher et al., 2005). Epileptic seizures can take on the form of tonic or clonic movements accompanied sporadically by convulsions and other neurological and physical and psychic symptoms. Seizures occur transiently and can occur through provocation, though not necessarily (Aylwar R., 2008). The incidence of epilepsy is estimated at approximately 0.3 to 0.5 percent in different populations throughout the world, with the prevalence of epilepsy estimated at 5 to 10 people per 1000 which makes it one of the most prevalent neurological disorders (Shinnar and Pellock, 2002).

Epilepsy is classified by etiology, observable seizure activity, location of seizure activity in the brain, accompanying medical symptoms, and the initial event which provoked the seizure activity. The main characteristic that distinguishes the different categories of seizures is whether the seizure activity is partial (synonymous with focal) or generalized (Brodie et al., 2009). Currently, there are over 40 recognized epilepsy types classified by type of seizures, EEG recordings, physical manifestations, treatment and prognosis (Badawy et al., 2009). In vivo experiments have shown that genetic mutations in both voltage and receptor-gated ion channels are responsible for various types of seizure activities (Meisler M, and Keamey J., 2005). For example, dysregulation in voltage-gated sodium channel localized in GABAergic neurons have been implicated in severe myoclonic seizures of infants (SMEI) (Yu et al., 2009). Seizures can also occur from trauma such as ischemia or hypoxia, fever, and encephalitis, which then lead to dysregulation of balance in neuronal transmission (Bialer and White, 2010). Neuroinflammation has also been linked to the pathophysiology of epilepsy where inflammatory responses caused by cytokines lead to neuronal damage and changes in the neuronal environment, resulting in the hyperactivity observed in seizures (Ravizza et al., 2008).

Drugs to treat epilepsy are based on anticonvulsant medications. Currently, there are more than 20 antiepileptic drugs available. However, they have been reported to have side effects on patients including mood changes, sleepiness, or unsteadiness in gait (Schmitz, 2006). While the new generation of antiepileptic drugs has considerable improvements in terms of safety, tolerability and pharmacokinetics to control epileptic seizures, an estimated 30% of patients suffer from pharmacoresistant epilepsy and thus fail to respond to multiple medications (Andres and Antoaneta, 2007). The development of new drug candidates is necessary to offer alternative targets for the control of seizures with fewer or no side effects, and better efficacy is required to offer complete control of seizures in epileptic patients.

Therefore, there is a need to identify and/or to develop compounds that are capable of (i) preventing and/or treating CNS disorders, such as excitotoxicity, epilepsy, neurodegenerative diseases and neuropathological conditions; (ii) promoting neuronal survival against apoptosis induced by nutrient withdrawal; and (iii) enhancing the brain's cognitive functions. The present invention satisfies this and other needs.

BRIEF SUMMARY OF THE INVENTION

In some embodiments, the present invention provides compounds of formula Ia:

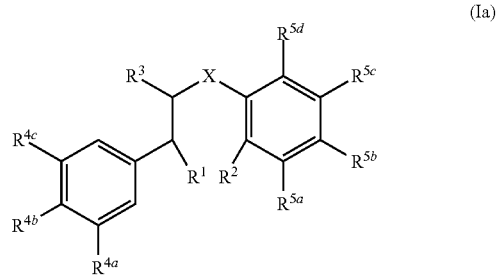

(Ia)

wherein radical X of formula Ia is a bond or —O—; $R^1$ of formula Ia is OH; or $R^2$ of formula Ia is H or OH. Alternatively, $R^1$ and $R^2$ of formula Ia are combined to form —O—. Radical $R^3$ of formula Ia is $C_{1-6}$ alkyl or $C_{1-6}$ alkyl-OH. Each of $R^{4a}$, $R^{4b}$ and $R^{4c}$ of formula Ia is independently H, OH, $C_{1-6}$ alkyl, or $C_{1-6}$ alkoxy. Each of $R^{5a}$, $R^{5b}$, $R^{5c}$ and $R^{5d}$ is independently H, OH, $C_{1-6}$ alkyl, $C_{1-6}$ alkoxy, $C_{2-6}$ alkenyl optionally substituted with $C_{1-6}$ alkoxy, or —C(O)—$C_{1-6}$ alkyl. The compounds of formula Ia include those such that when X is —O— and $R^1$ is OH, then $R^3$ is $C_{1-6}$ alkyl; $R^{4a}$ and $R^{5d}$ are each independently OH or $C_{1-6}$ alkoxy; $R^{4b}$ is OH; $R^{4c}$ is H, OH or $C_{1-6}$ alkoxy; $R^{5a}$ and $R^{5c}$ are each H; and $R^{5b}$ is $C_{2-6}$ alkenyl;

when X is —O—, and $R^1$ and $R^2$ are combined to form —O—, then $R^3$ is $C_{1-6}$ alkyl; $R^{4a}$ is $C_{1-6}$ alkoxy; $R^{4b}$ is OH; $R^{4c}$, $R^{5a}$, $R^{5c}$ and $R^{5d}$ are each H; and $R^{5b}$ is $C_{2-6}$ alkenyl;

when X is a bond, and $R^1$ is OH, then $R^2$, $R^{4b}$, $R^{5b}$ and $R^{5c}$ are each H; $R^3$ is OH; $R^{4a}$ and $R^{5a}$ are each $C_{1-6}$ alkyl; and $R^{4c}$ and $R^{5d}$ are each $C_{1-6}$ alkoxy;

when X is a bond and $R^1$ and $R^2$ are combined to form —O—, then $R^3$ is $C_{1-6}$ alkyl or $C_{1-6}$ alkyl-OH; $R^{4a}$ and $R^{5a}$ are each $C_{1-6}$ alkoxy; $R^{4b}$ is OH; $R^{4c}$ is H, OH or $C_{1-6}$ alkoxy; $R^{5b}$ is H; $R^{5c}$ is H or $C_{2-6}$ alkenyl substituted with $C_{1-6}$ alkoxy; and $R^{5d}$ is H or C(O)—$C_{1-6}$ alkyl, wherein when $R^3$ is $C_{1-6}$ alkyl, then $R^{5d}$ is —C(O)—$C_{1-6}$ alkyl, and when $R^3$ is $C_{1-6}$ alkyl-OH, then $R^{5d}$ is H; and when X is —O—, $R^1$ is OH, $R^2$, $R^{5a}$ and $R^{5c}$ are each H, $R^3$ is Me, $R^{4a}$ and $R^{5d}$ are both OMe, $R^{4b}$ is OH, and $R^{5b}$ is $C_3$ alkenyl, then $R^{4c}$ is OH or $C_{1-6}$ alkyl.

The compounds of formula Ia include the salts and isomers thereof.

In other embodiments, the present invention provides compounds of formula IIa:

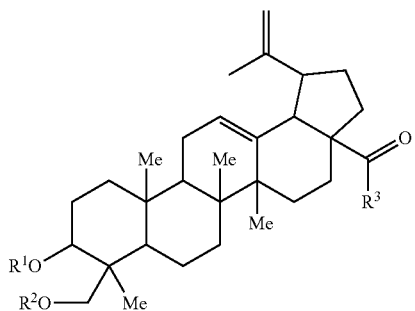

(IIa)

wherein $R^1$ of formula IIa is H, $C_{1-6}$ alkyl or a saccharide. Radical $R^2$ of formula IIa is H or $C_{1-6}$ alkyl. And radical $R^3$ of formula IIa is —OH or —$NH_2$. The compounds of formula IIa include the salts and isomers thereof.

In some other embodiments, the present invention provides compounds of formula III:

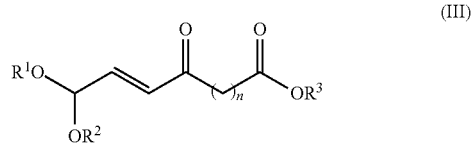

(III)

wherein each of $R^1$, $R^2$ or $R^3$ of formula III is independently H or $C_{1-6}$ alkyl. Subscript n of formula III is an integer from 8 to 20. The compounds of formula III include the salts and isomers thereof.

In still other embodiments, the present invention provides compounds of formula IVa:

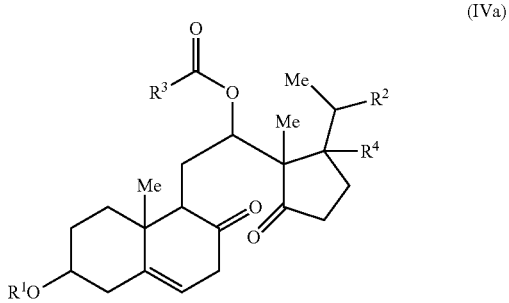

(IVa)

wherein $R^1$ of formula IVa is a saccharide, wherein the saccharide does not include a glucose moiety. Radical $R^2$ of formula IVa is OH, $C_{1-6}$ alkoxy, —OC(O)—$C_{1-6}$ alkyl, —OC(O)O—$C_{1-6}$ alkyl, $C_{0-6}$ alkyl-aryl substituted with 1-3 $R^{2a}$ groups, or is combined with the hydrogen on the carbon to which each is attached to form (=O). Each $R^{2a}$ of formula IVa is independently H, $C_{1-6}$ alkyl, halogen, OH, nitro or —$NH_2$. Radical $R^3$ of formula IVa is H, $C_{1-6}$ alkyl, $C_{2-10}$ alkenyl, aryl, heteroaryl, or $C_{2-6}$ alkenyl-aryl, wherein the aryl or heteroaryl groups are optionally substituted with 1-4 $R^{3a}$ groups. Each $R^{3a}$ group of formula IVa is independently $C_{1-6}$ alkyl, $C_{1-6}$ alkoxy or OH. Each $R^4$ of formula IVa is H, $C_{1-6}$ alkyl, $C_{1-6}$ alkoxy, $C_{1-6}$ alkylamine, $C_{0-6}$ alkyl—OH, $C_{1-6}$ alkyl—$CO_2$H, or $C_{1-6}$ alkyl—C(O)$NH_2$. The compounds of formula IVa include the salts and isomers thereof.

In some embodiments, a compound of the present invention as described herein (e.g., compound of formula I, Ia, Ib, Ic, Id, Ie, II, IIa, III, IV, IVa, IVb, IVc, V, VI or VII) is an isolated compound.

In yet other embodiments, the present invention also provides compositions comprising a compound of the present invention and a pharmaceutically acceptable excipient.

In some embodiments, the present invention provides a method of preparing a *Adelostemma gracillimum* refined fraction, including contacting *Adelostemma gracillimum* herb with methanol or ethanol, to form an alcohol extract; contacting the alcohol extract with an organic solvent to form an organic solvent fraction; and contacting the organic solvent fraction with a petroleum ether to form the *Adelostemma gracillimum* refined fraction. The organic solvent can be any suitable organic solvent described above. In other embodiments, the present invention provides an *Adelostemma gracillimum* refined fraction prepared by this method.

In some embodiments, the *Adelostemma gracillimum* refined fraction prepared above is further fractionated by eluting a first fraction of the *Adelostemma gracillimum* refined fraction from a resin column with a solution of about 30% ethanol in water; eluting a second fraction from the resin column with a solution of about 60% ethanol in water; and eluting a third fraction from the resin column with a solution of about 96% ethanol in water. In other embodiments, the present invention provides an *Adelostemma gracillimum* refined fraction prepared by the method above.

In another embodiment, the present invention provides a method of improving memory in a subject, the method comprising administering to a subject in need thereof, a therapeutically effective amount of a compound or composition or *Adelostemma gracillimum* refined fraction of the present invention.

In yet other embodiments, the present invention provides a method of treating a neurodegenerative disease or neuropathological condition in a subject, the method including administering to the subject a therapeutically effective amount of a compound or composition or *Adelostemma gracillimum* refined fraction of the present invention.

In still yet other embodiments, the present invention provides a method of inhibiting the activities of an NMDA receptor, the method including contacting the NMDA receptor with a compound or composition or *Adelostemma gracillimum* refined fraction of the present invention.

In another embodiment, the present invention provides a method of inhibiting the activities of an amyloid-beta peptide, the method including contacting the amyloid-beta peptide with a compound or composition or *Adelostemma gracillimum* refined fraction of the present invention.

In still another embodiment, the present invention provides a method of treating epilepsy in a subject, the method comprising administering to a subject in need thereof, a therapeutically effective amount of a *Adelostemma gracillimum* refined fraction.

DETAILED DESCRIPTION OF THE INVENTION

I. General

Figure 1:
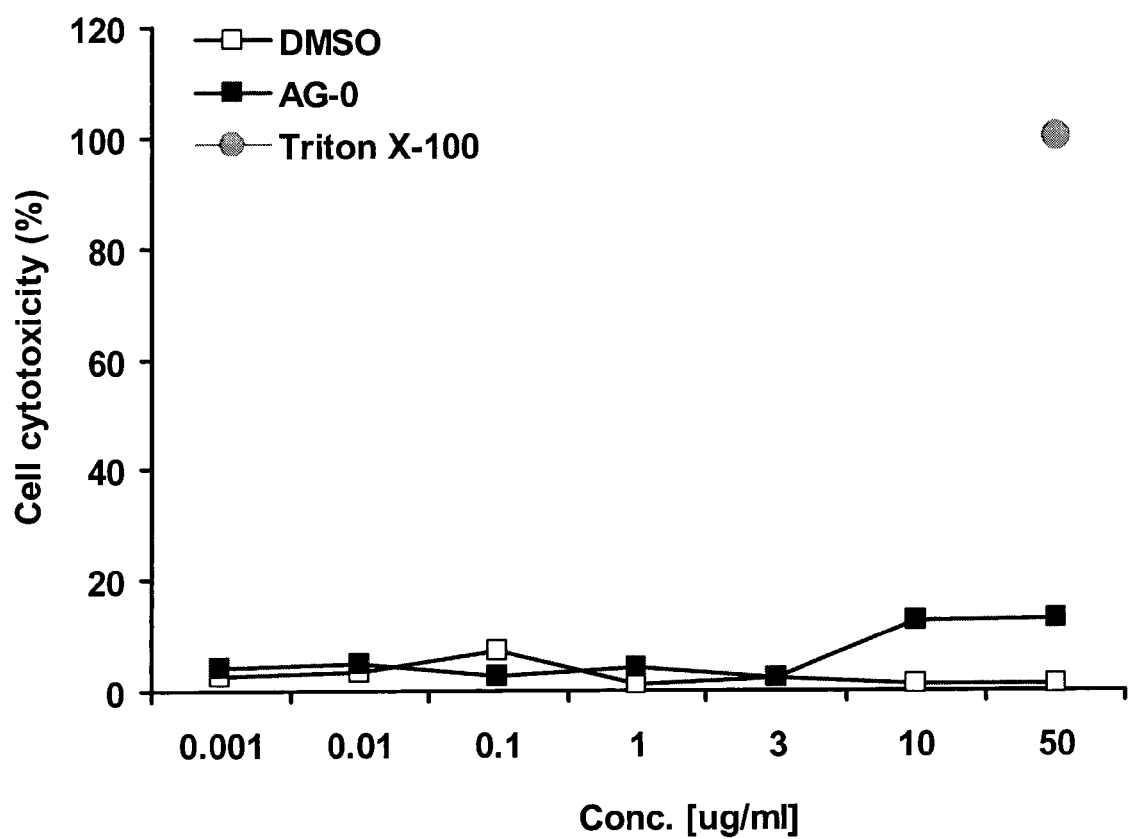
FIG. 1. *Adelostemma gracillimum* refined fraction does not cause cell death in neurons. Cortical neurons 7 days in vitro (DIV) were pre-treated with various concentrations of *Adelostemma gracillimum* refined fraction ("AG—0") for 24 hours and the level of lactate dehydrogenase (LDH) was measured. Quantification of cell survival is presented as a percentage compared to a positive control (Triton X—100, values set as 100% cell death). Assays were done in triplicate and repeated at least twice.

The present invention provides isolated compounds from *Adelostemma gracillimum* refined fraction. In the course of screening the *Adelostemma gracillimum* refined fraction ("AG-0") for neuroprotective activity, a less polar sub-fraction of AG-0, AG-3, was found to exhibit neuroprotective activities. Studies on the fraction AG-0 and its compounds also indicate their potencies in promoting neuronal survival against apoptosis and in activating intracellular signaling cascades that are important for neuronal survival and differentiation. AG-0 and its compounds are also able to prevent glutamate-induced neurotoxicity by inhibiting the activities of the N-methyl-D-aspartic acid (NMDA) receptor and prevent amyloid-beta peptide neurotoxicity by inhibiting caspase-3 activity. AG-0 and its compounds are also useful for treating a variety of disease states, can be used for improving memory, and can be used to treat or protect against epilepsy.

II. Definitions

As used herein, the term "alkyl" refers to a straight or branched, saturated, aliphatic radical having the number of carbon atoms indicated. For example, $C_1$-$C_6$ alkyl includes, but is not limited to, methyl, ethyl, propyl, isopropyl, butyl, isobutyl, sec-butyl, tert-butyl, pentyl, isopentyl, hexyl, etc. Other alkyl groups include, but are not limited to heptyl, octyl, nonyl, decyl, etc. Alkyl can include any number of carbons, such as 1-2, 1-3, 1-4, 1-5, 1-6, 1-7, 1-8, 1-9, 1-10, 2-3, 2-4, 2-5, 2-6, 3-4, 3-5, 3-6, 4-5, 4-6 and 5-6. The alkyl group is typically monovalent, but can be divalent, such as when the alkyl group links two moieties together.

As used herein, the term "alkylene" refers to an alkyl group, as defined above, linking at least two other groups, i.e., a divalent hydrocarbon radical. The two moieties linked to the alkylene can be linked to the same atom or different atoms of the alkylene. For instance, a straight chain alkylene can be the bivalent radical of —$(CH_2)_n$—, where n is 1, 2, 3, 4, 5 or 6. Alkylene groups include, but are not limited to, methylene, ethylene, propylene, isopropylene, butylene, isobutylene, sec-butylene, pentylene and hexylene.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R", —NR"C(O)$_2$R', —NR—C(NR'R")=NR"", —NR—C(NR'R")=NR"', —S(O)R', —S(O)$_2$R', —S(O)$_2$NR'R", —NRSO$_2$R', —CN and —NO$_2$ in a number ranging from zero to (2 m'+1), where m' is the total number of carbon atoms in such radical. R', R", R'" and R"" each preferably independently refer to hydrogen, alkyl, heteroalkyl, aryl, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl.

As used herein, the term "alkoxy" refers to an alkyl group having an oxygen atom that connects the alkyl group to the point of attachment. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. For example, the alkoxy groups can be substituted with halogens to form a "haloalkoxy" group.

As used herein, the term "alkenyl" refers to either a straight chain or branched hydrocarbon of 2 to 6 carbon atoms, having at least one double bond. Examples of alkenyl groups include, but are not limited to, vinyl, propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can also have from 2 to 3, 2 to 4, 2 to 5, 3 to 4, 3 to 5, 3 to 6, 4 to 5, 4 to 6 and 5 to 6 carbons. The alkenyl groups are typically monovalent, but can be divalent, such as when the alkenyl group links two moieties together.

As used herein, the term "alkenylene" refers to an alkenyl group, as defined above, linking at least two other groups, i.e., a divalent hydrocarbon radical. The two moieties linked to the alkenylene can be linked to the same atom or different atoms of the alkenylene. Alkenylene groups include, but are not limited to, ethenylene, propenylene, isopropenylene, butenylene, isobutenylene, sec-butenylene, pentenylene and hexenylene.

As used herein, the term "alkynyl" refers to either a straight chain or branched hydrocarbon of 2 to 6 carbon atoms, having at least one triple bond. Examples of alkynyl groups include, but are not limited to, acetylenyl, propynyl, 1-butynyl, 2-butynyl, isobutynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can also have from 2 to 3, 2 to 4, 2 to 5, 3 to 4, 3 to 5, 3 to 6, 4 to 5, 4 to 6 and 5 to 6 carbons. The alkynyl group is typically monovalent, but can be divalent, such as when the alkynyl group links two moieties together.

As used herein, the term "alkynylene" refers to an alkynyl group, as defined above, linking at least two other groups, i.e., a divalent hydrocarbon radical. The two moieties linked to the alkynylene can be linked to the same atom or different atoms of the alkynylene. Alkynylene groups include, but are not limited to, ethynylene, propynylene, isopropynylene, butynylene, sec-butynylene, pentynylene and hexynylene.

As used herein, the term "alkyl amine" refers to an alkyl groups as defined within, having one or more amino groups. The amino groups can be primary, secondary or tertiary. The alkyl amine can be further substituted with a hydroxy group. Alkyl amines useful in the present invention include, but are not limited to, ethyl amine, propyl amine, isopropyl amine, ethylene diamine and ethanolamine. The amino group can link the alkyl amine to the point of attachment with the rest of the compound, be at the omega position of the alkyl group, or link together at least two carbon atoms of the alkyl group. One of skill in the art will appreciate that other alkyl amines are useful in the present invention.

As used herein, the term "halogen" refers to fluorine, chlorine, bromine and iodine.

As used herein, the term "haloalkyl" refers to alkyl as defined above where some or all of the hydrogen atoms are substituted with halogen atoms. Halogen (halo) preferably represents chloro or fluoro, but may also be bromo or iodo. For example, haloalkyl includes trifluoromethyl, fluoromethyl, 1,2,3,4,5-pentafluoro-phenyl, etc. The term "perfluoro" defines a compound or radical which has at least two available hydrogens substituted with fluorine. For example, perfluorophenyl refers to 1,2,3,4,5-pentafluorophenyl, perfluoromethane refers to 1,1,1-trifluoromethyl, and perfluoromethoxy refers to 1,1,1-trifluoromethoxy.

As used herein, the term "halo-alkoxy" refers to an alkoxy group having at least one halogen. Halo-alkoxy is as defined for alkoxy where some or all of the hydrogen atoms are substituted with halogen atoms. The alkoxy groups can be substituted with 1, 2, 3, or more halogens. When all the hydrogens are replaced with a halogen, for example by fluorine, the compounds are per-substituted, for example, perfluorinated. Halo-alkoxy includes, but is not limited to, trifluoromethoxy, 2,2,2,-trifluoroethoxy, perfluoroethoxy, etc.

As used herein, the term "cycloalkyl" refers to a saturated or partially unsaturated, monocyclic, fused bicyclic or bridged polycyclic ring assembly containing from 3 to 12 ring atoms, or the number of atoms indicated Monocyclic rings include, for example, cyclopropyl, cyclobutyl, cyclopentyl, cyclohexyl, cycloheptyl and cyclooctyl. Bicyclic and polycyclic rings include, for example, norbornane, decahydronaphthalene and adamantane. For example, $C_{3-8}$cycloalkyl includes cyclopropyl, cyclobutyl, cyclopentyl, cyclohexyl, cycloheptyl, cyclooctyl, and norbornane.

As used herein, the term "cycloalkylene" refers to a cycloalkyl group, as defined above, linking at least two other groups, i.e., a divalent hydrocarbon radical. The two moieties linked to the cycloalkylene can be linked to the same atom or different atoms of the cycloalkylene. Cycloalkylene groups include, but are not limited to, cyclopropylene, cyclobutylene, cyclopentylene, cyclohexylene, cycloheptylene and cyclooctylene.

As used herein, the term "heterocycloalkyl" refers to a ring system having from 3 ring members to about 20 ring members and from 1 to about 5 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heterocycle includes, but is not limited to, tetrahydrofuranyl, tetrahydrothiophenyl, morpholino, pyrrolidinyl, pyrrolinyl, imidazolidinyl, imidazolinyl, pyrazolidinyl, pyrazolinyl, piperazinyl, piperidinyl, indolinyl, quinuclidinyl and 1,4-dioxa-8-aza-spiro[4.5]dec-8-yl.

As used herein, the term "heterocyclalkylene" refers to a heterocyclalkyl group, as defined above, linking at least two other groups. The two moieties linked to the heterocyclalkylene can be linked to the same atom or different atoms of the heterocyclalkylene.

As used herein, the term "aryl" refers to a monocyclic or fused bicyclic, tricyclic or greater, aromatic ring assembly containing 6 to 16 ring carbon atoms. For example, aryl may be phenyl, benzyl or naphthyl, preferably phenyl. "Arylene" means a divalent radical derived from an aryl group. Aryl groups can be mono-, di- or tri-substituted by one, two or three radicals selected from alkyl, alkoxy, aryl, hydroxy, halogen, cyano, amino, amino-alkyl, trifluoromethyl, alkylenedioxy and oxy-$C_2$-$C_3$-alkylene; all of which are optionally further substituted, for instance as hereinbefore defined; or 1- or 2-naphthyl; or 1- or 2-phenanthrenyl. Alkylenedioxy is a divalent substitute attached to two adjacent carbon atoms of phenyl, e.g. methylenedioxy or ethylenedioxy. Oxy-$C_2$-$C_3$-alkylene is also a divalent substituent attached to two adjacent carbon atoms of phenyl, e.g. oxyethylene or oxypropylene. An example for oxy-$C_2$-$C_3$-alkylene-phenyl is 2,3-dihydrobenzofuran-5-yl.

Preferred as aryl is naphthyl, phenyl or phenyl mono- or disubstituted by alkoxy, phenyl, halogen, alkyl or trifluoromethyl, especially phenyl or phenyl-mono- or disubstituted by alkoxy, halogen or trifluoromethyl, and in particular phenyl.

Examples of substituted phenyl groups as R are, e.g. 4-chlorophen-1-yl, 3,4-dichlorophen-1-yl, 4-methoxyphen-1-yl, 4-methylphen-1-yl, 4-aminomethylphen-1-yl, 4-methoxyethylaminomethylphen-1-yl, 4-hydroxyethylaminomethylphen-1-yl, 4-hydroxyethyl-(methyl)-aminomethylphen-1-yl, 3-aminomethylphen-1-yl, 4-N-acetylaminomethylphen-1-yl, 4-aminophen-1-yl, 3-aminophen-1-yl, 2-aminophen-1-yl, 4-phenyl-phen-1-yl, 4-(imidazol-1-yl)-phen-yl, 4-(imidazol-1-ylmethyl)-phen-1-yl, 4-(morpholin-1-yl)-phen-1-yl, 4-(morpholin-1-ylmethyl)-phen-1-yl, 4-(2-methoxyethylaminomethyl)-phen-1-yl and 4-(pyrrolidin-1-ylmethyl)-phen-1-yl, 4-(thiophenyl)-phen-1-yl, 4-(3-thiophenyl)-phen-1-yl, 4-(4-methylpiperazin-1-yl)-phen-1-yl, and 4-(piperidinyl)-phenyl and 4-(pyridinyl)-phenyl optionally substituted in the heterocyclic ring.

As used herein, the term "arylene" refers to an aryl group, as defined above, linking at least two other groups. The two moieties linked to the arylene are linked to different atoms of the arylene. Arylene groups include, but are not limited to, phenylene.

As used herein, the term "arylene-oxy" refers to an arylene group, as defined above, where one of the moieties linked to the arylene is linked through an oxygen atom. Arylene-oxy groups include, but are not limited to, phenylene-oxy.

Similarly, substituents for the aryl and heteroaryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)═NH, —NR'C(NH$_2$)═NH, —NH—C(NH$_2$)═NR', —S(O)R', —S(O)$_2$R', —S(O)$_2$NR'R", —N$_3$, —CH(Ph)$_2$, perfluoro ($C_1$-$C_4$)alkoxy, and perfluoro($C_1$-$C_4$)alkyl, in a number ranging from zero to the total number of open valences on the aromatic ring system; and where R', R" and R'" are independently selected from hydrogen, ($C_1$-$C_8$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl.

As used herein, the term "alkyl-aryl" refers to a radical having an alkyl component and an aryl component, where the alkyl component links the aryl component to the point of attachment. The alkyl component is as defined above, except that the alkyl component is at least divalent in order to link to the aryl component and to the point of attachment. In some instances, the alkyl component can be absent. The aryl component is as defined above. Examples of alkyl-aryl groups include, but are not limited to, benzyl.

As used herein, the term "alkenyl-aryl" refers to a radical having both an alkenyl component and a aryl component, where the alkenyl component links the aryl component to the point of attachment. The alkenyl component is as defined above, except that the alkenyl component is at least divalent in order to link to the aryl component and to the point of attachment. The aryl component is as defined above. Examples of alkenyl-aryl include ethenyl-phenyl, among others.

As used herein, the term "heteroaryl" refers to a monocyclic or fused bicyclic or tricyclic aromatic ring assembly containing 5 to 16 ring atoms, where from 1 to 4 of the ring atoms are a heteroatom each N, O or S. For example, heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g. alkyl, nitro or halogen. Pyridyl represents 2-, 3- or 4-pyridyl, advantageously 2- or 3-pyridyl. Thienyl represents 2- or 3-thienyl. Quinolinyl represents preferably 2-, 3- or 4-quinolinyl. Isoquinolinyl represents preferably 1-, 3- or 4-isoquinolinyl. Benzopyranyl, benzothiopyranyl represents preferably 3-benzopyranyl or 3-benzothiopyranyl, respectively. Thiazolyl represents preferably 2- or 4-thiazolyl, and most preferred, 4-thiazolyl. Triazolyl is preferably 1-, 2- or 5-(1,2,4-triazolyl). Tetrazolyl is preferably 5-tetrazolyl.

Preferably, heteroaryl is pyridyl, indolyl, quinolinyl, pyrrolyl, thiazolyl, isoxazolyl, triazolyl, tetrazolyl, pyrazolyl, imidazolyl, thienyl, furanyl, benzothiazolyl, benzofuranyl, isoquinolinyl, benzothienyl, oxazolyl, indazolyl, or any of the radicals substituted, especially mono- or di-substituted.

As used herein, the term "saccharide" refers to mono-, di-, and oligosaccharides.

Monosaccharides useful in the present invention include, but are not limited to, glucose, fructose, galactose, xylose, and ribose. Disaccharides useful in the present invention include, but are not limited to, sucrose, lactose, maltose, and trehalose. Oligosaccharides contain from 3-10 monosaccharides, and include, but are not limited to, fructooligosaccharides, galactooligosaccharides and mannan-oligosaccharides. Other saccharides useful in the present invention include, but are not limited to, Cym-Ole-Ole, Cym-Ole-Cym, and Cym-Dig.

As used herein, the term "glucose moiety" refers to a glucose molecule that is a component of a larger molecule.

As used herein, the term "salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

As used herein, the term "subject" refers to animals such as mammals, including, but not limited to, primates (e.g., humans), cows, sheep, goats, horses, dogs, cats, rabbits, rats, mice and the like. In certain embodiments, the subject is a human.

As used herein, the terms "therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). In sensitized cells, the therapeutically effective dose can often be lower than the conventional therapeutically effective dose for non-sensitized cells.

As used herein, the term "pharmaceutically acceptable excipient" refers to a substance that aids the administration of an active agent to and absorption by a subject. Pharmaceutical excipients useful in the present invention include, but are not limited to, binders, fillers, disintegrants, lubricants, coatings, sweeteners, flavors and colors. One of skill in the art will recognize that other pharmaceutical excipients are useful in the present invention.

As used herein, the terms "administer" or "administering" refer to oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject.

As used herein, the term "improving learning and/or memory" refers to an improvement or enhancement of at least one parameter that indicates learning and memory. Improvement or enhancement is change of a parameter by at least 10%, optionally at least about 20%, at least about 30%, at least about 40%, at least about 50%, at least about 60%, at least about 70%, at least about 80%, at least about 90%, at least about 100%, at least about 150%, at least about 200%, etc. The improvement of learning and memory can be measured by any methods known in the art. For example, compounds described herein that improve learning and memory can be screened using the Morris water maze (see, e.g., materials' and methods section). See also, Gozes et al., *Proc. Natl. Acad. Sci. USA* 93:427-432 (1996). Memory and learning can also be screened using any of the methods described herein or other methods that are well known to those of skill in the art, e.g., the Randt Memory Test, the Wechler Memory Scale, the Forward Digit Span test, or the California Verbal Learning Test.

As used herein, the term "memory" includes all medical classifications of memory, e.g., sensory, immediate, recent and remote, as well as terms used in psychology, such as reference memory, which refers to information gained from previous experience, either recent or remote (see, e.g., *Harrison's Principles of Internal Medicine*, volume 1, pp. 142-150 (Fauci et al., eds., 1988). Pathologies or neuropathologies that would benefit from therapeutic and diagnostic applications of this invention include, for example, the following: diseases of central motor systems including degenerative conditions affecting the basal ganglia (Huntington's disease, Wilson's disease, striatonigral degeneration, corticobasal ganglionic degeneration), Tourette's syndrome, Parkinson's disease, progressive supranuclear palsy, progressive bulbar palsy, familial spastic paraplegia, spinomuscular atrophy, ALS and variants thereof, dentatorubral atrophy, olivo-pontocerebellar atrophy, paraneoplastic cerebellar degeneration, and dopamine toxicity;

diseases affecting sensory neurons such as Friedreich's ataxia, diabetes, peripheral neuropathy, retinal neuronal degeneration;

diseases of limbic and cortical systems such as cerebral amyloidosis, Pick's atrophy, Retts syndrome;

neurodegenerative pathologies involving multiple neuronal systems and/or brainstem including Alzheimer's disease, AIDS-related dementia, Leigh's disease, diffuse Lewy body disease, epilepsy, multiple system atrophy, Guillain-Barre syndrome, lysosomal storage disorders such as lipofuscinosis, late-degenerative stages of Down's syndrome, Alper's disease, vertigo as result of CNS degeneration;

pathologies associated with developmental retardation and learning impairments, and Down's syndrome, and oxidative stress induced neuronal death;

pathologies arising with aging and chronic alcohol or drug abuse including, for example, with alcoholism the degeneration of neurons in locus coeruleus, cerebellum, cholinergic basal forebrain; with aging degeneration of cerebellar neurons and cortical neurons leading to cognitive and motor impairments; and with chronic amphetamine abuse degeneration of basal ganglia neurons leading to motor impairments;

pathological changes resulting from focal trauma such as stroke, focal ischemia, vascular insufficiency, hypoxic-ischemic encephalopathy, hyperglycemia, hypoglycemia, closed head trauma, or direct trauma; and pathologies arising as a negative side-effect of therapeutic drugs and treatments (e.g., degeneration of cingulate and entorhinal cortex neurons in response to anticonvulsant doses of antagonists of the NMDA class of glutamate receptor).

As used herein, the terms "treat" or "treating" or "treatment" refers to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom or condition. The treatment or amelioration of symptoms can be based on any objective or subjective parameter; including, e.g., the result of a physical examination.

As used herein, the term "organic solvent" refers to solvents that are water immiscible. The organic solvent can be any suitable organic solvent, such as, dichloromethane, chloroform, carbon tetrachloride, ethyl acetate, acetone, diethyl ether, pentane, hexanes and petroleum ether. One of skill in the art will appreciate that other organic solvents are useful in the present invention.

As used herein, the term "resin column" refers to a column, for use in column chromatography, including a solid material capable of binding a target of interest. The resin used in the column can be any material or combination of materials suitable for a particular type of column chromatography, including but not limited to alumina, silica, silica gel, octadecasilica (ODS), cellulose, dextran, agarose, heparin, proteins, or metal (e.g., nickel, cobalt, copper, zinc, iron, and gallium). One of skill in the art will recognize that the suitability of a particular type of resin column for a particular application will vary depending upon the type of column chromatography to be performed (e.g., affinity, ion exchange, size exclusion, reverse phase high performance liquid chromatography, etc.) and the target to be bound. One of skill in the art will also recognize that other types of resin columns are useful in the present invention.

As used herein, the term "epilepsy" refers to a disorder of brain function characterized by the periodic and unpredictable occurrence of seizures (see, *Goodman & Gilman's The Pharmacological Basis of Therapeutics* and *Harrison's Principles of Internal Medicine*).

As used herein, the terms "treating epilepsy" and "protecting against epilepsy" refer to treating or protecting against the occurrence of epileptic seizures or diminishing the severity of an epileptic seizure. Treating or protecting against the occurrence of epileptic seizures corresponds to a decrease in occurrence of seizures of at least 10%, optionally at least about 20%, at least about 30%, at least about 40%, at least about 50%, at least about 60%, at least about 70%, at least about 80%, at least about 90%, at least about 100%, etc. Diminishing the severity of an epileptic seizure is a decrease in intensity of a seizure of at least 10%, optionally at least about 20%, at least about 30%, at least about 40%, at least about 50%, at least about 60%, at least about 70%, at least about 80%, at least about 90%, at least about 100%, etc. The decrease in occurrence of or severity of epileptic seizures can be measured by any methods known in the art. For example, compounds described herein that improve learning and memory can be screened using the audiogenic seizure susceptibility test (see, e.g., materials and methods section).

III. Compounds

The present invention provides compounds isolated from a *Adelostemma gracillimum* refined fraction. In some embodiments, the present invention provides compounds of formula I:

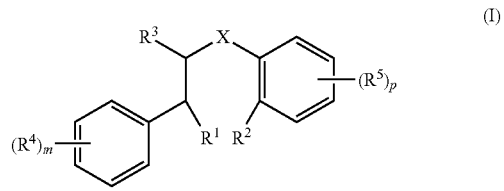

(I)

wherein radical X of formula I is a bond or —O—; $R^1$ of formula I is OH; and $R^2$ of formula I is H or OH. Alternatively, radicals $R^1$ and $R^2$ of formula I are combined to form —O—. Radical $R^3$ of formula I is H, $C_{1-6}$ alkyl, $C_{1-6}$ alkoxy or $C_{1-6}$ alkyl-OH. Each $R^4$ of formula I is independently H, OH, $C_{1-6}$ alkyl, or $C_{1-6}$ alkoxy. Each $R^5$ of formula I is independently H, OH, $C_{1-6}$ alkyl, $C_{1-6}$ alkoxy, $C_{2-6}$ alkenyl optionally substituted with one $R^6$ group, —C(O)$R^7$, or $C_{1-6}$ alkyl-C(O)$R^7$. Radical $R^6$ of formula I is $C_{1-6}$ alkoxy or —C(O)$R^7$. Each $R^7$ of formula I is H or $C_{1-6}$ alkyl. Subscript m of formula I is an integer from 1 to 5; and subscript p of formula I is an integer from 1 to 4. The compounds of formula I include the salts and isomers thereof.

Compounds of formula I include the following:

TABLE 1

Compounds of formula I

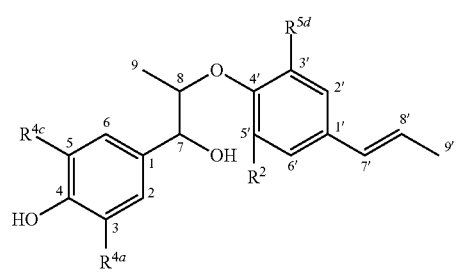

| COMPOUND | $R^2$ | $R^{4a}$ | $R^{4c}$ | $R^{5d}$ |
|---|---|---|---|---|
| GAG-C13 | H | OH | H | OCH$_3$ |
| GAG-C58 | H | OCH$_3$ | OH | OCH$_3$ |
| GAG-C59 | OH | OCH$_3$ | OCH$_3$ | OCH$_3$ |
| GAG-C114 | H | OCH$_3$ | H | OH |
| GAG-C121 | H | OCH$_3$ | OCH$_3$ | OCH$_3$ |

TABLE 2

Compounds of formula I

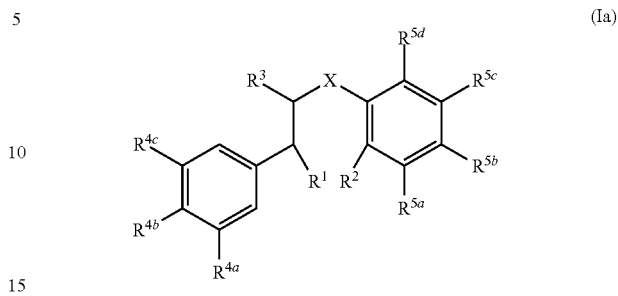

| COMPOUND | $R^3$ | $R^{5b}$ | $R^{5d}$ |
|---|---|---|---|
| GAG-C69 | $CH_3$ | CH=CHCH$_3$ | H |

TABLE 3

Compounds of formula I

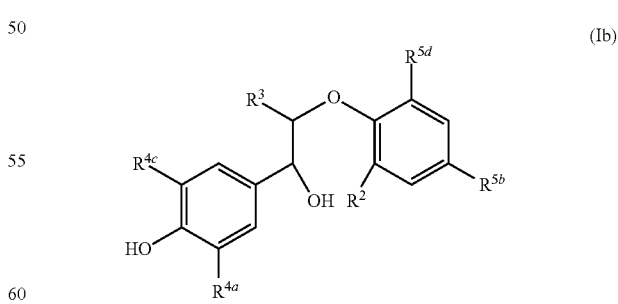

| COMPOUND | $R^3$ | $R^{5c}$ |
|---|---|---|
| GAG-C11 | CH$_2$OH | CH$_2$CH$_2$CHO |
| GAG-C12 | CH$_2$OH | CHO |
| GAG-C19 | CH$_2$OGlc | CH=CHCHO |
| GAG-C64 | CH$_3$ | CH=CHCHO |
| GAG-C76 | CH$_2$OH | CH=CHCH$_2$OCH$_2$CH$_3$ |
| GAG-C77 | CH$_3$ | CHO |

TABLE 4

Compounds of formula I

| COMPOUND | $R^{4c}$ |
|---|---|
| GAG-C51 | H |
| GAG-C109 | OH |
| GAG-C116 | OCH$_3$ |

In some other embodiments, the present invention provides compounds of formula Ia:

(Ia)

wherein radical X of formula Ia is a bond or —O—; $R^1$ of formula Ia is OH; or $R^2$ of formula Ia is H or OH. Alternatively, $R^1$ and $R^2$ of formula Ia are combined to form —O—. Radical $R^3$ of formula Ia is $C_{1-6}$ alkyl or $C_{1-6}$ alkyl-OH. Each of $R^{4a}$, $R^{4b}$ and $R^{4c}$ of formula Ia is independently H, OH, $C_{1-6}$ alkyl, or $C_{1-6}$ alkoxy. Each of $R^{5a}$, $R^{5b}$, $R^{5c}$ and $R^{5d}$ is independently H, OH, $C_{1-6}$ alkyl, $C_{1-6}$ alkoxy, $C_{2-6}$ alkenyl optionally substituted with $C_{1-6}$ alkoxy, or —C(O)—$C_{1-6}$ alkyl. The compounds of formula Ia include those such that
 when X is —O— and $R^1$ is OH, then $R^3$ is $C_{1-6}$ alkyl; $R^{4a}$ and $R^{5d}$ are each independently OH or $C_{1-6}$ alkoxy; $R^{4b}$ is OH; $R^{4c}$ is H, OH or $C_{1-6}$ alkoxy; $R^{5a}$ and $R^{5c}$ are each H; and $R^{5b}$ is $C_{2-6}$ alkenyl;
 when X is —O—, and $R^1$ and $R^2$ are combined to form —O—, then $R^3$ is $C_{1-6}$ alkyl; $R^{4a}$ is $C_{1-6}$ alkoxy; $R^{4b}$ is OH; $R^{4c}$, $R^{5a}$, $R^{5c}$ and $R^{5d}$ are each H; and $R^{5b}$ is $C_{2-6}$ alkenyl;
 when X is a bond, and $R^1$ is OH, then $R^2$, $R^{4b}$, $R^{5b}$ and $R^{5c}$ are each H; $R^3$ is OH; $R^{4a}$ and $R^{5a}$ are each $C_{1-6}$ alkyl; and $R^{4c}$ and $R^{5d}$ are each $C_{1-6}$ alkoxy;
 when X is a bond and $R^1$ and $R^2$ are combined to form —O—, then $R^3$ is $C_{1-6}$ alkyl or $C_{1-6}$ alkyl-OH; $R^{4a}$ and $R^{5a}$ are each $C_{1-6}$ alkoxy; $R^{4b}$ is OH; $R^{4c}$ is H, OH or $C_{1-6}$ alkoxy; $R^{5b}$ is H; $R^{5c}$ is H or $C_{2-6}$ alkenyl substituted with $C_{1-6}$ alkoxy; and $R^{5d}$ is H or C(O)—$C_{1-6}$ alkyl, wherein when $R^3$ is $C_{1-6}$ alkyl, then $R^{5d}$ is —C(O)—$C_{1-6}$ alkyl, and when $R^3$ is $C_{1-6}$ alkyl-OH, then $R^{5d}$ is H; and
 when X is —O—, $R^1$ is OH, $R^2$, $R^{5a}$ and $R^{5c}$ are each H, $R^3$ is Me, $R^{4a}$ and $R^{5d}$ are both OMe, $R^{4b}$ is OH, and $R^{5b}$ is $C_3$ alkenyl, then $R^{4c}$ is OH or $C_{1-6}$ alkyl.

The compounds of formula Ia include the salts and isomers thereof.

In other embodiments, the present invention provides compounds of formula Ib:

(Ib)

wherein $R^2$ is H; $R^3$ is $C_{1-6}$ alkyl; $R^{4a}$ and $R^{5d}$ are each independently OH or $C_{1-6}$ alkoxy; $R^{4c}$ is H, OH or $C_{1-6}$ alkoxy; and $R^{5b}$ is $C_{2-6}$ alkenyl. The compounds of formula Ib include the salts and isomers thereof. In some other embodiments, the compounds of formula Ib include compounds GAG-C13, GAG-C58 and GAG-C59:

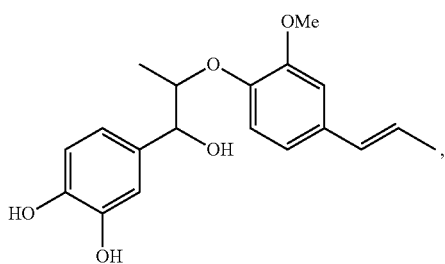,

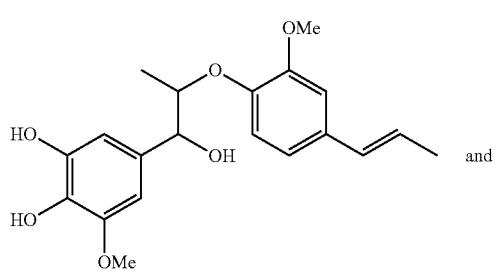 and

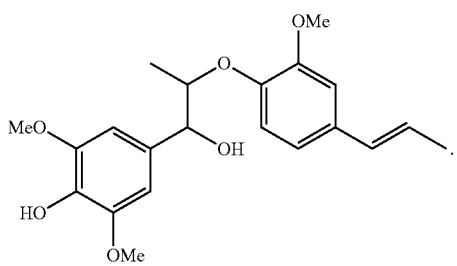.

In another embodiments, the present invention provides compounds of formula Ic:

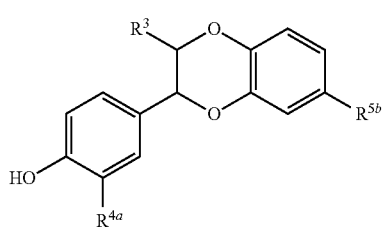

(Ic)

wherein $R^3$ is $C_{1-6}$ alkyl; $R^{4a}$ is $C_{1-6}$ alkoxy; and $R^{5b}$ is $C_{2-6}$ alkenyl. The compounds of formula Ic include the salts and isomers thereof. In other embodiments, the compounds of formula Ic include compound GAG-C69:

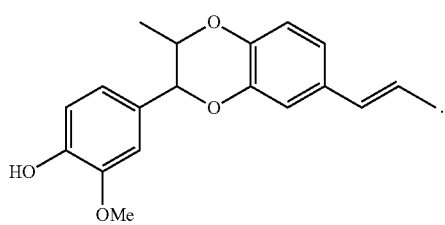 [SMILES: C/C=C/c1ccc2c(c1)OC(c1ccc(O)c(OC)c1)C(C)O2].

In some other embodiments, the present invention provides compounds of formula Id:

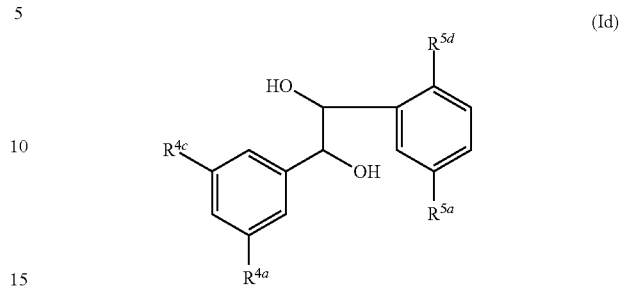

(Id)

wherein $R^{4a}$ and $R^{5a}$ are each $C_{1-6}$ alkyl; and $R^{4c}$ or $R^{5d}$ are each $C_{1-6}$ alkoxy. The compounds of formula Id include the salts and isomers thereof. Compounds of formula Id include GAG-C80:

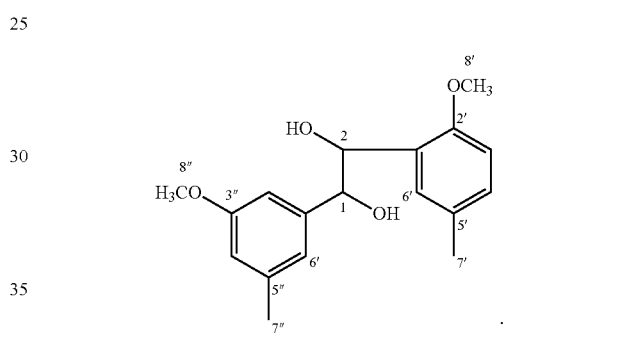.

In still other embodiments, the present invention provides compounds of formula Ie:

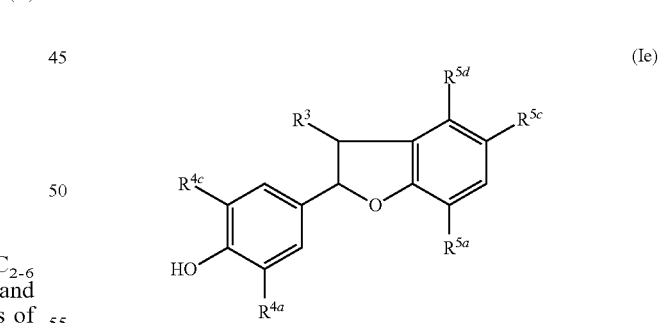

(Ie)

wherein $R^3$ is $C_{1-6}$ alkyl or $C_{1-6}$ alkyl-OH; $R^{4a}$ and $R^{5a}$ are each $C_{1-6}$ alkoxy; $R^{4c}$ is H, OH or $C_{1-6}$ alkoxy; $R^{5c}$ is H or $C_{2-6}$ alkenyl substituted with $C_{1-6}$ alkoxy; and $R^{5d}$ is H or C(O)—$C_{1-6}$ alkyl, wherein when $R^3$ is $C_{1-6}$ alkyl, then $R^{5d}$ is —C(O)—$C_{1-6}$ alkyl, and when $R^3$ is $C_{1-6}$ alkyl-OH, then $R^{5d}$ is H. The compounds of formula Ie include the salts and isomers thereof.

In other embodiments, the compounds of formula Ie include compounds GAG-C51, GAG-C76, GAG-C109 and GAG-C116:

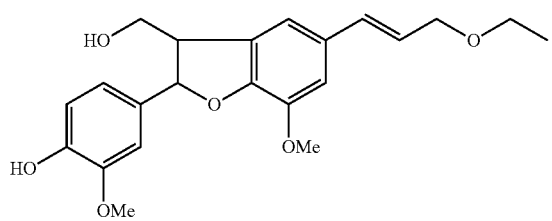

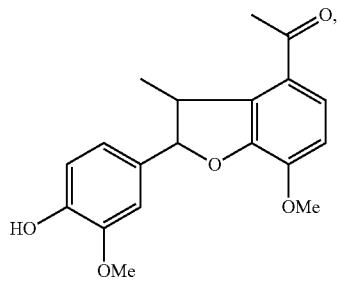

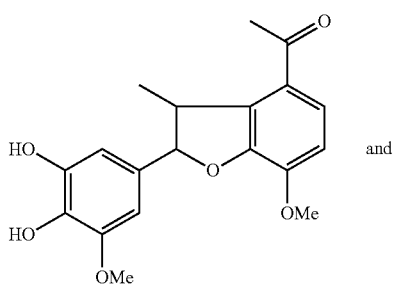

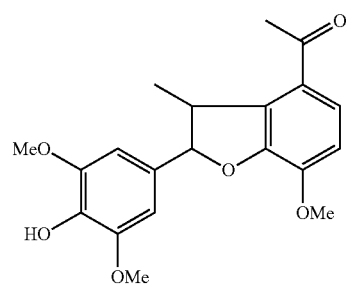

In yet other embodiments, the compounds of formula Ia include GAG-C13, GAG-C69 and GAG-C80:

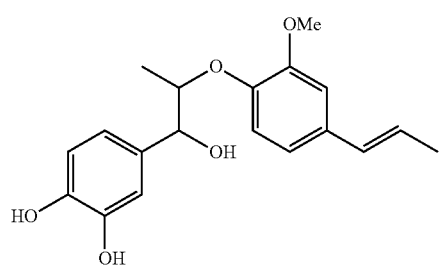

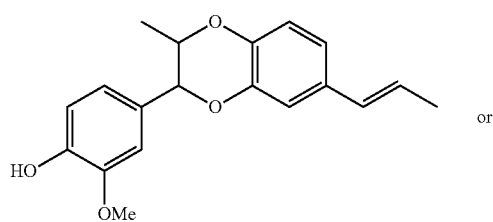 or

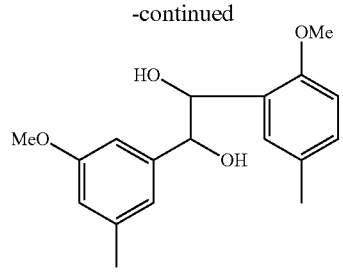

In another embodiment, the present invention provides compounds of formula II:

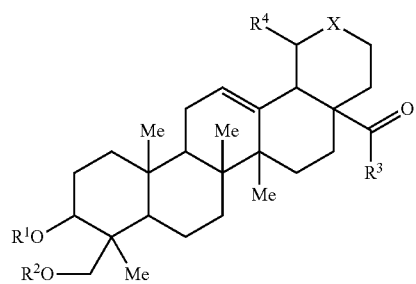

(II)

wherein X of formula II is a bond or —C(CH$_3$)$_2$—. Radical R$^1$ of formula II is H, C$_{1-6}$ alkyl or a saccharide. Radical R$^2$ of formula II is H or C$_{1-6}$ alkyl. Radical R$^3$ of formula II is —OH or —NH$_2$. Radical R$^4$ of formula II is H, C$_{1-6}$ alkyl, or C$_{2-6}$ alkenyl, such that when X is a bond, then R$^4$ is C$_{2-6}$ alkenyl. The compounds of formula II include the salts and isomers thereof. Compounds of formula II include GAG-C74:

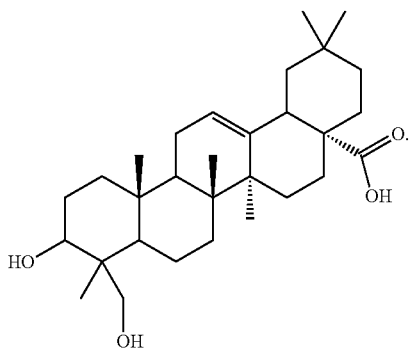

In other embodiments, the present invention provides compounds of formula IIa:

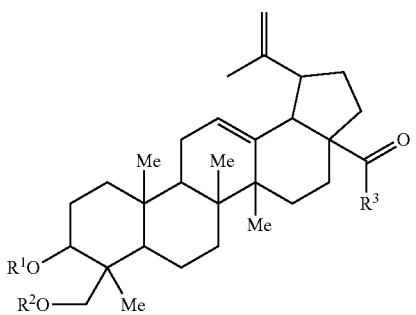

(IIa)

wherein $R^1$ of formula IIa is H, $C_{1-6}$ alkyl or a saccharide. Radical $R^2$ of formula IIa is H or $C_{1-6}$ alkyl. And radical $R^3$ of formula IIa is —OH or —NH$_2$. The compounds of formula IIa include the salts and isomers thereof. In some other embodiments, the compounds of formula IIa include compound GAG-C73:

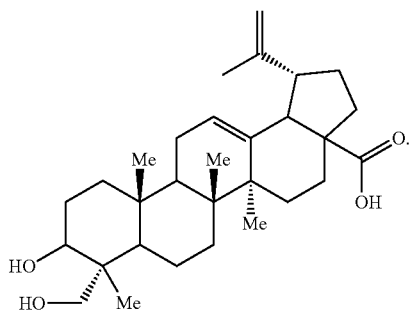

In still other embodiments, the present invention provides compounds of formula (III)

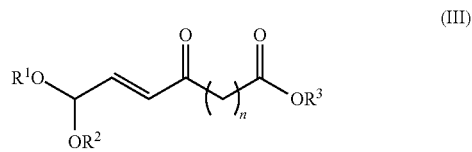

wherein each of $R^1$, $R^2$ or $R^3$ of formula III is independently H or $C_{1-6}$ alkyl. Subscript n of formula III is an integer from 8 to 20. The compounds of formula III include the salts and isomers thereof.

In yet other embodiments, $R^1$ of formula III is H. In still yet other embodiments, $R^1$ of formula III is H; each of $R^2$ and $R^3$ of formula III are Me; and subscript n of formula III is 10. In other embodiments, the compound of formula III is GAG-C78:

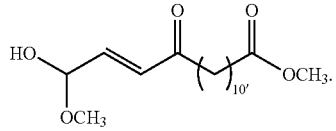

In another embodiment, the present invention provides compounds of formula IV:

(IV)

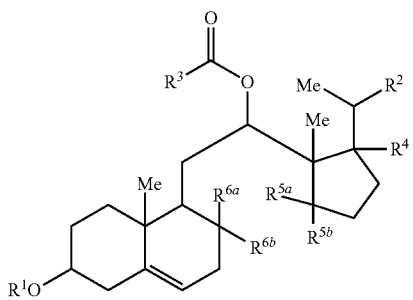

wherein $R^1$ of formula IV is a saccharide. Radical $R^2$ of formula IV is OH, $C_{1-6}$ alkoxy, —OC(O)—$C_{1-6}$ alkyl, —OC(O)O—$C_{1-6}$ alkyl, $C_{0-6}$ alkyl-aryl substituted with 1-3 $R^{2a}$ groups, or is combined with the hydrogen on the carbon to which each is attached to form (=O). Each Rea of formula IV is independently H, $C_{1-6}$ alkyl, halogen, OH, nitro or —NH$_2$. Radical $R^3$ of formula IV is H, $C_{1-6}$ alkyl, $C_{2-6}$ alkenyl, aryl, heteroaryl, or $C_{2-6}$ alkenyl-aryl, wherein the aryl or heteroaryl groups are optionally substituted with 1-4 $R^{3a}$ groups. Each $R^{3a}$ group of formula IV is independently $C_{1-6}$ alkyl, $C_{1-6}$ alkoxy or OH. Radical $R^4$ of formula IV is H, $C_{1-6}$ alkyl, $C_{1-6}$ alkoxy, $C_{1-6}$ alkylamine, $C_{0-6}$ alkyl-OH, $C_{1-6}$ alkyl-CO$_2$H, or $C_{1-6}$ alkyl-C(O)NH$_2$. Each of $R^{5a}$ and $R^{6a}$ of formula IV are OH. Each of $R^{5b}$ and $R^{6b}$ of formula IV are H, or $R^{5a}$ and $R^{5b}$, and $R^{6a}$ and $R^{6b}$, are combined to form (=O). Alternatively, $R^{5b}$ and $R^{6b}$ of formula IV are combined to form a bond. The compounds of formula IV include the salts and isomers thereof.

In other embodiments, the present invention provides compounds of formula IVa:

(IVa)

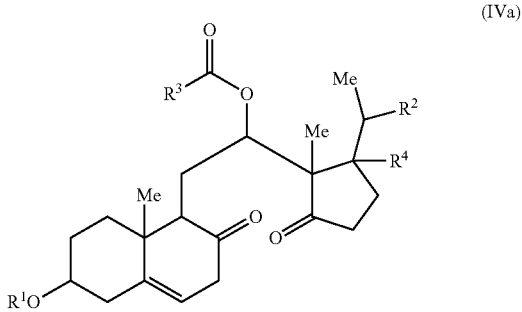

wherein $R^1$ of formula IVa is a saccharide, wherein the saccharide does not include a glucose moiety. Radical $R^2$ of formula IVa is OH, $C_{1-6}$ alkoxy, —OC(O)—$C_{1-6}$ alkyl, —OC(O)O—$C_{1-6}$ alkyl, $C_{0-6}$ alkyl-aryl substituted with 1-3 $R^{2a}$ groups, or is combined with the hydrogen on the carbon to which each is attached to form (=O). Each $R^{2a}$ of formula IVa is independently H, $C_{1-6}$ alkyl, halogen, OH, nitro or —NH$_2$. Radical $R^3$ of formula IVa is H, $C_{1-6}$ alkyl, $C_{2-10}$ alkenyl, aryl, heteroaryl, or $C_{2-6}$ alkenyl-aryl, wherein the aryl or heteroaryl groups are optionally substituted with 1-4 $R^{3a}$ groups. Each $R^{3a}$ group of formula IVa is independently $C_{1-6}$ alkyl, $C_{1-6}$ alkoxy or OH. Each $R^4$ of formula IVa is H, $C_{1-6}$ alkyl, $C_{1-6}$ alkoxy, $C_{1-6}$ alkylamine, $C_{0-6}$ alkyl-OH, $C_{1-6}$ alkyl-CO$_2$H, or $C_{1-6}$ alkyl-C(O)NH$_2$. The compounds of formula IVa include the salts and isomers thereof.

In some embodiments, radical $R^3$ of formula IVa can be combined with the —C(O)O— group to which it is attached to form a cinnamoyl, nicotinoyl, benzoyl, acetyl, salicyloyl, tigloyl or ikemaoyl group, among others.

In some other embodiments, the present invention provides compounds of formula IVb:

(IVb)

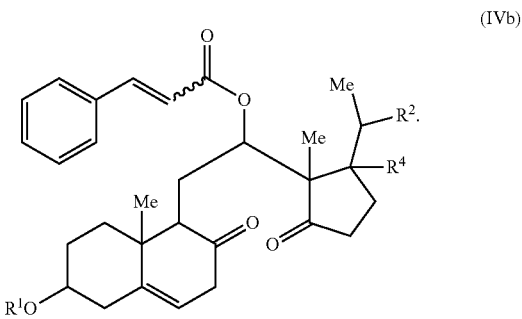

wherein radical $R^1$, $R^2$ and $R^4$ are as defined above for formula IVb. The compounds of formula IVb include the salts and isomers thereof.

TABLE 5
Glycoside compounds of formula IVb with Gracigenin as aglycone:
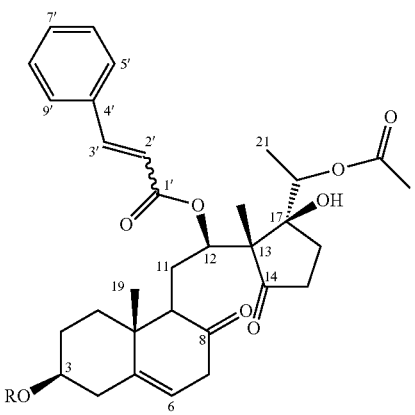
| COMPOUND | CINNAMOYL GROUP | R GROUP |
|---|---|---|
| GAG-C89 | mixture of cis and trans | |
| GAG-C90 | mixture of cis and trans | |
| GAG-C94 | mixture of cis and trans | β-D-Cym |
| GAG-C96 | mixture of cis and trans | |
| GAG-C95 | mixture of cis and trans | |
| GAG-C44 | mixture of cis and trans | |

TABLE 5-continued
Glycoside compounds of formula IVb with Gracigenin as aglycone:
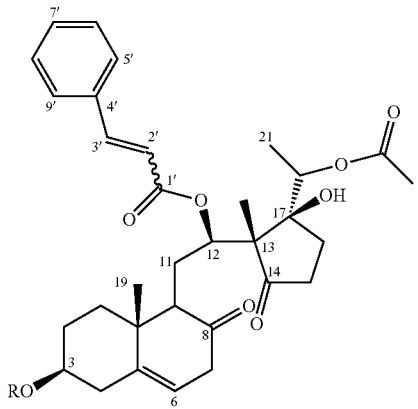
| COMPOUND | CINNAMOYL GROUP | R GROUP |
|---|---|---|
| GAG-C45 | mixture of cis and trans | |
| GAG-C46 | mixture of cis and trans | |
| GAG-C47 | mixture of cis and trans | |
| GAG-C102 | mixture of cis and trans | |
| GAG-C104 | mixture of cis and trans | |

TABLE 5-continued

Glycoside compounds of formula IVb with Gracigenin as aglycone:

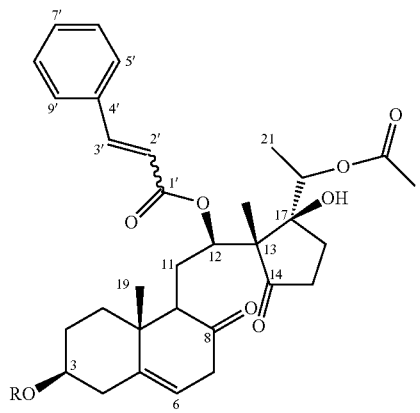

| COMPOUND | CINNAMOYL GROUP | R GROUP |
|---|---|---|
| GAG-C27 | cis | (disaccharide structure) |
| GAG-C28 | trans | (disaccharide structure) |
| GAG-C30 | trans | (monosaccharide structure) |

In still other embodiments, the present invention provides compounds of formula IVc:

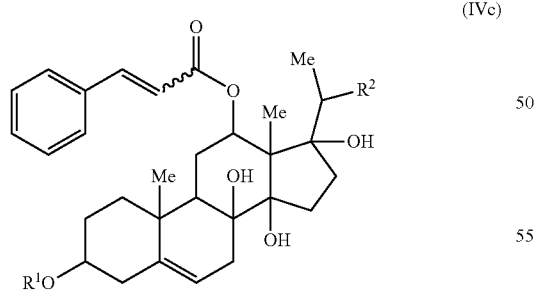

(IVc)

wherein radical $R^1$ of formula IVc is a saccharide Cym-Ole-Ole, Cym-Ole-Cym, or Cym-Dig. Radical $R^2$ of formula IVc is OH, $C_{1-6}$ alkoxy, —OC(O)—$C_{1-6}$ alkyl, or —OC(O)O—$C_{1-6}$ alkyl, or is combined with the hydrogen on the carbon to which each is attached to form (═O). The compounds of formula IVc include the salts and isomers thereof.

TABLE 6
Glycoside compounds of formula IVc with Penupogenin as aglycone
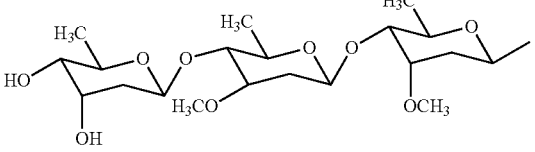
| COMPOUND | CINNAMOYL GROUP | R¹ GROUP |
|---|---|---|
| GAG-C43 | mixture of cis and trans | |
| GAG-C86 | mixture of cis and trans | |
| GAG-C99 | mixture of cis and trans | |
Other compounds of formula IVc include glycoside compounds with cynanforridin as the aglycone, such as in GAG-C87:
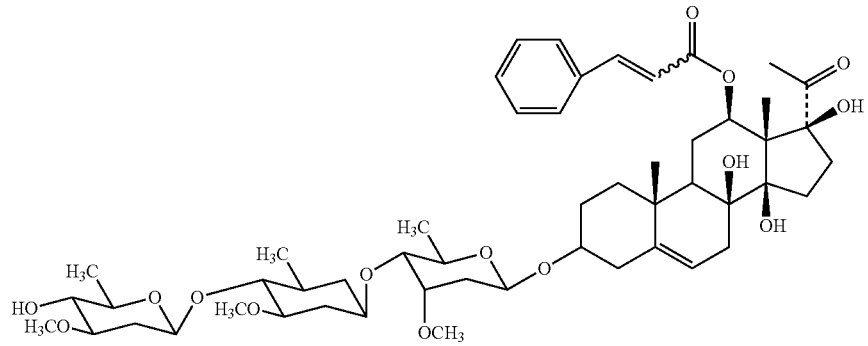

The present invention also provides compounds of formula V in Table 7.

TABLE 7

Acetophenone compounds

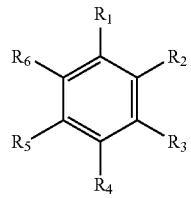

(V)

| COMPOUND | R₁ | R₂ | R₃ | R₄ | R₅ | R₆ |
|---|---|---|---|---|---|---|
| GAG-C02 | COCH₃ | H | OCH₃ | OH | H | H |
| GAG-C23 | COCH(OH) | H | OCH₃ | OH | OCH₃ | H |
| GAG-C113 | COCH₃ | OH | D-Cym | H | H | D-Ole |

The present invention also includes compounds of formula VI in Table 8.

TABLE 8

Steroid compounds

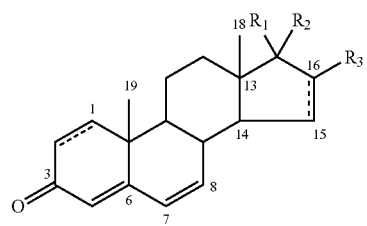

(VI)

| R₁ | R₂ | R₃ | COMPOUND |
|---|---|---|---|
| C=O | | H | GAG-C66/C72 |
| COHCH₃ | H | H | GAG-C68 |

TABLE 8-continued

| | | | |
|---|---|---|---|
| OH | H | H | GAG-C67 |
| H | H | COOH | GAG-C62/C63 |

The present invention also includes compounds of formula VII in Table 9.

TABLE 9

Furocoumarins

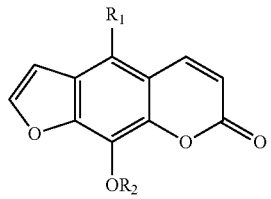

(VII)

| COMPOUND | R₁ | R₂ |
|---|---|---|
| GAG-C36 | H | CH₃ |
| GAG-C38 | OCH₃ | CH₃ |
| GAG-C50 | H | CH₂CH(OH)C(CH₂)CH₃ |
| GAG-C71 | H | CH₂CH(OH)C(CH₃)₂OCH₂CH₃ |
| GAG-C81 | H | CH₂CHC(CH₃)₂ |
| GAG-C82 | OCH₃ | CH₂CHC(CH₃)₂ |

The present invention also includes the following compounds:

| COMPOUND | STRUCTURE |
|---|---|
| GAG-C07 | 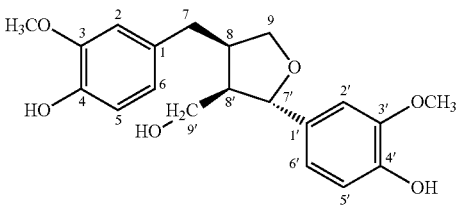 |
| GAG-C49 | 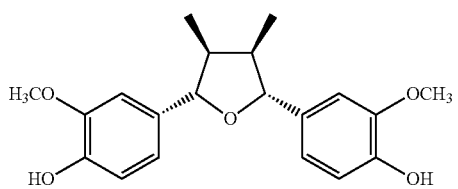 |

| COMPOUND | STRUCTURE |
|---|---|
| GAG-C70 | 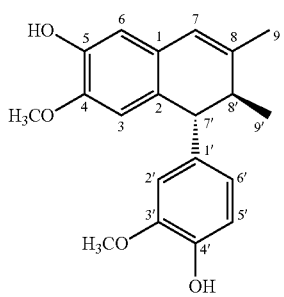 |
| GAG-C61 | 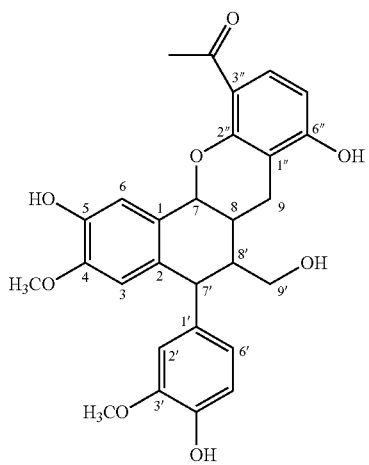 [SMILES: COc1cc(C2c3cc(OC)c(O)cc3C3Oc4c(C(C)=O)ccc(O)c4CC3C2CO)ccc1O] |
| GAG-C20 | 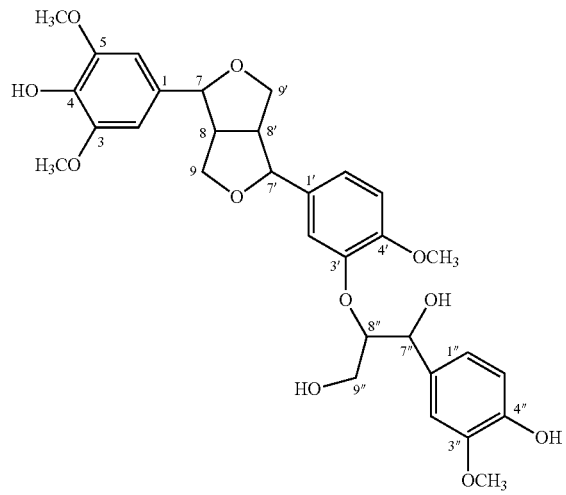 [SMILES: COc1cc(C(O)C(CO)Oc2cc(C3OCC4C(c5cc(OC)c(O)c(OC)c5)OCC34)ccc2OC)ccc1O] |
| GAG-C40 | 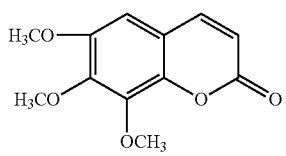 |

| COMPOUND | STRUCTURE |
|---|---|
| GAG-C65 | 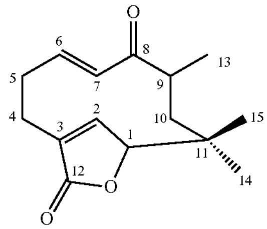 |
| GAG-C119 | 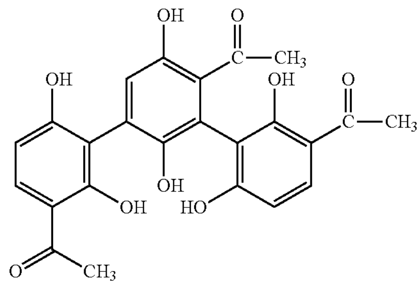 [SMILES: CC(=O)c1ccc(O)c(-c2cc(O)c(C(C)=O)c(-c3c(O)ccc(C(C)=O)c3O)c2O)c1O] |
| GAG-C120 | 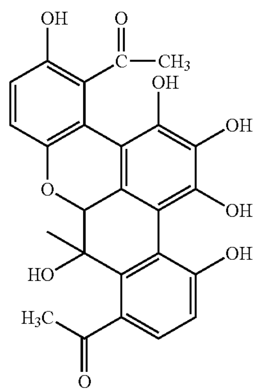 [SMILES: CC(=O)c1ccc(O)c2c1C(C)(O)C1Oc3ccc(O)c(C(C)=O)c3-c3c(O)c(O)c(O)c-2c31] |

The compounds of the present invention, including the compounds of formulas I, Ia, Ib, Ic, Id, Ie, II, IIa, III, IV, IVa, IVb, IVc, V, VI and VII, can be isolated compounds.

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention can be prepared by a variety of methods known to one of skill in the art, for example, see Richard C. Larock, *Comprehensive Organic Transformations* 1989, VCH Publishers, Inc.

In some embodiments, a compound of the present invention is an isolated compound. As used herein, the term "isolated" means substantially separated from nature. In some embodiments, an isolated compound of the present invention is isolated from a naturally occurring compound, e.g., *Adelostemma gracillimum*. Optionally, an isolated compound of the present invention has a higher concentration than occurs in nature. In some embodiments, an isolated compound has a degree of purity of at least 80%, at least 85%, at least 90%, at least 91%, at least 92%, at least 93%, at least 94%, at least 95%, at least 96%, at least 97%, at least 98%, or at least 99%, as determined by established analytical methods.

IV. Compositions and Administration

The present invention also provides compositions of a compound of the present invention and a pharmaceutically acceptable excipient. In some embodiments, the compound of the present invention is an isolated compound of formula I, Ia, Ib, Ic, Id, Ie, II, IIa, III, IV, IVa, IVb, IVc, V, VI or VII. Pharmaceutical excipients useful in the present invention include, but are not limited to, binders, fillers, disintegrants, lubricants, coatings, sweeteners, flavors and colors. One of skill in the art will recognize that other pharmaceutical excipients are useful in the present invention.

In some embodiments, a composition comprising an isolated compound comprises at least about 10%, at least 20%, at least 30%, at least 40%, at least 50%, at least 60%, at least 70%, at least 80%, at least 90% or more by weight of the compound. In some embodiments, a pharmaceutical composition comprising an isolated compound of the present invention is in unit dose form. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be an appropriate number of any of these in packaged form. The quantity of isolated compound in a unit dose preparation may be varied or adjusted from 0.1 mg to 10000 mg, from 1.0 mg to 1000 mg, or from 10 mg to 500 mg, according to the particular application and the potency of the isolated compound.

The compounds of the present invention can be administered as frequently as necessary, including hourly, daily, weekly or monthly. The compounds utilized in the pharmaceutical method of the invention are administered at the initial dosage of about 0.0001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound being employed. For example, dosages can be empirically determined considering the type and stage of disease diagnosed in a particular patient. The dose administered to a patient, in the context of the present invention should be sufficient to effect a beneficial therapeutic response in the patient over time. The size of the dose also will be determined by the existence, nature, and extent of any adverse side-effects that accompany the administration of a particular compound in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired. Doses can be given daily, or on alternate days, as determined by the treating physician. Doses can also be given on a regular or continuous basis over longer periods of time (weeks, months or years), such as through the use of a subdermal capsule, sachet or depot, or via a patch.

The pharmaceutical compositions can be administered to the patient in a variety of ways, including topically, parenterally, intravenously, intradermally, intramuscularly, colonically, rectally or intraperitoneally. Preferably, the pharmaceutical compositions are administered parenterally, topically, intravenously, intramuscularly or orally.

In practicing the methods of the present invention, the pharmaceutical compositions can be used alone, or in combination with other therapeutic or diagnostic agents. The additional anticancer drugs used in the combination protocols of the present invention can be administered separately or one or more of the anticancer drugs used in the combination protocols can be administered together, such as in an admixture. Where one or more anticancer drug is administered separately, the timing and schedule of administration of each drug can vary. The other therapeutic or diagnostic agents can be administered at the same time as the compounds, separately or at different times.

In clinical studies, number of lesions, tumor size, and tumor growth rate can be monitored by radiography, tomography, and, where possible, direct measurement of tumor mass. Anti-tumor effects can also be measured using molecular biology and biochemistry techniques, such as ELISA, PCR, western blotting, or immunocytochemistry.

The pharmaceutically effective amount of a composition required as a dose will depend on the route of administration, the type of cancer being treated, and the physical characteristics of the patient. The dose can be tailored to achieve a desired effect, but will depend on such factors as body surface area, weight, diet, concurrent medication and other factors which those skilled in the medical arts will recognize.

The foregoing are general guidelines only that can be expanded or altered based on, for example, disease type and grade, patient age, health status, and sex, the particular drugs used in combination, the route and frequency of administration, and experimental and clinical findings using a multidrug combination.

V. *Adelostemma gracillimum* Refined Fractions

Also useful in the present invention are refined fractions of *Adelostemma gracillimum*. These fractions include a fraction obtained by extracting compounds from the herb itself, *Adelostemma gracillimum* refined fraction (AG-0). Other fractions include AG-1, AG-2 and AG-3, prepared by further fractionating the *Adelostemma gracillimum* refined fraction.

The *Adelostemma gracillimum* refined fractions can be prepared by any means known in the art. For example, the *Adelostemma gracillimum* herb can be extracted with any suitable solvent, such as an alcohol, water, aqueous solvent or organic solvent. Alcohols useful as the solvent in the present invention include, but are not limited to, methanol, ethanol propanol, isopropanol, and ethylene glycol. The organic solvent can be any suitable organic solvent, such as, dichloromethane, chloroform, carbon tetrachloride, ethyl acetate, acetone, diethyl ether, pentane, hexanes and petroleum ether.

In some embodiments, the present invention provides a method of preparing a *Adelostemma gracillimum* refined fraction, including contacting *Adelostemma gracillimum* herb with methanol or ethanol, to form an alcohol extract; contacting the alcohol extract with an organic solvent to form an organic solvent fraction; and contacting the organic solvent fraction with a petroleum ether to form the *Adelostemma gracillimum* refined fraction. The organic solvent can be any suitable organic solvent described above. In other embodiments, the present invention provides an *Adelostemma gracillimum* refined fraction prepared by this method.

The *Adelostemma gracillimum* refined fraction can be further fractioned by any means known in the art, including via column chromatography, HPLC, and other methods. In some embodiments, the *Adelostemma gracillimum* refined fraction prepared above is further fractionated by eluting a first fraction of the *Adelostemma gracillimum* refined fraction from a resin column with a solution of about 30% ethanol in water; eluting a second fraction from the resin column with a solution of about 60% ethanol in water; and eluting a third fraction from the resin column with a solution of about 96% ethanol in water. In other embodiments, the present invention provides an *Adelostemma gracillimum* refined fraction prepared by the method above.

VI. Methods of Improving Memory

The present invention also provides methods of improving memory and learning by administration of a *Adelostemma*

*gracillimum* refined fraction (AG-0) or by administration of a compound isolated from the *Adelostemma gracillimum* refined fraction. In some embodiments the method comprises administering to a subject AG-0 or a first (AG-1), second (AG-2), or third (AG-3) fraction extracted from AG-0. In some embodiments, the method includes administering to a subject in need thereof, a therapeutically effective amount of a compound of any of formulas I, Ia, Ib, Ic, Id, or Ie. In some embodiments the method comprises administering to a subject a compound of formula II or IIa. In some embodiments, the method includes administering to a subject in need thereof, a therapeutically effective amount of a compound of formula III. In some embodiments, the method includes administering to a subject in need thereof, a therapeutically effective amount of a compound of any of formulas IV, IVa, Nb, or IVc. In some embodiments, the method includes administering to a subject in need thereof, a therapeutically effective amount of an isolated compound of any of formula I, Ia, Ib, Ic, Id, Ie, II, IIa, III, IV, Na, IVb, IVc, V, VI or VII, or a pharmaceutical composition thereof. In some embodiments, the method includes administering to a subject in need thereof, a therapeutically effective amount of an *Adelostemma gracillimum* refined fraction of the present invention.

Various parameters can be measured to determine if the compounds or *Adelostemma gracillimum* refined fraction (AG-0) of the present invention improves learning and memory of a subject. For example, the degree of learning and memory improvement can be compared between the control (e.g., untreated with the compounds or AG-0 of the present invention) and a group pretreated with the compounds or AG-0 of the present invention. Learning and memory improvement can be assessed using, for example, a Morris water maze for rodents (see, e.g., the Example section) or any suitable tests such as those described above for humans. If any one or more of these parameters are changed for the group treated with the compounds or AG-0 of the present invention by, e.g., about 10%, optionally at least about 20%, at least about 30%, at least about 40%, at least about 50%, at least about 60%, at least about 70%, at least about 80%, at least about 90%, at least about 100%, at least about 150%, at least about 200%, etc., compared to control, then it can be said that the compounds or AG-0 of the present invention improved learning and memory of the subject. Alternatively, statistical analysis using ANOVA for continuous variables, Mann-Whitney U for nonparametic data, Chi square for categorical variables or Fisher's exact test with $p<0.05$ is considered significant.

Generally, mice that are treated with AG-0 or the compounds of the present invention and control mice (that are not treated with the compounds of the present invention) are trained to escape the swimming task by learning the position of a hidden platform and climbing on it. The time it takes them to complete this task is defined as the escape latency. This test can be conducted one or more times daily for a number of days. One parameter that is indicative of improved learning and memory is the reduction in latency in escaping the swimming task by climbing onto the hidden platform (see the Examples section below). See also, methods described in Gozes et al., *Proc. Natl. Acad. Sci. USA* 93:427-432 (1996), incorporated herein by reference. Animals treated with a suitable compound or fraction of the present invention show improvement in their learning and memory capacities compared to the controls that are not treated with a compound or fraction of the present invention. Embodiments of the invention are not limited by examples of the test used to measure performance. Any suitable test methods can be used to measure performance such as learning and memory.

Other methods known in the art can be used in human subjects to determine if a compound or a combination of compounds or *Adelostemma gracillimum* refined fraction of the present invention improves performance (e.g., learning and memory) in vivo. For example, these methods include assessment of memory or learning over time by the Randt Memory Test (Randt et al., *Clin. Neuropsychol.*, 1980, 2:184), Wechsler Memory Scale (*J. Psych.* 19:87-95 (1945), Forward Digit Span test (Craik, Age Differences in Human Memory, in: *Handbook of the Psychology of Aging*, Birren, J., and Schaie, K. (Eds.), New York, Van Nostrand (1977), Mini-Mental State Exam (Folstein et al., *J. of Psych. Res.* 12:189-192 (1975), or California Verbal Learning Test (CVLT). See, also, U.S. Pat. No. 6,030,968. In these tests, factors unrelated to effects of the compounds or fractions of the present invention (e.g., anxiety, fatigue, anger, depression, confusion, or vigor) are controlled for. See, U.S. Pat. No. 5,063,206. Methods for assessing and controlling for subjective factors is known in the art and determined by such standard clinical tests such as the BECK Depression Scale, Spielberger Trait State Anxiety test, and POMS test (Profile of Mood State).

VII. Methods of Treating Diseases and Disorders Modulated by NMDA Receptors and Amyloid-Beta Peptides The present invention also provides a method of inhibiting the activities of a NMDA receptor for treating CNS disorders. In some embodiments, the present invention provides a method of inhibiting the activities of a NMDA receptor for treating CNS disorders by contacting a *Adelostemma gracillimum* refined fraction (AG-0) or a first (AG-1), second (AG-2), and/or third (AG-3) fraction extracted from AG-0 with the NMDA receptor. In some embodiments the method includes contacting a compound of formula I, Ia, Ib, Ic, Id, Ie, IIa, III, IV, IVa, IVb, IVc, V, VI or VII, or a pharmaceutical composition thereof, with the NMDA receptor. In some embodiments, the compound is an isolated compound. Preferably, the NMDA receptor is an activated NMDA receptor.

The present invention also provides a method of inhibiting the activities of amyloid-beta peptide, thereby protecting neurons against amyloid-beta induced toxicity. In some embodiments, the method includes contacting a neuron expressing amyloid-beta peptides with a *Adelostemma gracillimum* refined fraction (AG-0) or a first (AG-1), second (AG-2), and/or third (AG-3) fraction extracted from AG-0. In some embodiments the method includes contacting a neuron expressing amyloid-beta peptides with a compound of formula I, Ia, Ib, Ic, Id, Ie, II, IIa, III, IV, IVa, IVb, IVc, V, VI or VII, or a pharmaceutical composition thereof. In some embodiments, the compound is an isolated compound.

The present invention provides neuroprotection as well as improves cognitive deficits. The compounds and fractions of the present invention are useful in the treatment of acute and chronic disorders of CNS, ranging from neuropathological conditions to neurodegenerative diseases and conditions related to excitotoxicity. Disease states that can be treated using the compounds or fractions of the present invention include, but are not limited to, neurodegenerative disorders, head and brain trauma, genetic disorders, infectious disease, inflammatory disease, medication, drug and alcohol disorders, neuropathic pain, cancer, metabolic disorders, mental retardation, and learning and memory disorders, such as age related memory loss, Alzheimer's disease, mild cognitive impairment, amyotrophic lateral sclerosis, Huntington's chorea, amnesia, B1 deficiency, schizophrenia, depression and bipolar disorder, cerebrovascular disease, stroke, hydrocephalus, subarachnoid hemorrhage, vascular insufficiency, brain tumor, epilepsy, Parkinson's disease, cerebral microangiopathy, pain medication, chemotherapy, oxygen deprivation, e.g., caused by a heart-lung machine, anesthesia, or near drowning, dementia (vascular, frontotemporal, Lewy-body, semantic, primary progressive aphasia, Pick's), progressive supranuclear palsy, corticobasal degeneration, Hashimoto encephalopathy, ADD, ADHD, dyslexia, Down syndrome, fragile X syndrome, Turner's syndrome, fetal alcohol syndrome, depression, anxiety, anorexia, multiple sclerosis, autism, and cachexia, for example.

In some embodiments, the compounds and fractions of the present invention can be used for the treatment of diseases selected from the group consisting of amyotrophic lateral sclerosis, Alzheimer's disease, Parkinson's disease and Huntington's disease, acute or chronic neuropathic pain, stroke, brain trauma, epilepsy, stroke, dementia, multiple sclerosis, depression, schizophrenia, and autism. In other embodiments, the present invention provides a method of treating a neurodegenerative disease or neuropathological condition in a subject, the method including administering to the subject a therapeutically effective amount of a compound or composition or *Adelostemma gracillimum* refined fraction of the present invention.

In general, treatment methods provided herein comprise administering to a subjects an effective amount of a *Adelostemma gracillimum* refined fraction (AG-0) and/or first (AG-1) and/or second (AG-2) and/or third (AG-3) fraction extracted from AG-0 or one or more isolated compounds isolated from AG-0 provided herein. In some embodiments, the fraction(s) and/or compound(s) of the invention can be administered to a subject (e.g., a human) orally. The effective amount may be an amount sufficient to modulate the NMDA receptor and/or amyloid-beta peptide activity and/or an amount sufficient to reduce or alleviate the symptoms presented by the subject. The amount administered is sufficient to yield a plasma concentration of fraction or compound high enough to detectably inhibit the NMDA receptor and/or amyloid-beta peptide in vitro.

VIII. Methods of Treating Epilepsy

The present invention also provides methods of treating epilepsy by administration of a *Adelostemma gracillimum* refined fraction (AG-0) or by administration of a compound isolated from the *Adelostemma gracillimum* refined fraction. In some embodiments the method comprises administering to a subject AG-0 or a first (AG-1), second (AG-2), or third (AG-3) fraction extracted from AG-0. In some embodiments, the method includes administering to a subject in need thereof, a therapeutically effective amount of a compound of any of formulas I, Ia, Ib, Ic, Id, or Ie. In some embodiments the method comprises administering to a subject a compound of formula II or IIa. In some embodiments, the method includes administering to a subject in need thereof, a therapeutically effective amount of a compound of formula III. In some embodiments, the method includes administering to a subject in need thereof, a therapeutically effective amount of a compound of any of formulas IV, IVa, IVb, or IVc. In some embodiments, the method includes administering to a subject in need thereof, a therapeutically effective amount of an isolated compound of any of formula I, Ia, Ib, Ic, Id, Ie, II, IIa, III, IV, IVa, IVb, IVc, V, VI or VII, or a pharmaceutical composition thereof. In some embodiments, the method includes administering to a subject in need thereof, a therapeutically effective amount of an *Adelostemma gracillimum* refined fraction of the present invention.

Various parameters can be measured to determine if the compounds or *Adelostemma gracillimum* refined fraction (AG-0) of the present invention treat epilepsy in a subject. For example, the degree to which epilepsy is treated or protected against can be compared between the control (e.g., untreated with the compounds or AG-0 of the present invention) and a group pretreated with the compounds or AG-0 of the present invention. Protection against epileptic seizure can be assessed using, for example, an audiogenic seizure-susceptibility test for rodents (see, e.g., the Examples section); monitoring the subject for increase or decrease of seizure activity by EEG analysis or behavioral modeling (locomotor activity, contextual fear responses, muscular strength and coordination) or any other suitable tests such as those described above for humans. If any one or more of these parameters are changed for the group treated with the compounds or AG-0 of the present invention by, e.g., about 10%, optionally at least about 20%, at least about 30%, at least about 40%, at least about 50%, at least about 60%, at least about 70%, at least about 80%, at least about 90%, at least about 100%, at least about 150%, at least about 200%, etc., compared to control, then it can be said that the compounds or AG-0 of the present invention treated or protected against seizure in the subject. Alternatively, statistical analysis using ANOVA for continuous variables, Mann-Whitney U for nonparametric data, Chi square for categorical variables or Fisher's exact test with $p<0.05$ is considered significant.

The animal models used to assess protection against epileptic seizure generally are mammals of any kind, but usually mice. Specific examples of suitable animals include mice of the DRA/2J strain, or alternatively mice of the Frings mouse strain, which can be preferred due to the fact that Frings mice maintain susceptibility to audiogenic seizure to adulthood (Shradski et al., 1998, *Genomics* 49, 188-192). Generally, the mice that are treated with the compounds or AG-0 of the present invention are exposed to a stimulus, such as an audiogenic stimulus, and then scored for various indicators of seizure, including but not limited to wild running for a determined period of time, clonic seizure, forelimb extension/hindlimb flexion, forelimb and hindlimb extension, and/or motor impairment as assessed by the rotorod test (see, e.g., the Examples section). Animals treated with a suitable compound or fraction of the present invention show an increase in protection against epileptic seizure as compared to the controls that are not treated with a compound or fraction of the present invention.

IX. EXAMPLES

Example 1

*Adelostemma gracillimum* Refined Fraction does not Cause any Cytotoxicity

To examine the effect of the *Adelostemma gracillimum* refined fraction (AG-0) in primary rat neurons, cultures were treated with various concentrations of AG-0. As shown in FIG. 1, no observable cell death was found in all concentrations tested.

Example 2

Figure 2:
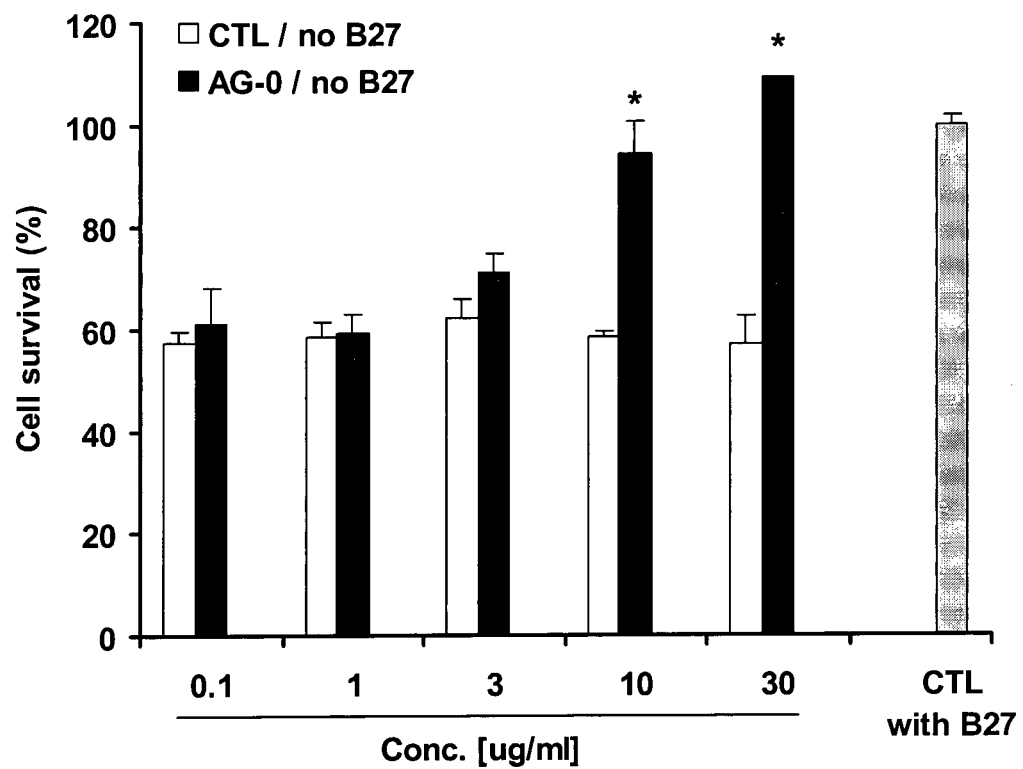
FIG. 2. *Adelostemma gracillimum* refined fraction promotes rat cortical neuron survival against B27 withdrawal. Cortical neurons isolated from embryonic day 18 rats were cultured in Neurobasal medium supplemented with 2 % B27. Neurons of 7 DIV were pre-treated with various concentrations of AG—0 for 24 hours, then the medium was changed to one lacking B27. A MTT assay was performed 24 hours later. Cell survival is presented as a percentage compared to a DMSO control in the presence of B27 ("CTL with B27"). Assays were conducted in triplicate and repeated at least twice. *=P<0.05.

*Adelostemma gracillimum* Refined Fraction Promotes Neuronal Survival Against B27 Withdrawal Primary cortical neurons were cultured in Neurobasal medium and supplemented with B27, a proprietary formula of Life Technologies. The combination of Neurobasal medium and B27 provides a stable growth environment for primary neurons to maturity in vitro. Neurons undergo apoptosis or cell death in the absence of B27. To study the neuroprotective effect of *Adelostemma gracillimum* refined fraction, neurons of 7DIV were treated with AG-0 and cell survival was measured as mitochondrial activity by the MTT assay. As shown in FIG. 2, a dose-dependent study on AG-0 showed its neuroprotective effect at 10-30 µg/ml on primary neurons cultured in the absence of B27. The level of neuronal survival observed in AG-0-treated cultures was similar to that in the presence of B27.

Example 3

Figure 3:
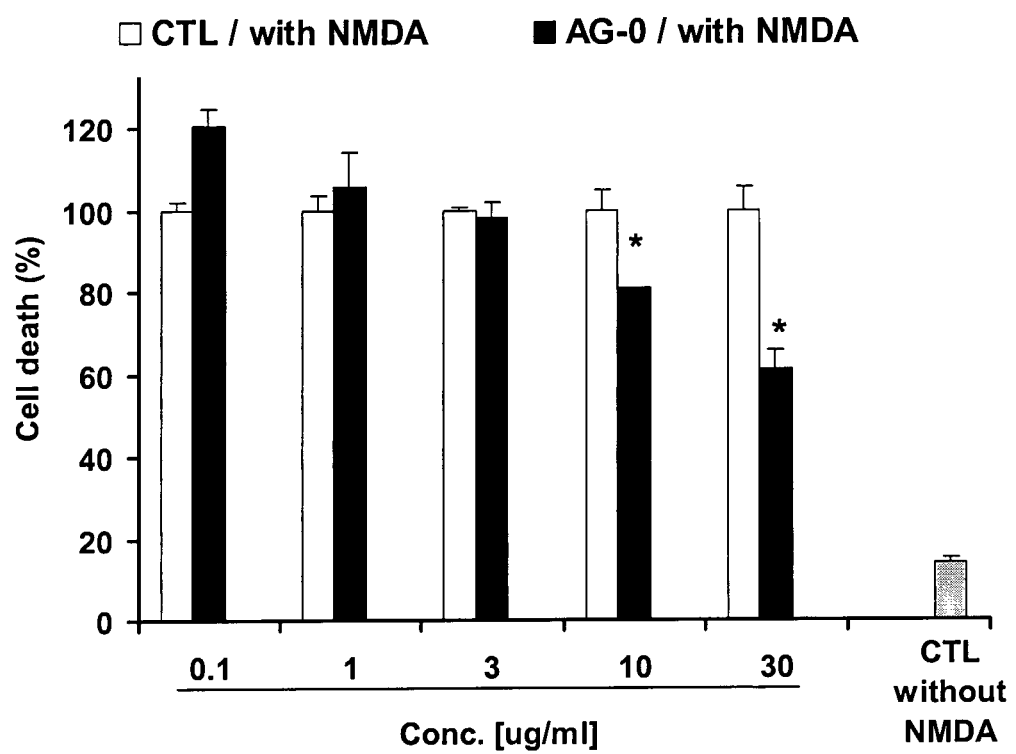
FIG. 3. *Adelostemma gracillimum* refined fraction protects rat cortical neurons against NMDA excitotoxicity. Embryonic rat cortical neurons (11 DIV) were pre-treated with various concentrations of AG—0 (0.1 -30 μg/mL) and then co-incubated with NMDA (20 μM). After 20 min, the medium was replaced with fresh medium, and after overnight incubation lactate dehydrogenase (LDH) released into the medium was measured. Cell death was calculated as a percentage compared to solvent control ("CTL without NMDA"). Assays were conducted in duplicate and repeated at least twice. *=P<0.05.

*Adelostemma gracillimum* Refined Fraction Promotes Neuronal Survival Against NMDA Excitoxicity in Rat Primary Cortical Neurons NMDA survival assays were performed to demonstrate the ability of *Adelostemma gracillimum* refined fraction to prevent NMDA receptor-induced excitotoxicity in primary cortical neuronal cells. FIG. 3 shows the effect of NMDA insults on cortical cells in the absence and presence of differing concentrations of AG-0. AG-0 (at 30 µg/ml) reduced cell death by more than 40% compared to the DMSO control.

Example 4

Figure 4:
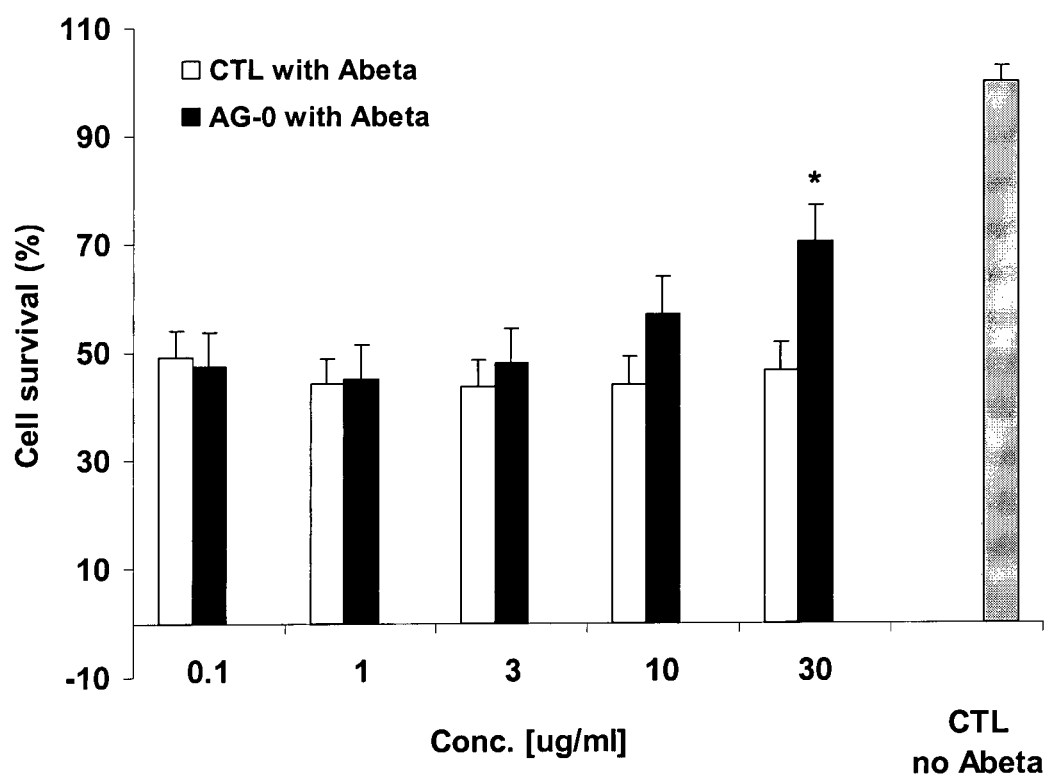
FIG. 4. *Adelostemma gracillimum* refined fraction protects rat cortical neurons against amyloid-beta peptide excitotoxicity. Embryonic rat cortical neurons (7 DIV) were pre-treated with various concentrations of AG- 0 (0.1 -50 μg/mL) and then co-incubated with $A\beta_{25-35}$ (10 μM). After overnight incubation, the MTT assay was performed. Cell survival was calculated as a percentage compared to vehicle control ("CTL no Abeta"). Assays were conducted in duplicate and repeated at least twice. *=P<0.05.

*Adelostemma gracillimum* Refined Fraction Promotes Neuronal Survival Against Amyloid-Beta Peptide Insult in Rat Primary Cortical Neurons Exogenous addition of amyloid beta peptide (Aβ) initiates cell death of neuronal cultures via apoptosis. The MTT assay was performed to study the ability of *Adelostemma gracillimum* refined fraction to prevent Aβ-induced excitotoxicity in primary cortical neuronal cells. FIG. 4 shows the effect of Aβ insults on cortical cells in the absence and presence of differing concentrations of AG-0. AG-0 (at 30-50 µg/ml) promotes cell survival compared to the DMSO control.

Example 5

*Adelostemma gracillimum* Refined Fraction Inhibits Caspase-3 Cleavage in Primary Neurons upon Amyloid-Beta Peptide Treatment Caspases are a family of cysteine-aspartic acid proteases that are involved in cell apoptosis through sequential activation by proteolytic processing of inactive proenzymes to form the active enzyme. Caspase-3 is considered as the executioner of the apoptotic pathway and is the predominant caspase that is involved in the cleavage of amyloid precursor protein as well as the production of amyloid beta peptide (Aβ), which is associated with neuronal death in Alzheimer's disease. Exogenous addition of Aβ into neuronal cultures initiates caspase-3 dependent apoptosis. Since *Adelostemma gracillimum* refined fraction protects against neuronal death induced by Aβ (as revealed by the MTT assay), the effect of AG-0 on caspase-3 activation in the presence of Aβ in cortical neurons was examined.

Figure 5:
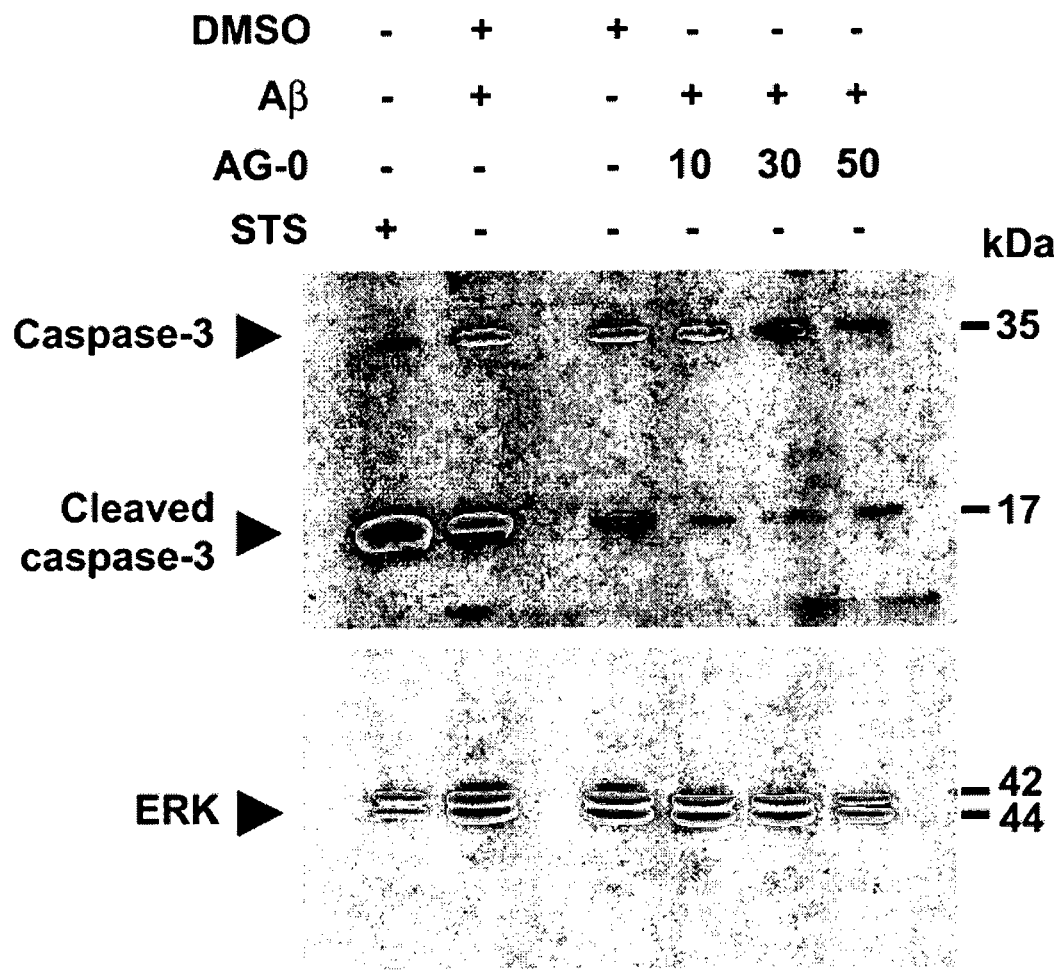
FIG. 5. *Adelostemma gracillimum* refined fraction inhibits caspase-3 production in primary cortical neurons induced by Aβ. Primary cortical neuron cultures (7DIV) were treated with various concentrations of AG-0 (10-50 μg/mL) in the presence of $A\beta_{25-35}$ (10 μM). Proteins were extracted after overnight incubation and Western blot analysis was performed. Blots were probed with antibodies against caspase-3 and ERK protein. Staurosporine (STS, 10 μM) was used as a positive control, while DMSO served as the vehicle control.

As shown in FIG. 5, the addition of Aβ resulted in an increase in protein expression of cleaved-caspase-3 (17 kDa, active form). However, in the presence of AG-0, the expression level of cleaved-caspase-3 significantly decreased in a dose-dependent manner comparable to that without addition of Aβ.

Example 6

Figure 6:
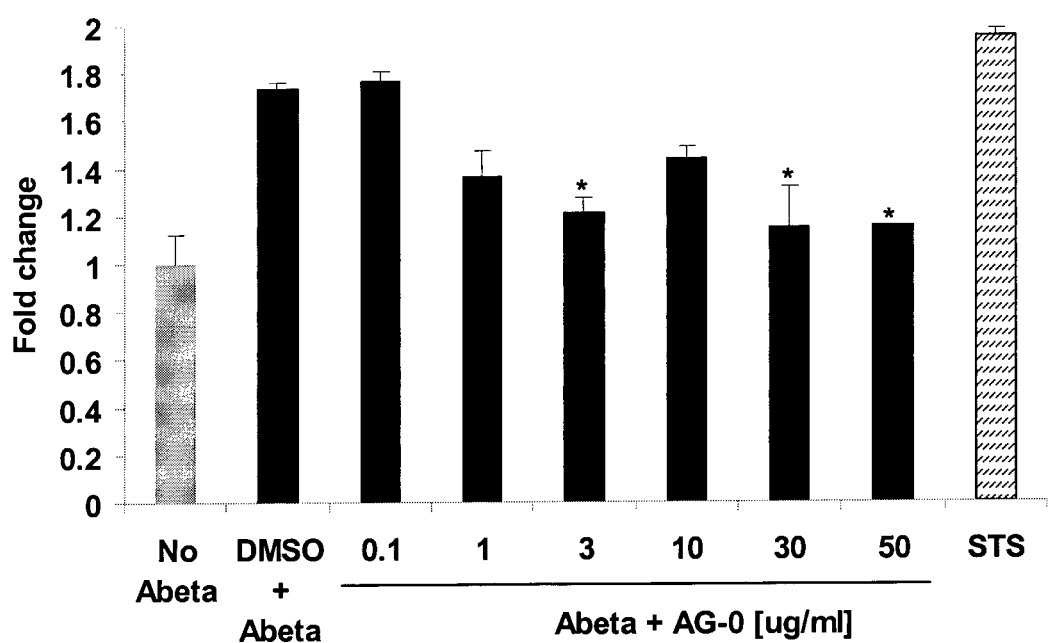
FIG. 6. *Adelostemma gracillimum* refined fraction inhibits caspase-3 enzyme activity in primary cortical neurons induced by Aβ. Primary cortical neuron cultures (7DIV) were treated with various concentrations of AG-0 (0.1-50 μg/mL) in the presence of $A\beta_{25-35}$ ("Abeta", 10 μM). A caspase-3 activity assay was subsequently performed. Fluorescence units measured was calculated with protein concentration and compared to DMSO+Abeta control, then represented as fold change. Staurosporine (STS, 10 μM) was used as a positive control to induce apoptosis.

*Adelostemma gracillimum* Refined Fraction Inhibits Caspase-3 Activity in Primary Neurons Upon Amyloid-Beta Peptide Treatment To further examine whether the reduction of caspase-3 cleavage product would lead to a decrease in caspase-3 enzyme activity, a fluorescence assay was employed to study the effect of *Adelostemma gracillimum* refined fraction on the caspase-3 activity. Caspases are cysteine-aspartic acid proteases and caspase-3 cleaves the substrate that contains DEVD (SEQ ID NO:1) amino acid sequence. To measure the activity of caspase-3 an artificial substrate DEVD (SEQ ID NO:1) was coupled to a fluorescence dye wherein cleavage results in the release of fluorescence dye and subsequent increase of arbitrary fluorescence units. As shown in FIG. 6, the addition of Aβ resulted in an increase in caspase-3 activity. However, in the presence of AG-0, the relative fluorescence unit was significantly decreased in a dose-dependent manner comparable to that without addition of Aβ.

Example 7

Figure 7:
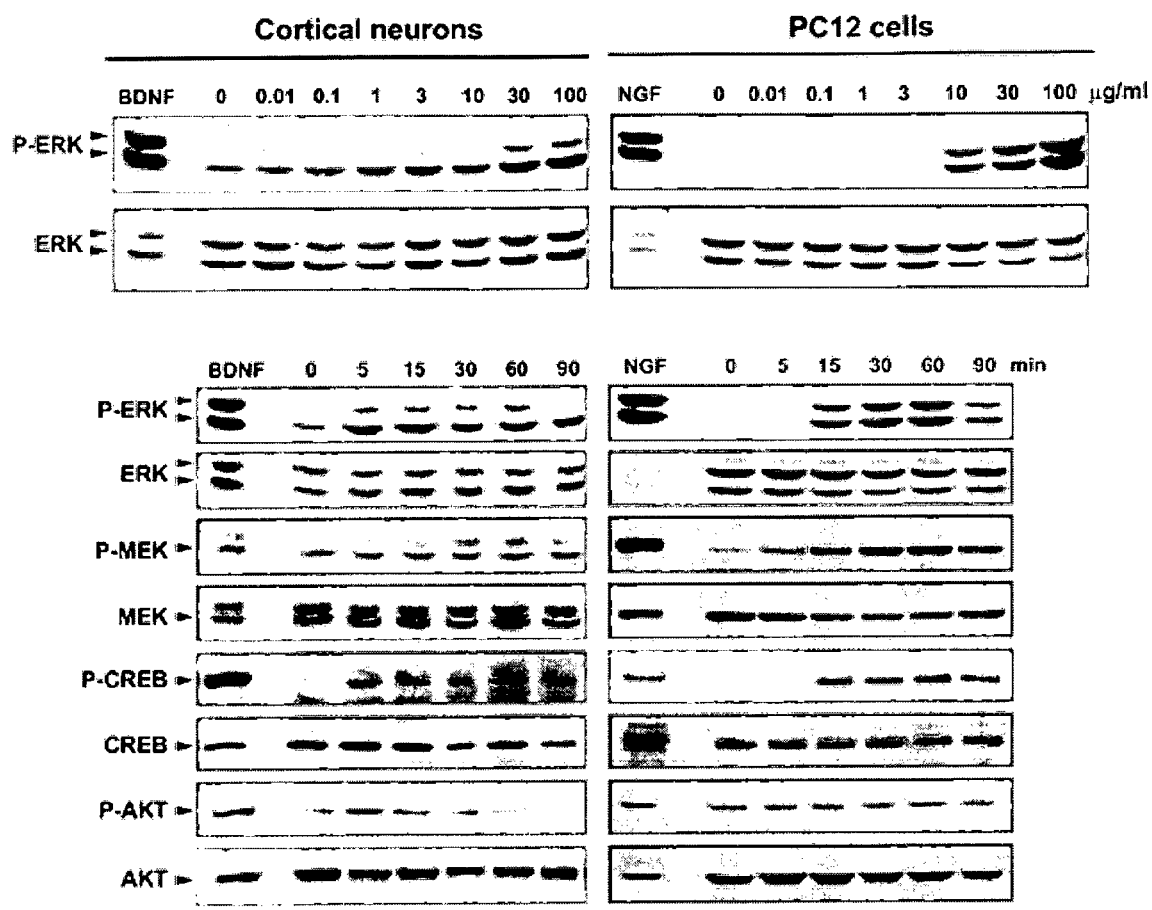
FIG. 7. *Adelostemma gracillimum* refined fraction induces phosphorylation of MEK/ERK/CREB pathway in embryonic rat cortical neurons and PC12 cells. Cortical neurons (7DIV) or PC12 cells were incubated with various concentrations of AG for 15 min (top panels), or were treated with AG-0 (30 μg/mL) at different time intervals (bottom panels). Total protein was collected and the expression of signaling proteins was analyzed by Western blot analysis. Nerve growth factor (NGF) and brain-derived neurotrophic factor (BDNF) were used as controls for PC12 and cortical neurons, respectively.

*Adelostemma gracillimum* Refined Fraction Activates MEK/ERK/CREB in Both Primary Cortical Neurons and PC12 Cells The MEK/ERK/CREB pathway has been shown to be involved in neuronal survival and differentiation. Thus, the effect of *Adelostemma gracillimum* refined fraction on these signaling proteins was investigated. Temporal and dose-dependent effects of AG-0 were examined in cortical neurons of 7DIV (A & B) and PC12 (C & D) of passages 12-15. As shown in FIG. 7, AG-0 significantly induced ERK phosphorylation in cortical neurons (1-100 µg/ml) and PC12 cells (10-100 µg/ml) after 15 min incubation. From the temporal studies, AG-0 induced activation of CREB via ERK and MEK phosphorylation.

Example 8

Figure 8:
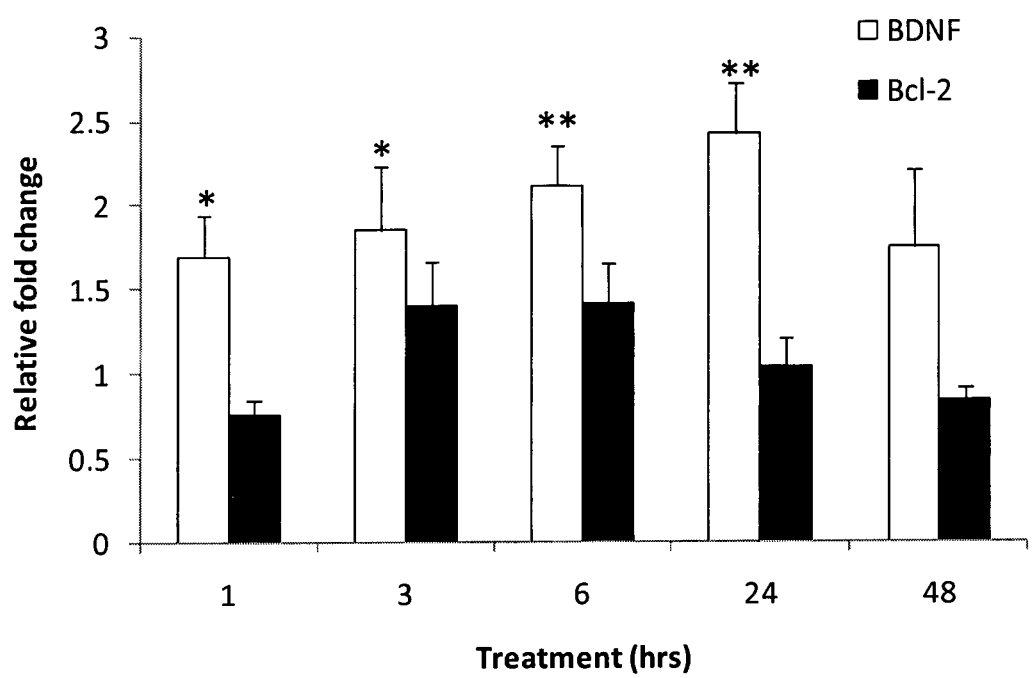
FIG. 8. *Adelostemma gracillimum* refined fraction increases BDNF expression in primary cortical neurons. Cortical neurons (7DIV) were incubated with AG-0 at various time intervals. Total RNA was extracted, followed by cDNA synthesis. Gene expression was normalized against the housekeeping genes hypoxanthine phosphoribosyltransferase 1 (HPRT1) and glyceraldehyde 3-phosphate dehydrogenase (GAPDH), and relative change in gene expression induced by AG-0 was compared to vehicle control. Assays were conducted in duplicate and repeated at least 3 times. *=P<0.005.

BDNF Expression is Induced in Neurons Treated with *Adelostemma gracillimum* Refined Fraction AG-0 induces ERK and CREB phosphorylation in primary cortical neurons. Therefore, the downstream effect of *Adelostemma gracillimum* refined fraction after CREB activation was examined on BDNF and bcl-2, both downstream target genes after CREB activation. Gene expression changes were studied in neuronal cultures treated with AG-0 at different time intervals using real-time PCR analysis. As shown in FIG. 8, AG-0 significantly increased expression of BDNF, but not bcl-2.

Example 9

Activity-Guided Fractionations

Figure 9:
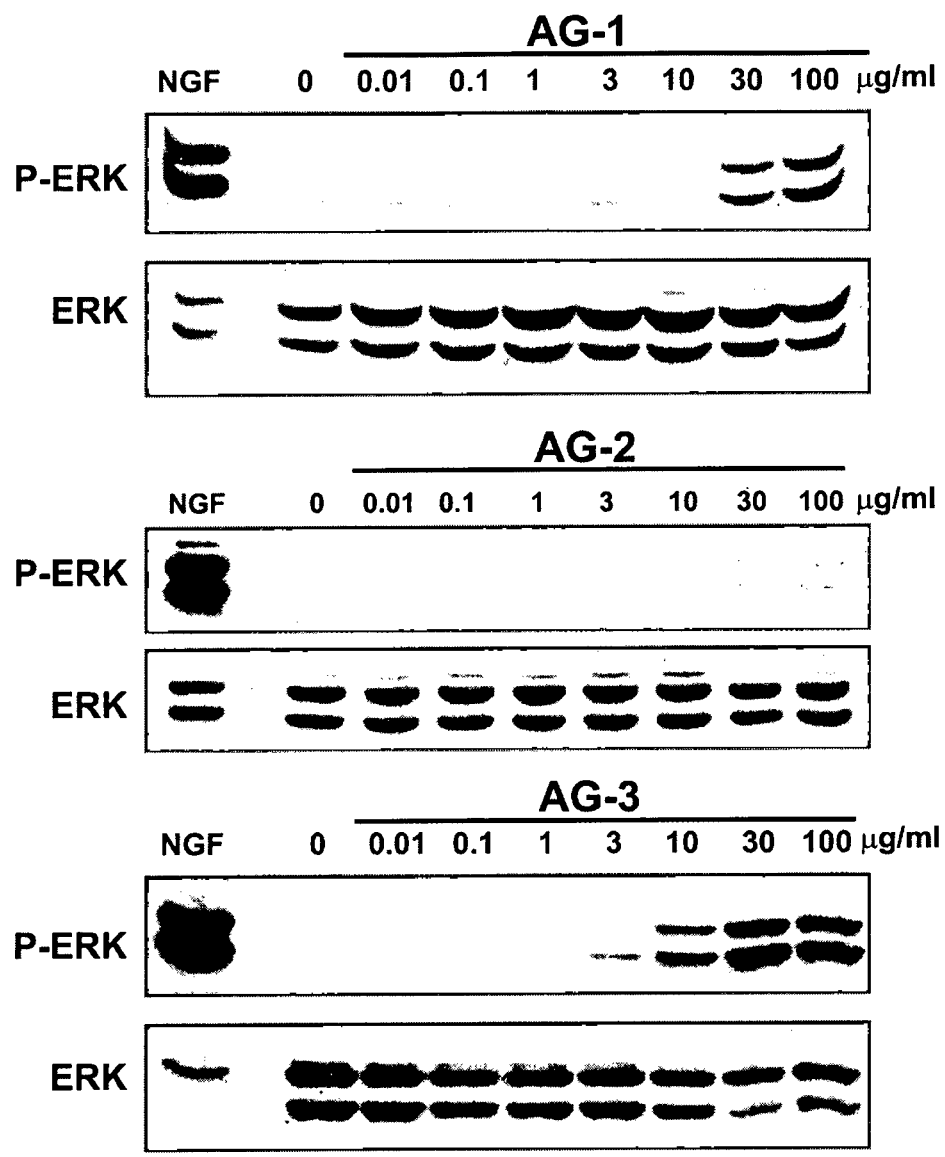
FIG. 9. Activity guided fractionation of *Adelostemma gracillimum* refined fraction and ERK phosphorylation in PC12 cells. AG-0 was further fractionated into three fractions by means of 30% ethanol (AG-1), 60% ethanol (AG-2) and 96% ethanol (AG-3). Strong ERK phosphorylation in PC12 cells was induced by AG-3, and a weaker signal was induced by AG-1 when compared at 10 μg/ml. Nerve growth factor (NGF, 10 ng/ml) was used as a control.

To isolate the compounds that contribute to the activities exhibited by *Adelostemma gracillimum* refined fraction, further fractionations of AG-0 were performed. AG-0 was further divided into first, second, and third fractions by means of 30% ethanol (AG-1), 60% ethanol (AG-2) and 96% ethanol (AG-3). Cortical neurons were pre-treated with the three fractions, and the expression of ERK was analyzed. As shown in FIG. 9, AG-3 exhibited strong ERK phosphorylation at 10 μg/ml while no activation was found for AG-1 and AG-2. ERK activation was observed for AG-1 only after 30 μg/ml.

Example 10

Immunofluorescence Staining of Cortical Neurons Treated with *Adelostemma gracillimum* Refined Fraction in the Absence of B27

Figure 10:
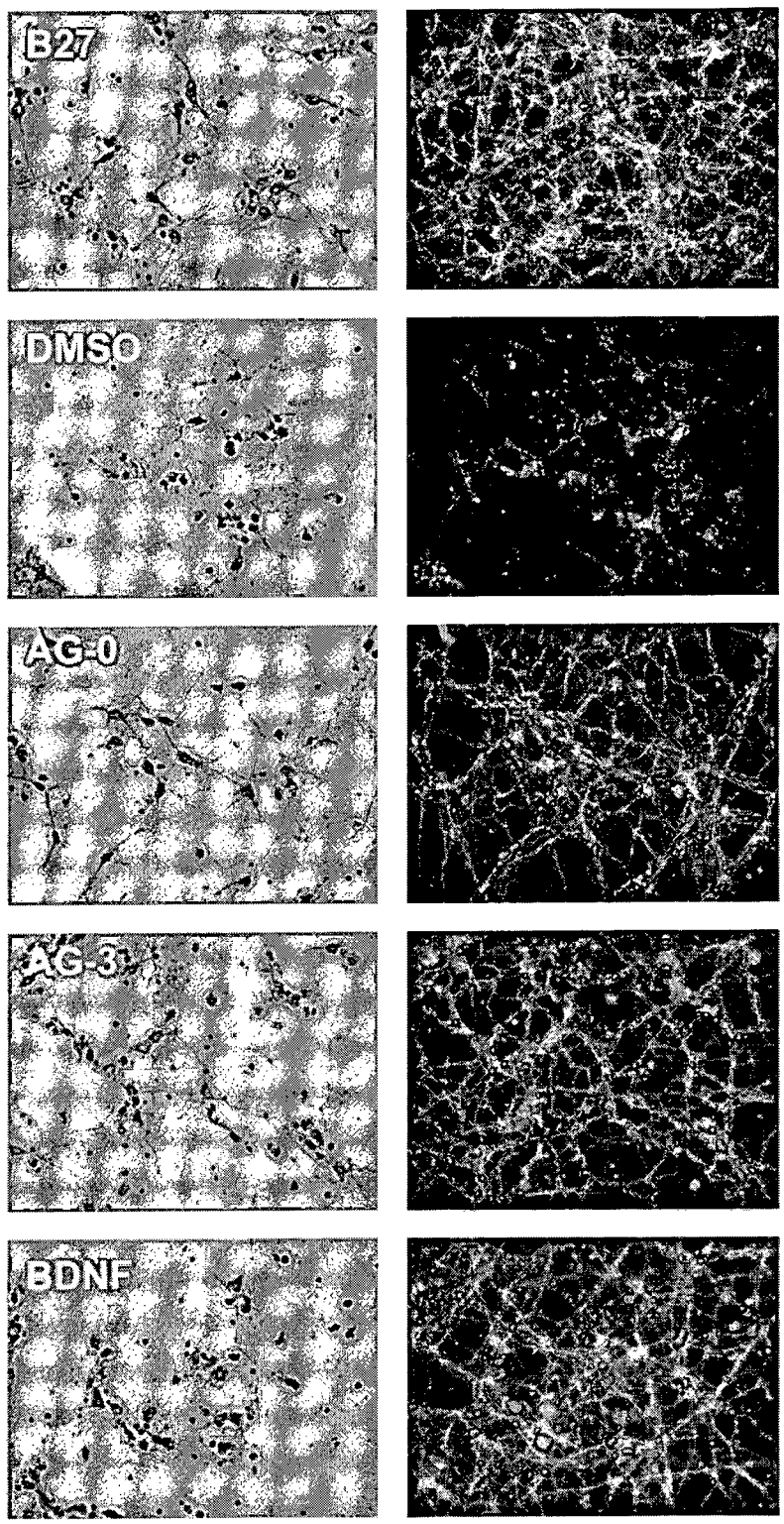
FIG. 10. Immunofluorescence staining of cortical neurons pretreated with *Adelostemma gracillimum* refined fraction or fraction AG-3 in the absence of B27. AG-0 was further fractionated into three fractions by means of 30% ethanol (AG-1), 60% ethanol (AG-2) and 96% ethanol (AG-3). Cortical neuronal cultures of 7DIV were pre-treated with AG-0 (30 μg/mL), AG-3 (30 μg/mL), or BDNF (50 ng/mL) for 24 hours, then the medium was changed to one lacking B27. Cultures were fixed with 4% paraformaldehyde, immunostained with beta-tubulin type III antibody, and visualized with FITC-conjugated anti-mouse antibody. Cell bodies were highlighted by DAPI staining. DMSO was used as a solvent control. Images are shown at 40× magnification.

The neuroprotective effect of AG-0 and AG-3 was visually exhibited via immunofluorescence staining in cortical neurons. Cortical neurons were pre-treated with AG-0 and AG-3 and the medium was changed to one that lacked B27. Neurons were fixed and immunostained with neuronal markers. As shown in FIG. 10, AG-0 and AG-3 protected primary cortical neurons from cell death after B27 withdrawal.

Example 11

AG-0, AG-1 and AG-3 Induce ERK Phosphorylation in PC12 Cells via Src Kinase

Figure 11:
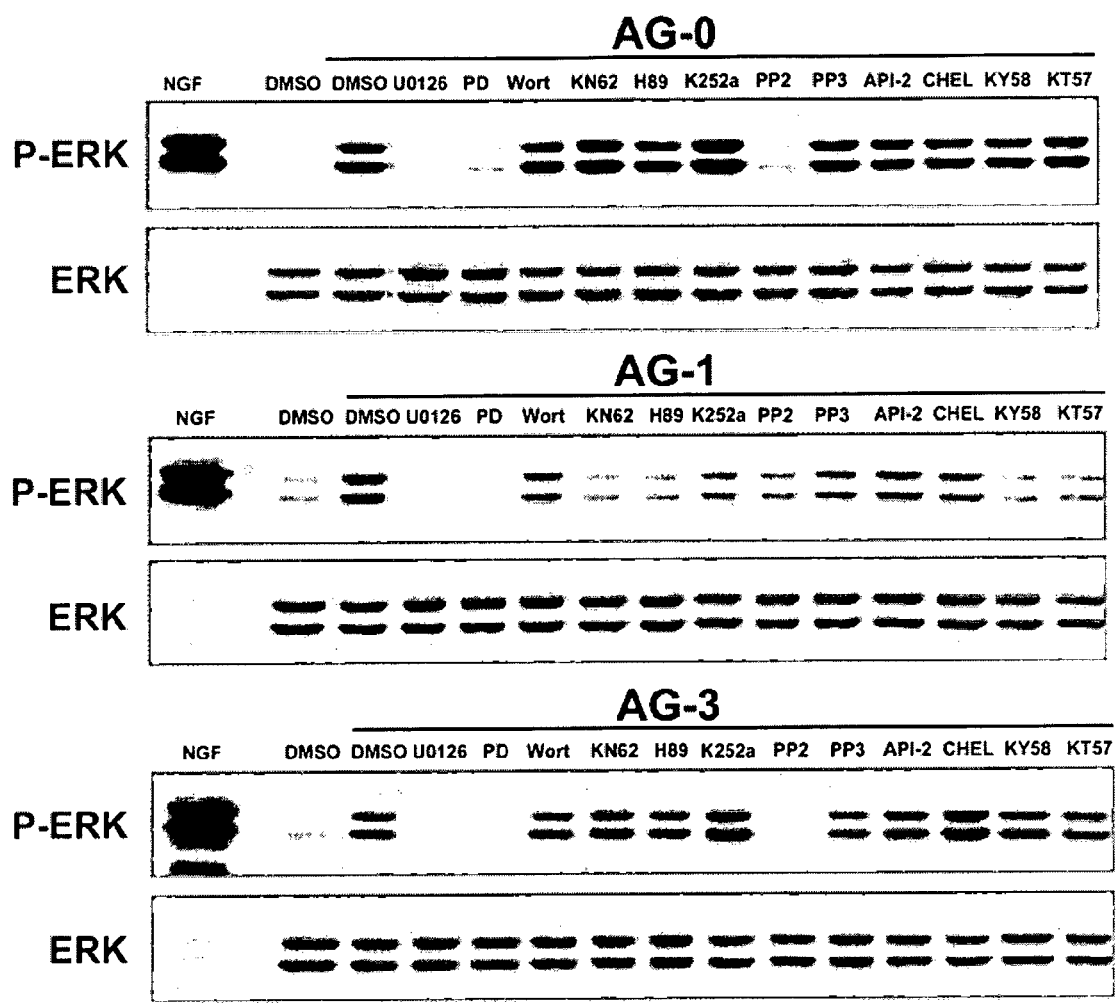
FIG. 11. *Adelostemma gracillimum* refined fraction and fractions AG-1 and AG-3 induce ERK phosphorylation in PC12 cells via Src kinase. PC12 cells were pre-treated with various inhibitors for 1 hour and then AG-0, AG-1, or AG-3 (30 μg/mL) were added to the cultures for 15 min. Total cell lysates were collected and Western blot analysis was performed. ERK phosphorylation induced by AG-0 was significantly attenuated by UO126 (1 μM), PD (PD98095, 25 μM), and PP2 (20 μM). While a similar inhibitory pattern was found for AG-3, ERK phosphorylation induced by AG-1 was also reduced by KN62 (10 μM), H89 (10 μM), K252a (100 nM), KT58 (KT5823, 1 μM), and KT57 (KT5720, 1 μM). ERK phosphorylation induced by these fractions was not affected by PP3 (20 μM), Wort (wortmannin, 100 nM), API-2 (10 μM), and CHEL (chelecythrine, 10 μM). Nerve growth factor (NGF, 20 ng/mL) was used as a positive control.

To examine the signaling mechanism of *Adelostemma gracillimum* refined fraction and the further fractions AG-1, AG-2, and AG-3 on ERK phosphorylation, various inhibitors were pre-treated with PC12 cells prior to treatment with AG-0, AG-1, AG-2, or AG-3. As shown in FIG. 11, ERK phosphorylation by AG-0 and AG-3 was found to be significantly attenuated by U0126 (MAP kinase, MEK-1 and MEK-2 inhibitor), PD98059 (MEK inhibitor) and PP2 (Src inhibitor), indicating the involvement of MEK and Src kinase. On the other hand, the ERK phosphorylation induced by AG-1 was attenuated by U0126, PD98059, KN62 (CAMKII inhibitor), H89 & KT5720 (PKA inhibitor), K252a (non-specific protein kinase inhibitor), PP2, and KY5823 (PKG inhibitor). No effect was observed for treatment with PP3 (inactive control for PP2), wortmannin (PI3K inhibitor), API-2 (Akt inhibitor), and chelerythrine (PKC inhibitor).

Example 12

Figure 12:
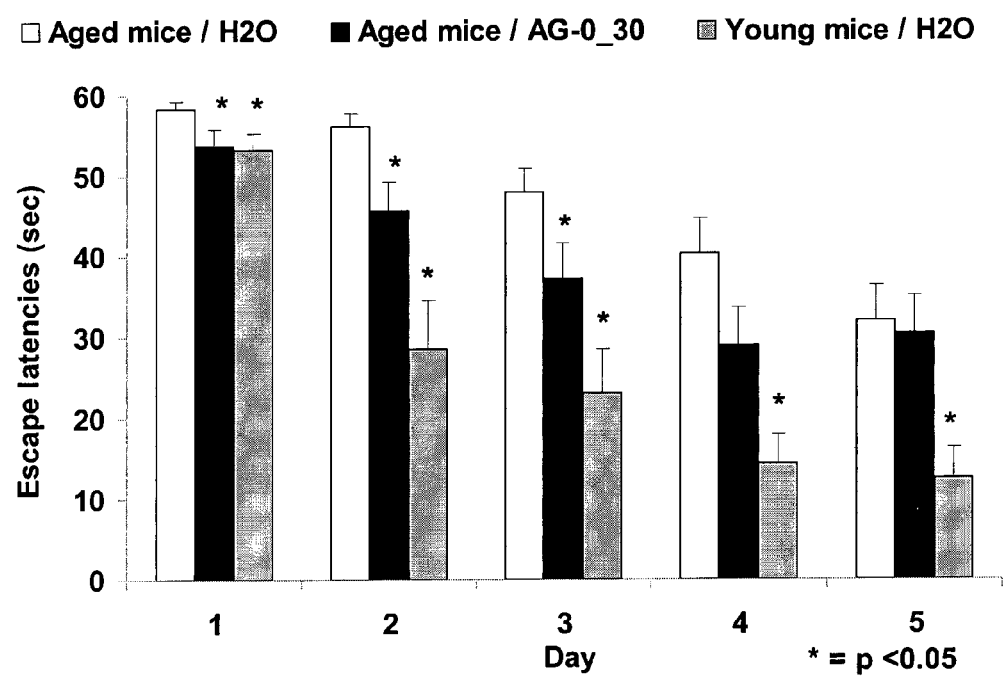
FIG. 12. *Adelostemma gracillimum* refined fraction significantly reduces the escape latency of aged mice in the Morris water maze model. AG-0 was administered orally at 30 mg/kg. Measurements were calculated as the mean latency periods for each mouse, n=14-16 per group. Data is expressed as mean±SEM, and is compared to the aged mice/water group.

*Adelostemma gracillimum* Refined Fraction Significantly Improves Learning Skills of Aged Mice in the Morris Water Maze As shown in FIG. 12, the therapeutic effect of the novel compounds on spatial learning and memory in mice was demonstrated using the Morris water maze task, the favored test to study hippocampal-dependant learning and memory. The Morris water maze is a popular animal model that measures learning and memory capabilities of the test subjects. It consists of a water pool with a hidden, submerged escape platform. The mice must learn, over a period of consecutive days, the location of the platform using either contextual or local cues. The time taken to locate the hidden platform (escape latency) is a measure of the animal's cognitive abilities.

Aged mice (18-month-old, orally administered with AG-0 or water) and young mice (4-week-old, oral administered with water) were subjected to the Morris water maze over a period of 5 days. On each day, the time taken for the mice to detect a hidden platform in the water maze was measured, in seconds. Aged mice can learn but take a longer time to reach the platform compared to young mice. AG-0-treated mice showed significant improvements in locating the hidden platform. As shown in FIG. 12, the escape latency was reduced from day 1-3 in AG-0-treated mice compared to the water-treated aged mice.

Example 13

*Adelostemma gracillimum* Refined Fraction Shows Anti-Depressant Effects in the Forced Swim Test

Figure 13:
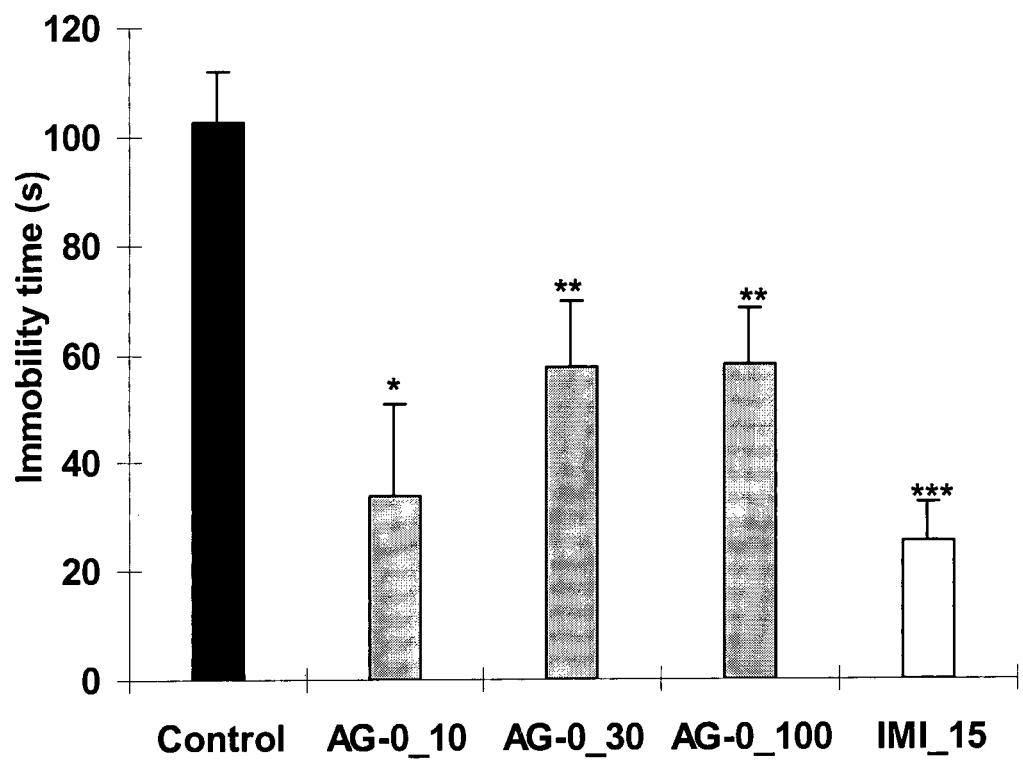
FIG. 13. *Adelostemma gracillimum* refined fraction reduces the immobility duration of mice in the Forced Swim Test. AG-0 was administered orally at 10, 30, or 100 mg/kg for 7 days. Measurements were calculated as the mean immobility duration for each mouse, n=5-25 per group. Data is expressed as mean±SEM, and is compared to the aged mice/ water group. Imipramine (Imi, 15 mg/kg administered intraperitoneally), an antidepressant with a well-documented ability to reduce immobility duration, is used as a control. *=P<0.005; **=P<0.0005.

*Adelostemma gracillimum* refined fraction has been shown to increase BDNF expression and CREB phosphorylation in neurons of rats. Recent findings have suggested that the expression of BDNF and CREB protein is a critical factor in the treatment of depression. Therefore, the effect of AG-0 was examined in a well-established animal model of depression, the Forced Swim Test (FST). Young mice were orally administered with AG-0 or water for 7 days. On day 8, mice were placed in a cylinder filled with water, thus creating an environment to prevent any escape and induce despair. 24 hours later, these mice were placed in the cylinder again and the amount of time where they ceased to struggle (immobility duration) was measured. Anti-depressants can effectively decrease the immobility duration. As shown in FIGS. 13, AG-0 (10, 30 and 100 mg/kg) significantly reduced the immobility time of mice in the FST.

Example 14

Figure 14:
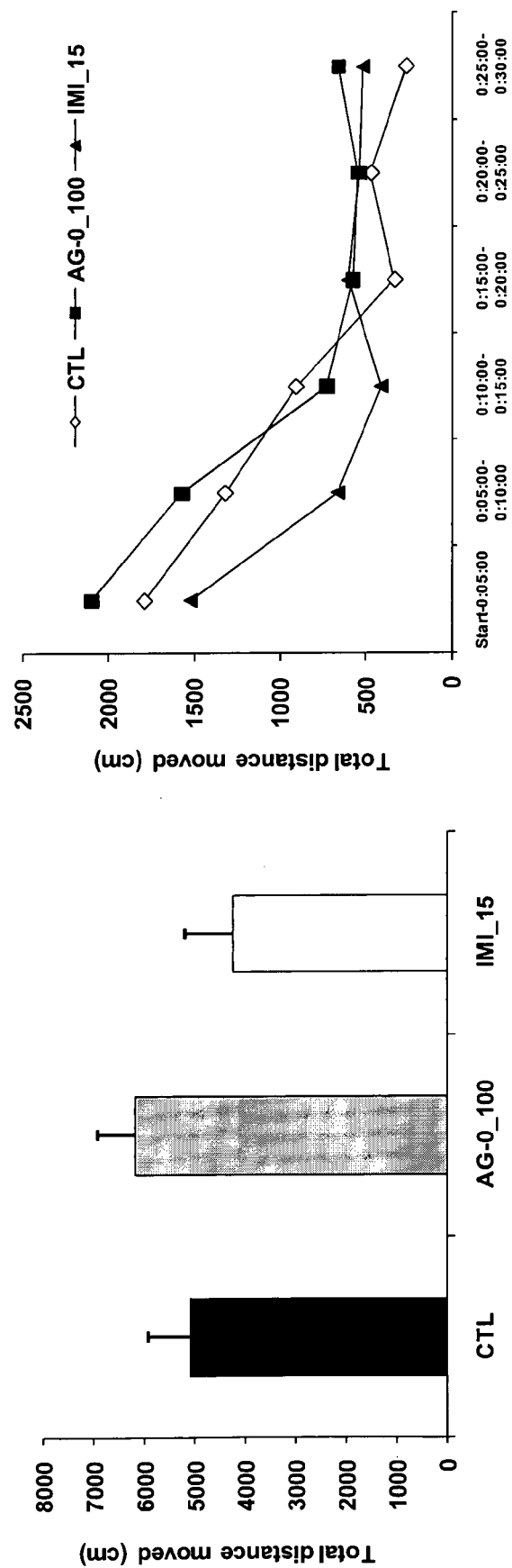
FIG. 14. *Adelostemma gracillimum* refined fraction does not have any effect on locomotor activity of mice in the Open Field Test. AG-0 was administered orally at 100 mg/kg and imipramine was given at 15 mg/kg intraperitoneally. Measurements were calculated as the mean total distance traveled in the field (left panel) or as the distance moved between each time interval (right panel), n=14-16 per group. Data is expressed as mean±SEM, and is compared to the vehicle control ("CTL") group.

*Adelostemma gracillimum* Refined Fraction Shows No Effect in Locomotor Activity in the Open Field Test To determine if the reduction in immobility time by AG-0-treated mice in the FST is due to an effect by AG-0 on locomotor activity of the test subject, AG-0-treated mice were subjected to the Open Field Test (OFT). The OFT is an established model to measure a compound's effect on the locomotor activity of test subjects. A similar treatment paradigm for AG-0 was followed for the test subjects, which were then subjected to the OFT. As shown in FIG. 14, there was no significant difference among the three groups of mice: control (CTL), AG-0-treated mice (AG__100) and imipramine (IMI__15).

Example 15

Figure 15:
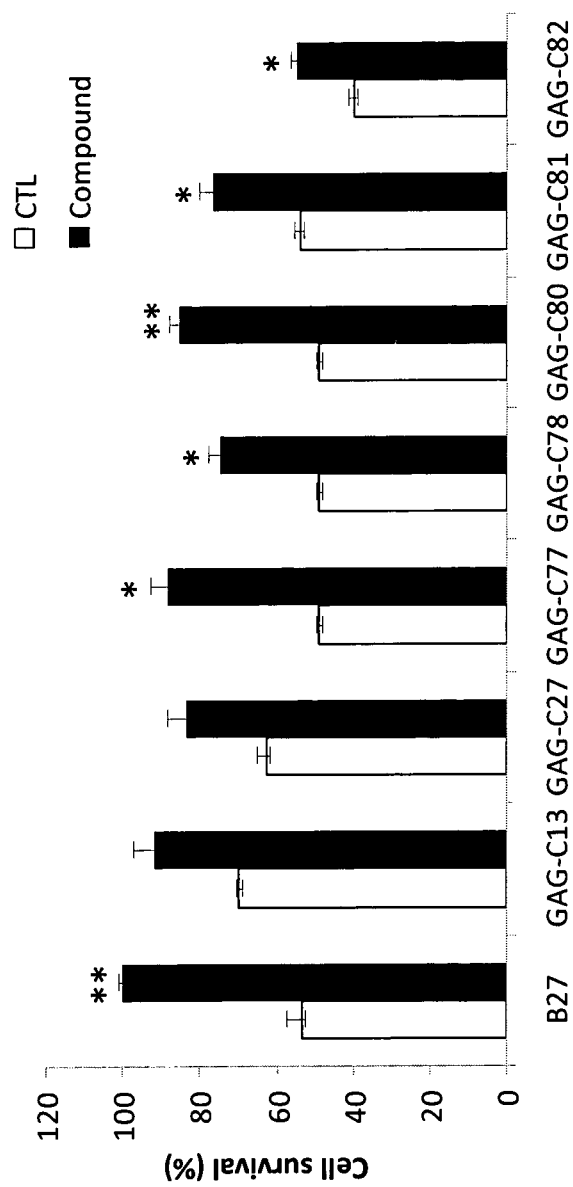
FIG. 15. Seven compounds isolated from *Adelostemma gracillimum* refined fraction promote rat cortical neuron survival against B27 withdrawal. Cortical neuron cultures of 7DIV were pre-treated with various compounds isolated from AG-0 (30 μM) for 24 hours and the medium was changed to one that lacked B27. A MTT assay was performed after 24 hours. Cell survival is presented as a percentage compared to a B27 positive control. Assays were conducted in duplicate and repeated at least 3 times. *=P<0.05; **=P<0.01.

Compounds Isolated from *Adelostemma gracillimum* Refined Fraction Promote Neuronal Survival Against B27 Withdrawal To identify the compounds which contribute to the neuroprotective effects of *Adelostemma gracillimum* refined fraction, 129 natural compounds were isolated from AG-0. All of the compounds were subjected to the B27 withdrawal assay. As shown in FIG. 15, seven of them promoted cell survival of cortical neurons in the absence of B27. They were designated as GAG-C13, GAG-C27, GAG-C77, GAG-C78, GAG-C80, GAG-C81 and GAG-C82. Characterization of these positive compounds identified GAG-C13, GAG-C27, GAG-C78 and GAG-C80 as novel structures.

Example 16

Figure 16:
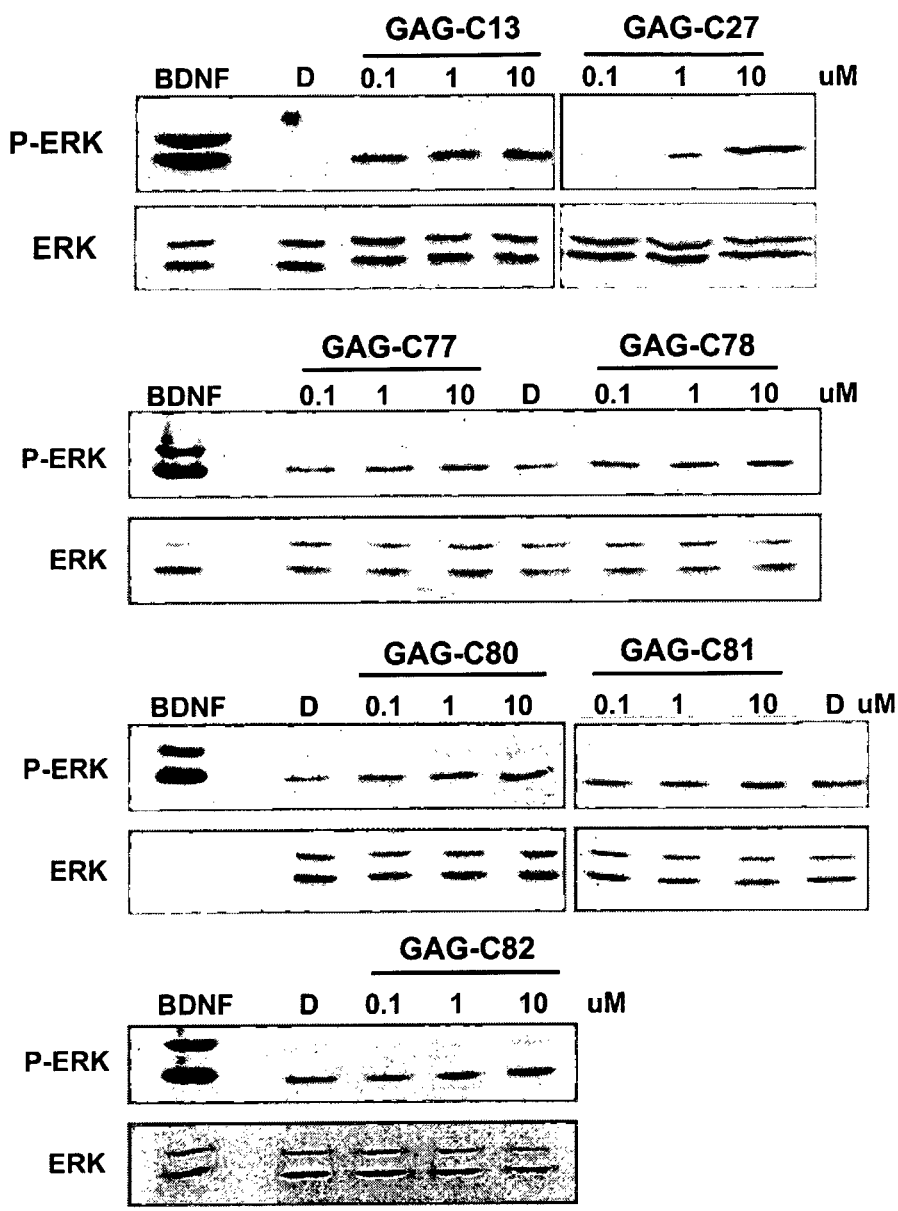
FIG. 16. Seven compounds from *Adelostemma gracillimum* refined fraction that protect primary neurons from B27 withdrawal induce ERK phosphorylation. Cortical neuron cultures of 7DIV were treated with various concentrations of compounds isolated from AG-0 (0.1-10 μM) for 15 min. Protein lysates were collected and Western blot analysis was performed with antibodies against phospho-ERK. Protein loading was indicated by total ERK expression. BDNF (50 ng/mL) was used as a positive control. "D" denotes lysates treated with DMSO for 15 min.

Compounds Isolated from *Adelostemma gracillimum* Refined Fraction Protect Neurons from B27 Withdrawal Induce ERK Phosphorylation Compounds that promote neuronal survival against B27 withdrawal were tested on their abilities to induce ERK phosphorylation. Western blot analysis was performed on neuronal lysates treated with various doses of the compounds for fifteen minutes. As shown in FIG. 16, all of them induced ERK phosphorylation in a dose-dependant manner, albeit to different extents.

Example 17

Figure 17:
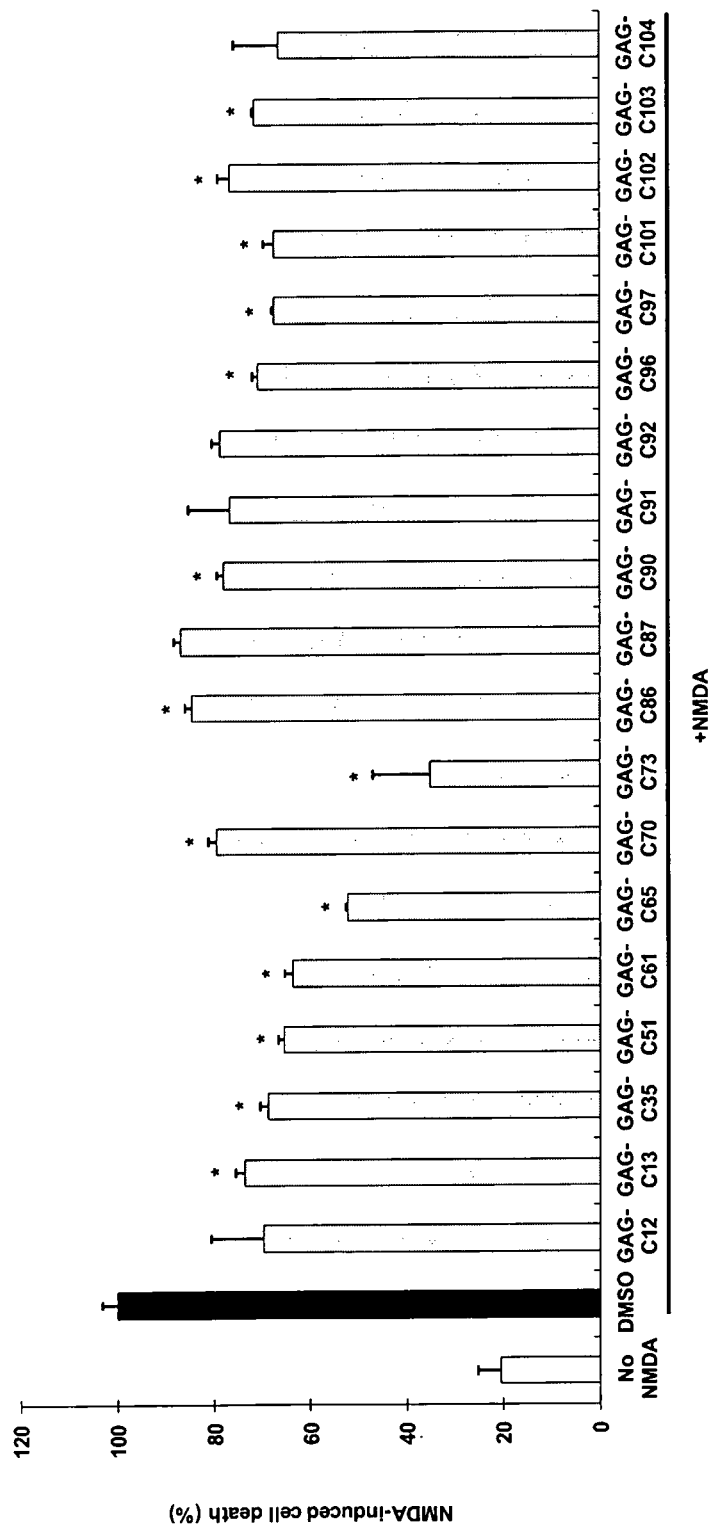
FIG. 17. Nineteen compounds isolated from *Adelostemma gracillimum* refined fraction promote rat cortical neuron survival against NMDA excitotoxicity. Cortical neuron cultures of 11DIV were pre-treated with various concentrations of compounds isolated from AG-0 (30-50 μM) for 2 hours, followed by treatment with NMDA for 20 min. The culture medium was then replaced with fresh medium, and a LDH assay was performed 24 hours later. Cell death is presented as a percentage compared to a vehicle control (DMSO, set as 100% cell death). Assays were conducted in duplicates. *=P<0.05.

Compounds Isolated from *Adelostemma gracillimum* Refined Fraction Promote Neuronal Survival Against NMDA Induced Cell Death To identify the compounds which contribute to the neuroprotective effect of *Adelostemma gracillimum* refined fraction, 129 natural compounds were isolated from AG-0. All of the compounds were subjected to the NMDA excitotoxicity assay and as shown in FIG. 17, nineteen of them promoted neuronal survival following NMDA treatment, albeit to different extents. These compounds were designated as GAG-C12, GAG-C13, GAG-C35, GAG-C51, GAG-C61, GAG-C65, GAG-C70, GAG-73, GAG-C86, GAG-C87, GAG-C90, GAG-C91, GAG-C92, GAG-C96, GAG-C97, GAG-C101, GAG-C102, GAG-C103, and GAG-C104. Upon characterization, GAG-C13, GAG-C51, GAG-C61, GAG-C65, GAG-C73, GAG-C90, GAG-C96, GAG-C102 and GAG-C104 were identified as novel structures.

Example 18

Figure 18:
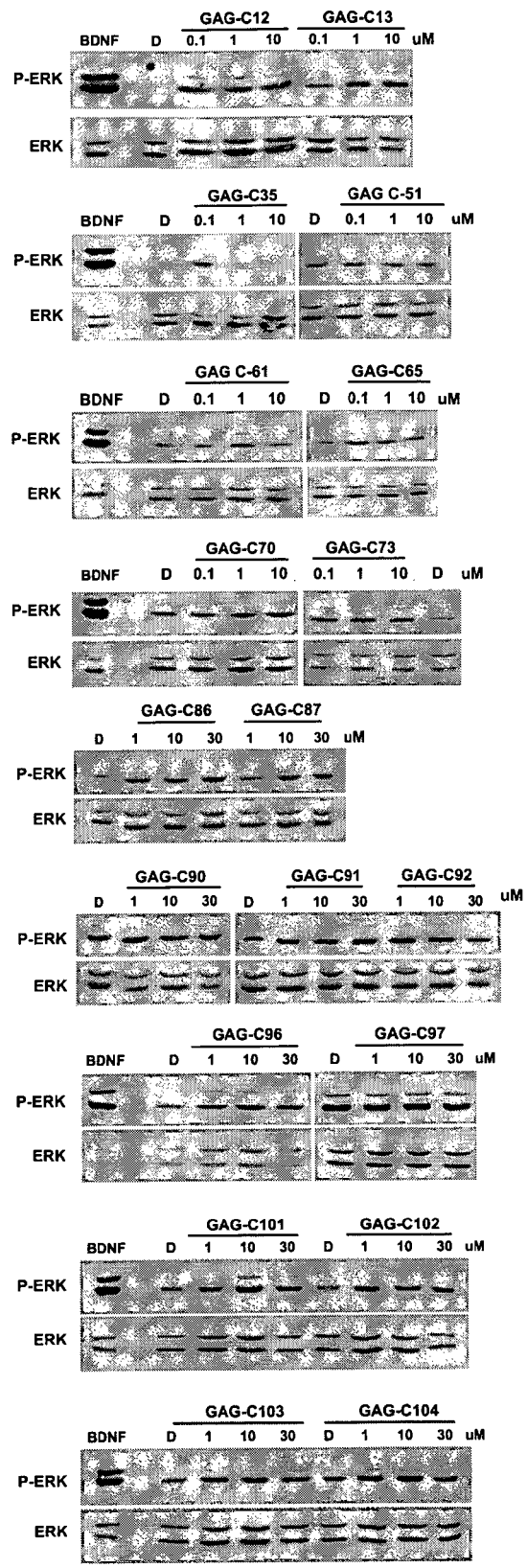
FIG. 18. Isolated compounds from *Adelostemma gracillimum* refined fraction that promote cortical neuron survival against NMDA-induced cell death induce ERK phosphorylation. Cortical neuron cultures of 7DIV were treated with various concentrations of compounds isolated from AG-0 (0.1-10 μM) for 15 min. Protein lysates were collected and Western blot analysis was performed with antibodies against phospho-ERK. Protein loading was indicated by total ERK expression. BDNF (50 ng/mL) was used as a positive control. "D" denotes lysates treated with DMSO for 15 min.

Compounds Isolated from *Adelostemma gracillimum* Refined Fraction that Promote Neuronal Survival Against NMDA Excitotoxicity Induce ERK Phosphorylation Compounds that promote neuronal survival against NMDA excitotoxicity were examined on their abilities to induce ERK phosphorylation. Western blot analysis was performed on neuronal lysates treated with various doses of the compounds for fifteen minutes. As shown in FIG. 18, with the exception of GAG-C51 and GAG-C97, all of the compounds induced ERK phosphorylation at certain dosages, albeit to different extents.

Example 19

Figure 19:
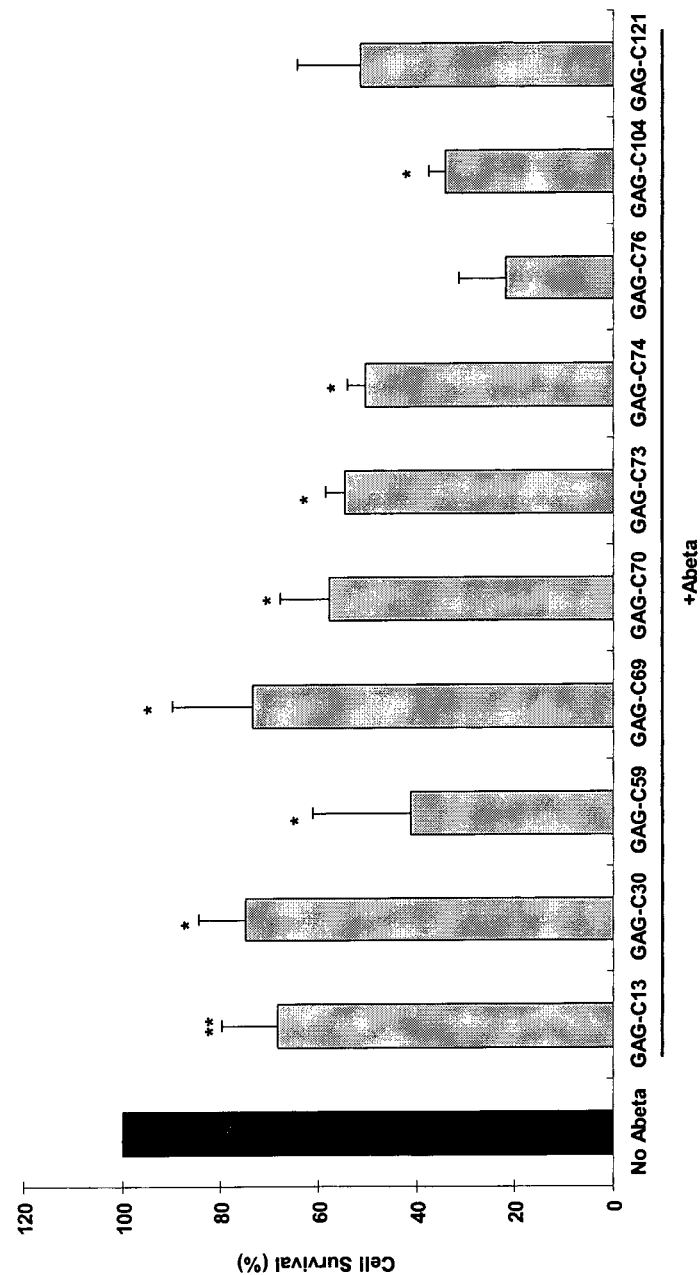
FIG. 19. Seven compounds isolated from *Adelostemma gracillimum* refined fraction protect rat cortical neurons against amyloid-beta peptide-induced cell death. Cortical neuron cultures of 7DIV were treated with various concentrations of compounds isolated from AG-0 (50 μM, except GAG-C69 at 30 μM) for 2 hours, then the medium was changed to medium containing $A\beta_{25-35}$ ("Abeta", 10 μM). A MTT assay was performed after 24 hours. Cell survival is presented as a percentage compared to a positive control (no Abeta). Assays were conducted in duplicate and repeated at least twice. *=P<0.05; **=P<0.005.

Isolated Compounds from *Adelostemma gracillimum* Refined Fraction Promote Neuronal Survival Against Amyloid-Beta Peptide-Induced Cell Death To identify the compounds that contribute to the neuroprotective effects of *Adelostemma gracillimum* refined fraction, 129 natural compounds were isolated from AG-0. The effect of these compounds on amyloid-beta peptide ($A\beta_{25-35}$)-treated primary cortical neurons was investigated. As shown in FIG. 19, ten of the compounds (GAG-C13, GAG-C30, GAG-C59, GAG-C69, GAG-C70, GAG-73, GAG-C74, GAG-C76, GAG-C104 and GAG-C121) promoted cell survival of cortical neurons treated with $A\beta_{25-35}$. Upon further characterization, GAG-C13, GAG-C30, GAG-C59, GAG-C69, GAG-C73, GAG-C76 and GAG-C104 were identified as novel structures.

Example 20

Figure 20:
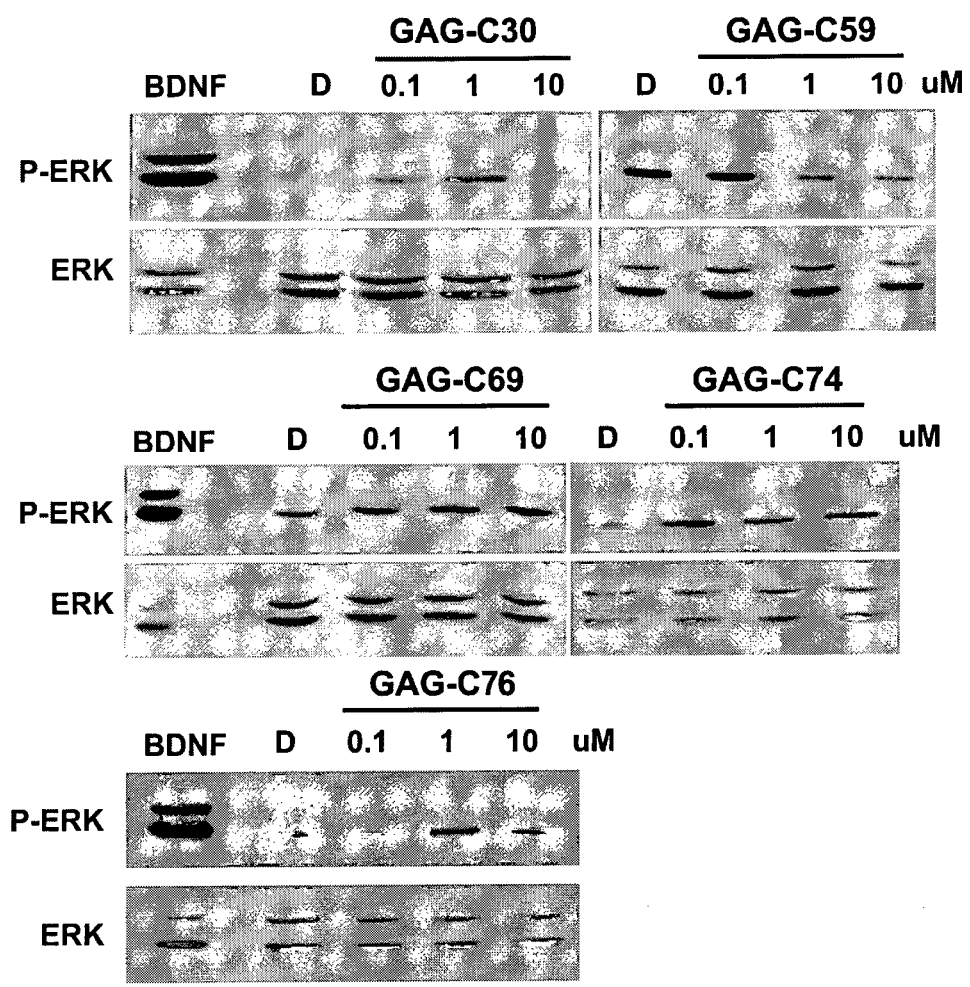
FIG. 20. Compounds isolated from *Adelostemma gracillimum* refined fraction that promote cortical neuron survival against amyloid-beta peptide insult induce ERK phosphorylation. Cortical neuron cultures of 7DIV were treated with various concentrations of compounds isolated from AG-0 (0.1-10 μM) for 15 min. Protein lysates were collected and Western blot analysis was performed with antibodies against phosphorylated-ERK. Protein loading was indicated by total ERK expression. BDNF (50 ng/mL) was used as a positive control. "D" denotes lysates treated with DMSO for 15 min.

Isolated Compounds from *Adelostemma gracillimum* Refined Fraction that Promote Neuronal Survival Against Amyloid-Beta Peptide Excitotoxicity Also Induce ERK Phosphorylation Isolated compounds that promoted neuronal survival against amyloid-beta peptide insult were examined on their abilities to induce ERK phosphorylation. Western blot analysis was performed on neuronal lysates that had been treated with various doses of compounds for fifteen minutes. With the exception of GAG-C59, all of the compounds (GAG-C70 and GAG-C73 were shown in example 18) induced ERK phosphorylation albeit to different extents, as shown in FIG. 20.

Example 21

GAG-C27 Protects Neurons Against B27 Withdrawal

Figure 21:
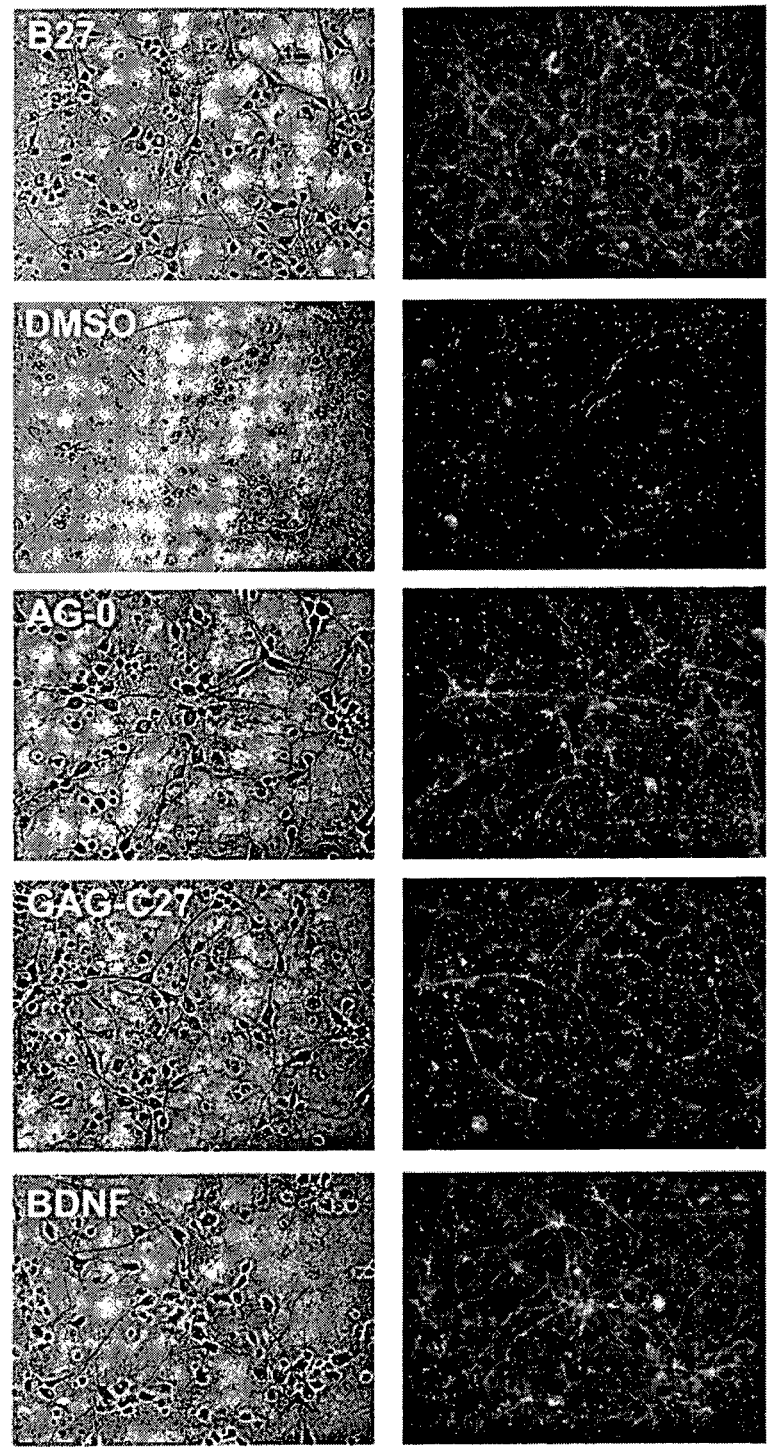
FIG. 21. Immunofluorescence staining of GAG-C27-treated cortical neurons in the absence of B27. Cortical neuronal cultures of 7DIV were pre-treated with AG-0 (30 μg/mL), GAG-C27 (30 μM), or BDNF (50 ng/mL) for 24 hours, after which the medium was changed to one lacking B27. Cultures were fixed with 4% paraformaldehyde, immunostained with beta-tubulin type III antibody, and visualized with FITC-conjugated anti-mouse antibody. Cell bodies were highlighted by DAPI staining. DMSO was used as a solvent control. Images are shown at 40× magnification.

Cortical neurons were pre-treated with GAG-C27 and the medium was changed to one lacking B27. Neurons were fixed and immunostained with neuronal markers. As shown in FIG. 21, GAG-C27 protected cortical neurons from cell death after B27 withdrawal. GAG-C27 is composed of a novel structure.

Example 22

GAG-C27 Promotes Cortical Neuronal Survival in the Absence of B27

Figure 22:
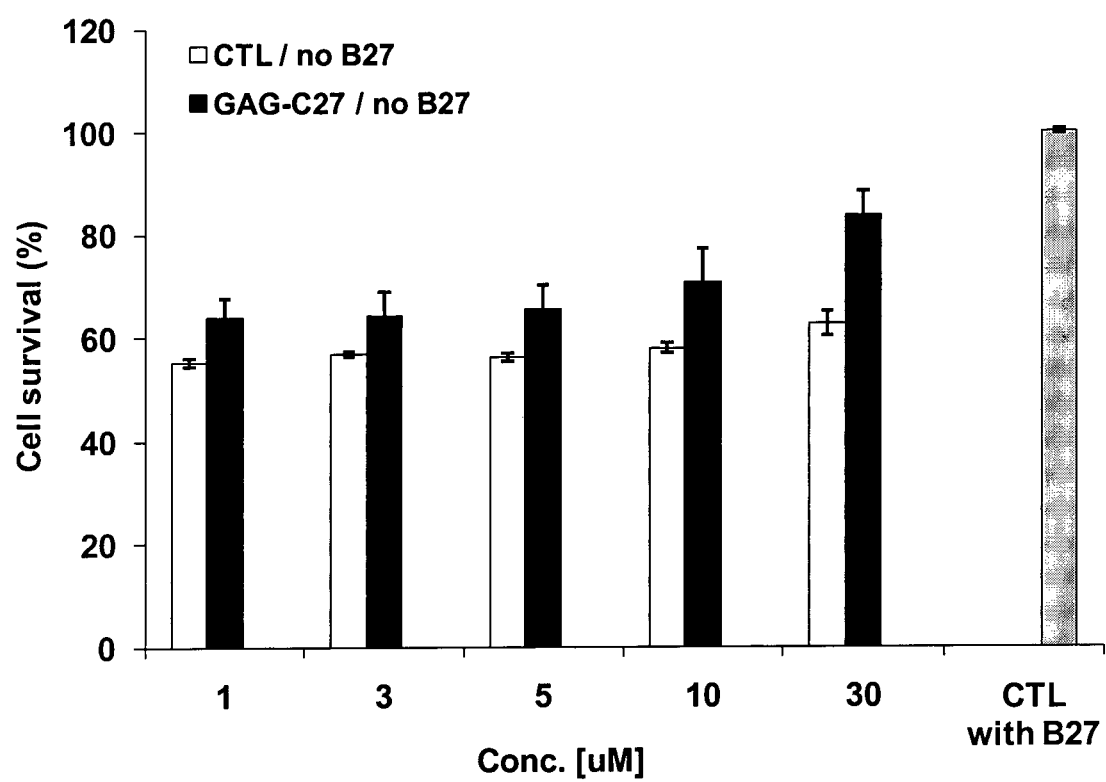
FIG. 22. GAG-C27 promotes rat cortical neuron survival against B27 withdrawal. Cortical neurons isolated from embryonic day 18 rat were cultured in Neurobasal medium supplemented with 2% B27. Neuron cultures of 7DIV were pre-treated with various concentrations of GAG-C27 (1-30 μM) for 24 hours, after which the medium was changed to one lacking B27. A MTT assay was performed 24 hours later. Cell survival is presented as a percentage compared to a DMSO control in the presence of B27 ("CTL with B27"). Assays were conducted in triplicate and repeated at least 3 times.

The neuroprotective effect of compound GAG-C27 was studied using primary neurons of 7DIV and cell survival was measured as mitochrondial activity by the MTT assay. A dose-dependent study on GAG-C27 showed its neuroprotective effect at 30 µM on primary neurons cultured in the absence of B27, as shown in FIG. 22.

Example 23

GAG-C27 Induces ERK Phosphorylation in Primary Cortical Neurons

Figure 23:
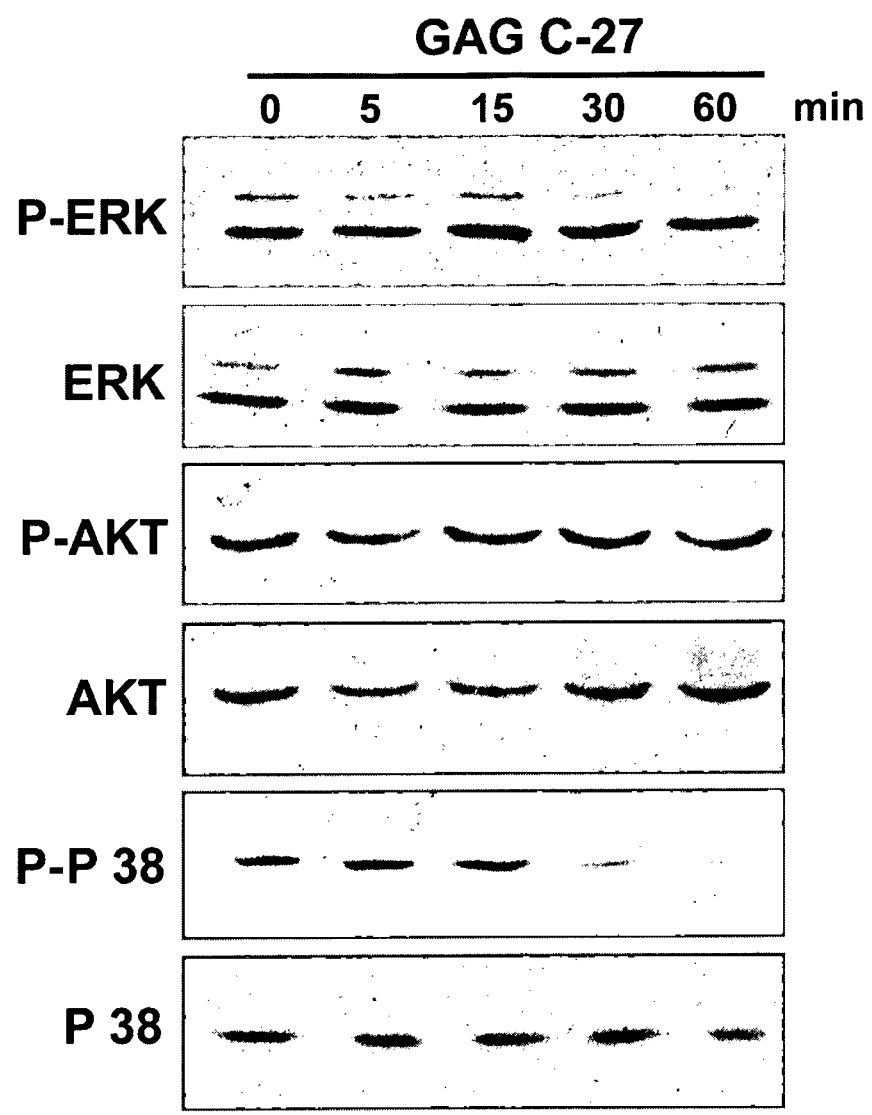
FIG. 23. GAG-C27 induces ERK phosphorylation in embryonic rat cortical neurons. Cortical neurons (7DIV) were incubated with GAG-C27 (10 μM) for various time intervals. Total protein was collected and the expression of signaling proteins was analyzed by Western blot analysis.

The effect of GAG-C27 on ERK phosphorylation was examined in cortical neurons of 7DIV using Western blot analysis. As shown in FIG. 23, GAG-C27 induced ERK phosphorylation in cortical neurons after 15 min, which was sustained for 60 min. There was no effect on AKT protein phosphorylation, while a reduction in phosphorylated P38 was observed for GAG-C27-treated lysates after 30 min of incubation.

Example 24

GAG-C77 Promotes Neuronal Survival Against B27 Withdrawal

Figure 24:
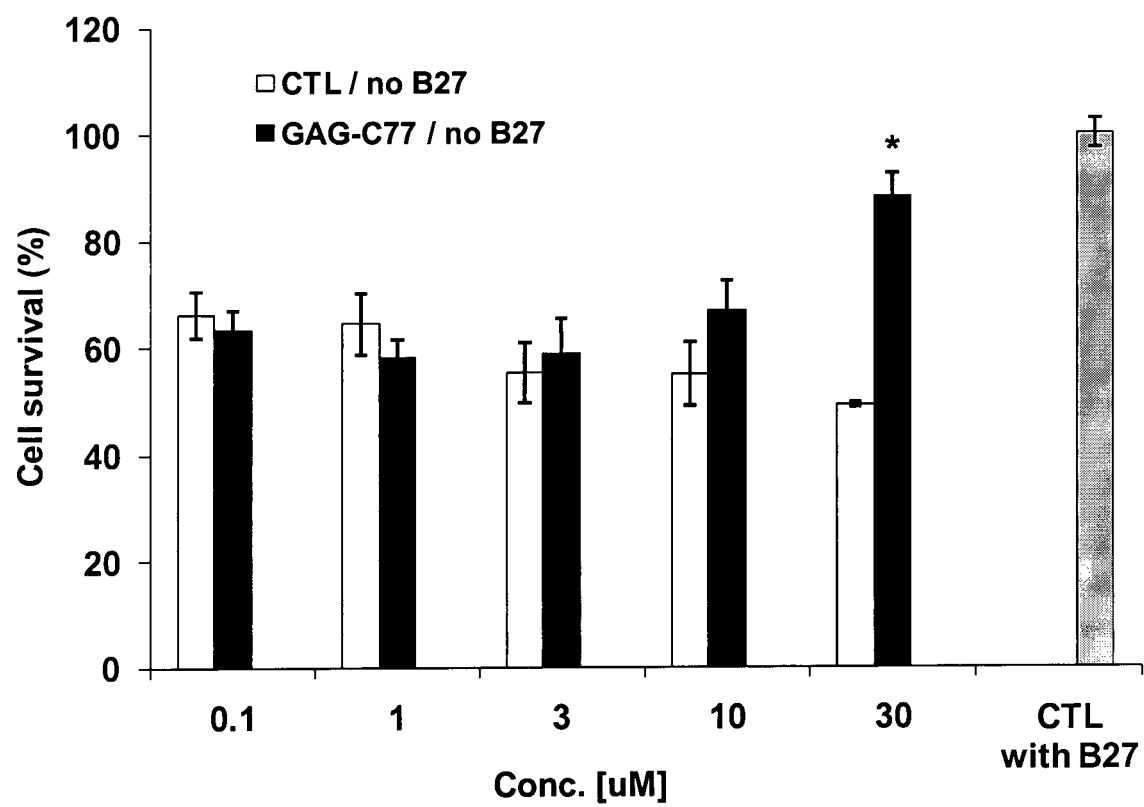
FIG. 24. GAG-C77 promotes rat cortical neuron survival against B27 withdrawal. Cortical neurons isolated from embryonic day 18 rat were cultured in Neurobasal medium supplemented with 2% B27. Neuron cultures of 7DIV were pre-treated with various concentrations of GAG-C77 (1-30 μM) for 24 hours, after which the medium was changed to one lacking B27. A MTT assay was performed 24 hours later. Cell survival is presented as a percentage compared to a DMSO control in the presence of B27 ("CTL with B27"). Assays were conducted in triplicate and repeated at least 3 times. *=P<0.05.

The neuroprotective effect of compound GAG-C77 was studied using primary cortical neurons of 7DIV. Neuronal cells were subjected to B27 withdrawal upon which cell survival was measured as mitochondrial activity by the MTT assay. As shown in FIG. 24, dose-dependent studies indicated GAG-C77 exerted its neuroprotective effect at 10-30 µM on primary cortical neurons cultured in the absence of B27.

Example 25

GAG-C77 Induces ERK Phosphorylation in Primary Cortical Neurons

Figure 25:
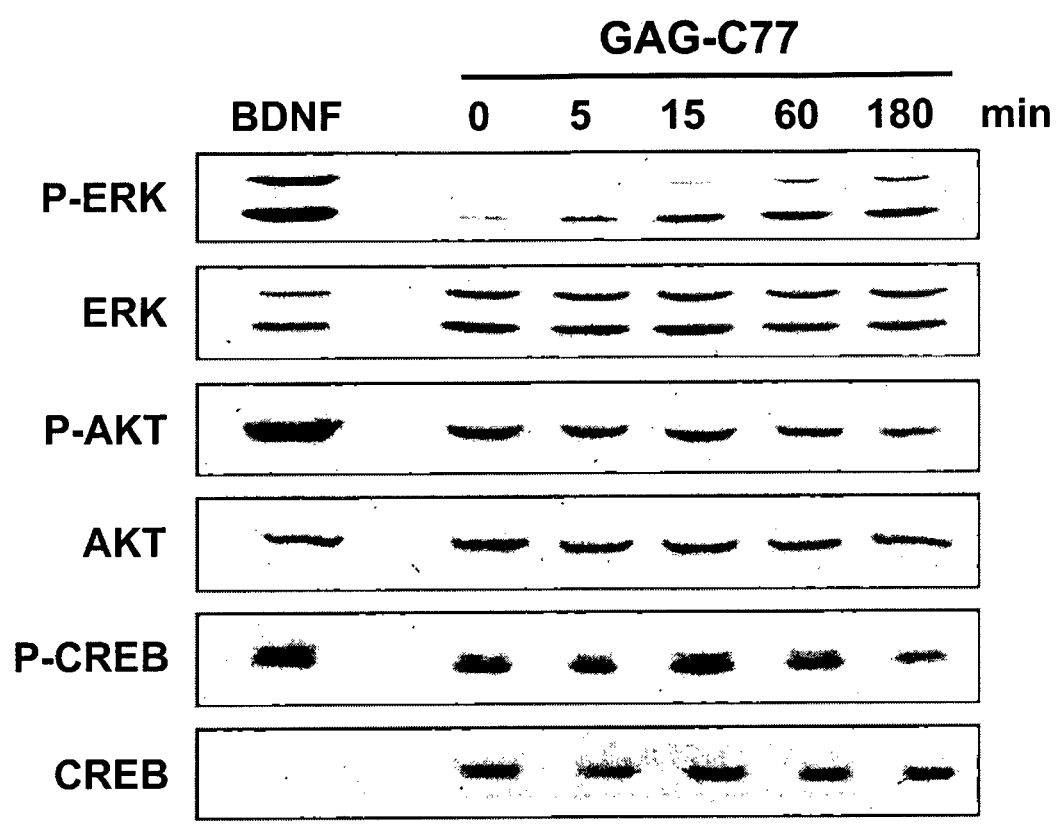
FIG. 25. GAG-C77 induces phosphorylation of ERK and CREB in embryonic rat cortical neurons. Cortical neurons (7DIV) were incubated with GAG-C77 (30 μM) for various time intervals. Total protein was collected and the expression of signaling proteins was analyzed by Western blot analysis. Brain-derived neurotrophic factor (BDNF, 50 ng/mL, 15 min treatment) was used as a control.

The effect of GAG-C77 on ERK phosphorylation was examined. As shown in FIG. 25, GAG-C77 (30 µM) significantly induced ERK phosphorylation in cortical neurons from 15 min and persistently to 180 min. Furthermore, GAG-C77 also induced CREB phosphorylation at 15 min of incubation.

Example 26

GAG-C77 Induces CREB-Promoter Activity

Figure 26:
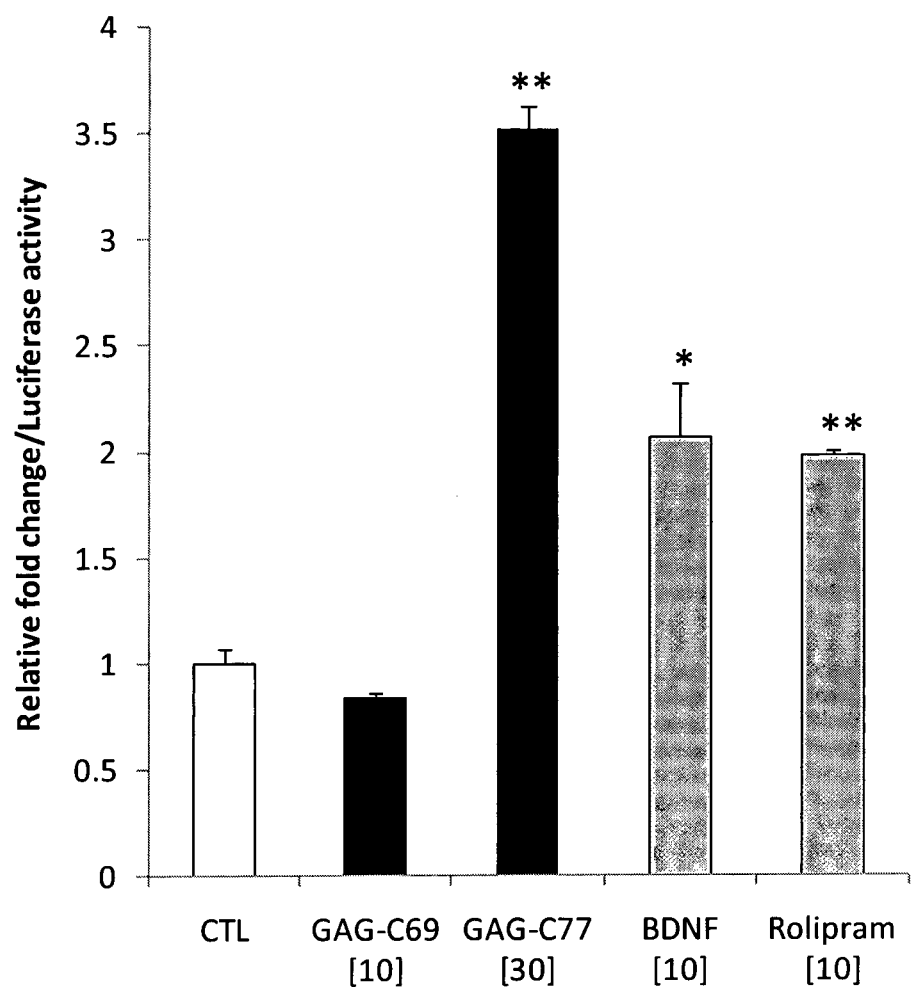
FIG. 26. GAG-C77 increases CREB-promoter activity in primary cortical neurons. Primary cortical neuronal cultures (7DIV) transfected with a luciferase-CREB promoter construct were treated with GAG-C69 or GAG-C77 (concentration depicted in [μM]). Cell lysates were collected after 6 hours incubation and luciferase activity was measured. BDNF [ng/mL] and rolipram [μM] were used as positive controls. Assays were conducted in triplicate. *=P<0.05; **=P<0.005.

GAG-C77 induces ERK and CREB phosphorylation in primary cortical neurons. Therefore, the downstream effect of GAG-C77 after CREB activation was examined. Using a reporter gene (luciferase)-linked CREB promoter assay, GAG-C77 was found to significantly induce luciferase activity driven by the CREB promoter (see FIG. 26).

Example 27

GAG-C78 Promotes Neuronal Survival Against B27 Withdrawal

Figure 27:
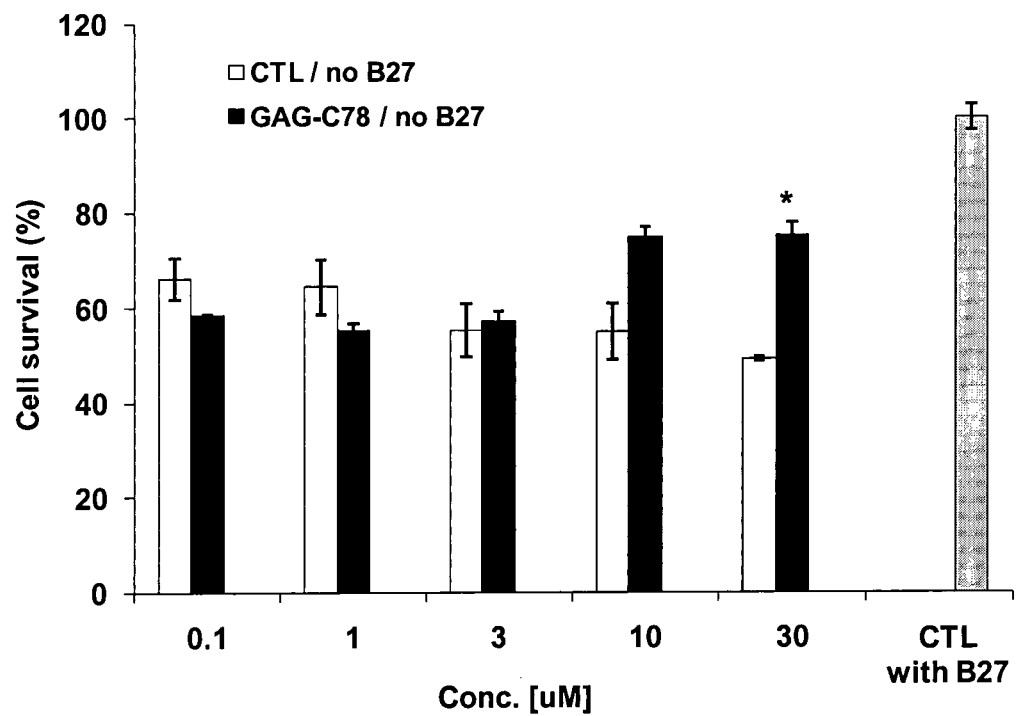
FIG. 27. GAG-C78 promotes rat cortical neuron survival against B27 withdrawal. Cortical neurons isolated from embryonic day 18 rat were cultured in Neurobasal medium supplemented with 2% B27. Neuron cultures of 7DIV were pre-treated with various concentrations of GAG-C78 (1-30 μM) for 24 hours, then the medium was changed to one lacking B27. A MTT assay was performed 24 hours later. Cell survival is presented as a percentage compared to a DMSO control in the presence of B27 ("CTL with B27"). Assays were conducted in duplicate and repeated at least 3 times. *=P<0.05.

The neuroprotective effect of compound GAG-C78 was studied using primary cortical neurons of 7DIV. Neuronal cells were subjected to B27 withdrawal upon which cell survival was measured as mitochondrial activity by the MTT assay. As shown in FIG. 27, dose-dependent studies indicated GAG-C78 exerted its neuroprotective effect at 10-30 µM on primary cortical neurons cultured in the absence of B27.

Example 28

GAG-C78 Induces ERK Phosphorylation in Primary Cortical Neurons

Figure 28:
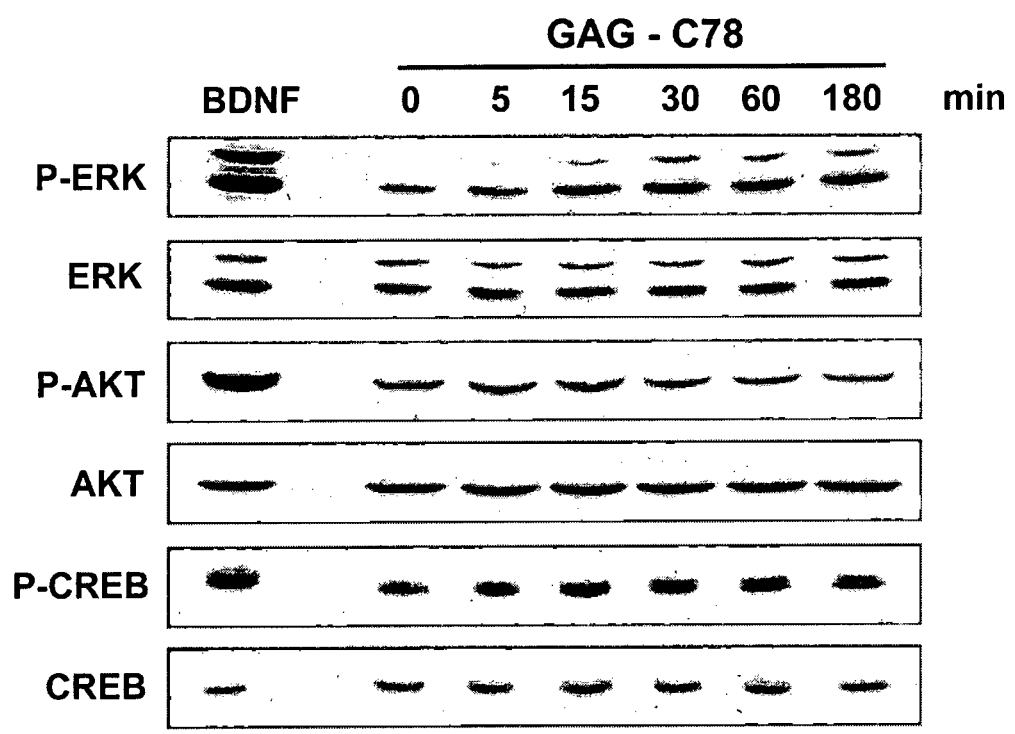
FIG. 28. GAG-C78 induces phosphorylation of ERK and CREB in embryonic rat cortical neurons. Cortical neurons (7DIV) were incubated with GAG-C78 (30 µM) for various time intervals. Total protein was collected and the expression of signaling proteins was analyzed by Western blot analysis. Brain-derived neurotrophic factor (BDNF, 50 ng/mL, 15 min treatment) was used as a control.

The effect of GAG-C78 on ERK phosphorylation was examined. As shown in FIG. 28, GAG-C78 (30 µM) significantly induced ERK phosphorylation in cortical neurons from 15 min and persistently to 180 min. Furthermore, GAG-C78 also induced CREB phosphorylation at 15 min of incubation.

Example 29

GAG-C80 Dose-Dependently Promotes Neuronal Survival Against B27 Withdrawal

Figure 29:
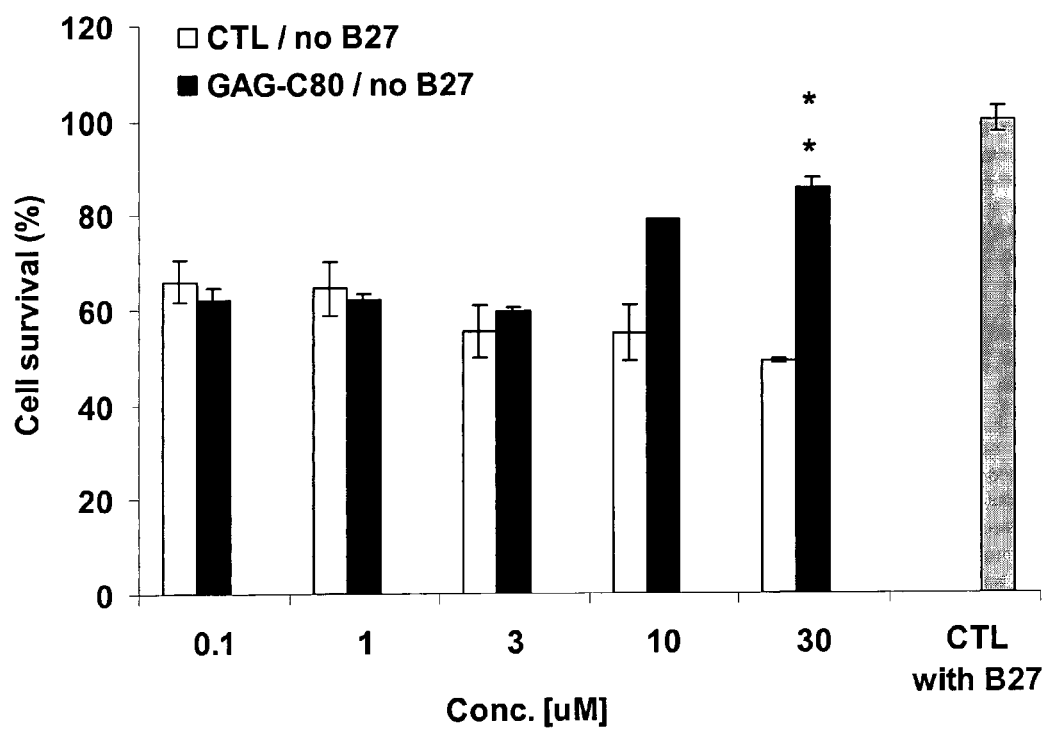
FIG. 29. GAG-C80 promotes rat cortical neuron survival against B27 withdrawal. Cortical neurons isolated from embryonic day 18 rat were cultured in Neurobasal medium supplemented with 2% B27. Neuron cultures of 7DIV were pre-treated with various concentrations of GAG-C80 (1-30 µM) for 24 hours, after which the medium was changed to one lacking B27. A MTT assay was performed 24 hours later. Cell survival is presented as a percentage compared to a DMSO control in the presence of B27 ("CTL with B27"). Assays were conducted in duplicate and repeated at least 3 times. *=P<0.01.

The neuroprotective effect of compound GAG-C80 was examined using primary cortical neurons of 7DIV and cell survival was measured as mitochondrial activity by the MTT assay. As shown in FIG. 29, GAG-C80 exhibited neuroprotective effects in a dose-dependent manner (10-30 µM) on primary neurons cultured in the absence of B27. The level of neuronal survival observed in GAG-C80-treated cultures was similar to the neurons cultured in the presence of B27.

Example 30

GAG-C81 Promotes Neuronal Survival Against B27 Withdrawal

Figure 30:
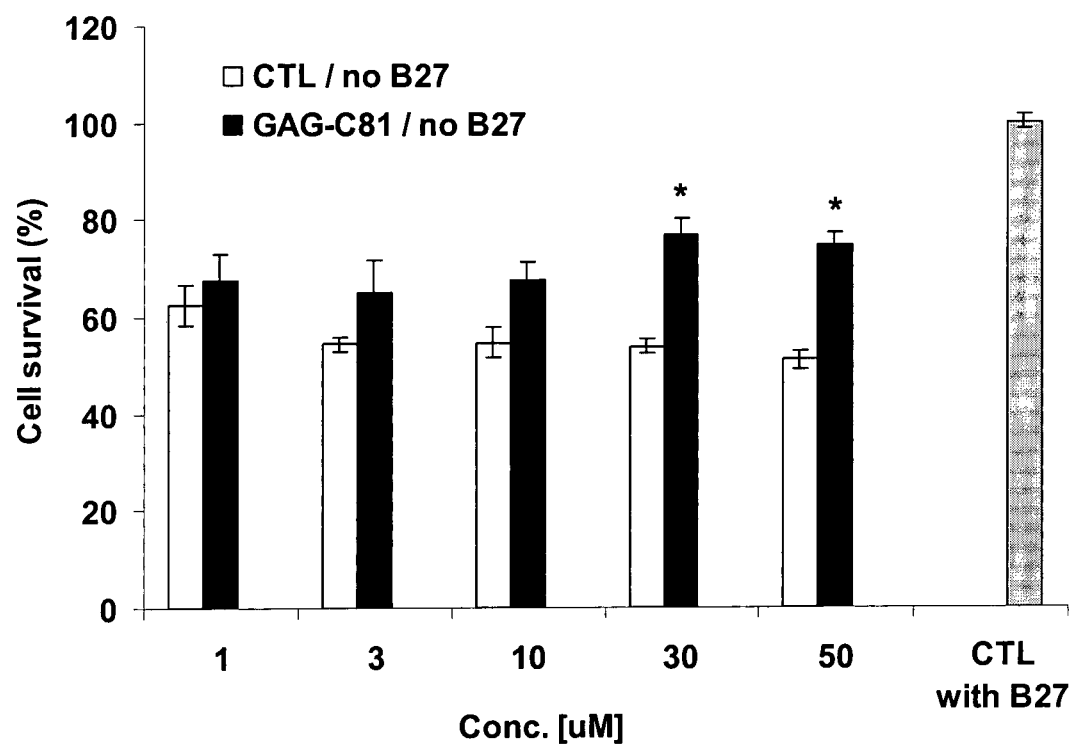
FIG. 30. GAG-C81 promotes rat cortical neuron survival against B27 withdrawal. Cortical neurons isolated from embryonic day 18 rat were cultured in Neurobasal medium supplemented with 2% B27. Neuron cultures of 7DIV were pre-treated with various concentrations of GAG-C81 (1-50 µM) for 24 hours, after which the medium was changed to one lacking B27. A MTT assay was performed 24 hours later. Cell survival is presented as a percentage compared to a DMSO control in the presence of B27 ("CTL with B27"). Assays were conducted in duplicate and repeated at least 3 times. *=P<0.05.

The neuroprotective effect of compound GAG-C81 was examined using primary cortical neurons of 7DIV and cell survival was measured as mitochondrial activity by the MTT assay. As shown in FIG. 30, GAG-C81 exhibited neuroprotective effects in a dose-dependent manner on primary neurons cultured in the absence of B27.

Example 31

Figure 31:
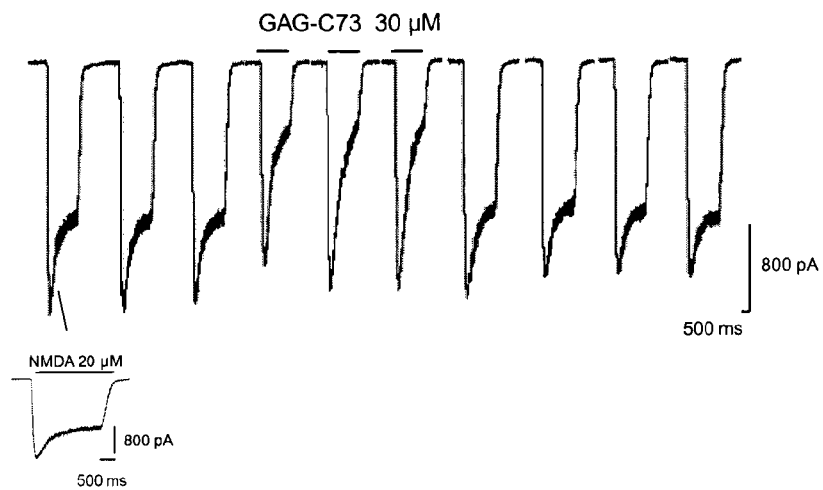
FIG. 31. GAG-C73 inhibits NMDA-induced current in hippocampal neurons. The effects of GAG-C73 on NMDA-activated currents in rat hippocampal neurons (11DIV) were examined using whole-cell patch clamp studies. Addition of NMDA induced depolarization and initiated an inward current in pyramidal cells. A. Examples of NMDA-activated currents before, during, and after application of GAG-C73 (30 µM) are shown. Horizontal bars denote GAG-C73 application. B-C. Co-treatment of NMDA with GAG-C73 (30 µM) reduced the current induced by NMDA, for both peak and plateau currents (B). Increasing doses of GAG-C73 further decreased the NMDA-induced current (C). DMSO was used as a solvent control. The concentration of glycine was 0.1 µM, and membrane potential was held at −70 mV. n=10; three independent experiments were performed. *=P<0.05.
Figure 31:
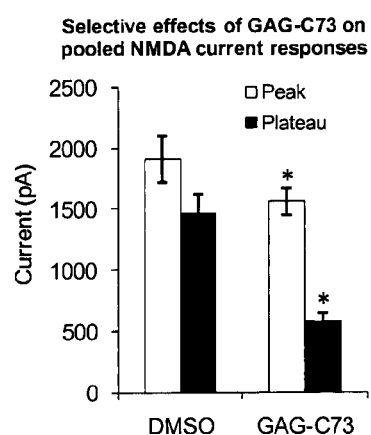
Figure 31:
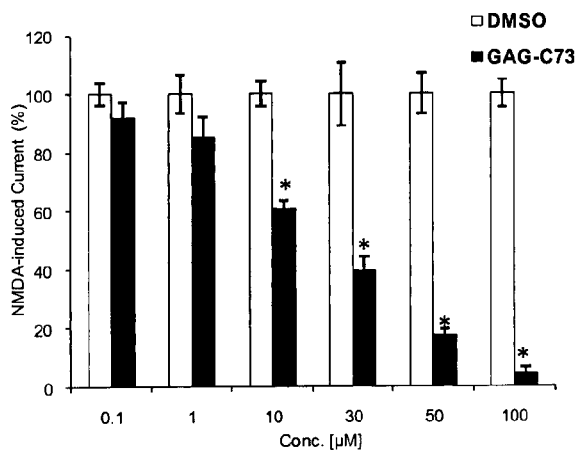

GAG-C73 Exhibits NMDA Receptor Antagonist Activity in Whole-Cell Patch Clamp Study Whole cell patch clamp studies were conducted to measure the ion current across the surface of hippocampal neurons in the presence and absence of the novel compounds to demonstrate NMDA receptor activity. The NMDA receptor is a gated ion channel, which allows inflow of current during a nerve impulse. Antagonists to the receptor would prevent the inflow of current. As shown in FIG. 31, the addition of NMDA induced depolarization and initiated an inward current in pyramidal cells.

Example 32

Figure 32:
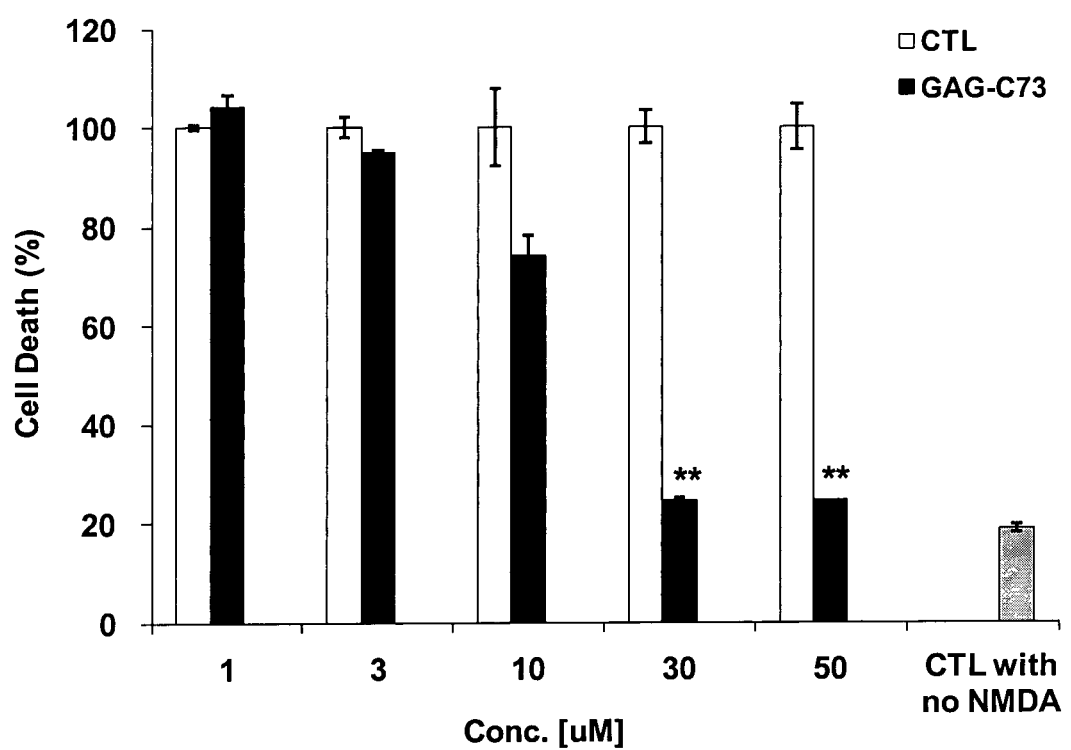
FIG. 32. GAG-C73 decreases cortical neuron cell death induced by NMDA insult in a dose-dependent manner. Cortical neurons were pre-incubated with different concentrations of GAG-C73 or DMSO control ("CTL with no NMDA") for 2 hrs, followed by co-treatment with NMDA (20 µM) for 20 min. After overnight incubation, LDH release into the medium was measured. Assays were conducted in duplicate and repeated at least 3 times. *=P<0.05; **=P<0.005.

GAG-C73 Protects Neurons Against NMDA-Induced Cell Death in a Dose-Dependent Manner Cortical neurons were pre-treated with varying concentrations of GAG-C73 and subsequently subjected to a toxic dose of NMDA (20 µM). Survival assays were then conducted to examine the ability of GAG-C73 to effectively protect neuronal cells from NMDA-induced excitotoxicity. As indicated in FIG. 32, there was a significant dose-dependent reduction in cell death upon pre-treatment with GAG-C73 compared to the DMSO control.

Example 33

GAG-C73 Protects Neurons Against Differing Concentrations of NMDA

Figure 33:
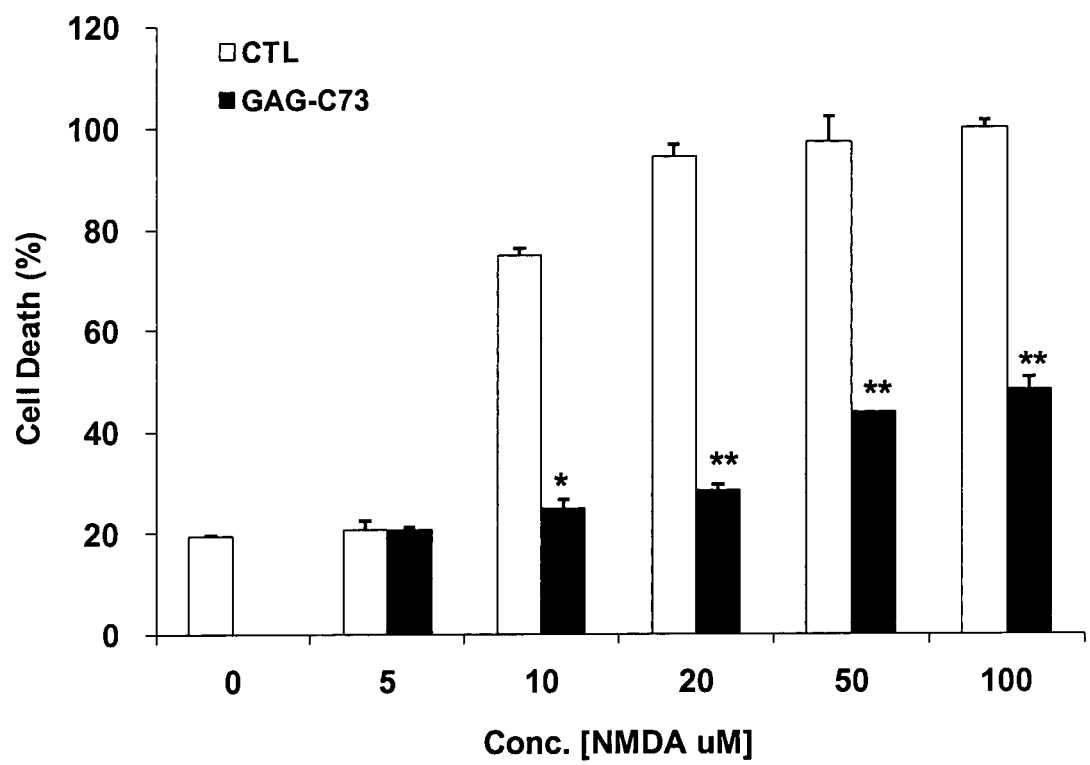
FIG. 33. GAG-C73 decreases primary neuron cell death induced by high doses of NMDA. Cortical neurons were incubated with GAG-C73 (30 µM) or DMSO control for 2 hrs, followed by co-treatment with differing concentrations of NMDA (5-100 µM) for 20 min. LDH release into the medium was then measured. Assays were conducted in duplicate and repeated at least 3 times. *=P<0.05; **=P<0.005.

Cortical neurons were pre-treated with GAG-C73 and subsequently subjected to varying concentrations of NMDA. Survival assays were then conducted to determine the ability of GAG-C73 to effectively protect neuronal cells from NMDA-induced excitotoxicity. As indicated in FIG. 33, there was a significant reduction in cell death upon pre-treatment with GAG-C73 compared to the DMSO control at toxic dosages of NMDA.

Example 34

GAG-C73 Protects Neurons Against Glutamate Insults

Figure 34:
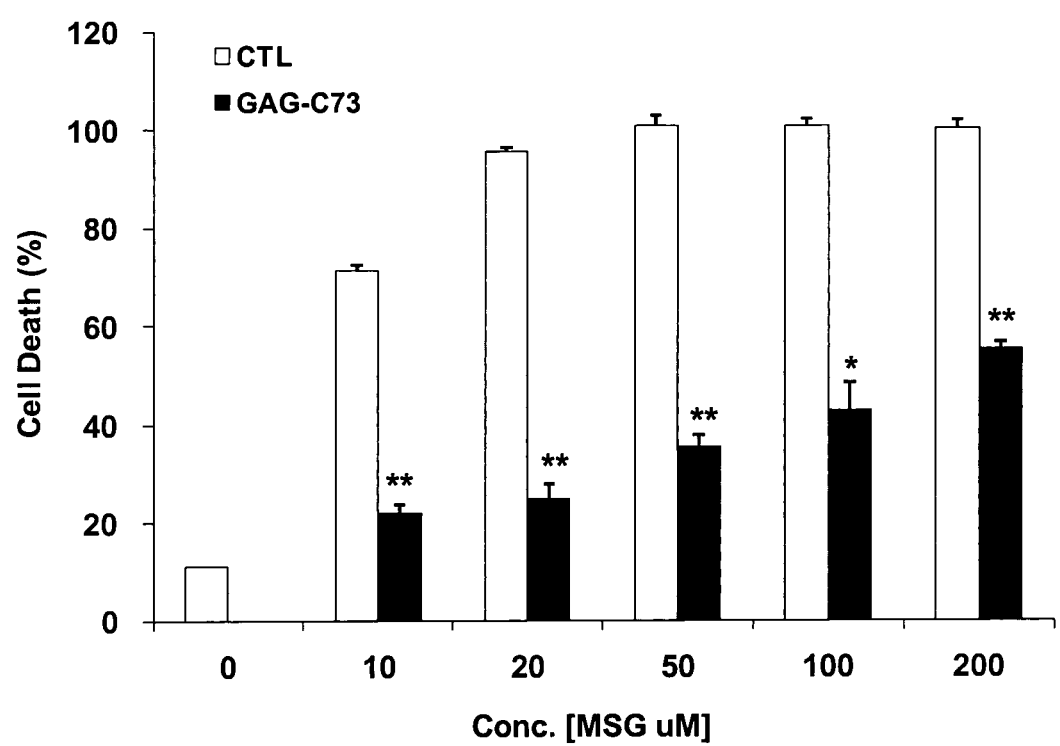
FIG. 34. GAG-C73 decreases primary neuron cell death induced by high doses of glutamate. Cortical neurons were incubated with GAG-C73 (30 µM) or DMSO control for 2 hrs, followed by co-treatment with differing concentrations of glutamate (10-200 µM) for 20 min. LDH release into the medium was then measured. Assays were conducted in duplicate and repeated at least 3 times. *=P<0.05; **=P<0.005.

Glutamate is the physiological neurotransmitter that activates NMDA receptors. However, excess amounts of glutamate can result in excitotoxicity and potential cell death. Survival assays were conducted to determine the ability of GAG-C73 to effectively protect neuronal cells from glutamate-induced excitotoxicity. As indicated in FIG. 34, there was a significant reduction in cell death upon pre-treatment with GAG-C73 compared to the DMSO control at all concentrations of glutamate examined.

Example 35

GAG-C69 Protects Neurons Against Amyloid-Beta Peptide Insults

Figure 35:
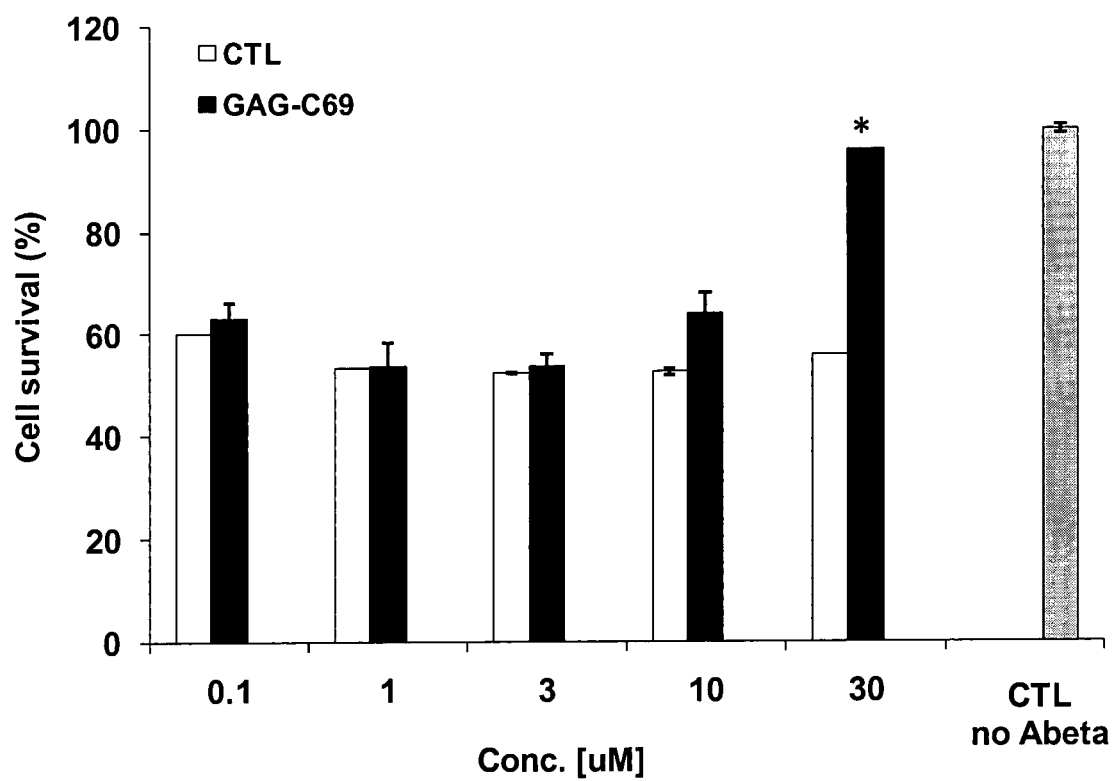
FIG. 35. GAG-C69 protects cortical neurons from amyloid-beta peptide-induced toxicity. Embryonic rat neuron cultures (7DIV) were pre-treated with various concentrations of GAG-C69 and then co-incubated with $A\beta_{25-35}$ (10 µM). After overnight incubation, a MTT assay was performed. Cell survival is presented as a percentage compared to a DMSO solvent control ("CTL no Abeta"). Assays were conducted in triplicate and repeated at least 3 times. *=P<0.05.

GAG-C69 is one of the compounds isolated from AG that promotes the survival of neurons against Aβ insult. As shown in FIG. 35, GAG-C69 increases the survival of neurons against Aβ insult comparable to control levels (without Aβ treatment).

Example 36

Figure 36:
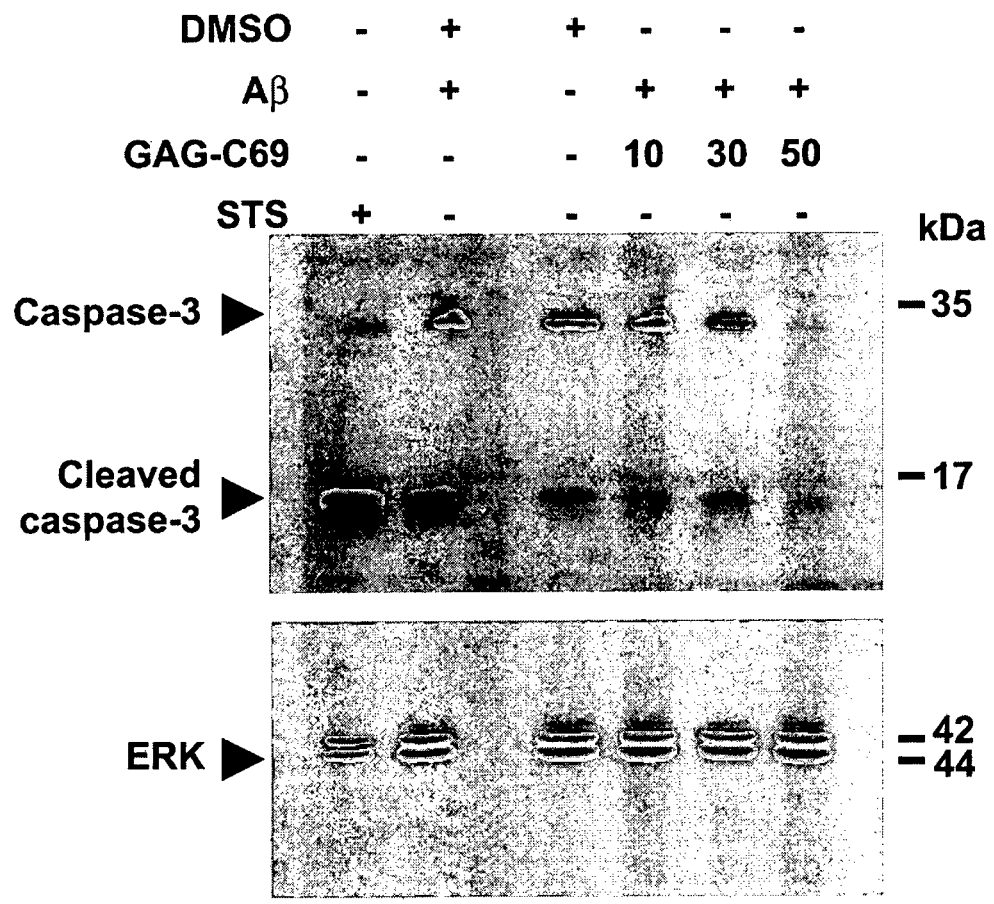
FIG. 36. GAG-C69 inhibits caspase-3 activation in primary cortical neurons induced by Aβ. Primary cortical neuron cultures (7DIV) were treated with various concentrations of GAG-C69 (10-50 µg/mL) in the presence of $A\beta_{25-35}$ (10 µM). Proteins were extracted after overnight incubation and Western blot analysis was performed. Blots were probed with antibodies against caspase-3 and ERK protein. Staurosporine (STS, 10 µM) was used as a positive control, while DMSO served as the vehicle control.

GAG-C69 Inhibits Caspase-3 Activity in Primary Neurons Upon Amyloid-Peptide Treatment GAG-C69 protects against neuronal death induced by Aβ as revealed by the MTT assay. Thus, the effect of the compound on caspase-3 activation in the presence of Aβ in cortical neurons was examined through Western blot analysis. As indicated in FIG. 36, the protein expression of cleaved-caspase-3 (17 kDa, active form of caspase-3) increased in the presence of Aβ treatment. With the addition of GAG-C69, the expression level of cleaved-caspase-3 was significantly decreased to levels comparable to that without Aβ.

Example 37

GAG-C14 Induces ERK Phosphorylation in Primary Cortical Neurons

Figure 37:
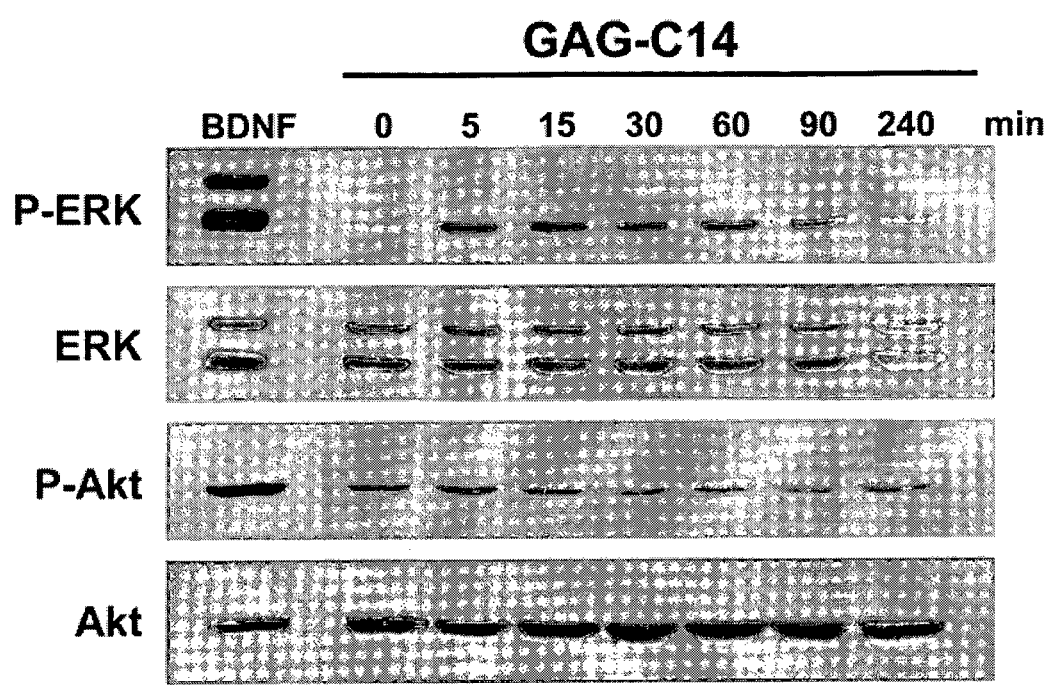
FIG. 37. GAG-C14 induces phosphorylation of ERK in embryonic rat cortical neurons. Cortical neurons (7DIV) were incubated with GAG-C14 (10 µM) for various time intervals. Total proteins were collected and the expression of signaling proteins was analyzed by Western blot analysis. Brain-derived neurotrophic factor (BDNF, 50 ng/mL, 15 min treatment) was used as a control.

The effect of GAG-C14 on ERK phosphorylation was examined in cortical neurons of 7DIV using Western blot analysis. As indicated in FIG. 37, GAG-C14 induced ERK phosphorylation in cortical neurons after 15 min and the effect remained for 90 min. The compound had no observable effect on AKT protein phosphorylation.

Example 38

GAG-C14 Modulates Spine Morphogenesis

A dendritic spine, a small membranous protrusion from a neuron's dendrite that typically receives input from a single synapse of an axon, serves as a storage site for synaptic strength and helps transmit electrical signals to the neuron's cell body. Two classes of dendritic spines (spines) are identified in hippocampal neurons: mature spines (mushroom shaped) and immature spines (filopodia). Immature spines, which have impaired signaling capabilities, typically only have necks and either lack or have very small "heads". Mature spines have both heads and necks, and spines with strong synaptic contacts typically have a large spine head that connects to the dendrite via a membranous, mushroom-shaped neck. Decreased spine density has been reported in aged neurons of the CA1 area of the hippocampus as well as the layer III pyramidal layer (Duan et al., 2003; von Bohlen und Halbach et al., 2009). Spine reduction is also associated with major depression as well as schizophrenia (Law et al., 2004). Cognitive disorders such as autism, mental retardation, Fragile X Syndrome, stroke, and chronic alcoholism may be resultant from abnormalities in dendritic spines, especially in regards to the number of spines and their maturity (Bhatt et al., 2009; von Bohlen und Halbach et al., 2009).

Figure 38:
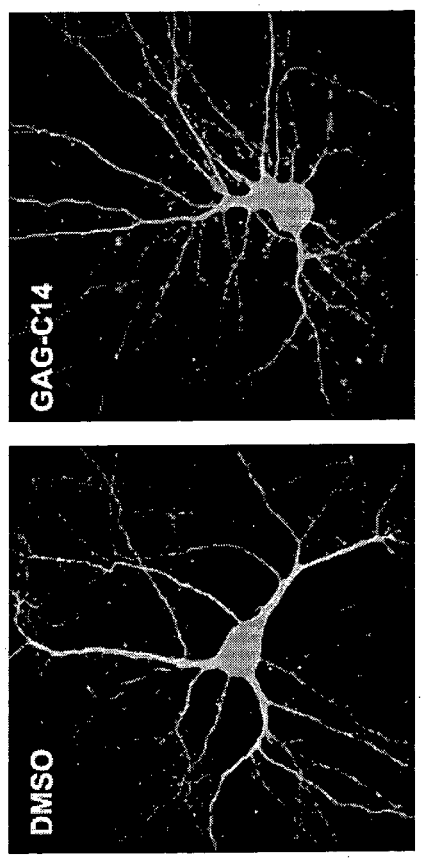
FIG. 38. GAG-C14 modulates spine morphogenesis. Hippocampal neurons were transfected with enhanced green fluorescent protein (EGFP) construct at 7DIV by calcium phosphate precipitation. The GFP-expressing neurons at 14DIV were then treated with 10 µM GAG-C14 or DMSO vehicle control for 24 hr. The dendritic spine morphology of hippocampal neurons was examined by confocal microscopy. GAG-C14 significantly increased spine density (bottom middle panel) and the percentage of large spines (head>1 µm) (bottom left panel), while the percentage of filopodia was significantly reduced (bottom right panel), as compared to the DMSO control. n=20; *=P<0.05.
Figure 38:
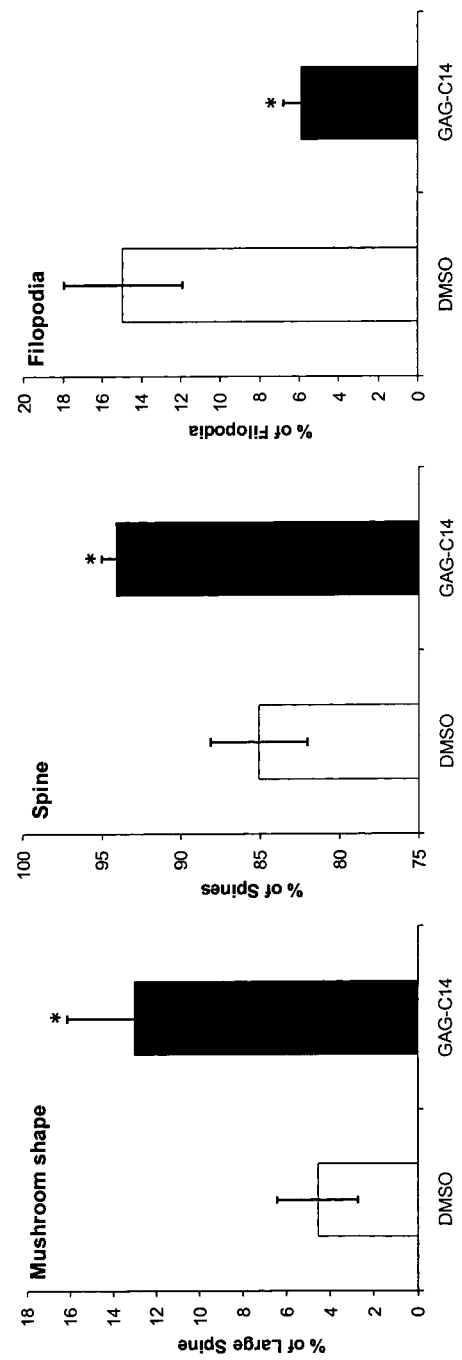

As indicated in FIG. 38, when neuronal cells were treated with GAG-C14, there was an increase in spine density in the GAG-C14-treated neurons, especially for spine heads larger than 1 μm. Furthermore, there was a reduction in the frequency of filopodia compared to the control.

Example 39

Figure 39:
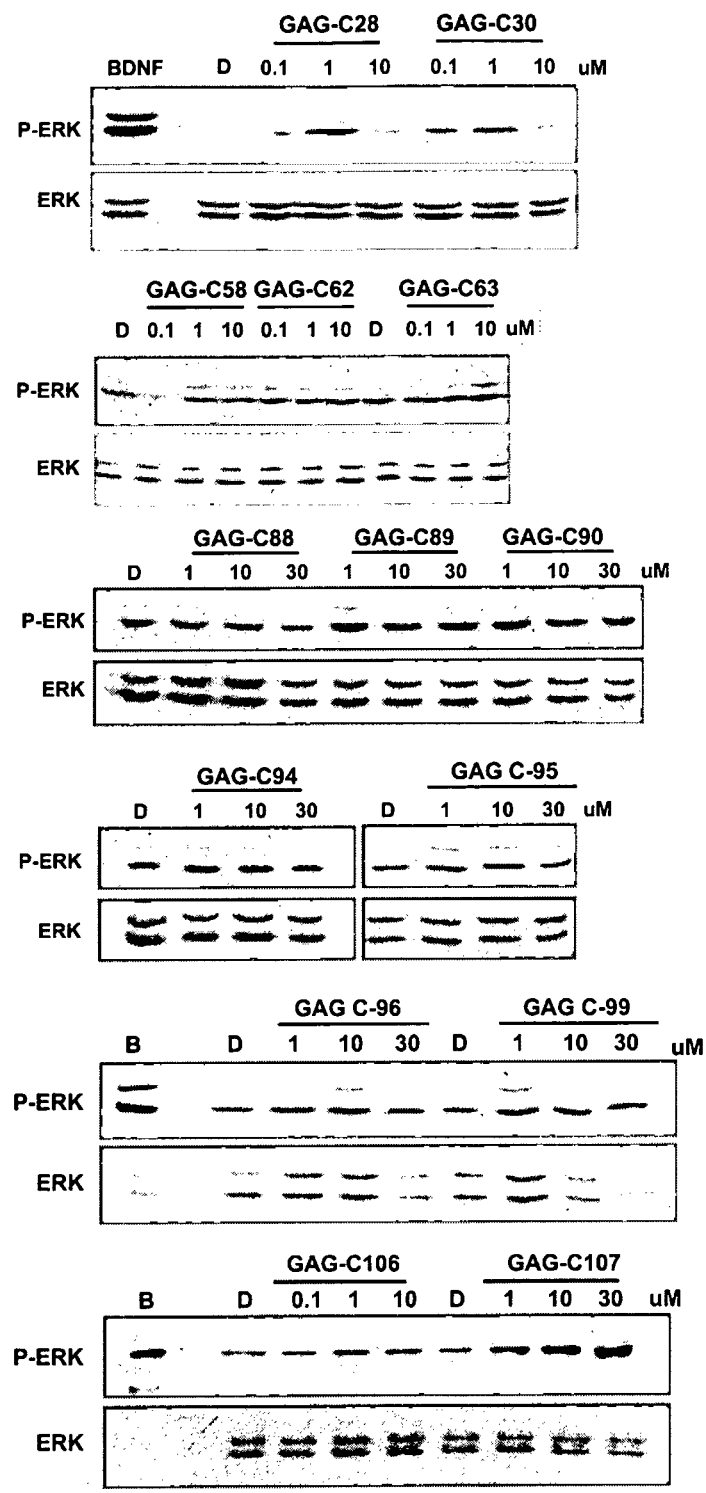
FIG. 39. Novel compounds isolated from *Adelostemma gracillimum* refined fraction induce phosphorylation of ERK in embryonic rat cortical neurons. Cortical neurons (7DIV) were incubated with various compounds isolated from AG-0 for 15 min. Total protein was collected and the expression of phosphorylated-ERK was analyzed by Western blot analysis. Protein loading was indicated by total ERK expression. BDNF (50 ng/mL) was used as a positive control. "D" denotes lysates treated with DMSO for 15 min.

Novel Compounds from *Adelostemma gracillimum* Refined Fraction Induce ERK Phosphorylation in Primary Cortical Neurons The effect of the compounds isolated from *Adelostemma gracillimum* refined fraction on ERK phosphorylation was examined in cortical neurons of 7DIV using Western blot analysis. Various concentrations of the compounds were applied to the cultures and ERK phosphorylation was examined in cortical neurons after treatment for 15 min. As indicated in FIG. 39, ERK phosphorylation was stimulated upon treatment with these compounds, albeit to different extents. The optimal dosages of each compound also varied.

Example 40

*Adelostemma gracillimum* Refined Fraction Shows Anti-Convulsant Effects in Frings Mice To determine the effect of the *Adelostemma gracillimum* refined fraction (AG-0) on the animal epileptic model, the audiogenic seizure susceptibility of Frings mice were evaluated following intraperitoneal administration of AG-0. Frings mice are susceptible to audiogenic seizure and their seizure phenotypes include wild running, loss of righting reflex, tonic flexion, and tonic extension in response to high-intensity sound stimulation. Test subjects that did not show hindlimb tonic extension after the sound stimulus were considered as protected.

To determine the time of peak effect of AG-0 in Frings mice against audiogenic seizure, seizure was induced at various time intervals after AG-0 treatment. As shown in Table 10, the effect of AG-0 peaked for administration 4 hours prior to audiogenic seizure. Intraperitoneal injection of AG-0 (50 mg/kg) to Frings mice 4 hours prior to inducing the seizure resulted in a protective effect on 50% of the test subjects.

TABLE 10

Time effect of AG-0 against audio seizure susceptibility of Frings mice following i.p. injection

| | | AG-0 administration prior to audiogenic stimuli (hours) | | | | |
|---|---|---|---|---|---|---|
| Test Subjects | Dose | 0.5 | 1 | 2 | 4 | 6 |
| # Protected/# Tested | 50 mg/kg | 1/4 | 1/4 | 1/4 | 2/4 | 0/4 |
| # Toxic/# Tested | 50 mg/kg | 0/8 | 0/8 | 0/8 | 0/8 | 0/4 |

Further quantitative data on the anti-convulsant effects of AG-0 was obtained by treating Frings mice with various concentrations of AG-0, Scoring of mice was conducted 4 hours after treatment. As shown in Table 11, administration of AG-0 at 100 mg/kg and 150 mg/kg exhibited protective effect on 63% and 100% of the test subjects, respectively.

TABLE 11

Dose effect of AG-0 on audiogenic seizure susceptibility of Frings mice following i.p. injection

| Dose (mg/kg) | Seizure score ± SEM | # Protected/# Tested at 4 hr | $ED_{50}$ (mg/kg) |
| --- | --- | --- | --- |
| 25 | 4.5 ± 0.5 | 1/8 | 62.35 (38.29-91.40)[a] |
| 50 | 3.5 ± 0.73 | 3/8 | |
| 100 | 2.38 ± 0.78 | 5/8 | |
| 150 | 0 ± 0 | 8/8 | |

[a]indicates 95% confidence interval.

Example 41

Characterization of AG-3 as Containing GAG-C77, GAG-C13, GAG-C14, and GAG-C69

Figure 40:
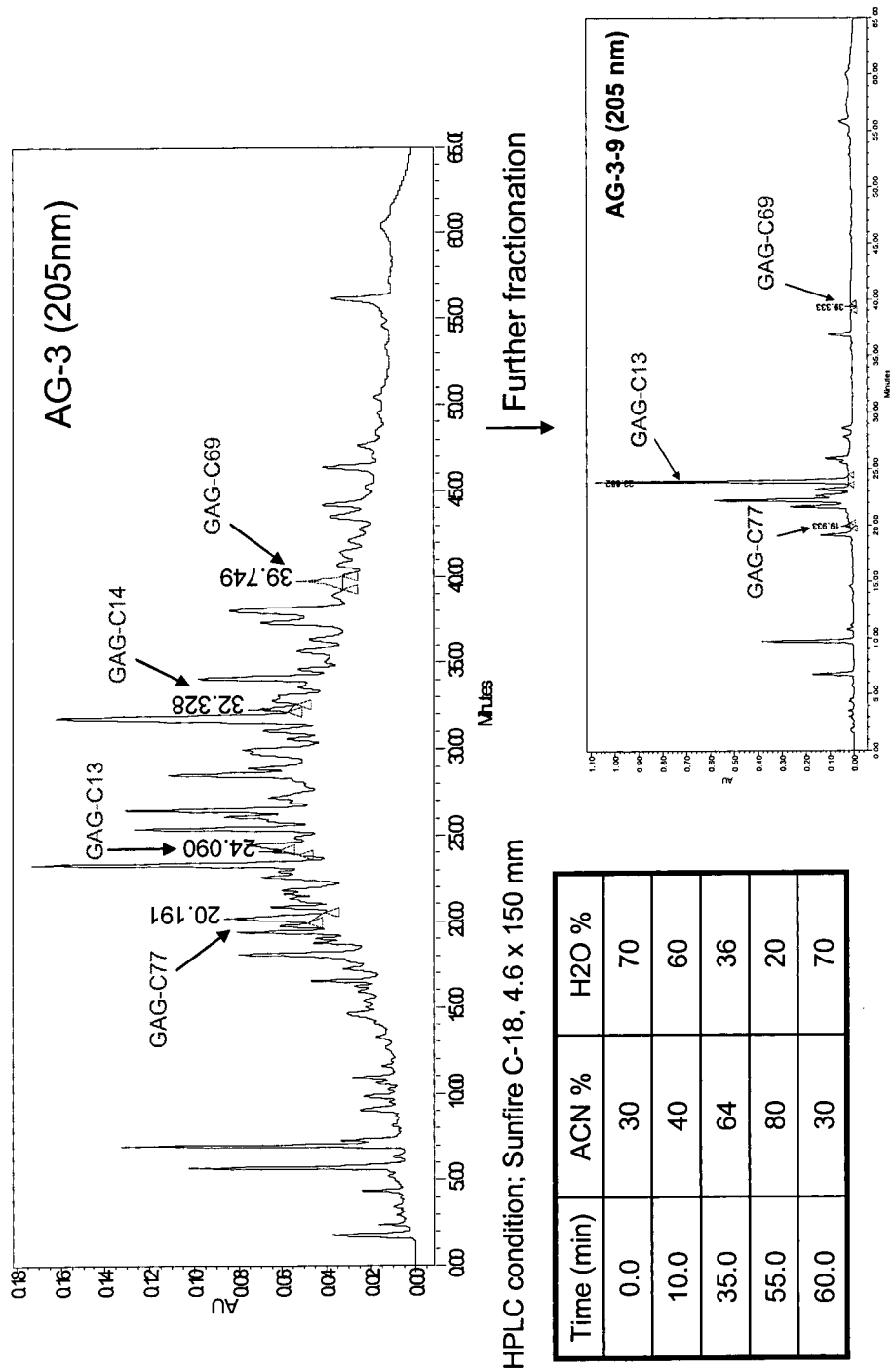
FIG. 40. Characterization of AG-3 as containing GAG-C77, GAG-C13, GAG-C14, and GAG-C69. AG-3 was fractionalized by column chromatography on a silica gel eluted with a mixture of petroleum ether/ethyl acetate stepwise from 90/10 to 50/50, followed by a mixture of chloroform/methanol from 100/1 to 70/30. Based on the TLC analysis, a total of 26 fractions were obtained. These fractions were further analyzed by HPLC (upper panel). Elution with 80/20 of petroleum ether/ethyl acetate resulted in fraction AG-3-9. Further, the retention time of the HPLC chromatogram and UV spectrum of individual peaks showed that fraction AG-3-9 contains compounds GAG-C13, GAG-C77 and GAG-C69 with GAG-C13 as the major components (lower right panel).

AG-3 was fractionalized by column chromatography on a silica gel eluted with a mixture of petroleum ether/ethyl acetate stepwise from 90/10 to 50/50, followed by a mixture of chloroform/methanol from 100/1 to 70/30. As shown in FIG. 40, based on the TLC analysis, a total of 26 fractions were obtained. These fractions were further analyzed by HPLC. Elution with 80/20 of petroleum ether/ethyl acetate resulted in fraction AG-3-9. Further, the retention time of the HPLC chromatogram and UV spectrum of individual peaks showed that fraction AG-3-9 contains compounds GAG-C13, GAG-C77 and GAG-C69 with GAG-C13 as the major components.

Example 42

GAG Compounds Enhance CRE-Dependent Transcription Activity

Long-term memory storage involves long-lasting changes in synaptic strength. This modification of synaptic strength requires the synthesis of de novo proteins. The cAMP-response element binding protein (CREB) is a transcription factor that plays an important role in regulating the expression of proteins involved in synaptic plasticity and memory formation. CREB conveys the neural signals from the membrane to the nucleus to regulate gene transcription through binding of genes that contain the cAMP-responsive element (CRE) domain at the promoter region. As CREB is necessary for memory formation, the CREB pathway is one of the targets for searching for cognitive enhancers. The CRE promoter assay is a functional readout to study the activation of the CREB pathway.

Figure 41:
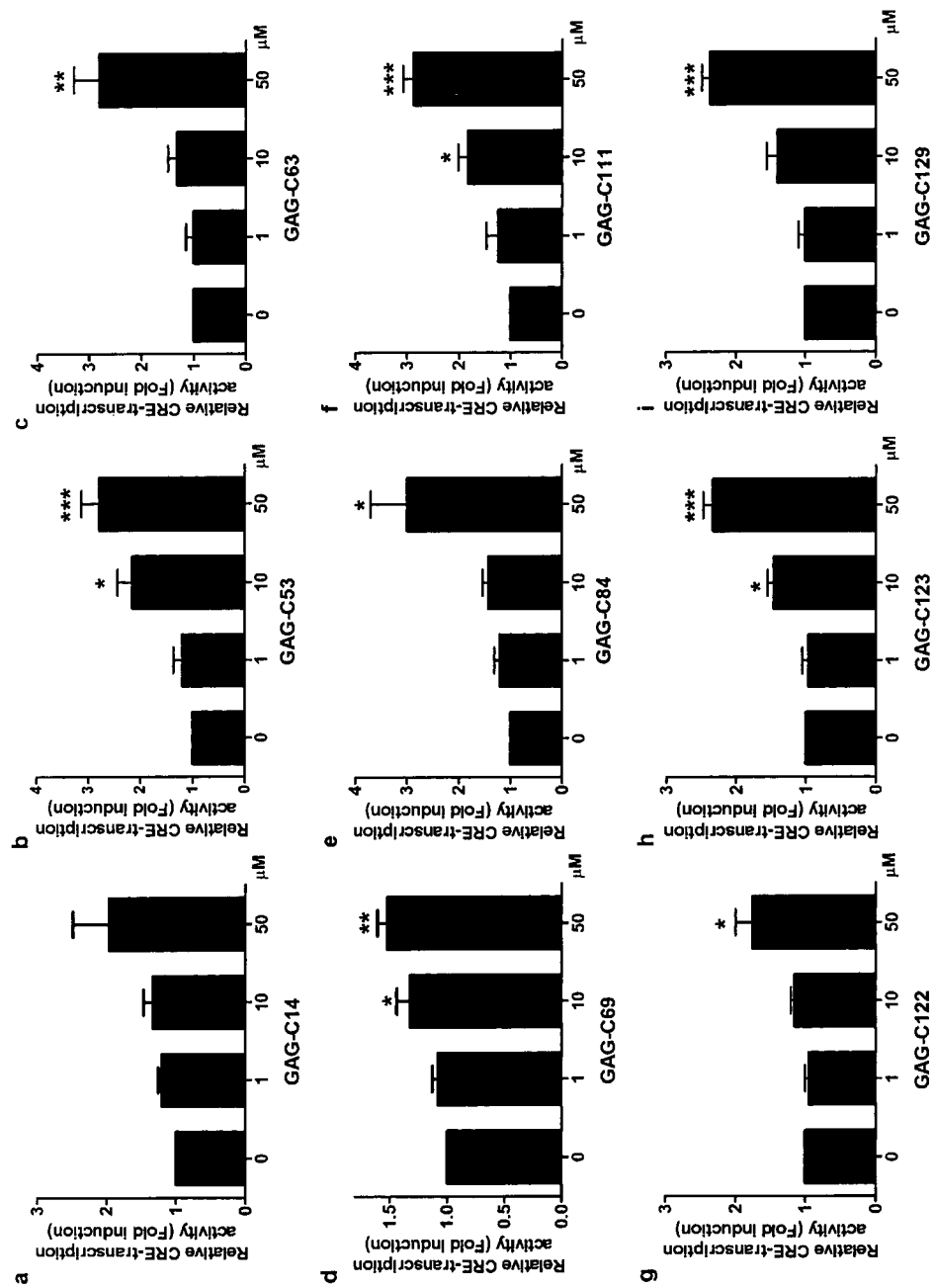
FIG. 41. GAG compounds enhance CRE-dependent transcription activity. GAG-C14 (a), GAG-C53 (b), GAG-C63 (c), GAG-C69 (d), GAG-C84 (e), GAG-C111 (f), GAG-C122 (g), GAG-C123 (h), and GAG-C129 (i) induce CRE-dependent transcriptional activity in cultured hippocampal neurons. On the day of cell seeding, hippocampal neurons were transfected with a firefly luciferase reporter plasmid containing cyclic AMP response (CRE)-element. The cells at 12 DIV were then treated with 50 µM of AG compounds for 6 hours. Data are mean±SEM (n=3-4), *=P<0.05, =P<0.01, and *=P<0.005 versus vehicle-treated cells (0 µM), student's t test.

Cultured hippocampal neurons were transfected with a firefly luciferase reporter plasmid containing a cyclic AMP response (CRE) element. At 12DIV, the cells were treated with 50 µM of compound for 6 hours, then CRE-dependent transcription activity was assayed by measuring luciferase levels. As shown in FIG. 41, each of the GAG compounds GAG-C14, GAG-C53, GAG-C63, GAG-C69, GAG-C84, GAG-C111, GAG-C122, GAG-C123, and GAG-C129 enhances CRE-dependent transcription in hippocampal neurons.

Example 43

Preparation of Compounds

Preparation of Compounds of the Present Invention.

The root of *Adelostemma gracillimum* Hook f. (Asclepiadaceae) was collected in July 1997 in Zhongdian of northwest Yunnan province, People's Republic of China, and identified by Prof. Mu, Quan-zhang, Kunming Institute of Botany, Chinese Academy of Science.

The root of *Adelostemma gracillimum* was washed, dried and pulverized. It was then immersed in ethanol (or methanol) at w/v 1:5 for 30 min, and refluxed for 1.5 hr 3 times or for 2 hr 2 times. The ethanol extract was suspended in water and partitioned using chloroform (or dichloromethane or ethylacetate) at v/v 1:1 3 times. These crude chloroform fractions were then combined and dried by evaporation. The combined chloroform fraction was then refined by reflux with petroleum ether (PE, 60-80° C.) at w/v 1:10 for 1 h. The PE-insoluble substances were collected and dried and were found to contain mainly the total glycosides of the herb. The refined chloroform fraction was re-dissolved in 70% ethanol at w/v 1:10, passed through filter paper (3M) and allowed to dry in a rotary evaporator. The refined chloroform fraction was then dissolved in 100% dimethylsulfoxide and subjected to different in vitro and in vivo bioactivity assays. The refined chloroform fraction is abbreviated herein as "AG-0."

The refined chloroform fraction of *Adelostemma gracillimum* (AG-0~200 g) was subjected to micropore resin column (D-101) chromatography. The column was washed by water (discarded) and then eluted consecutively with 30% ethanol (EtOH)/$H_2O$ (AG-1), 60% EtOH/$H_2O$ (AG-2), and 96% EtOH/$H_2O$ (AG-3) to yield first, second, and third fractions AG1-AG3. These three fractions AG1-AG3 were dried into 6 g (AG-1), 28 g (AG-2), and 170 g (AG-3). Compound GAG-C02 and GAG-C23 were isolated from fraction AG-1 and the rest of the compounds were isolated from fraction AG-3.

The fraction AG-3 was chromatographed on a silica gel column eluted with a stepwise gradient of petroleum ether/ethylacetate and chloroform/methanol to obtain 26 fractions. The additional sub-fractions obtained from AG-3 were subjected to next step separation procedure as follows: (1) silica gel column chromatography, (2) silica gel column chromatography and Sephadex LH-20 column chromatography (3) silica gel column chromatography and Sephadex LH-20 column chromatography and final semi-prep and/or prep-HPLC, (4) silica gel column chromatography and ODS column chromatography, (5) silica gel column chromatography and ODS column chromatography and final semi-prep and/or prep-HPLC, (6) silica gel column chromatography and semi-prep and/or prep-HPLC. The pure compounds can be obtained by applying one of the above isolation procedures. For some compounds like GAG-C27 and GAG-C28, extra step purification by prep-HPLC separation was needed to obtain the pure compound.

Analysis of compounds of the present invention. Optical rotation was measured with PERKIN-ELMER 241 polarimeter in MeOH at room temperature. UV was recorded at 2996 PDA detector of Waters HPLC system. $^1H$, $^{13}C$ and 2D NMR spectra was recorded on Varian Mercury 300 MHz NMR spectrometer. Compounds were dissolved in $CD_3OD$ or $CDCl_3$ (3-10 mg/ml) and all spectra were acquired at room temperature 22° C. Chemical shifts were reported as ppm using the solvent peak as a reference ($^1H$ 3.31 ppm and $^{13}C$ 49.05 ppm for $CD_3OD$, $^1H$ 7.19 ppm, $^{13}C$ 77.0 ppm for $CDCl_3$). HR-MS spectra were measured with three different ion sources, ESI, MALDI and CI according to the samples properties. For ESI HR-MS, QSTAR XL™ by Applied Biosystem equipped with turbo-ion spray source was used, $N_2$ as curtain gas, $MeCH_3/H_2O$ (1:1) mixed with 0.1% formic acid as solvent. Both positive and negative mode were used for acquiring mass spectra as represented by $[M+H]^+/[M+Na]^+$ or $[M-H]^-$ at room temperature. MALDI-TOF spectra were acquired by MALDI micro MX™ (Waters micromas) using CHCA as matrix. GCT Premier by Waters micromass was used for CI spectra using $CH_4$ as carrier gas at pressure $1.5\times 10^{-4}$ tort Finnigan MAT LCQ was used for acquiring ESI-MS spectra at Sheath gas 60 psi, auxiliary gas 20 psi, spray voltage 4.5 kV and capillary voltage 30V.

Column chromatography was performed with macropore resin D101 (Tianjin Le Tai Chemical Ltd., China) silica gel (40-63 μm, Merck, Darmstadt, Germany), Sephadex LH-20 (40-70 μm, Amersham Pharmacia Biotech AB, Uppsala, Sweden) and LiChroprep RP-C18 gel (40-63 μm, Merck, Darmstadt, Germany). Preparative Reversed-phase HPLC was carried out on a Waters 2545 Binary Gradient Module pump system equipped with 2996 photodiode Array Detector using X-bridge ODS column (19×150 mm i.d., 5 μm Waters) and Nova-Pak C-18 column (19×300 mm i.d., 6 μm, Waters). Semi-prep HPLC was carried out by the same Waters system with Nova-Pak C-18 column (7.8×300 mm, i.d., Waters).

Compound GAG-C13 was obtained as light yellow oil and optical rotation was $[\alpha]_D$+1.5 (C=0.4, MeOH). UV absorption was at $\lambda_{max}$ ($CH_3CN$): 259 nm. The molecular formula of GAG-C13 was found to be $C_{19}H_{22}O_5$, based on a molecular ion at m/z $[M+Na]^+$ 353.1380 and $[M+H-H_2O]^+$ 313.1190 in positive HR MALDI-MS. GAG-C13 was identified by NMR and MS to be 3,4,7-trihydroxyl-3'-methoxy-(7'E)-(8-O-4')-neolignan-7'-en according to IUPAC nomenclature.

$^1$H-NMR (300 MHz, $CD_3OD$, ppm) [delta]: 6.98 (1H, d, 1.8, H-2), 6.73 (1H, d, 8.1, H-5), 6.81 (1H, d, 1.8, H-6), 6.84, 6.85 (2H, d, 1.2, 6.6, H-2'5'), 6.70 (1H, dd, 2.1, 8.1, H-6'), 6.26 (1H, dd, 1.5, 15.6, H-7'), 6.07 (1H, m, H-8'), 4.61 (1H, d, 6.6, H-7), 4.24 (1H, m, H-8), 3.83 (3 H, s, $OCH_3$-3'), 1.14 (3 H, d, 6.2, $CH_3$-9), 1.82 (3H, d, 6.6, $CH_3$-9'). $^{13}$C-NMR (75 MHz, $CD_3OD$, ppm) [delta]: 149.1 (C-3), 148.8 (C-3'), 146.3 (C-4) 147.2 (C-4'), 133.9 (C-1), 134.2 (C-1'), 120.9 (C-6), 118.0 (C-6'), 115.8 (C-5), 118.5 (C-5'), 111.4 (C-2), 113.9 (C-2'), 131.7 (C-7'), 124.5 (C-8'), 78.5 (C-7), 82.5 (C-8), 17.2 (C-9), 18.5 (C-9'), 56.3 ($OCH_3$-3').

Compound GAG-C51 was obtained as viscous oil and optical rotation was $[\alpha]_D$+2.3 (C=0.94, MeOH). UV absorption was at $\lambda_{max}$ ($CH_3CN$): 346 and 231 nm. The molecular formula of GAG-C51 was found to be $C_{18}H_{18}O_5$, based on a molecular ion at m/z
$[M+H]^+$315.1241 in positive HR ESI-MS. The structure of GAG-C51 was identified by NMR and MS to be 3-methoxyl-4,4'-dihydroxy-1''-athanone-3'7-epoxy-8,2''-neolignane according to IUPAC nomenclature.

$^1$H-NMR (300 MHz, $CD_3OD$, ppm) [delta]:]: 6.86 (1H, H-2), 6.74 (2H, H-5,6), 6.84 (1H, d, 8.7, H-5'), 6.70 (1H, d, 8.7, H-6'), 2.59 (3H, $CH_3$-8'), 5.14 (1H, d, 4.5, H-7), 3.69 (1H, H-8), 3.79 (3H, s, $OCH_3$-3), 1.30 (3 H, d, 6.9, $CH_3$-9). $^{13}$C-NMR (75 MHz, $CD_3OD$, ppm) [delta]: 147.3 (C-3), 149.0 (C-4), 153.6 (C-3'), 153.4 (C-4'), 134.5 (C-1), 119.3 (C-6), 116.0 (C-5), 110.1 (C-2), 120.8 (C-1'), 132.4 (C-2'), 117.4 (C-6'), 115.0 (C-5'), 204.8 (C-7'), 32.1 (C-8'), 92.6 (C-7), 47.3 (C-8), 20.7 (C-9), 56.4 ($OCH_3$-3).

Compound GAG-C58 was obtained as viscous oil and optical rotation was $[\alpha]_D$+24.6 (C=0.38, MeOH). LTV absorption was at $\lambda_{max}$ ($CH_3CN$): 258 nm. The molecular formula of GAG-C58 was found to be, $C_{20}H_{24}O_6$, based on a molecular ion at m/z $[M+Na]^+$ 383.1478 and $[M+H-H_2O]^+$ 343.1551 in positive HR ESI-MS. GAG-C58 was identified by NMR and MS to be 3,3'-dimethoxy-4,5,7-trihydroxyl-(7'E)-(8-O-4')-neolignan-7' en according to IUPAC nomenclature.

$^1$H-NMR (300 MHz, $CD_3OD$, ppm) [delta]: 6.84 (1H, d, 1.8, H-2), 6.72 (1H, d, 1.8, H-6), 6.70 (1H, d, 1.8, H-2'), 6.83 (1H, d, 8.4, H-5'), 6.69 (1H, dd, 1.8, 8.4, H-6'), 6.27 (1H, dd, 1.2, 15.6, H-7'), 6.09 (1H, m, H-8'), 4.62 (1H, d, 6.3, H-7), 4.28 (1H, m, H-8), 3.82 (6H, s, $OCH_3$-3,3'), 1.17 (3H, d, 6.3, $CH_3$-9), 1.82 (3H, dd, 1.2, 6.6, $CH_3$-9'). $^{13}$C-NMR (75 MHz, $CD_3OD$, ppm) [delta]: 149.0 (C-3), 149.1 (C-3', C-5) 146.2 (C-4'), 133.2 (C-1), 134.2 (C-1'), 136.2 (C-4), 118.6 (C-6'), 117.8 (C-5'), 113.9 (C-2'), 105.6 (C-2), 105.7 (C-6), 131.8 (C-7'), 124.5 (C-8'), 78.6 (C-7), 82.2 (C-8), 17.2 (C-9), 18.6 (C-9'), 56.8 ($OCH_3$-3,3').

Compound GAG-C59 was obtained as viscous oil and optical rotation was $[\alpha]_D$−5.3 (C=0.34, MeOH). UV absorption was at $\lambda_{max}$ ($CH_3CN$): 260 nm. The ESI-MS spectra showed a molecular ion at m/z $[M+Na]^+$ 413.11 for positive mode and $[M-H]^-$ 389.07 for negative mode. However, HR MALDI-MS spectrum gave the most abundant ion at m/z 373.1660, which corresponded to $[M+H-H_2O]^+$. The molecular ions of $[M+H]^+$391.1743 and $[M+Na]^+$413.1576 were also observed but with intensity of 25% and 30%, respectively. Thus the molecular formula of GAG-C59 was deduced to be $C_{21}H_{26}O_7$ based on the above information. The structure of GAG-C59 was identified by NMR and MS to be 4,5',7-trihydroxyl-3, 3',5-trimethyoxyl-hydroxy-(7'E)-(8-O-4)-neolignan-7' en according to IUPAC nomenclature.

$^1$H-NMR (300 MHz, $CD_3OD$, ppm) [delta]: 6.67 (2H, s, H-2,6), 6.50 (1H, dd, 2.0, 6.5, H-2'), 6.51 (1H, dd, 2.0, 6.5, H-6'), 6.27 (1H, dd, 1.5, 15.5, H-7'), 6.16 (1H, m, H-8'), 4.58 (1H, d, 6.3, H-7), 3.98 (1H, m, H-8), 3.80 (3H, s, $OCH_3$-5), 3.83 (6H, s $OCH_3$-3,3'), 1.13 (3H, d, 6.3, $CH_3$-9), 1.84 (3H, dd, 1.5, 6.5, $CH_3$-9'). $^{13}$C-NMR (75 MHz, $CD_3OD$, ppm) [delta]: 152.1 (C-5'), 154.7 (C-3'), 149.2 (C-3, 5), 133.2 (C-1), 135.8 (C-5), 135.9 (C-4'), 132.3 (C-1'), 105.5 (C-2,6), 102.6 (C-2'), 107.9 (C-6'), 132.2 (C-7'), 125.6 (C-8'), 79.9 (C-7), 86.7 (C-8), 17.9 (C-9), 18.5 (C-9'), 56.3 ($OCH_3$-5), 56.8 ($OCH_3$-3,3').

Compound GAG-C69 was obtained as light yellow oil and optical rotation was $[\alpha]_D$−12.7 (C=0.3, MeOH); UV absorption was at $\lambda_{max}$ ($CH_3CN$): 261 nm. The molecular formula of GAG-C69 was found to be, $C_{19}H_{20}O_4$, based on a molecular ion at m/z $[M+H]^+$313.1408 in positive HR MALDI-MS. GAG-C69 was identified by NMR and MS to be 3-methoxyl-4-hydroxyl-(7'-E)-5'7-epoxy-8,4'-oxyneolignane-7' en according to IUPAC nomenclature.

$^1$H-NMR (300 MHz, $CD_3OD$, ppm) [delta]: 6.96 (1H, d, 1.5, H-2), 6.87 (1H, d, 1.8, H-6'), 6.82 (1H, d, 1.8, H-2'), 6.83 (1H, H-3'), 6.76 (1H, d, 8.4, H-5), 6.84 (1H, m, H-6), 6.28 (1H, dd, 1.5, 15.9, H-7'), 6.10 (1H, m, H-8'), 4.54 (1H, d, 8.1, H-7), 4.11 (1H, dd, 6.6, 8.1, H-8), 3.87 (3H, s, $OCH_3$-3), 1.13 (3H, d, 6.3, $CH_3$-9), 1.82 (3H, dd, 1.5, 6.3, $CH_3$-9'). $^{13}$C-NMR (75 MHz, $CD_3OD$, ppm) [delta]: 148.3 (C-4), 149.2 (C-3), 145.5 (C-4'), 144.0 (C-5'), 133.0 (C-1), 130.1 (C-1'), 111.9 (C-2), 117.7 (C-5), 121.8 (C-6), 116.2 (C-3'), 120.2 (C-2'), 114.9 (C-6'), 131.8 (C-7'), 124.4 (C-8'), 82.3 (C-7), 75.5 (C-8), 17.6 (C-9), 18.5 (C-9'), 56.5 ($OCH_3$-3).

Compound GAG-C76 was obtained as light yellow oil and optical rotation was $[\alpha]_D$+14.6 (C=0.82, MeOH); UV absorption was at $\lambda_{max}$ ($CH_3CN$) was 220 and 278 nm. The molecular formula of GAG-C76 was found to be $C_{22}H_{26}O_6$ based on a molecular ion at m/z $[M+Na]^+$ 409.1627, in positive HR MALDI-MS. The HRMS spectrum revealed the ion peaks at m/z 357.1358 $[M+Na-29]^+$ and 341.1415 $[M+Na-45]^+$, corresponding to fragments lost of ethyl group (—$CH_2CH_3$) and ethoxyl group (—$OCH_2CH_3$) from parent molecular, respectively. Thus, the structure of GAG-C76 was identified by NMR and MS to be the 4,9-dihydroxy-9'-ethoxyl-3,5'-dimethoxy-(7'E)-4'7-epoxy-8,3'-neolignane-7'-en according to IUPAC nomenclature.

$^1$H-NMR (300 MHz, $CD_3OD$, ppm) [delta]: 6.94 (1H, d, 1.5, H-2), 6.77 (1H, d, 8.1, H-5), 6.82 (1H, dd, 1.5, 8.1, H-6), 6.96 (1H, d, 1.8, H-2'), 6.93 (1H, d, 1.8, H-6'), 6.54 (1H, d, 15.9, H-7'), 6.17 (1H, dtt, 15.9, 6.0, 6.3, H-8'), 5.51 (1H, d, 6.3, H-7), 3.49 (1H, m, H-8), 3.75, 3.82 (2H, m, H-9), 4.08 (2H, dd, 1.5, 6.3, H-9'), 3.79, 3.85 (6H, s, OCH$_3$-3,3'), 3.54 (2H, q, 6.9, OCH$_2$—), 1.20 (3H, t, 6.9, CH$_3$-9). $^{13}$C-NMR (75 MHz, CD$_3$OD, ppm) [delta]: 149.1 (C-3), 149.3 (C-4'), 147.5 (C-4), 145.4 (C-5'), 130.4 (C-3'), 134.4 (C-1), 134.1 (C-1'), 119.8 (C-6), 116.2 (C-2'), 116.6 (C-5), 110.5 (C-2), 112.1 (C-6'), 132.3 (C-7'), 124.6 (C-8'), 89.3 (C-7), 55.1 (C-8), 64.8 (C-9), 72.4 (C-9'), 66.4 (OCH$_2$—), 15.5 (—CH$_3$), 56.7, 56.4 (OCH$_3$-3,3').

Compound GAG-C78 was obtained as light yellow gum and optical rotation was [α]$_D$+5.8 (C=0.2, MeOH). UV absorption was at λ$_{max}$ (CH$_3$CN): 267 nm. The molecular formula of GAG-C78 was determined as C$_{17}$H$_{30}$O$_5$, based on HR ESI-MS peak at m/z 315.2147 ([M+H]$^+$, calc. 314.2093). The structure of GAG-C78 was identified by NMR and MS to be (K)-methyl 15-hydroxy-15-methoxy-12-oxopentadec-13-enoate according to IUPAC nomenclature.

$^1$H-NMR (300 MHz, CD$_3$OD, ppm) [delta]: 2.32 (2H, m, H-2), 1.60 (4H, m, H-3, H-10), 1.29 (12H, m, H-4 to H-9), 2.65 (2H, t, H-11), 6.34 (1H, d, H-13), 6.62 (1H, dd, H-14), 4.97 (1H, d, H-15), 3.34 (3H, s, OCH$_3$-15), 3.65 (3H, s, OCH$_3$-1). $^{13}$C-NMR (75 MHz, CD$_3$OD, ppm) [delta]: 175.9 (C-1), 34.8 (C-2), 26.0 (C-3), 30.1 (C-4 to C-9), 25.1 (C-10), 41.3 (C-11), 202.7 (C-12), 132.5 (C-13), 141.7 (C-14), 102.6 (C-15), 53.6 (OCH$_3$-15), 52.0 (OCH$_3$-1).

Compound GAG-C80 was obtained as light yellow gum and optical rotation was [α]$_D$+11.1 (C=0.1, MeOH). UV absorption was at λ$_{max}$ (CH$_3$CN): 236 and 186 nm. The molecular formula of GAG-C80 was determined as C$_{18}$H$_{22}$O$_4$, based on HR ESI-MS peak at m/z 325.1441 ([M+Na]$^+$, calc. 302.1518). GAG-C80 was identified by NMR and MS to be the 2-(2-methoxy-5-methylphenyl)-1-(3-methoxy-5-methylphenyl)-ethane-1,2-diol according to IUPAC nomenclature.

$^1$H-NMR (300 MHz, CD$_3$OD, ppm) [delta]: 2.09 (3H, s, H-7'), 2.40 (3H, s, H-7"), 4.08 (1H, d, H-1), 3.81 (1H, d, H-2), 3.66 (3H, s, H-8'), 3.85 (3H, s, H-8"), 6.65 (1H, d, H-3'), 6.94 (1H, d, H-4'), 7.38 (1H, H-6'), 7.03 (1H, s, H-2"), 6.64 (1H, H-4"), 6.76 (1H, d, H-6"). $^{13}$C-NMR (75 MHz, CD$_3$OD, ppm) [delta]: 70.9 (C-1), 79.4 (C-2), 128.9 (C-1'), 148.8 (C-2'), 106.5 (C-3'), 116.6 (C-4'), 134.2 (C-5'), 126.8 (C-6'), 131.5 (C-1"), 110.4 (C-2"), 148.6 (C-3"), 124.3 (C-4"), 138.5 (C-5"), 115.1 (C-6"), 56.7 (OCH$_3$-8"), 55.9 (OCH$_3$-8'), 21.2 (C-7"), 17.9 (C-7').

Compound GAG-C61 was obtained as light yellow gum and optical rotation was [α]$_D$+7.9 (C=0.1, MeOH). UV absorption was at λ$_{max}$ (CH$_3$CN): 269 nm. The molecular formula of GAG-C61 was determined as C$_{28}$H$_{28}$O$_8$, based on HR MALDI-MS peak at m/z 493.1872 ([M+H]$^+$, calc. 492.1784). The structure of GAG-C61 was identified by NMR and MS to be 4-hydroxy-3'-methoxy-(7'E)-5'7-epoxy-8,4'-oxyneolignane-7' en according to IUPAC nomenclature.

$^1$H-NMR (400 MHz, CD$_3$OD, ppm) [delta]: 6.94 (1H, H-2), 6.79 (1H, H-5), 6.50 (1H, d, H-3'), 7.74 (1H, d, H-4'), 6.77 (1H, H-2"), 6.69, 6.73 (2H, H-5", 6"), 3.32 (1H, H-7), 2.42 (1H, H-8), 2.80, 2.87 (2H, H-9), 2.84 (1H, H-7'), 2.75, (1H, H-8'), 3.96, 4.13 (2H, H-9'), 2.71 (3H, s, CH$_3$), 3.78, 3.84 (6H, s, OCH$_3$-3, 3"). $^{13}$C-NMR (100 MHz, CD$_3$OD, ppm) [delta]: 129.8 (C-1), 109.6 (C-2), 149.3 (C-3), 148.7 (C-4), 116.8 (C-5), 133.0 (C-6), 113.6 (C-1'), 162.1 (C-2'), 115.2 (C-3'), 132.5 (C-4'), 108.5 (C-5'), 164.3 (C-6'), 132.8 (C-1"), 116.3 (C-2"), 149.6 (C-3"), 146.6 (C-4"), 122.7 (C-5"), 120.1 (C-6"), 80.6 (C-7), 43.6 (C-8), 39.5 (C-9), 41.7 (C-7'), 55.3 (C-8'), 74.1 (C-9'), 205.3 (C=O), 27.6 (CH$_3$), 56.9, 56.8 (OCH$_3$-3, 3")

Compound GAG-C62 was obtained as white amorphous powder and optical rotation was [α]$_D$+49.1 (C=0.0.37, MeOH). UV absorption was at λ$_{max}$ (CH$_3$CN): 286 nm and 224 nm. The molecular formula of GAG-C62 was found to be the C$_{20}$H$_{24}$O$_3$, based on a molecular ion at m/z [M+H]$^+$ 313.1852 in positive HR ESI-MS. The structure of GAG-C62 was identified by mainly NMR and MS to be 4, 6,15-triene-16-carboxylic acid-3-oxo-androstane according to IUPAC nomenclature.

$^1$H-NMR (300 MHz, CD$_3$OD, ppm) [delta]: 5.66 (1 H, H-4), 6.21 (1 H, H-6), 6.27 (1 H, H-7), 6.77 (1 H, H-15), 1.72, 2.05 (2 H, H-1), 2.37, 2.62 (2 H, H-2), 1.33 (1 H, H-8), 2.49 (1 H, H-9), 1.43, 1.67 (2 H, H-11), 1.57, 2.33 (2 H, H-12), 1.64 (1 H, H-14), 2.24, 2.47 (2 H, H-17), 1.02 (3 H, s, CH$_3$-18), 1.18 (3 H, s, CH$_3$-19). $^{13}$C-NMR (75 MHz, CD$_3$OD, ppm) [delta]: 202.2 (C-3), 168.1 (C-20), 123.9 (C-4), 167.1 (C-5), 129.0 (C-6), 142.7 (C-7), 144.1 (C-15), 148.6 (C-16), 34.8 (C-1), 34.9 (C-2), 52.7 (C-8), 37.63 (C-9), 37.59 (C-10), 21.7 (C-11), 35.9 (C-12), 47.7 (C-13), 55.4 (C-14), 32.2 (C-17), 16.4 (C-18), 16.6 (C-19).

Compound GAG-C63 was obtained as white amorphous powder and optical rotation was [α]$_D$+50.5 (C=0.22, MeOH). UV absorption was at λ$_{max}$ (CH$_3$CN): 287 nm. The molecular formula of GAG-C63 was found to be the C$_{20}$H$_{26}$O$_3$, based on a molecular ion at m/z [M+H]$^+$ 315.1994 in positive HR ESI-MS. The structure of GAG-C63 was identified by mainly NMR and MS to be 4,6-diene-16-carboxylic acid-3-oxo-androstane according to IUPAC nomenclature.

$^1$H-NMR (300 MHz, CD$_3$OD, ppm) [delta]: 5.65 (1 H, H-4), 6.18 (1 H, H-6), 6.24 (1 H, H-7), 1.74, 2.07 (2 H, H-1), 2.38, 2.63 (2 H, H-2), 1.28 (1 H, H-8), 1.34 (1 H, H-9), 1.49, 1.64 (2 H, H-11), 1.35, 1.87 (2 H, H-12), 1.37 (1 H, H-14), 1.94, 2.13 (2 H, H-15), 2.42 (1H, H-16), 2.12, 2.28 (2 H, H-17), 0.82 (3H, s, CH$_3$-18), 1.16 (3 H, s, CH$_3$-19). $^{13}$C-NMR (75 MHz, CD$_3$OD, ppm) [delta]: 202.6 (C-3), 177.2 (C-20), 124.1 (C-4), 167.4 (C-5), 129.1 (C-6), 143.3 (C-7), 34.9 (C-1), 35.2 (C-2), 52.4 (C-8), 39.4 (C-9), 37.6 (C-10), 21.8 (C-11), 25.1 (C-12), 45.8 (C-13), 54.5 (C-14), 24.9 (C-15), 56.4 (C-16), 39.5 (C-17), 13.8 (C-18), 16.8 (C-19)

Compound GAG-C65 was obtained as crystal and optical rotation was [α]$_D$−94.3 (C=0.67, MeOH). UV absorption was at λ$_{max}$ (CH$_3$CN): 214 nm. The molecular formula of GAG-C65 was found to be C$_{15}$H$_{20}$O$_3$ based on a molecular ion at m/z [M+H]$^+$ 249.1537 in positive HR ESI-MS. The structure of GAG-C65 was identified by mainly NMR and MS to be 8-oxohumula-2, 6(E)-dien-1,12-olide according to IUPAC nomenclature.

$^1$H-NMR (300 MHz, CD$_3$OD, ppm):]: 4.73 (1H, H-1), 7.10 (1 H, H-2), 6.27 (1 H, H-6), 6.00 (1H, H-7), 2.72 (1 H, H-9), 1.73, 1.87 (2 H, H-4), 2.46, 1.82 (2 H, H-5), 1.78, 0.56 (2 H, H-10), 0.96 (3H, s, CH$_3$-13), 1.24 (3 H, s, CH$_3$-14), 1.38 (3 H, CH$_3$-15).

$^{13}$C-NMR (75 MHz, CD$_3$OD, ppm) [delta]: 88.1 (C-1), 148.5 (C-2), 135.4 (C-3), 144.6 (C-6), 133.3 (C-7), 204.7 (C-8), 174.5 (C-12), 42.27 (C-11), 46.6 (C-9), 29.8 (C-4), 26.1 (C-5), 21.3 (C-10), 12.5 (C-13), 22.2 (C-14), 24.8 (C-15).

Compound GAG-C73 was obtained as amorphous powder and optical rotation was [α]$_D$+21 (C=0.2, CHCl$_3$). UV absorption was at λ$_{max}$ (CH$_3$CN): 201 and 278 nm. The molecular formula of GAG-C73 was found to be C$_{30}$H$_{46}$O$_4$ based on a molecular ion at m/z [M−H]$^-$ 469.65 in negative ESI-MS. The structure of GAG-C73 was identified by NMR and MS to be 3,23-dihydroxyl-12(13)-en-Lup-20(29)-en-28-oic acid according to IUPAC nomenclature.

$^1$H-NMR (300 MHz, CDCl$_3$, ppm) [delta]: 1.88, 1.68 (2 H, H-1), 1.62, 1.25 (2 H, H-2), 3.65 (1 H, H-3), 0.89 (1 H, H-5), 1.37 (2 H, H-6), 1.49, 1.31 (2 H, H-7), 1.55 (1 H, H-9), 1.94 (2 H, H-11), 5.29 (1 H, H-12), 1.87, 1.15 (2 H, H-15), 2.20, 1.78 (2 H, H-16), 2.30 (1 H, H-18), 2.34 (1 H, H-19), 1.3 (2 H, H-21), 2.28, 2.23 (2 H, H-22), 3.43, 3.73 (2 H, H-23), 0.89 (3 H, s, $CH_3$-24), 0.80 (3 H, s, $CH_3$-25), 0.88 (3 H, s, $CH_3$-26), 1.14 (3 H, s, $CH_3$-27), 4.64, 4.70 (2 H, H-29), 0.99 (3 H, s, $CH_3$-30).

$^{13}$C-NMR (75 MHz, $CDCl_3$, ppm) [delta]: 38.3 (C-1), 26.8 (C-2), 77.1 (C-3), 42.1 (C-4), 49.8 (C-5), 18.4 (C-6), 32.6 (C-7), 39.4 (C-8), 47.6 (C-9), 36.9 (C-10), 23.5 (C-11), 126.1 (C-12), 137.6 (C-13), 38.8 (C-14), 27.8 (C-15), 24.3 (C-16), 50.9 (C-17), 54.6 (C-18), 37.3 (C-19), 152.6 (C-20), 22.7 (C-21), 32.6 (C-22), 72.2 (C-23), 11.4 (C-24), 17.1 (C-25), 15.8 (C-26), 123.3 (C-27), 174.3 (C-28), 104.9 (C-29), 16.1 (C-30).

The active neuroprotective compounds GAG-C27 and GAG-C28 were obtained as white amorphous powder. GAG-C27 had optical rotation $[\alpha]_D$–22.5 (C=0.41, MeOH) and UV absorbsion at $\lambda_{max}$ ($CH_3CN$): 276 and 220 nm. GAG-C28 had $[\alpha]_D$–18.2 (C=0.34, MeOH) and UV $\lambda_{max}$ ($CH_3CN$): 286 and 218 nm. The molecular formula of GAG-C27 and GAG-C28 were found to be the same as $C_{45}H_{62}O_{14}$, based on a molecular ion at m/z $[M+Na]^+$ 849.4635 in positive HR MALDI-MS. The structures of GAG-C27/-C28 were identified by mainly NMR and MS to be 3-O-β-D-Cymaropyranose-(1→4)-β-D-Digitoxopyranose-12-cis-cinnamyl-20-acetyl-8,14-seco-sacrostin and 3-O-β-D-Cymaropyranose-(1→4)-β-D-Digitoxopyranose-12-trans-cinnamyl-20-acetyl-8,14-seco-sacrostin respectively according to IUPAC nomenclature. The difference between the two compounds is Cis-cinnamic acid substituted at C-12 of aglycone for GAG-C27 and trans-cinnamic acid at C-12 for GAG-C28.

Comparison of proton and carbon signal from GAG-C27 and GAG-C28 with data given for the gracigenin moiety substituted with oligosaccharide at C-3 (Tripetch Kanchanapoom, etc., Chem. Pharm. Bull. 50 (8) 1031-1034, 2002) demonstrated that both GAG-C27 and GAG-C28 was gracigenin substituted at C-3 with disaccharide.

Two anomeric signals in NMR spectra corresponding to Cymarose and Digitoxose were observed in both GAG-C27/-C28. By performing the ESI-MS/MS analysis of GAG-C27, a partial and complete loss of saccharide chain was generated. The ions observed at m/z 557.12 and 701.23 corresponded to the ions of aglycone $[M–18+Na]^+$ and to the same species but still carrying one cymaropyranose unit $[M–18+Na]^+$, respectively. The sequence of the saccharide chain was then revered, which was the molecular ion at m/z 849.46 $[M+Na]^+$ loss of one Digitoxose (130 Da) and $H_2O$ (18 Da) and further loss of Cymanorose (144 Da) leading to ions at m/z 701.23 and at m/z 557.12 respectively. This was supported by NMR data obtained from different 1D and 2D spectra. The cross peak between 3.26 (H-3) and 97.2 (C-1 for Cym) observed from HMBC spectra showed the glycosidic linkage between the cymarose and C-3 of gracignin. The linkage of Digitoxose at 4 position of Cym was determined based on HMBC correlations between H-4 of Cym (δ 3.22) and C-1 of Dig (δ 102.2) and also between C-4 of Cym (δ 83.5) and anomeric proton of Dig (δ 4.65).

The anomeric configuration of cymaropyranoside and digitoxopyranoside was determined to be β form, based on the $^3J_{H-1,H-2}$ value of the anomeric proton at 9.5 Hz for both Cym and Dig. The absolute configuration was determined to be the same as those of previously reported which were D-Cymarose and D-Digitoxose. $^1H$ and $^{13}C$ NMR signals of compounds GAG-C27 and GAG-C28 are listed in Table 12.

TABLE 12

$^1H$ and $^{13}C$ NMR chemical shifts for compounds GAG-C27 and GAG-C28

| No. | GAG-C27 | | GAG-C28 | |
|---|---|---|---|---|
| | $^{13}C$ | $^1H$ | $^{13}C$ | $^1H$ |
| 1 | 41.82 | 2.53, 2.85 | 41.77 | 2.52, 2.85 |
| 2 | 30.25 | 1.89, 2.04 | 30.21 | 1.90, 2.04 |
| 3 | 73.27 | 3.26 | 73.15 | 3.24 |
| 4 | 43.98 | 1.93, 2.46 | 44.02 | 1.92, 2.47 |
| 5 | 142.54 | | 142.69 | |
| 6 | 119.37 | 5.35 | 118.87 | 5.41 |
| 7 | 30.02 | 2.24, 2.42 | 30.08 | 2.15(2H) |
| 8 | 211.38 | | 211.37 | |
| 9 | 56.73 | 2.29 | 56.77 | 2.31 |
| 10 | 37.30 | | 37.21 | |
| 11 | 26.60 | 1.39, 1.75 | 26.53 | 1.51, 1.80 |
| 12 | 76.80 | 5.14 | 76.80 | 5.24 |
| 13 | 62.88 | | 63.22 | |
| 14 | 219.65 | | 219.33 | |
| 15 | 38.22 | 1.89, 2.30 | 38.92 | 1.92, 2.47 |
| 16 | 34.90 | 2.36, 2.54 | 34.35 | 2.4, 2.55 |
| 17 | 82.99 | | 83.07 | |
| 18 | 12.32 | 1.17 | 11.91 | 1.21 |
| 19 | 19.19 | 0.71 | 19.63 | 0.76 |
| 20 | 75.21 | 4.74 | 75.06 | 4.77 |
| 21 | 14.46 | 1.24 | 14.33 | 1.24 |
| Cin | | | | |
| 1' | 167.54 | | 168.57 | |
| 2' | 120.58 | 5.91 | 119.35 | 6.44 |
| 3' | 144.89 | 7.07 | 146.74 | 7.62 |
| 4' | 136.20 | | 135.45 | |
| 5' | 129.0 | 7.35 | 129.25 | 7.36 |
| 6' | 130.61 | 7.36 | 130.0 | 7.41 |
| 7' | 130.72 | 7.55 | 131.62 | 7.62 |
| 8' | 130.09 | 7.36 | 129.96 | 7.62 |
| 9' | 129.33 | 7.35 | 129.35 | 7.66 |
| Ac., CO | 171.57 | | 171.42 | |
| $CH_3$ | 21.48 | 2.04 | 21.38 | 1.97 |
| β-D-Cyn | 97.16 | 4.92 | 96.95 | 4.91 |
| | 38.89 | 1.62, 1.93 | 38.84 | 1.62, 1.92 |
| | 78.03 | 2.98 | 76.82 | 2.99 |
| | 83.55 | 3.22 | 83.54 | 3.20 |
| | 69.38 | 3.83 | 69.4 | 3.83 |
| | 18.58 | 1.13 | 18.50 | 1.14 |
| 3'-$OCH_3$ | 57.45 | 3.41 | 57.43 | 3.42 |
| β-D-Dig | 102.21 | 4.65 | 102.07 | 4.62 |
| | 37.30 | 1.41, 2.29 | 37.21 | 1.39, 2.31 |
| | 68.30 | 4.19 | 68.38 | 4.21 |
| | 81.48 | 3.21 | 81.49 | 3.20 |
| | 69.46 | 3.5 | 69.40 | 3.45 |
| | 18.63 | 1.21 | 18.46 | 1.26 |

Compound GAG-C30 was obtained as amorphous white powder and optical rotation was $[\alpha]_D$+2.7 (C=0.2, MeOH). UV absorption was at $\lambda_{max}$ (CH3CN): 277 and 218 nm. The molecular formula of GAG-C30 was found to be $C_{38}H_{51}O_{11}$, based on a molecular ion at m/z $[M+Na]^+$ 705.4148 in positive HR MALDI-MS. GAG-C30 was identified by mainly NMR and MS to be 3-O-β-D-Cymaropyranose-(1→4)-β-D-Digitoxopyranose-12-trans-cinnamyl-20-acetyl-8,14-seco-sacrostin according to IUPAC nomenclature.

The $^1H$ NMR spectrum of GAG-C30 showed there is only one anomeric signal corresponding to Digitoxose (δ $^1H$, 4.93, $^{13}C$ 97.2 ppm). The anomeric configuration of digitoxose was determined to be β form, based on the $^3J_{H-1,H-2}$ value of the anomeric proton at 9.5 Hz. The Digitoxopyranoside was substituted at 3 position of aglycone, based on the HMBC correlations between H-3/C-3 of aglycone (δ 3.24/83.1) and C-1/H-1 of Dig (δ 97.2/4.93). ESI-MS/MS analysis of GAG-C30 generated the daughter ion at m/z 557.11$[M+Na]^+$ corresponding to loss of one Dig (130Da) and $H_2O$ (18 Da) from parent ion, which was confirmed the linkage position of Digitoxose.

$^1H$ and $^{13}C$ NMR signals of compound GAG-C30 are listed in Table 13.

TABLE 13

$^{1}$H and $^{13}$C NMR chemical shifts for compounds GAG-C30 GAG-C30

| No. | $^{13}$C | $^{1}$H | Cin | $^{13}$C | $^{1}$H |
|---|---|---|---|---|---|
| 1 | 41.77 | 2.52, 2.85 | 1' | 168.55 | |
| 2 | 30.21 | 1.90, 2.04 | 2' | 119.35 | 6.44 |
| 3 | 83.08 | 3.24 | 3' | 144.92 | 7.62 |
| 4 | 44.02 | 1.92, 2.47 | 4' | 135.43 | |
| 5 | 142.56 | | 5' | 129.25 | 7.36 |
| 6 | 118.87 | 5.41 | 6' | 130.0 | 7.41 |
| 7 | 30.08 | 2.15(2H) | 7' | 131.62 | 7.62 |
| 8 | 211.37 | | 8' | 129.96 | 7.62 |
| 9 | 56.77 | 2.31 | 9' | 129.35 | 7.66 |
| 10 | 37.21 | | Ac., CO | 171.42 | |
| 11 | 26.53 | 1.51, 1.80 | CH$_3$ | 21.38 | 1.97 |
| 12 | 75.29 | 5.24 | β-D-Dig | 97.19 | 4.93 |
| 13 | 63.22 | | | 37.21 | 1.39, 2.31 |
| 14 | 219.33 | | | 68.38 | 4.21 |
| 15 | 38.92 | 1.92, 2.47 | | 81.49 | 3.20 |
| 16 | 34.35 | 2.4, 2.55 | | 69.40 | 3.45 |
| 17 | 81.49 | | | 18.46 | 1.26 |
| 18 | 11.91 | 1.21 | | | |
| 19 | 19.63 | 0.76 | | | |
| 20 | 75.06 | 4.77 | | | |
| 21 | 14.33 | 1.24 | | | |

Compound GAG-C44 was obtained as white amorphous powder and optical rotation was [α]$_D$–20.1 (C=0.2, MeOH). UV absorption was at λ$_{max}$ (CH$_3$CN) 273 nm. The molecular formula of GAG-C44 was determined to be C$_{52}$H$_{74}$O$_{17}$, based on a molecular ion at m/z [M+Na]$^+$ 993.5052 in positive HR MALDI-MS (calculated as 970.4926). The structure of GAG-C44 was identified by different 1D and 2D NMR spectroscopies and HR-MS spectrometry to be 12-O-cis/trans-cinnamoyl-20-acetyl-8,14-seco-sarcostin 3-O-β-D-Cymaropyranosyl-(1→4)-β-D-Digitoxopyranosyl-(1→4)-β-D-Oleandropyranoside according to IUPAC nomenclature.

The $^1$H NMR spectrum of GAG-C44 showed there are 3 anomeric signals corresponding to Cymarose (δ $^1$H, 4.93, $^{13}$C 97.2 ppm), Digitoxose (δ $^1$H, 4.93, $^{13}$C 97.2 ppm) and Oleandrose (δ $^1$H, 4.93, $^{13}$C 97.2 ppm). The anomeric configurations of three monosaccharides were determined to be β form, based on the $^3J_{H-1,H-2}$ value of the anomeric proton at 9.5 Hz. The glycoside position and sequence of trisaccharides were established based on H—H and C—H correlations observed from 2D COSY, HSQC and HMBC spectra. $^1$H and $^{13}$C NMR signals of compound GAG-C44 are listed in Table 15 and Table 16.

Compound GAG-C45 was obtained as white amorphous powder and optical rotation was [α]$_D$–22.0 (C=0.15, MeOH). UV absorption was at λ$_{max}$ (CH$_3$CN) 273 nm. The molecular formula of GAG-C45 was determined to be C$_{59}$H$_{86}$O$_{20}$, based on a molecular ion at m/z [M+Na]$^+$ 1137.6625 in positive HR MALDI-MS (calculated as 1114.5713). The structure of GAG-C45 was identified by different 1D, 2D NMR spectroscopy and HR-MS spectrometry to be 12-O-cis/trans-cinnamoyl-20-acetyl-8,14-seco-sarcostin 3-O-β-D-Cymaropyranosyl-(1→4)-O-β-D-Digitoxopyranosyl-(1→4)-β-D-Oleandropyranosyl-(1→4)-β-3-D-Cymaropyranoside according to IUPAC nomenclature. $^1$H and $^{13}$C NMR signals of compound GAG-C45 are listed in Table 15 and Table 16.

Compound GAG-C89 was obtained as white amorphous powder and optical rotation was [α]$_D$–20.8 (C=0.1, MeOH). UV absorption was at λ$_{max}$ (CH$_3$CN) 283 nm. The molecular formula of GAG-C89 was determined to be C$_{46}$H$_{64}$O$_{14}$, based on a molecular ion at m/z [M+Na]$^+$ 863.4650 in positive HR MALDI-MS (calc. 863.4296). The structure of GAG-C89 was identified by different 1D, 2D NMR and MS to be 12-O-cis/trans-cinnamoyl-20-acetyl-8,14-seco-sarcostin 3-O-β-D-Cymaropyranosyl-(1→4)-β-D-Oleandropyranoside according to IUPAC nomenclature. $^1$H and $^{13}$C NMR signals of compound GAG-C89 are listed in Table 15 and Table 16.

Compound GAG-C90 was obtained as white amorphous powder and optical rotation was [α]$_D$–22.3 (C=0.12, MeOH). UV absorption was at λ$_{max}$ (CH$_3$CN) 282 nm. The molecular formula of GAG-C90 was determined to be C$_{53}$H$_{76}$O$_{17}$, based on a molecular ion at m/z [M+Na]$^+$ 1007.5393 and [M+K]$^+$ 1023.5203 in positive HR MALDI-MS (calc. 984.5083). The structure of GAG-C90 was identified by different 1D, 2D NMR and MS to be 12-O-cis/trans-cinnamoyl-20-acetyl-8,14-seco-sarcostin 3-O-β-D-Cymaropyranosyl-(1→4)-β-D-Oleandropyranosyl-(1→4)-O-D-Oleandropyranoside according to IUPAC nomenclature. $^1$H and $^{13}$C NMR signals of compound GAG-C90 are listed in Table 15 and Table 16.

Compound GAG-C94 was obtained as white amorphous powder and optical rotation was [α]$_D$–16.9 (C=0.1, MeOH). UV absorption was at λ$_{max}$ (CH$_3$CN) 282 nm. The molecular formula of GAG-C94 was determined to be C$_{60}$H$_{88}$O$_{20}$, based on a molecular ion at m/z [M+Na]$^+$ 1007.5579 in positive HR MALDI-MS (calc. 984.5083). The structure of GAG-C94 was identified by different 1D, 2D NMR and MS to be 12-O-cis/trans-cinnamoyl-20-acetyl-8,14-seco-sarcostin 3-O-β-D-Cymaropyranosyl-(1→4)-β-D-Cymaropyranosyl-(1→4)-β-D-Cymaropyranosyl-(1→4)-β-D-Oleandropyranoside according to IUPAC nomenclature. $^1$H and $^{13}$C NMR signals of compound GAG-C94 are listed in Table 15 and Table 16.

Compound GAG-C95 was obtained as white amorphous powder and optical rotation was [α]$_D$+5.9 (C=0.15, MeOH). UV absorption was at λ$_{max}$ (CH$_3$CN): 281 nm. The molecular formula of GAG-C95 was determined to be C$_{66}$H$_{98}$O$_{23}$, based on a molecular ion at m/z [M+Na]$^+$ 1281.7705 in positive HR MALDI-MS (calc. 1258.6499). The structure of GAG-C95 was identified by different 1D, 2D NMR and MS to be 12-O-cis/trans-cinnamoyl-20-acetyl-8,14-seco-sarcostin 3-O-β-D-Cymaropyranosyl-(1→4)-β-D-Cymaropyranosyl-(1→4)-β-D-Digitoxopyranosyl-(1→4)-β-D-Oleandropyranosyl-(1→4)-β-D-Cymaropyranoside according to IUPAC nomenclature. $^1$H and $^{13}$C NMR signals of compound GAG-C95 are listed in Table 15 and Table 16.

Compound GAG-C96 was obtained as white amorphous powder and optical rotation was [α]$_D$+26.5 (C=0.1, MeOH). UV absorption was at λ$_{max}$ (CH$_3$CN): 279 nm. The molecular formula of GAG-C96 was determined to be C$_{60}$H$_{88}$O$_{20}$, based on a molecular ion at m/z [M+Na]$^+$ 1151.6057 in positive HR MALDI-MS (calc. 1128.5869). The structure of GAG-C96 was identified by different 1D, 2D NMR and MS to be 12-O-cis/trans-cinnamoyl-20-acetyl-8,14-seco-sarcostin 3-O-β-D-Cymaropyranosyl-(1→4)-β-D-Cymaropyranosyl-(1→4)-β-D-Oleandropyranosyl-(1→4)-β-D-Oleandropyranoside according to IUPAC nomenclature. $^1$H and $^{13}$C NMR signals of compound GAG-C96 are listed in Table 15 and Table 16.

Compound GAG-C104 was obtained as white amorphous powder and optical rotation was [α]$_D$-23.1 (C=0.15, MeOH). UV absorption was at λ$_{max}$ (CH$_3$CN): 271 nm. The molecular formula of GAG-C104 was determined to be C$_{66}$H$_{98}$O$_{23}$, based on a molecular ion at m/z [M+Na]$^+$ 1281.62 in positive ESI-MS. The structure of GAG-C104 was identified by different 1D, 2D NMR and MS to be 12-O-cis/trans-cinnamoyl-20-acetyl-8,14-seco-sarcostin 3-O-β-D-Cymaropyranosyl-(1→4)-β-D-Cymaropyranosyl-(1→4)-β-D-Digitoxopyranosyl-(1→4)-β-D-Cymaropyranosyl-(1→4)-β-D-Oleandropyranoside according to IUPAC nomenclature. $^1$H and $^{13}$C NMR signals of compound GAG-C104 are listed in Table 15 and Table 16.

Compound GAG-C86 was obtained as white amorphous powder and optical rotation was [α]$_D$+10.1 (C=0.1, MeOH). UV absorption was at λ$_{max}$ (CH$_3$CN): 280 nm. The molecular formula of GAG-C86 was determined to be C$_{51}$H$_{76}$O$_{16}$, based on a molecular ion at m/z [M+Na]$^+$ 967.52 and [2M+Na]$^+$ 1912.43 in positive ESI-MS (calculated as 944.5133). The structure of GAG-C86 was identified by different 1D, 2D NMR and MS to be 12-O-cis/trans-cinnamoylsacrostin 3-O-β-D-Cymaropyranosyl-(1→4)-β-D-Oleandropyranosyl-(1→4)-β-D-Oleandropyranoside according to IUPAC nomenclature. $^1$H and $^{13}$C NMR signals of compound GAG-C86 are listed in Table 15 and Table 17.

Compound GAG-C87 was obtained as white amorphous powder and optical rotation was [α]$_D$+25.0 (C=0.1, MeOH). UV absorption was at λ$_{max}$ (CH$_3$CN): 281 nm. The molecular formula of GAG-C87 was determined to be C$_{51}$H$_{74}$O$_{16}$, based on a molecular ion at m/z [M+Na]$^+$ 965.53 and [2M+Na]$^+$ 1907.26 in positive ESI-MS (calculated as 942.4977). The structure of GAG-C87 was identified by different 1D, 2D NMR and MS to be Ikemagenin 3-O-β-D-Cymaropyranosyl-(1→4)-β-D-Oleandropyranosyl-(1→4)-β-D-Oleandropyranoside according to IUPAC nomenclature. $^1$H and $^{13}$C NMR signals of compound GAG-C87 are listed in Table 15 and Table 17.

Compound GAG-C99 was obtained as white amorphous powder and optical rotation was [α]$_D$+18.1 (C=0.1, MeOH). UV absorption was at λ$_{max}$ (CH$_3$CN): 280 nm. The molecular formula of GAG-C99 was determined to be C$_{43}$H$_{62}$O$_{13}$, based on a molecular ion at m/z [M+Na]$^+$ 809.41 in positive ESI-MS (calculated as 786.4190). The structure of GAG-C99 was identified by different 1D, 2D NMR and MS to be 12-O-cis/trans-cinnamoylsacrostin 3-O-β-D-Cymaropyranosyl-(1→4)-β-D-Digitoxopyranoside according to IUPAC nomenclature. $^1$H and $^{13}$C NMR signals of compound GAG-C99 are listed in Table 15 and Table 17.

Compound GAG-C91 was obtained as white amorphous powder and UV absorption was at λ$_{max}$ (CH$_3$CN): 281 nm. The molecular formula of GAG-C91 was determined to be C$_{56}$H$_{90}$O$_{19}$, based on a molecular ion at m/z [M+Na]$^+$ 1089.71 in positive ESI-MS. The structure of GAG-C91 was identified by different 1D, 2D NMR and MS data and compared with previously reported data to be Caudatin 3-O-β-D-Cymaropyranosyl-(1→4)-β-D-Cymaropyranosyl-(1→4)-β-D-Cymaropyranosyl-(1→4)-β-D-Oleandropyranoside (Wilfoside C1N) according to IUPAC nomenclature (Tsukamoto Sachiko; etc.; *Tetrahedron* 1985, 41(5), 927-34). $^1$H and $^{13}$C NMR signals of sugar moieties for GAG-C91 are listed in Table 14. Compound GAG-C91:

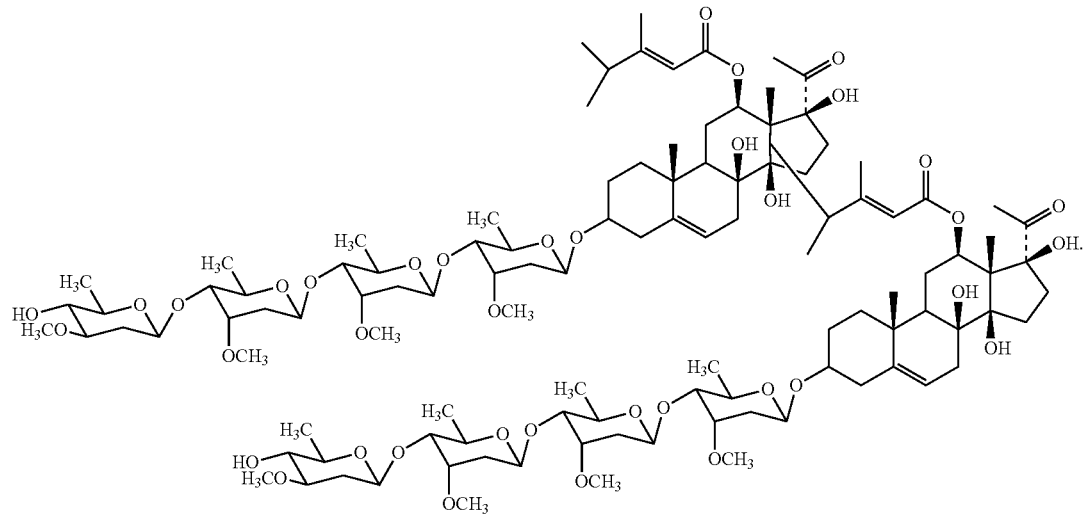

Compound GAG-C92 was obtained as white amorphous powder and UV absorption was at λ$_{max}$ (CH$_3$CN): 281 nm. The molecular formula of GAG-C92 was determined to be C$_{56}$H$_{90}$O$_{19}$, based on a molecular ion at m/z [M+Na]$^+$ 1089.71 in positive ESI-MS. The structure of GAG-C92 was identified by different 1D, 2D NMR and MS data and compared with previously reported data to be Caudatin 3-O-β-D-Cymaropyranosyl-(1→4)-β-D-Cymaropyranosyl-(1→4)-β-D-Oleandropyranosyl-(1→4)-β-D-Oleandropyranoside according to IUPAC nomenclature (Tsukamoto Sachiko; etc.; *Chem. Pharm. Bull.* 1985, 33 (6), 2294-2304). $^1$H and $^{13}$C NMR signals of sugar moieties for GAG-C92 are listed in Table 14. Compound GAG-C92:

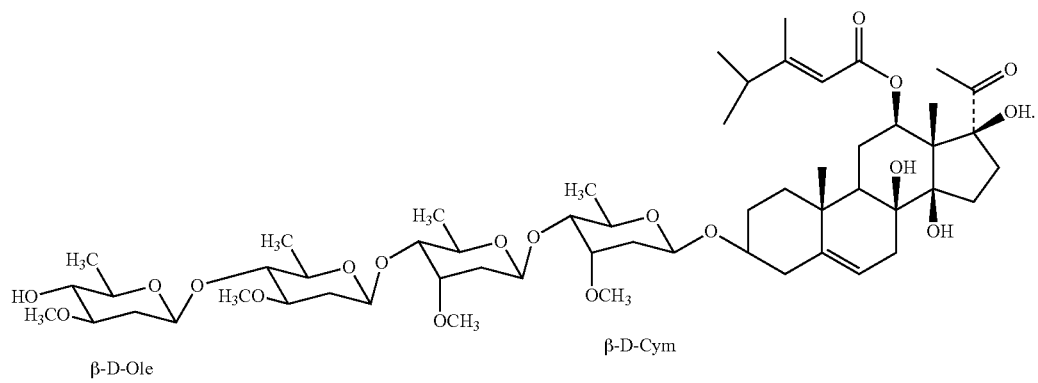

β-D-Ole        β-D-Cym

TABLE 14

$^1$H and $^{13}$C NMR chemical shifts for sugar moieties of compounds GAG-C91 and GAG-C92

| Position | GAG-C91 $^{13}$C | GAG-C91 $^1$H | GAG-C92 $^{13}$C | GAG-C92 $^1$H |
|---|---|---|---|---|
| D-Cym 1 | 97.26 | 4.88(dd, 9.5, 1.9) | 97.21 | 4.89 (dd, 9.6, 1.8) |
| 2 | 36.65 | 1.52, 2.09 | 36.65 | 2.15, 1.55 |
| 3 | 78.51 | 3.80 | 78.50 | 3.82 |
| 4 | 82.87 | 3.28 | 83.83 | 3.29 |
| 5 | 69.88 | 3.78 | 69.96 | 3.80 |
| 6 | 18.56 | 1.19 | 18.52 | 1.18 |
| -OMe | 57.66 | 3.43 | 57.68 | 3.44 |
| D-Cym 1 | 99.74 | 4.90 (dd, 9.6, 1.8) | 99.74 | 4.90(dd, 9.6,1.8) |
| 2 | 38.33 | 1.44, 2.39 | 38.13 | 1.39, 2.35 |
| 3 | 79.35 | 3.36 | 79.28 | 3.35 |
| 4 | 84.00 | 3.18 | 84.08 | 3.16 |
| 5 | 70.02 | 3.76 | 72.27 | 3.39 |
| 6 | 18.61 | 1.25 | 18.57 | 1.27 |
| -OMe | 58.58 | 3.44 | 58.02 | 3.43 |
| D-Cym 1 | 101.23 | 4.81(dd, 9.6,1.8) | | |
| 2 | 38.18 | 1.29, 2.36 | | |
| 3 | 80.06 | 3.38 | | |
| 4 | 83.89 | 3.17 | | |

TABLE 14-continued $^1$H and $^{13}$C NMR chemical shifts for sugar moieties of compounds GAG-C91 and GAG-C92

| Position | GAG-C91 $^{13}$C | GAG-C91 $^1$H | GAG-C92 $^{13}$C | GAG-C92 $^1$H |
|---|---|---|---|---|
| 5 | 71.70 | 3.35 | | |
| 6 | 18.74 | 1.28 | | |
| -OMe | 58.73 | 3.43 | | |
| D-Ole 1 | | | 101.28 | 4.69 (dd, 9.6, 1.8) |
| 2 | | | 37.92 | 1.44, 2.39 |
| 3 | | | 80.07 | 3.36 |
| 4 | | | 84.09 | 3.18 |
| 5 | | | 72.33 | 3.49 |
| 6 | | | 18.57 | 1.26 |
| -OMe | | | 57.73 | 3.44 |
| D-Ole 1 | 102.75 | 4.60(dd, 9.6, 1.8) | 102.66 | 4.59(dd, 9.6, 1.8) |
| 2 | 37.76 | 1.44, 2.36 | 37.74 | 1.44, 2.35 |
| 3 | 80.12 | 3.19 | 80.12 | 3.20 |
| 4 | 79.32 | 3.22 | 79.27 | 3.22 |
| 5 | 73.31 | 3.33 | 73.26 | 3.32 |
| 6 | 18.64 | 1.29 | 18.69 | 1.29 |
| -OMe | 58.47 | 3.45 | 58.51 | 3.44 |

TABLE 15

$^{13}$C NMR chemical shifts for aglycone moieties of compounds GAG-C44, GAG-C45, GAG-C89, GAG-C90, GAG-C94, GAG-C95, GAG-C96, GAG-C104, GAG-C86, GAG-C87 and GAG-C99

| Position | GAG-C44 | GAG-C45 | GAG-C89 | GAG-C90 | GGA-C94 | GAG-C95 | GAG-C96 | GAG-C104 | GAG-C86 | GAG-C87 | GAG-C99 |
|---|---|---|---|---|---|---|---|---|---|---|---|
| 1 | 41.80 | 41.77 | 41.85 | 41.86 | 41.81 | 41.80 | 41.80 | 41.81 | 38.2 | 39.8 | 38.9 |
| 2 | 30.20 | 30.12 | 30.24 | 30.26 | 30.16 | 30.16 | 30.15 | 30.14 | 30.3 | 30.1 | 30.2 |
| 3 | 73.27 | 73.17 | 73.24 | 73.37 | 73.25 | 73.12 | 73.24 | 73.77 | 79.26 | 79.26 | 79.4 |
| 4 | 43.97 | 44.06 | 44.06 | 44.05 | 44.02 | 44.04 | 44.02 | 44.01 | 37.8 | 39.7 | 37.3 |
| 5 | 142.61/ 142.48 | 142.69 | 142.71 | 142.72/ 142.59 | 142.85/ 142.72 | 142.85/ 142.73 | 142.83/ 142.71 | 142.87 | 139.9 | 140.2 | 140.1 |
| 6 | 119.43/ 118.84 | 118.87 | 119.52 | 119.52/ 118.94 | 119.63/ 118.99 | 119.95/ 119.00 | 119.67 | 119.62/ 119.02 | 119.9 | 119.7 | 119.3 |
| 7 | 30.00 | 29.94 | 30.05 | 30.08 | 29.99 | 29.98 | 29.98 | 29.97 | 34.4 | 35.1 | 29.95 |
| 8 | 211.36/ 211.30 | 212.16 | 211.60 | 211.39/ 211.32 | 211.75 | 211.80 | 211.75/ 211.69 | 211.73 | 75.0 | 74.8 | 75.0 |
| 9 | 56.64 | 56.91 | 56.78 | 56.74 | 56.74 | 56.75 | 56.72 | 56.74 | 44.9 | 45.1 | 44.9 |
| 10 | 37.55 | 37.49 | 37.44 | 37.67 | 37.70 | 37.69 | 37.68 | 37.37 | 38.1 | 37.7 | 38.1 |
| 11 | 26.51 | 26.21 | 26.58 | 26.59/ 26.18 | 26.51/ 26.08 | 26.50/ 26.07 | 26.49/ 26.07 | 26.49/ 26.09 | 25.9 | 25.0 | 26.0 |
| 12 | 76.89 | 76.97 | 76.91 | 77.00 | 76.93 | 76.9 | 76.91 | 76.84 | 77.0 | 74.4 | 76.9 |
| 13 | 63.19/ 62.86 | 63.91/ 62.99 | 63.28/ 62.95 | 63.26/ 62.93 | 63.27/ 62.94 | 63.27/ 62.93 | 63.25/ 62.92 | 63.21 | 57.4 | 57.5 | 57.4 |
| 14 | 219.63/ 219.32 | 219.88 | 219.35 | 219.65/ 219.34 | 220.12/ 219.80 | 219.77 | 219.73 | 219.70 | 88.7 | 89.9 | 89.2 |
| 15 | 39.79 | 39.84 | 38.96 | 38.99 | 39.77 | 39.77 | 39.77 | 39.79 | 35.1 | 34.1 | 39.9 |

TABLE 15-continued $^{13}$C NMR chemical shifts for aglycone moieties of compounds GAG-C44, GAG-C45, GAG-C89, GAG-C90, GAG-C94, GAG-C95, GAG-C96, GAG-C104, GAG-C86, GAG-C87 and GAG-C99

| | GAG-C44 | GAG-C45 | GAG-C89 | GAG-C90 | GGA-C94 | GAG-C95 | GAG-C96 | GAG-C104 | GAG-C86 | GAG-C87 | GAG-C99 |
|---|---|---|---|---|---|---|---|---|---|---|---|
| 16 | 34.38 | 34.44 | 34.42 | 34.48 | 34.35 | 34.34 | 34.41 | 34.33 | 33.7 | 33.1 | 33.8 |
| 17 | 83.05 | 83.24 | 83.06 | 83.04 | 83.09 | 83.08 | 83.06 | 83.06 | 89.3 | 93.0 | 89.4 |
| 18 | 12.32/11.93 | 11.91 | 12.36/11.94 | 12.35/11.94 | 12.27/11.84 | 12.25/11.83 | 12.25/11.83 | 12.23/11.82 | 11.31 | 10.4/10.0 | 11.2 |
| 19 | 19.19 | 19.63 | 19.22 | 19.24 | 19.14 | 19.14 | 19.13 | 19.14 | 18.4 | 18.3 | 18.4 |
| 20 | 75.12 | 75.29 | 75.22 | 75.20 | 75.25 | 75.23 | 75.22 | 75.23 | 74.9 | 211.2 | 74.9 |
| 21 | 14.47/14.41 | 14.41 | 14.48/14.42 | 14.49/14.43 | 14.39/14.32 | 14.38/14.32 | 14.38/14.31 | 14.39/14.32 | 18.8 | 27.6 | 18.6 |
| Cin | | | | | | | | | | | |
| 1' | 168.50/167.51 | 168.91/167.89 | 168.64/167.62 | 168.60/167.59 | 168.84/167.82 | 168.83/167.81 | 168.80/167.78 | 168.81/167.80 | 168.2/167.3 | 167.4/166.9 | 168.5/167.6 |
| 2' | 120.59 | 120.67 | 120.64 | 120.66 | 120.73 | 120.74 | 120.72 | 120.77 | 120.67 | 120.8 | 120.0 |
| 3' | 146.71/144.88 | 145.26 | 146.79/145.02 | 146.74/144.97 | 146.95/145.18 | 146.93/145.16 | 146.90/145.13 | 146.89 | 146.7 | 144.5 | 146.5 |
| 4' | 136.15/135.38 | 136.35 | 136.26/135.47 | 136.26/135.50 | 136.38/135.59 | 136.38/135.60 | 136.55/135.58 | 136.39/135.62 | 136.5/135.7 | 136.6 | 136.1 |
| 5' | 129.25/129.00 | 129.21 | 129.05 | 129.04 | 129.17 | 129.17 | 129.15 | 129.18 | 129.0 | 129.1 | 129.2 |
| 6' | 130.70/130.62 | 130.32 | 130.72 | 130.74 | 130.85 | 130.85 | 130.83 | 130.85 | 130.6 | 130.1 | 130.0 |
| 7' | 131.67/131.60 | 130.80 | 131.68 | 131.65 | 131.82 | 131.85 | 131.79 | 131.79 | 131.4 | 130.6 | 130.7 |
| 8' | 130.08 | 130.13 | 130.14 | 130.12 | 130.13 | 130.12 | 130.11 | 130.12 | 130.0 | 130.0 | 130.1 |
| 9' | 129.94/129.31 | 129.47 | 129.34 | 129.34 | 129.47 | 129.46 | 129.45 | 129.47 | 129.9 | 129.2 | 129.5 |
| Ac, CO | 171.55/171.38 | 171.45 | 171.69/171.53 | 171.58/171.44 | 171.89/171.73 | 171.88/171.72 | 171.84/171.68 | 171.83/171.67 | | | |
| CH$_3$ | 21.51/21.45 | 21.50 | 21.50 | 21.51 | 21.42 | 21.41 | | 21.41 | | | |

TABLE 16

$^{13}$C NMR chemical shifts for sugar moieties of compounds GAG-C44, GAG-C45, GAG-C89, GAG-C90, GAG-C94, GAG-C95, GAG-96 and GAG-C104.

| Position | | GAG-C44 | GAG-C45 | GAG-C89 | GAG-C90 | GAG-C94 | GAG-C95 | GAG-C96 | GAG-C104 |
|---|---|---|---|---|---|---|---|---|---|
| D-Cym | 1 | 97.06/4.9 | 97.19/4.95 | 97.33 | 97.31 | 97.20 | 97.39/4.84 | 97.38 | 97.24/4.9 |
| | 2 | 37.55 | 37.59 | 36.65 | 36.68 | 36.54 | 36.54 | 36.55 | 36.47 |
| | 3 | 78.11 | 78.33 | 78.20 | 78.18 | 78.47 | 78.44 | 78.44 | 78.36 |
| | 4 | 83.81 | 83.58 | 83.71 | 83.81 | 83.96 | 83.97 | 83.95 | 83.94 |
| | 5 | 69.36 | 69.49 | 69.91 | 69.94 | 69.96 | 70.22 | 70.21 | 70.26 |
| | 6 | 18.49 | 18.50 | 18.51 | 18.46 | 18.44 | 18.46 | 18.45 | 18.43 |
| —OMe | | 57.45 | 57.50 | 58.46 | 58.50 | 57.45 | 58.52 | 58.55 | 58.46 |
| D-Dig | 1 | 101.17/4.70 | 101.50/4.71 | | | | | | |
| | 2 | 38.88 | 38.84 | | | | | | |
| | 3 | 65.93 | 65.32 | | | | | | |
| | 4 | 83.52 | 81.63 | | | | | | |
| | 5 | 68.32 | 68.32 | | | | | | |
| | 6 | 18.42 | 18.37 | | | | | | |
| D-Ole | 1 | 102.02/4.6 | 102.17/4.60 | 102.69 | 101.3 | | | | |
| | 2 | 38.18 | 38.20 | 38.25 | 38.33 | | | | |
| | 3 | 81.57 | 79.92 | 81.57 | 80.09 | | | | |
| | 4 | 79.96 | 83.27 | 78.47 | 83.77 | | | | |
| | 5 | 72.29 | 72.42 | 72.43 | 72.31 | | | | |
| | 6 | 18.71 | 18.72 | 18.66 | 18.68 | | | | |
| —OMe | | 57.72 | 57.75 | 57.46 | 57.47 | | | | |
| D-Cym | 1 | | 98.75/4.85 | | | 99.73/4.90 | 99.73/4.90 | 99.71 | 98.75/4.85 |
| | 2 | | 35.13 | | | 38.27 | 38.19 | 35.70 | 37.15 |
| | 3 | | 79.12 | | | 79.99 | 79.26 | 79.24 | 79.96 |
| | 4 | | 74.48 | | | 83.78 | 83.80 | 83.79 | 83.64 |
| | 5 | | 71.49 | | | 69.78 | 69.95 | 69.93 | 69.95 |
| | 6 | | 18.37 | | | 18.58 | 18.76 | 18.56 | 18.55 |
| —OMe | | | 58.05 | | | 57.64 | 57.63 | 58.34 | 56.96 |

TABLE 16-continued $^{13}$C NMR chemical shifts for sugar moieties of compounds GAG-C44, GAG-C45, GAG-C89, GAG-C90, GAG-C94, GAG-C95, GAG-96 and GAG-C104.

| Position | | GAG-C44 | GAG-C45 | GAG-C89 | GAG-C90 | GAG-C94 | GAG-C95 | GAG-C96 | GAG-C104 |
|---|---|---|---|---|---|---|---|---|---|
| D-Dig | 1 | | | | | | 101.19 | | 102.81/4.58 |
| | 2 | | | | | | 38.89 | | 38.89 |
| | 3 | | | | | | 70.02 | | 65.21 |
| | 4 | | | | | | 83.66 | | 83.23 |
| | 5 | | | | | | 69.84 | | 66.65 |
| | 6 | | | | | | 18.68 | | 18.60 |
| D-Ole | 1 | | | | 102.56 | 102.65 | 102.7/4.60 | 101.24 | |
| | 2 | | | | 37.79 | 38.90 | 38.38 | 38.86 | |
| | 3 | | | | 81.68 | 79.25 | 80.00 | 79.98 | |
| | 4 | | | | 78.01 | 83.17 | 83.17 | 83.15 | |
| | 5 | | | | 72.42 | 72.41 | 72.40 | 71.63 | |
| | 6 | | | | 18.86 | 18.71 | 18.71 | 18.70 | |
| —OMe | | | | | 57.73 | 58.51 | 58.32 | 58.03 | |
| D-Cym | 1 | | | | | 101.20 | 101.26/4.79 | | 100.01/4.85 |
| | 2 | | | | | 35.70 | 35.70 | | 38.04 |
| | 3 | | | | | 78.22 | 78.18 | | 78.36 |
| | 4 | | | | | 74.46 | 74.46 | | 83.15 |
| | 5 | | | | | 71.64 | 71.64 | | 68.35 |
| | 6 | | | | | 18.58 | 18.59 | | 18.15 |
| —OMe | | | | | | 58.03 | 58.03 | | 56.85 |

TABLE 17

$^{1}$H and $^{13}$C NMR chemical shifts for sugar moieties of compounds GAG-C86, GAG-C87 and GAG-C99

| | | GAG-C87 | | GAG-C86 | | GAG-C99 | |
|---|---|---|---|---|---|---|---|
| Position | | $^{13}$C | $^{1}$H | $^{13}$C | $^{1}$H | $^{13}$C | $^{1}$H |
| D-Cym | 1 | 97.18 | 4.90 (dd, 9.6, 1.8) | 97.15 | 4.95 (dd, 9.5, 1.9) | 97.06 | 4.90 (dd, 9.5, 1.9) |
| | 2 | 36.68 | 2.15, 1.55 | 36.76 | 1.52, 2.09 | 35.24 | 1.55, 2.12 |
| | 3 | 78.47 | 3.80 | 78.49 | 3.80 | 79.41 | 3.58 |
| | 4 | 83.77 | 3.29 | 83.83 | 3.28 | 83.70 | 3.26 |
| | 5 | 69.94 | 3.80 | 69.43 | 3.81 | 69.51 | 3.82 |
| | 6 | 18.41 | 1.18 | 18.50 | 1.19 | 18.50 | 1.16 |
| —OMe | | 57.69 | 3.44 | 57.62 | 3.45 | 57.51 | 3.44 |
| D-Ole | 1 | 101.37 | 4.72 (dd, 9.6, 1.8) | 101.31 | 4.69 (dd, 9.6, 1.8) | | |
| | 2 | 38.11 | 1.39, 2.35 | 38.12 | 1.44, 2.39 | | |
| | 3 | 80.11 | 3.35 | 80.10 | 3.36 | | |
| | 4 | 84.01 | 3.16 | 84.01 | 3.18 | | |
| | 5 | 72.30 | 3.50 | 72.33 | 3.49 | | |
| | 6 | 18.57 | 1.38 | 18.63 | 1.35 | | |
| —OMe | | 58.48 | 3.43 | 58.54 | 3.44 | | |
| D-Dig | 1 | | | | | 102.31 | 4.62 (d, 9.1) |
| | 2 | | | | | 37.29 | 1.40, 2.37 |
| | 3 | | | | | 68.43 | 4.24 |
| | 4 | | | | | 81.60 | 3.21 |
| | 5 | | | | | 73.32 | 3.31 |
| | 6 | | | | | 18.58 | 1.28 |
| D-Ole | 1 | 102.62 | 4.58 (dd, 9.6, 1.8) | 102.60 | 4.60 (dd, 9.6, 1.8) | | |
| | 2 | 37.58 | 1.44, 2.36 | 37.68 | 1.44, 2.35 | | |
| | 3 | 81.67 | 3.20 | 81.69 | 3.20 | | |
| | 4 | 78.40 | 3.22 | 74.87 | 3.22 | | |
| | 5 | 73.24 | 3.33 | 73.38 | 3.32 | | |
| | 6 | 18.74 | 1.27 | 18.71 | 1.29 | | |
| —OMe | | 58.53 | 3.44 | 58.51 | 3.44 | | |

Compound GAG-C43 was obtained as white amorphous powder and optical rotation was $[\alpha]_D$+12.9 (C=0.1, MeOH). UV absorption was at $\lambda_{max}$ (CH$_3$CN): 281 nm. The molecular formula of GAG-C43 was determined to be $C_{50}H_{74}O_{16}$, based on a molecular ion at m/z [M+Na]$^+$ 953.4889 in positive HR MALDI-MS (calculated as 930.4977). The structure of GAG-C43 was identified by different 1D, 2D NMR and MS to be 12-O-cis/trans-cinnamoylsacrostin 3-O-β-D-Cymaropyranosyl-(1→4)-β-D-Oleandropyranosyl-(1→4)-β-D-Digitoxopyranoside according to IUPAC nomenclature. $^1$H and $^{13}$C NMR signals of compound GAG-C43 are listed in Table 18 and Table 19.

Compound GAG-C46 was obtained as white amorphous powder and optical rotation was $[\alpha]_D$−11.6 (C=0.18, MeOH). UV absorption was at $\lambda_{max}$ (CH$_3$CN): 274 nm. The molecular formula of GAG-C46 was determined to be $C_{52}H_{74}O_{17}$, based on a molecular ion at m/z [M+Na]$^+$ 993.5181 in positive HR MALDI-MS. The structure of GAG-C46 was identified by different 1D, 2D NMR and MS to be 12-O-cis/trans-cinnamoyl-20-acetyl-8,14-seco-sarcostin 3-O-β-D-Cymaropyranosyl-(1→4)-β-D-Digitoxopyranosyl-(1→4)-β-D-Cymaropyranoside according to IUPAC nomenclature. $^1$H and $^{13}$C NMR signals of compound GAG-C46 are listed in Table 18 and Table 19.

Compound GAG-C47 was obtained as white amorphous powder and optical rotation was $[\alpha]_D$–15.1 (C=0.1, MeOH). UV absorption was at $\lambda_{max}$ (CH$_3$CN): 274 nm. The molecular formula of GAG-C47 was determined to be C$_{52}$H$_{74}$O$_{17}$, based on a molecular ion at m/z [M+Na]$^+$ 993.4927 in positive HR MALDI-MS. The structure of GAG-C47 was identified by different 1D, 2D NMR and MS to be 12-O-cis/trans-cinnamoyl-20-acetyl-8,14-seco-sarcostin 3-O-β-D-Cymaropyranosyl-(1→4)-β-D-Oleandropyranosyl-(1→4)-β-D-Digitoxopyranoside according to IUPAC nomenclature. $^1$H and $^{13}$C NMR signals of compound GAG-C47 are listed in Table 18 and Table 19.

Compound GAG-C102 was obtained as white amorphous powder and optical rotation was $[\alpha]_D$–8.2 (C=0.2, MeOH). UV absorption was at $\lambda_{max}$ (CH$_3$CN): 275 nm. The molecular formula of GAG-C102 was determined to be C$_{59}$H$_{86}$O$_{20}$, based on a molecular ion at m/z [M+Na]$^+$ 1137.68 in positive HR MALDI-MS (calc. 1114.5713). The structure of GAG-C102 was identified by different 1D, 2D NMR and MS to be 12-O-cis/trans-cinnamoyl-20-acetyl-8,14-seco-sarcostin 3-O-β-D-Cymaropyranosyl-(1→4)-β-D-Digitoxopyranosyl-(1→4)-β-D-Oleandropyranosyl-(1→4)-β-D-Oleandropyranoside according to IUPAC nomenclature. $^1$H and $^{13}$C NMR signals of compound GAG-C102 are listed in Table 18 and Table 19.

TABLE 18

$^{13}$C NMR chemical shifts for aglycone moiety of compounds GAG-C46, GAG-C47, GAG-C102 and GAG-C43

| Position | GAG-C46 | GAG-C47 | GAG-C102 | GAG-C43 |
|---|---|---|---|---|
| 1 | 41.79 | 41.80 | 41.78 | 38.9 |
| 2 | 30.15 | 30.15 | 30.21 | 30.7 |
| 3 | 73.37 | 73.3 | 73.80 | 79.4 |
| 4 | 43.99 | 44.01 | 44.05 | 37.5 |
| 5 | 142.71 | 142.55 | 142.88 | 140.0 |
| 6 | 118.69 | 119.34 | 119.55 | 119.9 |
| 7 | 29.95 | 29.99 | 30.00 | 30.1 |
| 8 | 211.73/211.76 | 211.37/211.31 | 211.45 | 75.6 |
| 9 | 56.71 | 56.74 | 56.75 | 44.8 |
| 10 | 37.51 | 37.50 | 37.66 | 38.0 |
| 11 | 26.48/26.07 | 26.2 | 26.35 | 26.0 |
| 12 | 76.97 | 76.9 | 76.87 | 77.0 |
| 13 | 63.26/62.93 | 63.22/62.89 | 63.33 | 57.4 |
| 14 | 220.13/219.81 | 219.63 | 219.72 | 89.2 |
| 15 | 39.74 | 38.88 | 39.85 | 39.8 |
| 16 | 34.34 | 34.41 | 34.24 | 33.6 |
| 17 | 83.12 | 83.07 | 83.12 | 89.3 |
| 18 | 12.25/11.83 | 11.9 | 12.22 | 11.2 |
| 19 | 19.13 | 19.15 | 19.16 | 18.3 |
| 20 | 75.19 | 74.40 | 75.34 | 75.0 |
| 21 | 14.38 | 14.48 | 14.41 | 18.5 |
| Cin-1' | 168.82/167.81 | 168.56/167.54 | | 168.5/167.6 |
| 2' | 120.72 | 120.6 | | 120.3 |
| 3' | 146.93/145.13 | 146.68/144.91 | | 146.6 |
| 4' | 136.36/135.60 | 136.20/135.44 | | 136.2 |
| 5' | 129.16 | 129.29 | | 129.1 |
| 6' | 130.25 | 130.67 | | 130.0 |
| 7' | 130.81 | 131.60 | | 130.6 |
| 8' | 130.11 | 130.07 | | 130.1 |
| 9' | 129.45 | 129.94 | | 129.4 |
| Ac., CO | 171.89/171.72 | 171.57/171.41 | | |
| CH$_3$ | 21.43 | 21.47 | | |

TABLE 19

$^1$H and $^{13}$C NMR chemical shifts for sugar moieties of compounds GAG-C46, GAG-C47, GAG-C102 and GAG-C43

| Position | GAG-C46 | GAG-C47 | GAG-C102 | GAG-C43 13C | GAG-C43 1H |
|---|---|---|---|---|---|
| D-Cym 1 | 97.19/4.9 | 97.2/4.94 | 97.38 | 97.0 | 4.94(dd, 9.5, 1.9) |
| 2 | 37.59 | 37.50 | 36.55 | 35.20 | 1.53, 2.11 |
| 3 | 78.10 | 79.11 | 78.44 | 79.35 | 3.62 |
| 4 | 83.61 | 83.84 | 83.95 | 83.62 | 3.27 |
| 5 | 69.46 | 69.48 | 70.21 | 69.43 | 3.83 |
| 6 | 18.54 | 18.57 | 18.45 | 18.53 | 1.19 |
| -OMe | 57.47 | 57.61 | 58.55 | 57.54 | 3.45 |
| D-Dig 1 | 101.36 | | 101.36 | | |
| 2 | 38.87 | | 38.87 | | |
| 3 | 66.01 | | 66.01 | | |
| 4 | 81.66 | | 81.66 | | |
| 5 | 68.34 | | 68.34 | | |
| 6 | 18.38 | | 18.38 | | |
| D-Ole 1 | | | | 101.36 | 4.62(dd, 9.5, 1.9) |
| 2 | | | | 38.02 | 1.40, 2.40 |
| 3 | | | | 80.06 | 3.41 |
| 4 | | | | 83.93 | 3.20 |
| 5 | | | | 72.37 | 3.53 |
| 6 | | | | 18.43 | 1.36 |
| -OMe | | | | 57.72 | 3.44 |
| D-Cym 1 | 98.66 | 99.76/4.85 | | | |
| 2 | 37.20 | 35.69 | | | |
| 3 | 80.06 | 79.27 | | | |
| 4 | 73.87 | 83.54 | | | |
| 5 | 72.96 | 71.66 | | | |
| 6 | 18.70 | 18.69 | | | |
| -OMe | 57.72 | 57.70 | | | |
| D-Dig 1 | | 102.2/4.6 | | 102.14 | 4.60(d, 9.2) |
| 2 | | 38.21 | | 37.56 | 1.39, 2.38 |
| 3 | | 68.90 | | 68.36 | 4.21 |
| 4 | | 79.88 | | 81.65 | 3.25 |
| 5 | | 72.39 | | 73.36 | 3.40 |
| 6 | | 18.48 | | 18.48 | 1.42 |
| D-Ole 1 | | | 101.24 | | |
| 2 | | | 38.86 | | |
| 3 | | | 79.98 | | |
| 4 | | | 83.15 | | |
| 5 | | | 71.63 | | |
| 6 | | | 18.70 | | |
| -OMe | | | 58.03 | | |
| D-Ole 1 | | | 102.69 | | |
| 2 | | | 37.36 | | |
| 3 | | | 81.57 | | |
| 4 | | | 74.98 | | |
| 5 | | | 72.38 | | |
| 6 | | | 18.75 | | |
| -OMe | | | 57.63 | | |

The polyoxygranane glycosides isolated from *Adelostemma gracillimum* refined fraction were glycosylated at 3 position of aglycone by different oligosaccharides started with the β-D-cymarose, which was supported by the cross-peaks in HMBC spectra between Cym-1(δ 4.90~4.95 ppm) and C-3 aglycone (δ 73.2 ppm for gracigenin and δ 79.3 ppm for penupogenin and ikemagenin). NMR data showed that all compounds contain both cis-(δ 5.80 and 7.05, d, J=16 Hz) and trans-(δ 6.34 and 7.55, d, J=12.8 Hz) form of cinnamic acid ester with variable ratios. On the basis of C—H correlation of HMBC spectra, the cinnamic acid ester linkage was substituted at 12 position of aglycone (δ 5.1~5.2 ppm/δ 167.5~168.9 ppm) for all compounds. The chemical shift values for cis- or trans-form compound showed up to 0.1 ppm difference for $^1$H signal and 2 ppm difference for $^{13}$C signal at certain positions (Table 12 to Table 19) of aglycone.

The aglycone obtained by acid analysis for compounds GAG-C44, GAG-C45, GAG-C46, GAG-C47, GAG-C89, GAG-C90, GAG-C94, GAG-C95, GAG-96, GAG-C102 and GAG-C104, was identified as gracigenin, 12-cis/trans-cinnamoyl-20-acetyl-8,14-seco-sacrostin, by comparison of its $^1$H and $^{13}$C NMR chemical shifts with those published NMR data for gracigenin moiety (Mu, Quanzhang, etc., *Planta Med.*, 58(2), 200-4 (English) 1992).

The aglycone obtained by acid analysis for compounds GAG-C43, C86 and C99 were determined to be 12-cinnamoylsacrostin (penupogenin), which was confirmed by comparing their NMR data with those reported NMR data of penupogenin. The aglycone obtained by acid analysis for GAG-C87 was elucidated as kidjolanin by comparison of its NMR data with those in literature. The aglycone obtained by acid analysis for compounds GAG-C91 and C92 was determined to be 12-ikeamoylsacrostin (caudatin), which was confirmed by comparison of their NMR data with reported NMR data for caudatin.

Three sugar units, cymarose, oleandrose and digitoxose, were observed in $^1$H NMR spectrum. The anomeric configuration of the three sugar moieties was determined to be the β form based on the $^3J_{H-1,H-2}$ value of the anomeric proton at 9.5 Hz. The absolute configuration was determined to be the same as those of previously reported which were D-Cymarose, D-Oleandrose and D-Digitoxose.

Compound GAG-C114 was obtained as light yellow oil and optical rotation was $[\alpha]_D$+2.4 (C=0.63, MeOH). UV absorption was at $\lambda_{max}$ (CH$_3$CN) 220 and 278 nm. The molecular formula of GAG-C114 was found to be C$_{19}$H$_{22}$O$_5$, based on a molecular ion at m/z [M+Na]$^+$ 353.1369 and [M+H–H$_2$O]$^+$ 313.1455 in positive HR MALDI-MS. The structure of GAG-C114 was determined to be 3-methoxyl-3', 4,7-trihydroxyl-(7'E)-(8-O-4')-neolignan-7' en according to IUPAC nomenclature.

$^1$H-NMR (300 MHz, CD$_3$OD, ppm) [delta]: 6.96 (1H, d, 1.5, H-2), 6.76 (1H, d, 8.4, H-5), 6.77 (1H, m, H-6), 6.87 (1H, d, 1.2, H-2'), 6.76 (1H, H-5'), 6.66 (1H, d, 8.1, H-6'), 6.18 (1H, d, 15.6, H-7'), 6.00 (1H, m, H-8'), 4.59 (1H, d, 6.3, H-7), 4.21 (1H, m, H-8), 3.72 (3H, s, OCH$_3$-3), 1.09 (3 H, d, 6.0, CH$_3$-9), 1.72 (3H, d, 6.3, CH$_3$-9'). $^{13}$C-NMR (75 MHz, CD$_3$OD, ppm) [delta]: 148.8 (C-3), 148.6 (C-4'), 145.9 (C-4) 146.9 (C-3'), 133.8 (C-1), 134.0 (C-1'), 120.8 (C-6), 118.8 (C-6'), 115.9 (C-5), 115.8 (C-5'), 111.2 (C-2), 113.9 (C-2'), 131.6 (C-7'), 124.7 (C-8'), 78.3 (C-7), 82.1 (C-8), 17.1 (C-9), 18.5 (C-9'), 56.2 (OCH$_3$-3).

Compound GAG-C109 was obtained as light yellow oil and optical rotation was $[\alpha]_D$–12.7 (C=0.3, MeOH). UV absorption was at $\lambda_{max}$ (CH$_3$CN) 220 and 278 nm. The molecular formula of GAG-C109 was found to be C$_{18}$H$_{18}$O$_6$, based on a molecular ion at m/z [M+H]$^+$ 331.1190 in positive HR MALDI-MS. The structure of GAG-C109 was identified by NMR and MS to be 3-methoxyl-4,4',5-trihydroxyl-1'-athanone-3'7-epoxy-8,2"-neolignane according to IUPAC nomenclature.

$^1$H-NMR (300 MHz, CD$_3$OD, ppm) [delta:]: 6.46 (1H, d, 1.5, H-2), 6.44 (1H, d, 1.5, H-6), 6.86 (1H, d, 8.7, H-5'), 6.73 (1H, d, 8.7, H-6'), 2.60 (3H, s, CH$_3$-8'), 5.08 (1H, d, 4.6, H-7), 3.68 (1H, dd, H-8), 3.79 (3H, s, OCH$_3$-3), 1.30 (3H, d, 6.9, CH$_3$-9). $^{13}$C-NMR (75 MHz, CD$_3$OD, ppm) [delta]: 149.5 (C-3), 146.6 (C-5), 134.0 (C-4), 153.8 (C-3'), 153.6 (C-4'), 135.0 (C-1), 107.1 (C-6), 102.1 (C-2), 123.8 (C-1'), 132.6 (C-2'), 117.6 (C-6'), 115.3 (C-5'), 205.2 (C-7'), 32.1 (C-8'), 92.8 (C-7), 47.4 (C-8), 20.9 (C-9), 56.6 (OCH$_3$-3).

Compound GAG-C116 was obtained as light yellow oil and optical rotation was $[\alpha]_D$–12.7 (C=0.3, MeOH). UV absorption was at $\lambda_{max}$ (CH$_3$CN) 220 and 278 nm. The molecular formula of GAG-C116 was found to be C$_{19}$H$_{20}$O$_6$, based on a molecular ion at m/z [M+H]$^+$ 345.1340 and [M+Na]$^+$ 367.1162 in positive HR MALDI-MS. The structure of GAG-C116 was identified by NMR and MS to be 3,5-dimethoxyl-4,4'-dihydroxy-1'-athanone-3'7-epoxy-8,2'-neolignane according to IUPAC nomenclature.

$^1$H-NMR (300 MHz, CD$_3$OD, ppm) [delta:]: 6.59 (2H, H-2,6), 6.87 (1H, d, 8.7, H-5'), 6.74 (1H, d, 8.7, H-6'), 2.60 (3H, s, CH$_3$-8'), 5.15 (1H, d, 4.5, H-7), 3.68 (1H, H-8), 3.78 (6H, s, OCH$_3$-3.5), 1.30 (3H, d, 6.9, CH$_3$-9). $^{13}$C-NMR (75 MHz, CD$_3$OD, ppm) [delta]: 149.3 (C-3.5), 133.8 (C-4), 153.6 (C-3'), 153.5 (C-4'), 132.5 (C-1), 103.8 (C-6), 103.9 (C-2), 120.8 (C-1'), 132.4 (C-2'), 117.6 (C-6'), 115.1 (C-5'), 205.3 (C-7'), 32.2 (C-8'), 92.9 (C-7), 47.4 (C-8), 20.9 (C-9), 56.7 (OCH$_3$-3.5).

Compound GAG-C113 was obtained as white amorphous powder and UV absorption was at $\lambda_{max}$ (CH$_3$CN) 202 and 274 nm. The molecular formula of GAG-C113 was found to be C$_{22}$H$_{32}$O$_{10}$, based on a molecular ion at m/z [M+Na]$^+$479.52 in positive ESI-MS. The structure of GAG-C113 was identified by NMR and MS data to be 1-(2-hydroxyl-3-O-β-D-Cymaropyranosyl-6-O-β-D-Oleandropyranosyl-phenyl)-ethanone according to IUPAC nomenclature.

$^1$H-NMR (300 MHz, CD$_3$OD, ppm) [delta]: 7.26 (1H, d, 8.7, H-4), 6.92 (1H, d, 8.6, H-5), 2.62 (3H, s, CH$_3$-8), 4.88 (1H, Cym-1), 1.50, 2.14 (2H, Cym-2), 3.48 (1H, Cym-3), 3.18 (1H, Cym-4), 3.84 (1H, H-5), 1.22 (3H, Cym-6), 3.42 (3H, Cym-OCH$_3$-3), 4.62 (1H, dd, Ole-1), 1.53, 2.20 (2H, Ole-2) 3.61 (1H, Ole-3), 3.82 (1H, Ole-4), 3.71 (1H, Ole-5), 1.24 (3H, Ole-6), 3.42 (3H, Ole-OCH$_3$-3), ($^{13}$C-NMR (100 MHz, CD$_3$OD, ppm) [delta]: 124.1 (C-1), 159.6 (C-2), 142.2 (C-3) 120.3 (C-4), 117.1 (C-5), 154.4 (C-6), 204.8 (C-7), 32.4 (C-8), 96.2 (Cym-1), 35.5 (Cym-2), 78.7 (Cym-3), 74.6 (Cym-4), 70.5 (Cym-5), 18.8 (Cym-6), 58.1 (Cym-OCH$_3$-3), 100.4 (Ole-1), 35.3 (Ole-2), 79.2 (Ole-3), 75.2 (Ole-4), 71.4 (Ole-5), 18.6 (Ole-6), 58.0 (Ole-OCH$_3$-3).

Compound GAG-C119 was obtained as white amorphous powder. UV absorption was $\lambda_{max}$ (CH$_3$CN): 213 nm and 275 nm. The molecular formula of GAG-C119 was found to be C$_{24}$H$_{20}$O$_9$, based on a molecular ion at m/z [M–H]$^-$ 451.9203 in negative HR-ESI-MS. The structure of GAG-C119 was identified to be 3,6,2',6',2'',6''-hexhydroxyl-acetophenone (Cynandione F) according to IUPAC nomenclature.

$^1$H-NMR (300 MHz, CD$_3$OD, ppm) [delta]: 6.56 (1H, H-4), 7.87 (1H, d, H-4'), 6.53 (1H, d, H-5'), 7.81 (1H, d, 9 Hz, H-4"), 6.51 (1H, d, 9 Hz, H-5"), 2.56 (3H, CH$_3$-8), 2.18 (3H, CH$_3$-8'), 2.57 (3H, CH$_3$-8").

$^{13}$C-NMR (100 MHz, CD$_3$OD, ppm) [delta]: 120.5 (C-1), 123.8 (C-2), 154.1 (C-3), 110.1 (C-4), 134.3 (C-5), 148.2 (C-6), 114.5 (C-1'), 163.6 (C-2'), 115.9 (C-3'), 134.2 (C-4'), 106.3 (C-5'), 163.7 (C-6'), 112.6 (C-1"), 164.9 (C-2"), 116.9 (C-3"), 134.4 (C-4"), 108.8 (C-5"), 165.7 (C-6"), 207.0 (C-7), 204.6 (C-7'), 204.9 (C-7"), 30.8 (C-8), 26.7 (C-8'), 26.3 (C-8").

Compound GAG-C120 was obtained as white amorphous powder. UV absorption was at $\lambda_{max}$ (CH$_3$CN): 213 and 280 nm. The molecular formula of GAG-C120 was found to be C$_{25}$H$_{20}$O$_9$, based on a molecular ion at m/z [M–H]$^-$ 463.9558 in negative HR-ESI-MS. The structure of GAG-C120 was identified to be Cynandione G.

$^1$H-NMR (300 MHz, CD$_3$OD, ppm) [delta]: 6.79 (1H, d, 9 Hz, H-4), 6.93 (1H, d, 9 Hz, H-5), 7.78 (1H, d, 9 Hz, H-4"), 6.51 (1H, d, 9 Hz, H-5"), 5.01 (1H, H-7'), 2.56 (3H, CH$_3$-8), (3H, CH$_3$-8'), 2.18 (3H, CH$_3$-8"), 1.41 (3H, H-9').

$^{13}$C-NMR (100 MHz, CD$_3$OD, ppm) [delta]: 127.1 (C-2), 119.9 (C-1), 152.1 (C-3), 118.3 (C-4), 121.8 (C-5), 149.3 (C-6), 119.6 (C-1'), 149.0 (C-2'), 134.3 (C-3'), 149.1 (C-4'), 120.5 (C-5'), 131.5 (C-6'), 116.0 (C-1"), 146.0 (C-2"), 121.7 (C-3"), 134.0 (C-4"), 108.9 (C-5"), 163.7 (C-6"), 206.9 (C-7), 204.8 (C-7"), 92.9 (C-7'), 95.6 (C-8'), 30.9 (C-8), 26.4 (C-8"), 30.2 (C-9'), Compound GAG-C02 was obtained as white powder and the molecular weight was 166.17 with molecular formula C$_9$H$_{10}$O$_3$. GAG-C02 was identified by NMR and MS to be 1-(4-hydroxyl-3-methoxyl-phenyl)-ethanone (acetovanillone) according to IUPAC nomenclature.

$^1$H-NMR (400 MHz, CD$_3$OD, ppm) [delta]: 7.53 (1H, H-2), 6.84 (1H, H-5), 7.57 (1H, H-6), 2.53 (3H, s, CH$_3$-8), 3.89 (3H, s, OCH$_3$-3), $^{13}$C-NMR (100 MHz, CD$_3$OD, ppm) [delta]: 125.0 (C-1), 107.3 (C-2), 154.7 (C-3) 143.7 (C-4), 111.8 (C-5), 115.7 (C-6), 199.2 (C-7), 26.27 (C-8), 56.34 (OCH$_3$-3').

Compound GAG-C23 was obtained as white powder and the molecular weight was 226.23 and molecular formula C$_{11}$H$_{14}$O$_5$. The structure of GAG-C23 was identified by NMR and MS to be 3-hydroxyl-evofolin A.

$^1$H-NMR (400 MHz, CD$_3$OD, ppm) [delta]: 7.30 (2H, H-2.6), 5.17 (1H, H-8), 1.41 (3H, d, CH$_3$-9), 3.90 (6H, s, OCH$_3$-3.5), $^{13}$C-NMR (100 MHz, CD$_3$OD, ppm) [delta]: 125.8 (C-1), 107.6 (C-2, 6), 148.8 (C-3, C-4, C-5), 210.5 (C-7), 69.8 (C-8), 22.1 (C-9), 56.9 (OCH$_3$-3, OCH$_3$-5).

Compound GAG-007 was obtained as viscous oil. The molecular formula of GAG-C07 was found to be C$_{20}$H$_{24}$O$_6$ based on a molecular ion at m/z [M+Na]$^+$ 383.07 in positive ESI-MS. GAG-C07 was identified by NMR and MS to be 3,3'-dimethoxyl-4,5,9'-trihydroxyl-(7'E)-(9-7')-epoxylignane according to IUPAC nomenclature.

$^1$H-NMR (400 MHz, CD$_3$OD, ppm) [delta]: 6.80 (1H, H-2), 6.90 (1H, H-2'), 6.75 (1H, H-6), 6.63 (1H-6'), 6.72 (1H, H-5), 6.65 (1H, H-5'), 2.38, 2.45 (2H, H-7), 2.72 (1H, H-8), 3.72, 3.97 (2H, H-9), 4.75 (1H, H-7'), 2.92 (1H, H-8'), 3.61, 3.79 (2H, H-9'), 3.81, 3.83 (6H, s, OCH$_3$-3.3'). $^{13}$C-NMR (100 MHz, CD$_3$OD, ppm) [delta]: 149.0 (C-4,4'), 145.7 (C-3) 147.0 (C-3'), 135.7 (C-1), 116.2 (C-2), 113.5 (C-5), 122.7 (C-6), 133.6 (C-1'), 110.8 (C-2'), 116.0 (C-5'), 119.8 (C-6'), 33.6 (C-7), 43.8 (C-8), 73.5 (C-9), 84.0 (C-7'), 54.0 (C-8'), 60.4 (C-9') 56.5 (OCH$_3$-3,3').

Compound GAG-C11 was obtained as viscous oily paste. The molecular formula of GAG-C11 was found to be C$_{20}$H$_{22}$O$_6$ and molecular weight 358.39. The structure of GAG-C11 was determined by NMR and MS to be the 4,9-dihydroxyl-3,3'-dimethoxyl-4',7epoxy-8,5'-neoligna-9'-al according to IUPAC nomenclature.

$^1$H-NMR (400 MHz, CD$_3$OD, ppm) [delta]: 6.77, 6.80 (2H, H-5.6), 6.94 (1H, H-2), 7.45 (1H, H-2'), 7.52 (1H, H-6'), 5.65 (1H, H-7), 3.55 (1H, H-8), 3.48, 3.75 (2H, H-9), 3.91, 3.81 (6H, s OCH$_3$-3.3'), 9.78 (1H, H-9'). $^{13}$C-NMR (100 MHz, CD$_3$OD, ppm) [delta]: 149.0, 149.1 (C-3,3'), 146.1 (C-4), 147.7 (C-4'), 132.6 (C-1), 131.0 (C-1'), 133.5 (C-5'), 110.4 (C-2), 116.1 (C-5), 122.2 (C-6), 113.6 (C-2'), 119.7 (C-6'), 90.5 (C-7), 54.3 (C-8), 64.4 (C-9), 32.6 (C-7'), 42.7 (C-8'), 192.5 (C-9'), 56.6, 56.4 (OCH$_3$-3,3').

Compound GAG-C12 was obtained as light yellow paste. The molecular formula of GAG-C12 was found to be C$_{18}$H$_{18}$O$_6$ and molecular weight 330.33. The structure of GAG-C12 was identified by NMR and MS to be 4,9-dihydroxyl-3,3'-dimethyoxyl-4',7-epoxy-8,5'-neoligna-7'-al according to IUPAC nomenclature.

$^1$H-NMR (400 MHz, CD$_3$OD, ppm) [delta]: 6.94 (1 H, H-2), 7.45 (1H, H-2'), 7.52 (1H, H-6'), 6,78, 6.81 (2H, H-5.6), 5.64 (1H, H-7), 3.61 (1H, H-8), 3.59, 3.86 (2H, H-9), 9.78 (1 H, H-7'), 3.82, 3.92 (6H, s, OCH$_3$-3,3'). $^{13}$C-NMR (100 MHz, CD$_3$OD, ppm) [delta]: 149.0, 149.1 (C-3,3'), 146.1 (C-4), 147.7 (C-4'), 132.6 (C-1), 131.0 (C-1'), 133.5 (C-5'), 110.4 (C-2), 116.1 (C-5), 122.2 (C-6), 113.6 (C-2'), 119.7 (C-6'), 90.5 (C-7), 54.3 (C-8), 64.4 (C-9), 192.5 (C-7'), 56.6, 56.4 (OCH$_3$-3,3').

Compound GAG-C19 was obtained as light yellow paste. The molecular formula of GAG-C19 was found to be C$_{26}$H$_{30}$O$_{11}$ and molecular weight 518.51. The structure of GAG-C19 was determined by NMR and MS to be 4-hydroxyl-3,3'-dimethyoxyl-9(-O-β-D-glucopyranoside)-(7'E)-4',7epoxy-8,5'-neoligna-7'-en-9'-al according to IUPAC nomenclature.

$^1$H-NMR (400 MHz, CD$_3$OD, ppm) [delta]: 6.78, 6.84 (2H, H-5.6), 6.98 (1H, H-2), 7.23 (1H, H-2'), 7.34 (1H, H-6'), 5.67 (1H, H-7), 3.65 (1H, H-8), 3.79, 4.11 (2H, H-9), 7.62 (1H, d, H-7'), 6.65 (1H, dd, H-8'), 9.58 (1H, H-9'), 3.91, 3.81 (6H, s OCH$_3$-3,3'), 4.33 (1H, d, Glc-1), 3.41 (1H, Glc-2), 3.33 (1H, Glc-3), 3.50 (1H, Glc-4), 3.29 (1H, Glc-5), 3.22, 3.76 (2H, Glc-6). $^{13}$C-NMR (100 MHz, CD$_3$OD, ppm) [delta]: 148.9 (C-3), 145.8 (C-3'), 147.5 (C-4), 152.6 (C-4"), 129.5 (C-1), 130.9 (C-1'), 133.5 (C-5'), 110.5 (C-2), 116.0 (C-5), 120.1 (C-6), 114.2 (C-2'), 119.6 (C-6'), 89.8 (C-7), 52.5 (C-8), 71.8 (C-9), 155.9 (C-7'), 126.9 (C-8'), 195.9 (C-9'), 56.6, 56.4 (OCH$_3$-3,3'), 105.1 (Glc-1), 77.9 (Glc-2), 74.9 (Glc-3), 71.1 (Glc-4), 74.8 (Glc-5), 66.9 (Glc-6).

Compound GAG-C20 was obtained as light yellow gum and optical rotation was [α]$_D$+10.8 (C=0.1, MeOH). The molecular formula of GAG-C20 was determined to be C$_{31}$H$_{36}$O$_{11}$ based on ESI-MS peak at m/z 607.28 ([M+Na]$^+$), 1191([2M+Na]$^+$). The structure GAG-C20 was identified by NMR and MS to be 4,4',7",9"-tetrahydroxy-3,3",4',5-tetramethyxy-3',8"-oxy-7,9',7',9-diepoxylignan (Ficussesquilignan B) according to IUPAC nomenclature.

$^1$H-NMR (400 MHz, CD$_3$OD, ppm) [delta]: 6.67-6.96 (8H, aromatic proton), 4.74 (2H, H-7,7'), 3.13 (2H, H-8,8'), 3.89, 4.28 (2H×2, H-9, H-9'), 4.90 (1H, H-7"), 4.26 (1H, H-8"), 3.61, 3.90 (2H, H-9"), 3.82 (6H, s, OCH$_3$-3', 4'), 3.85 (6H, s, OCH$_3$-3",5).

$^{13}$C-NMR (100 MHz, CD$_3$OD, ppm) [delta]: 133.5 (C-1), 104.1 (C-2,6), 154.3 (C-3, 5), 130.5 (C-4), 132.2 (C-1'), 110.8 (C-2'), 147.1 (C-3'), 148.9 (C-4'), 115.5 (C-5'), 120.5 (C-6'), 132.5 (C-1"), 111.2 (C-2"), 152.4 (C-3"), 146.6 (C-4"), 115.9 (C-5"), 122.3 (C-6"), 87.2 (C-7,7'), 55.2 (C-8,8'), 72.7 (C-9, 9), 87.9 (C-7"), 74.8 (C-8"), 61.6 (C-9"), 56.6 56.4, 56.3, 55.7 (OCH$_3$).

Compound GAG-C49 was obtained as white paste. The molecular formula of GAG-C49 was found to be the C$_{20}$H$_{24}$O$_5$ and molecular weight was 344.16 which were deduced from a molecular ion at m/z [M+Na]$^+$ 367.30 in positive ESI-MS. GAG-C49 was elucidated by mainly NMR and MS to (7α,7'α,8β,8'β)-4,4'-dihydroxyl-3,3'-dimethyoxyl-7,4'-epoxylignane according to IUPAC nomenclature.

$^1$H-NMR (400 MHz, CD$_3$OD, ppm) [delta]: 6.98 (2H, H-2, 2'), 6.78, 6.83 (4H, H-4, 4', H-5,5'), 4.64 (2H, d, H-7, H-7'), 1.82 (2H, m, H-8,8'), 1.32 (3H, s, CH$_3$-9), 3.88 (6H, s, OCH$_3$-3,3'), 1.02 (6H, d, CH$_3$-9,9'). $^{13}$C-NMR (100 MHz, CD$_3$OD, ppm) [delta]: 148.7 (C-3, C-3'), 148.2 (C-4, C-4'), 134.7 (C-1, C-1'), 109.6 (C-2, C-2'), 110.8 (C-5, C-5'), 118.5 (C-6, C-6'), 87.1 (C-7, C-7'), 44.4 (C-8, C-8'), 12.9 (C-9, C-9'), 55.8, 55.9 (OCH$_3$-3,3').

Compound GAG-C64 was obtained as white paste. The molecular formula of GAG-C64 was found to be $C_{20}H_{20}O_5$ and molecular weight was 340.13 which were deduced from a molecular ion at m/z [M+Na]$^+$ 363.22 in positive ESI-MS. GAG-C64 was elucidated by mainly NMR and MS to be 4-hydroxyl-3,3'-dimethoxyl-(7'E)-4',7-epoxy-8,5'-neoligna-7'-en-9'-al according to IUPAC nomenclature.

$^1$H-NMR (400 MHz, CD$_3$OD, ppm) [delta]: 6.79, 6.87 (2H, H-5, 6), 6.99, 7.19, 7.20 (3H, H-2, H-2', H-6'), 7.62 (1H, d, H-7'), 6.68 (1H, dd, H-8'), 5.18 (1H, d, H-7), 3.53 (1H, H-8), 1.32 (3H, s, CH$_3$-9), 3.74, 3.71 (6H, s OCH$_3$-3,3'), 9.58 (1H, H-9'). $^{13}$C-NMR (100 MHz, CD$_3$OD, ppm) [delta]: 149.0 (C-3), 145.8 (C-3'), 147.9 (C-4), 152.0 (C-4"), 129.6 (C-1), 132.5 (C-1'), 135.5 (C-5'), 110.4 (C-2), 116.1 (C-5), 120.3 (C-6), 113.8 (C-2'), 118.8 (C-6'), 95.4 (C-7), 46.4 (C-8), 18.2 (C-9), 155.9 (C-7'), 126.9 (C-8'), 195.5 (C-9'), 56.7, 56.4 (OCH$_3$-3,3').

Compound GAG-C70 was obtained as white paste. The molecular formula of GAG-C70 was found to be $C_{20}H_{22}O_4$ and molecular weight was 326.15 which were deduced from a molecular ion at m/z [M+Na]$^+$ 349.40 in positive ESI-MS. GAG-C70 was elucidated by mainly NMR and MS to be (7'α,8'β)-4,4'-dihydroxyl-3,3'-dimethoxyl-6,7'-cyclo-ligane-7-en according to IUPAC nomenclature.

$^1$H-NMR (300 MHz, CD$_3$OD, ppm) [delta]: 6.46-6.62 (5H, m, H-2,5, H-2',5',6'), 6.07 (1H, d, H-7), 3.66 (1H, H-7'), 2.33 (1H, H-8'), 3.74, 3.71 (6H, s OCH$_3$-3,3'), 1.76 (3H, s, CH$_3$-9), 1.05 (3H, s, CH$_3$-9'). $^{13}$C-NMR (75 MHz, CD$_3$OD, ppm) [delta]: 147.3 (C-3), 146.4 (C-3'), 144.7 (C-4), 144.3 (C-4'), 126.9 (C-1), 137.7 (C-1'), 112.4 (C-2), 114.6 (C-5), 127.7 (C-6), 113.1 (C-2'), 119.9 (C-5'), 121.0 (C-6'), 111.2 (C-7), 138.4 (C-8), 18.1 (C-9), 51.0 (C-7'), 42.6 (C-8'), 21.3 (C-9'), 55.4, 55.2 (OCH$_3$-3,3').

Compound GAG-C77 was obtained as light yellow paste. The molecular formula of GAG-C77 was found to be $C_{18}H_{18}O_5$ and molecular weight 314.33. The structure of GAG-C77 was identified by NMR and MS to be 4-hydroxyl-3,3'-dimethoxyl-4",7-epoxy-8,5'-oxyneoligna-7'-al according to IUPAC nomenclature.

$^1$H-NMR (300 MHz, CD$_3$OD, ppm) [delta]: 6.99 (1H, H-2), 7.44 (2H, H-2', H-6'), 6,81, 6.87 (2H, dd, H-5.6), 5.26 (H, d, H-7), 3.55 (1H, H-8), 1.28 (3H, d, H-9), 9.79 (1H, H-7'), 3.83, 3.92 (6H, s, OCH$_3$-3,3'). $^{13}$C-NMR (75 MHz, CD$_3$OD, ppm) [delta]: 149.0 (C-3), 155.7 (C-3'), 145.1 (C-4), 143.6 (C-4'), 148.1.0 (C-5'), 130.2 (C-1), 133.0 (C-1'), 110.8 (C-2), 111.8 (C-2'), 116.1 (C-5), 120.4 (C-6), 115.5 (C-6'), 95.0 (C-7), 46.1 (C-8), 18.1 (C-9), 192.5 (C-7'), 56.7, 56.5 (OCH$_3$-3,3').

Compound GAG-C121 was obtained as viscous oil and UV absorption was at $\lambda_{max}$ (CH$_3$CN): 258 nm. The molecular formula of GAG-C121 was found to be $C_{21}H_{26}O_6$ based on a molecular ion at m/z [M+Na]$^+$ 397.37 in positive ESI-MS. GAG-C121 was identified by NMR and MS to be 3,3',5-trimethoxy-4,7-dihydroxyl-(7'E)-(8-O-4')-neolignan-7'en according to IUPAC nomenclature.

$^1$H-NMR (300 MHz, CD$_3$OD, ppm) [delta]: 6.97 (1H, d, 1.5, H-2), 6.81 (1H, d, 1.5, H-6), 6.69 (1H, H-2'), 6.83 (1H, d, 8.1, H-5'), 6.75 (1H, d, 8.4, H-6'), 6.34 (1H, d, 15.9, H-7'), 6.24 (1H, m, H-8'), 4.60 (1H, d, 6.9, H-7), 4.08 (1H, m, H-8), 3.86, 3.84 (9H, s, OCH$_3$-3,3',5), 1.07 (3H, d, 6.3, CH$_3$-9), 1.86 (3H, dd, 1.2, 6.3, CH$_3$-9'). $^{13}$C-NMR (75 MHz, CD$_3$OD, ppm) [delta]: 149.0 (C-3), 149.1 (C-3', C-5) 146.2 (C-4'), 133.2 (C-1), 134.2 (C-1'), 136.2 (C-4), 121.3 (C-6'), 115.8 (C-5'), 111.8 (C-2'), 105.6 (C-2), 104.3 (C-6), 132.1 (C-7'), 126.2 (C-8'), 79.6 (C-7), 86.3 (C-8), 17.3 (C-9), 18.5 (C-9'), 56.5, 56.4 (OCH$_3$-3,3',5).

Compound GAG-C66 was obtained as white paste. The molecular formula of GAG-C66 was found to be $C_{19}H_{24}O_2$ and molecular weight was 284.39 which were deduced from a molecular ion at m/z [M+H]$^+$ 285.1921 in positive HRESI-MS. The structure of GAG-C66 was elucidated by mainly NMR and MS to be 4,6-diene-3,17-dioxo-androstane according to IUPAC nomenclature.

$^1$H-NMR (300 MHz, CD$_3$OD, ppm) [delta]: 5.69 (1H, s, H-4), 6.25 (1H, dd, H-6), 6.34 (1H, dd, H-7), 1.64, 2.17 (2H, m, H-1), 2.54, 2.69 (2H, m, H-2), 1.32 (1H, H-8), 1.59 (1H, H-9), 1.54, 1.75 (2H, m, H-11), 1.82, 2.36 (2H, m, H-12), 2.48 (1H, H-14), 1.24, 2.13 (2H, m, H-15), 2.17, 2.63 (2H, m, H-16), 0.99 (3H, s, CH$_3$-18), 1.19 (3H, s, CH$_3$-19). $^{13}$C-NMR (75 MHz, CD$_3$OD, ppm) [delta]: 201.0 (C-3), 221.2 (C-17), 123.0 (C-4), 165.5 (C-5), 128.1 (C-6), 139.9 (C-7), 33.6 (C-1), 35.4 (C-2), 51.1 (C-8), 49.7 (C-9), 37.4 (C-10), 20.0 (C-11), 21.3 (C-12), 50.1 (C-13), 36.5 (C-14), 31.4 (C-15), 33.9 (C-16), 13.1 (C-18), 15.6 (C-19)

Compound GAG-C67 was obtained as amorphous powder. The molecular formula of GAG-C67 was found to be $C_{19}H_{24}O_2$ and exact mass was 284.18 which were deduced from a molecular ion at m/z [M+H]$^+$ 285.1903 in positive HRESI-MS. The structure of GAG-C67 was elucidated by mainly NMR and MS to be 4,6,16-triene-17-hydroxy-3-oxo-androstane according to IUPAC nomenclature.

$^1$H-NMR (300 MHz, CD$_3$OD, ppm) [delta]: 5.67 (1H, s, H-4), 6.22 (1H, dd, H-6), 6.43 (1H, d, H-7), 5.74 (1H, m, H-15), 6.12 (1H, d, H-16), 4.28 (1H, H-17), 1.72, 2.05 (2H, m, H-1), 2.37, 2.65 (2H, m, H-2), 1.29 (1H, H-8), 2.47 (1H, H-9), 1.56, 1.64 (2H, m, H-11), 1.55, 1.93 (2H, m, H-12), 1.99 (1H, H-14), 0.91 (3H, s, CH$_3$-18), 1.18 (3H, s, CH$_3$-19). $^{13}$C-NMR (75 MHz, CD$_3$OD, ppm) [delta]: 201.1 (C-3), 122.8 (C-4), 165.9 (C-5), 127.8 (C-6), 141.3 (C-7), 135.3 (C-15), 129.8 (C-16), 84.6 (C-17), 33.6 (C-1), 33.8 (C-2), 52.2 (C-8), 35.5 (C-9), 36.5 (C-10), 20.3 (C-11), 34.5 (C-12), 51.7 (C-13), 55.0 (C-14), 13.8 (C-18), 16.8 (C-19)

Compound GAG-C68 was obtained as amorphous powder. The molecular formula of GAG-C68 was found to be $C_{21}H_{30}O_2$ and molecular weight was 314.46 which were deduced from a molecular ion at m/z [M+H]$^+$ 315.1990 in positive HRESI-MS. The structure of GAG-C68 was elucidated by mainly NMR and MS to be 4,6-diene-20-hydroxy-3-oxo-pregnane according to IUPAC nomenclature.

$^1$H-NMR (300 MHz, CD$_3$OD, ppm) [delta]: 5.65 (1H, s, H-4), 6.18 (1H, dd, H-6), 6.25 (1H, dd, H-7), 4.09 (1H, dd, H-20), 1.71, 2.05 (2H, m, H-1), 2.37, 2.60 (2H, m, H-2), 1.35 (1H, m, H-8), 2.36 (1H, m, H-9), 1.47, 1.64 (2H, m, H-11), 1.55, 1.85 (2H, m, H-12), 1.47 (1H, H-14), 1.96, 2.32 (2H, m, H-15), 2.04, 2.62 (2H, m, H-16), 2.28 (1H, H-17), 0.79 (3H, s, CH$_3$-18), 1.15 (3H, s, CH$_3$-19), 1.21 (3H, d, CH$_3$-21). $^{13}$C-NMR (75 MHz, CD$_3$OD, ppm) [delta]: 202.1 (C-3), 123.7 (C-4), 167.2 (C-5), 128.6 (C-6), 143.4 (C-7), 70.8 (C-20), 34.8 (C-1), 35.0 (C-2), 52.2 (C-8), 40.0 (C-9), 37.5 (C-10), 21.6 (C-11), 24.7 (C-12), 43.6 (C-13), 54.8 (C-14), 27.4 (C-15), 38.9 (C-16), 59.5 (C-17), 12.8 (C-18), 16.7 (C-19), 24.1 (C-21).

Compound GAG-C72 was obtained as amorphous powder. The molecular formula of GAG-C72 was found to be $C_{19}H_{22}O_2$ and molecular weight was 282.38 which were deduced from a molecular ion at m/z [M+H]$^+$ 283.1921 in positive HRESI-MS. The structure of GAG-C72 was elucidated by mainly NMR and MS to be 1,4,6-triene-3,17-dioxo-androstane according to IUPAC nomenclature.

$^1$H-NMR (300 MHz, CD$_3$OD, ppm) [delta]: 7.31 (1H, d, H-1), 6.24 (1H, d, H-2), 6.03 (1H, s, H-4), 6.27 (1H, d, H-6), 6.41 (1H, d, H-7), 2.55 (1H, H-8), 1.21 (1H, H-9), 1.95, 2.14 (2H, m, H-11), 1.81, 1.93 (2H, m, H-12), 1.58 (1H, H-14), 1.32, 1.87 (2H, m, H-15), 2.16, 2.51 (2H, m, H-16), 0.99 (3H, s, $CH_3$-18), 1.19 (3H, s, $CH_3$-19). $^{13}$C-NMR (75 MHz, $CD_3OD$, ppm) [delta]: 188.3 (C-3), 221.8 (C-17), 128.2 (C-1), 156.0 (C-2), 124.1 (C-4), 165.8 (C-5), 128.9 (C-6), 138.6 (C-7), 39.0 (C-8), 50.1 (C-9), 43.0 (C-10), 22.3 (C-11), 22.4 (C-12), 49.3 (C-13), 50.2 (C-14), 32.5 (C-15), 36.5 (C-16), 14.3 (C-18), 21.3 (C-19).

Compound GAG-C38 was obtained as light yellow oil. The molecular formula of GAG-C38 was found to be $C_{13}H_{10}O_5$ and molecular weight 246.22. The structure of GAG-C38 was identified by NMR and MS to be the 5,8-dimethoxyl-psoralen.

$^1$H-NMR (400 MHz, $CD_3OD$, ppm) [delta]: 6.29 (1H, d, H-2), 8.25 (1H, d, H-3), 7.23 (1H, H-2'), 7.83 (1H, H-3'), 4.10 (3H, s, $OCH_3$), 4.21 (3H, s, $OCH_3$). $^{13}$C-NMR (100 MHz, $CD_3OD$, ppm) [delta]: 160.5 (C-2), 112.8 (C-3), 139.5 (C-4), 144.4 (C-5), 114.9 (C-6), 149.9 (C-7), 128.3 (C-8), 143.7 (C-9), 107.7 (C-10), 145.3 (C-2'), 105.3 (C-3'), 61.9 (3H, $OCH_3$), 61.7 (3H, $OCH_3$).

Compound GAG-C40 was obtained as light yellow oil. The molecular formula of GAG-C40 was found to be $C_{12}H_{12}O_5$ and molecular weight 236.22. The structure of GAG-C40 was identified by NMR and MS to be 6,7,8-trimethoxyl-coumarin.

$^1$H-NMR (400 MHz, $CD_3OD$, ppm) [delta]: 6.33 (1H, d, H-2), 7.87 (1H, d, H-3), 6.97 (1H, s, H-5), 3.88 (3H, s, $OCH_3$), 3.93 (3H, s, $OCH_3$), 3.97 (3H, s, $OCH_3$). $^{13}$C-NMR (100 MHz, $CD_3OD$, ppm) [delta]: 162.5 (C-2), 115.4 (C-3), 145.8 (C-4), 105.6 (C-5), 151.6 (C-6), 143.8 (C-7), 147.1 (C-8), 142.0 (C-9), 116.0 (C-10), 61.8, 62.2, 62.3 ($OCH_3$)

Compound GAG-C50 was obtained as yellow oil. The molecular formula of GAG-C50 was found to be $C_{16}H_{14}O_5$ and molecular weight 286.28. The structure of GAG-C50 was identified by NMR and MS to be 8-(2-hydroxy-3-methylbut-3-enyloxy)-psoralen.

$^1$H-NMR (300 MHz, $CD_3OD$, ppm) [delta]: 6.38 (1H, d, H-2), 8.03 (1H, d, H-3), 7.58 (1H, s, H-5), 6.96 (1H, d, H-2'), 7.89 (1H, d, H-3'), 4.42, 4.46 (2H, m, H-2"), 4.54 (1H, m, H-3"), 5.13, 4.96 (2H, H-4"), 1.67 (3H, s, $CH_3$-4"), 1.83 (3H, s, $CH_3$-5"). $^{13}$C-NMR (75 MHz, $CD_3OD$, ppm) [delta]: 161.5 (C-2), 113.9 (C-3), 144.4 (C-4), 113.8 (C-5), 126.7 (C-6), 147.9 (C-7), 131.7 (C-8), 143.1 (C-9), 116.8 (C-10), 147.3 (C-2'), 106.8 (C-3'), 145.5 (C-3"), 111.9 (C-4"), 76.3 (C-1"), 74.2 (C-2"), 17.8 (C-5").

Compound GAG-C71 was obtained as light yellow oil. The molecular formula of GAG-C71 was found to be $C_{18}H_{20}O_6$ and molecular weight 332.35. The structure of GAG-C71 was identified by NMR and MS to be 8-(3-Ethoxy-2-hydroxy-3-methylbutyloxy)-psoralen.

$^1$H-NMR (300 MHz, $CD_3OD$, ppm) [delta]: 6.38 (1H, d, H-2), 8.04 (1H, d, H-3), 7.58 (1H, s, H-5), 6.96 (1H, d, H-2'), 7.89 (1H, d, H-3"), 4.45 (1H, t, H-2"), 4.04, 4.77 (2H, H-1"), 1.21 (6H, s, $CH_3$-4"), 1.27 (3H, s, $CH_3$-5"), 3.49 (2H, m, $CH_2$-6"), 1.11 (3H, t, $CH_3$-7"). $^{13}$C-NMR (75 MHz, $CD_3OD$, ppm) [delta]: 162.1 (C-2), 115.0 (C-3), 147.3 (C-4), 114.8 (C-5), 126.7 (C-6), 149.7 (C-7), 131.3 (C-8), 144.9 (C-9), 115.1 (C-10), 146.6 (C-2'), 107.9 (C-3'), 66.9 (C-1"), 76.5 (C-2"), 81.0 (C-3"), 22.5 (C-4"), 21.9 (C-5"), 63.2 (C-6"), 15.8 (C-7").

Compound GAG-C81 was obtained as light yellow oil. The molecular formula of GAG-C81 was found to be $C_{16}H_{14}O_4$ and molecular weight 270.28. The structure of GAG-C81 was identified by NMR and MS to be 8-(3-methylbut-2-enyloxy)-psoralen (Imperatorin).

$^1$H-NMR (300 MHz, $CD_3OD$, ppm) [delta]: 6.37 (1H, d, H-2), 8.01 (1H, d, H-3), 7.56 (1H, d, H-5), 6.95 (1H, d, H-2'), 7.88 (1H, d, H-3'), 5.55 (1H, m, H-2"), 4.96, 4.98 (2H, H-1"), 1.67 (3H, s, $CH_3$-4"), 1.71 (3H, s, $CH_3$-5"). $^{13}$C-NMR (75 MHz, $CD_3OD$, ppm) [delta]: 162.6 (C-2), 115.1 (C-3), 148.3 (C-4), 114.8 (C-5), 127.7 (C-6), 149.9 (C-7), 132.3 (C-8), 144.9 (C-9), 115.1 (C-10), 146.6 (C-2'), 107.9 (C-3'), 120.8 (C-2"), 140.9 (C-3"), 70.9 (C-1"), 23.8 (C-4"), 18.1 (C-5").

Compound GAG-C82 was furanocoumarin obtained as light yellow oil. The molecular formula of GAG-C82 was found to be $C_{17}H_{16}O_5$ and molecular weight 330.31. The structure of GAG-C82 was identified by NMR and MS to be 8-(3-methylbut-2-enyloxy)-5-methoxyl-psoralen (Phellopterin).

$^1$H-NMR (300 MHz, $CD_3OD$, ppm) [delta]: 6.29 (1H, d, H-2), 8.25 (1H, d, H-3), 7.19 (1H, d, H-2'), 7.80 (1H, d, H-3'), 5.55 (1H, m, H-2"), 4.96, 4.98 (2H, H-1"), 4.21 (3H, $OCH_3$), 1.64 (3 H, s, $CH_3$-4"), 1.70 (3 H, s, $CH_3$-5"). $^{13}$C-NMR (75 MHz, $CD_3OD$, ppm) [delta]: 162.5 (C-2), 112.8 (C-3), 141.0 (C-4), 141.3 (C-5), 115.8 (C-6), 145.9 (C-7), 128.5 (C-8), 130.6 (C-9), 108.3 (C-10), 146.6 (C-2'), 106.2 (C-3'), 120.6 (C-2"), 140.7 (C-3"), 71.0 (C-1"), 23.7 (C-4"), 18.2 (C-5"), 61.4 (—$OCH_3$)

Compound GAG-C74 was obtained as amorphous powder. The molecular weight of GAG-C74 was 472.70 and molecular formula was found to be $C_{30}H_{48}O_4$ based on reported data. The structure of GAG-C74 was identified by NMR and MS to be 3β,23-dihydroxyolean-12-en-28-oic acid according to IUPAC nomenclature.

$^1$H-NMR (300 MHz, $CD_3OD$, ppm) [delta]: 1.10, 1.72 (2H, m, H-1), 1.78, 2.01 (2H, m, H-2), 3.66 (1H, H-3), 1.30 (1H, m, H-5), 0.93, 1.4 (2H, m, H-6), 1.3, 1.5 (2H, m, H-7), 1.74 (1H, m, H-9), 1.91 (2H, m, H-11), 5.23 (1H, t, H-12), 1.1, 1.9 (2H, m, H-15), <1.2> (2H, H-16), 2.85 (1H, H-18), 1.05, 2.30 (2H, H-19), 1.2, 1.9 (2H, H-21), 1.8, 2.2 (2H, H-22), 3.50, 3.61 (2H, H-23), 1.16 (3H, s, $CH_3$-24), 0.97 (3H, s, $CH_3$-25), 0.70 (3H, s, $CH_3$-26), 0.93 (3H, s, $CH_3$-27), 0.81 (3H, s, $CH_3$-29), 0.90 (3H, s, $CH_3$-30).

$^{13}$C-NMR (75 MHz, $CD_3OD$, ppm) [delta]: 39.5 (C-1), 27.5 (C-2), 77.1 (C-3), 40.5 (C-4), 55.5 (C-5), 18.8 (C-6), 33.6 (C-7), 39.4 (C-8), 47.7 (C-9), 37.9 (C-10), 24.0 (C-11), 126.1 (C-12), 138.6 (C-13), 42.9 (C-14), 28.9 (C-15), 24.6 (C-16), 48.3 (C-17), 53.6 (C-18), 43.0 (C-19), 43.3 (C-20), 31.6 (C-21), 34.9 (C-22), 65.4 (C-23), 12.8 (C-24), 16.3 (C-25), 17.8 (C-26), 24.5 (C-27), 181.3 (C-28), 33.5 (C-29), 24.1 (C-30).

The active neuro protective compound GAG-C14 was obtained as oil. The molecular weight of GAG-C14 was 330.50 and molecular formula was found to be $C_{19}H_{38}O_4$ based on a molecular ion at m/z $[M+Na]^+$353.31 in positive ESI-MS. The structure of GAG-C14 was identified by NMR spectroscopy to be 2,3-dihydroxypropyl palmitate (palmitic ester of glycerol).

$^1$H-NMR (300 MHz, $CD_3OD$, ppm) δ: 0.88 (3H, s), 1.65 (2H, m), 1.29 (2H, m), 1.31 (2H, m), 1.30 (20H, m), 2.35 (2H, m), 4.20 (2H, m), 3.68, 3.59 (2H, m, —OH), 3.92 (1H, m, —OH). $^{13}$C-NMR (75 MHz, $CD_3OD$, ppm) δ: 174.2, (C-1), 70.3 (C-2), 65.1 (C-3), 63.3 (C-4), 34.2 (C-5), 25.0 (C-6), 32.0 (C-7), 22.8 (C-8), 14.1 (C-9), 29.2-29.7 (C-10).

Preparation of aglycone of pregnane glycosides by acid hydrolysis. The polyoxypregnana glycosides (~5 mg) were dissolved in 1 ml MeOH and 0.3 ml 0.1 M $H_2SO_4$ was added. The solution was heated to 80° C. for 50 min and then 1 ml $H_2O$ was added to it. After removing the methanol, the aqueous layer was extracted with diethyl ether (3×2 ml). Evaporation of diethyl ether gave ~2.5 mg of aglycone. The aglycone was analyzed and identified by HPLC chromatography and NMR spectroscopy.

Example 44

Assays, Detections, and Tests

Primary Neuronal Cultures

Cortices and hippocampi were dissected from embryonic day 18 (E18) Sprague-Dawley rats in Hanks Balanced Salt Solution. Tissues were minced with a razor blade and trypsinized followed by treatment with heat-inactivated horse serum. Isolated cells were then plated onto poly d-Lysine (PDL) (Sigma)-coated plates (12.5 µg/ml). Neurons were incubated in Neurobasal medium supplemented with 2% B27, penicillin/streptomycin and 1 mM L-glutamine at 37° C. in a humidified atmosphere of 5% $CO_2$ in air. Medium was changed to growth medium (Neurobasal Medium with penicillin/streptomycin and B27 supplement) after 3 hours. Half of the volume of the culture medium was changed once every 2-3 days for maintenance. All reagents for primary neuronal cultures were purchased from Invitrogen unless otherwise indicated.

Cell Toxicity Test

Cortical neurons of 7 days in vitro (7 DIV) were treated with various concentrations of test samples that were serially diluted in Neurobasal medium. After 24 hrs incubation, lactate dehydrogenase (LDH) release into the medium was measured via a Cytotoxicity Detection Kit (Roche). Data was calculated as the percentage of cell death compared to 1% Triton X-100.

NMDA or Glutamate Survival Assay

Cortical neurons were plated on 48-well plate (Nunc) at a density of $1.1 \times 10^5$ cells per well and cultured for 11-12 days (11-12 DIV). Neurons were pre-treated with the test compounds for 2 hours prior to N-Methyl-D-Aspartate (NMDA, Sigma) or glutamate (MSG, Sigma) treatment. Briefly, the neurons were rinsed with Locke's solution (5 mM potassium chloride, 128 mM sodium chloride, 2.7 mM calcium chloride, 1 mM di-sodium hydrogen orthophosphate, 5 mM HEPES and 10 mM glucose in Milli-Q water) without $Mg^{2+}$, followed by incubation in Locke's solution with addition of glycine (0.1 µM) for 15 minutes. After the incubation, the neurons were co-treated with the test compound (dissolved in Locke's plus glycine solution) and NMDA (20 µM) or glutamate for 20 min. Neurons were then rinsed with Locke's solution containing $Mg^{2+}$ and replaced with fresh growth medium. Cell death was assayed and quantified using the lactate dehydrogenase release assay (Cytotoxicity Detection Kit, Roche). Data was compared to a DMSO vehicle control and represented in mean±SEM. The student t-test was used for statistical analysis.

Cortical Neuron Survival Assay with B27 Withdrawal

Neurons were plated on a 48-well plate (Nunc) at a density of $1.2 \times 10^5$ cells per well were cultured for 7-8 days (7-8DIV). Neurons were pre-treated with the test compounds for 2 hours in normal growth medium. The cells were then washed with Hanks' solution twice and replaced with test samples that were serial diluted in Neurobasal medium. A tetrazole, 3-(4,5-Dimethylthiazol-2-yl)-2,5-diphenyltetrazolium bromide (MTT, 5 mg/ml) was added to the medium at a ratio of 1:10 after a 2-day incubation. MTT is reduced by living cells into purple formazan and further solubilized in 20% SDS solution; therefore, the colored solution was measured by spectrophotometer and cell viability was quantified. Data was compared to a DMSO vehicle control in the presence of B27 and represented in mean±SEM. The student t-test was used for statistical analysis.

Cortical Neuron Survival Assay with Amyloid-Beta Peptide Insult

Neurons were plated on a 48-well plate (Nunc) at a density of $1.1 \times 10^5$ cells per well were cultured for 7-8 days (7-8DIV). Neurons were pre-treated with the test compounds for 2 hours in normal growth medium. The cells were then incubated with test samples and amyloid-beta peptide fragment 25-35 (Aβ, 10 µM, Sigma) in growth medium. A tetrazole, 3-(4,5-Dimethylthiazol-2-yl)-2,5-diphenyltetrazolium bromide (MTT, 5 mg/ml) was added to the medium at a ratio of 1:10 after 24-hr incubation. MTT is reduced by living cells into purple formazan and further solubilized in 20% SDS solution; therefore, the colored solution was measured by spectrophotometer and cell viability was quantified. Data was compared to a DMSO vehicle control and represented in mean±SEM. The student t-test was used for statistical analysis.

Caspase-3 Expression in Cortical Neuron with the Presence of Amyloid-Beta Peptide Neurons plated on 60 mm plate (TPP, Corning) at a density of $3 \times 10^6$ cells per plate were cultured for 7-8 days (7-8DIV). Neurons were pre-treated with the test compounds for 2 hours in normal growth medium. The cells were then incubated with test samples and amyloid-beta peptide fragment 25-35 (Aβ, 10 uM, Sigma) in growth medium. After 24 hours incubation, cultures were immediately placed on ice and rinsed with cold D-PBS with the addition of protease inhibitors. Total protein lysates were collected by RIPA buffer addition and debris was removed by centrifugation. Lysates were quantified and aliquots were stored at −80° C. before use. Before being loaded, the lysates were heated to 95° C. for 10 min, then vortexed and centrifuged for 7 min at 15,000×g. Extracted proteins were electrophoresed on 10% SDS-polyacrylamide gel and transblotted onto nitrocellulose membrane. The membranes were washed with 5% (w/v) powdered milk dissolved in PBS with 0.1% Triton X-100, followed by incubation at 4° C. overnight with primary antibodies against caspase-3 that also detected cleaved caspase-3 (1:1000, Cell Signaling Technology). The membranes were washed and incubated with horseradish peroxidase (HRP)-conjugated secondary antibodies. The signal was visualized using ECL Western Blotting Kit. Blots were then stripped and probed for total ERK expression.

Whole-Cell Patch Clamp

Hippocampal neurons were plated onto PDL-coated 35 mm dishes (NUNC) at a density of $3 \times 10^5$ cells per plate. Half of the medium was changed with NB, B27 and 50 mM L-glutamine every 2 to 3 days. On day 12 in vitro (12DIV), whole-cell patch clamp study was performed. The internal solution contained 120 mM cesium chloride, 20 mM tetraethylammonium chloride, 2 mM magnesium chloride, 1 mM calcium chloride and 10 mM HEPES (pH 7.2). The external solution contained 137 mM sodium chloride, 1 mM sodium bicarbonate, 0.34 mM sodium phosphate dibasic, 5.37 mM potassium chloride, 0.44 mM potassium phosphate monobasic, 2.5 mM HEPES (pH 7.4) and 22.2 mM glucose. Optimized concentrations of test samples mixed with NMDA (20 µM) were arranged in linear array of up to 8 individual controlled pipes (List Medical, Germany) which were connected to solution reservoirs. Pipettes were fire-polished to produce a pipette resistance of 3-5 MΩ. Holding potential of patched cells was kept at −70 mV and currents were recorded using Axopatch-200B amplifier (Axon Instruments, USA). Tetrodotoxin (5 µM) and bicuculline methiodide (20 µM) (Tocris) were present in the bath solution to block synaptic transmission mediated by voltage-gated sodium channels and GABAergic channels, respectively. Data was analyzed by pClamp9 software and percentage of inhibition on NMDA-induced current was' represented in comparison to a DMSO solvent control.

Fluorescent Calcium Assay on Cortical Neuron Cultures

Cortical neurons were plated at $3 \times 10^4$ per well onto clear-bottomed 96-well black plates (BD Bioscience) coated with poly-lysine. Cultures of 9 days in vitro (9DIV) to 13DIV were used for NMDA receptor activity assay. On the day of the assay, primary cultures were incubated in a balanced salt solution buffer consisting of 10 μM HEPES pH 7.4, probenecid, and the calcium sensitive fluorescent dye Fluo-4-AM (Molecular Probes) (4 μM) for 1 hr at 37° C. Cells were then placed onto a Fluorimetric Imaging Plate Reader (FLIPR, Molecular Devices), along with a corresponding plate that contained serially diluted test samples. FLIPR automatically transferred the test compounds into the wells at an injection speed of 50 μl per second. The subsequent calcium ion movements from extracellular membrane to the intracellular membrane were monitored via the fluorescent dye for 2 minutes. Relative fluorescence changes were measured by FLIPR; data was compared to a DMSO vehicle control and represented in mean±SEM. The student t-test was used for statistical analysis.

Immunocytochemical Analysis of Neurons After B27 Withdrawal

Cortical neurons were plated on 35-mm dishes (NUNC) at a density of $1 \times 10^6$ cells per plate using Neurobasal medium (Invitrogen) supplemented with 2% B27 (Invitrogen). Neurons at 7-8 days in vitro (7-8DIV) were subjected to treatment with the test compounds. Neurons were pre-treated with the test compound for 2 hours prior to B27 withdrawal as described above. After 48-hr incubation, neurons were fixed with 4% paraformaldehyde for 20 minutes at room temperature, permeabilized and blocked with 4% goat serum and 0.4% Triton X-100. Double staining was performed by incubating the neurons with mouse monoclonal antibody specific for β-tubulin isotype III (1:1000; Sigma) at 4° C. overnight followed by FITC-conjugated goat anti-mouse antibody (1:1000; Invitrogen). Neurons were counter-stained with DAPI (1:5000) to visualize nuclei before mounting. Cell morphology was then analyzed using a fluorescence microscope with a 40× objective (DMRA; Leica). Fluorescent images were acquired with a RT Slider digital camera (#2.3.1, Diagnostics Instruments), collected with SPOT software (Diagnostics Instruments) and composited with Adobe Photoshop software.

Western Blot Detection for Signaling Proteins

PC12 cells and cortical neurons were used in Western blot analysis. Stock of PC12 cells was obtained from ATCC and maintained in DMEM supplemented with 5% horse serum and 6% fetal bovine serum in the presence of streptomycin and penicillin. PC12 cells were sub-cultured once every 3 days and discarded after passage 25. Cortical neurons were plated onto 60 mm plates (TPP, Corning) at a density of $3 \times 10^6$ cells per plate. Experiments were performed after 7-8 days in vitro (DIV). Both neurons and PC12 cells were treated with test samples at different concentrations for 15 min or at optimal concentration for various time intervals. Cultures were immediately placed on ice and rinsed with cold D-PBS with the addition of protease inhibitors. Total protein lysates were collected by RIPA buffer addition and debris was removed by centrifugation. Lysates were quantified and aliquots were stored at −80° C. before use. Before being loaded, the lysates were heated to 95° C. for 10 min, vortexed and centrifuged for 7 min at 15,000×g. Extracted proteins were electrophoresed on 10% SDS-polyacrylamide gel and transblotted onto nitrocellulose membrane. The membranes were washed with 5% (w/v) powdered milk dissolved in PBS with 0.1% Triton ×100, followed by incubation at 4° C. overnight with primary antibodies against phosphorylated ERK (P-ERK, 1:1000), P-CREB Ser$^{133}$ (1:1000), P-Akt (1:1000), P-P38 (1:1000), or P-MEK (1:1000), purchased from Cell Signaling Technology. The membranes were washed and incubated with horseradish peroxidase (HRP)-conjugated secondary antibodies. Signal was visualized using ECL Western Blotting Kit. Blots were then stripped and probed for total ERK, CREB, Akt, P38 and MEK expression.

Quantification of Spine

Cultured hippocampal neurons were seeded on 18 mm coverslips coated with poly-D-lysine in 12-well-plates (Falcon). The neurons were then grown in Neurobasal medium (Invitrogen) supplemented with 2% B27 (Invitrogen) and 0.5 mM glutamine. To visualize the morphology of dendritic spines, the neurons were transfected with GFP DNA construct between 7-9 DIV by using calcium phosphate precipitation. To examine the development of dendritic spines, the neurons were treated with the test compound on 14 DIV. The neurons were then fixed with 4% paraformaldehyde and morphology was examined using confocal microscopy. To quantify spine density in cultured hippocampal neurons, a stack of images (z step, 0.5 μm) was collected using a 60× objective. Images were merged and analyzed using MetaMorph software (Universal Imaging Corp). Dendritic spines, defined as protrusions at least 0.5 μm from the dendritic surface, were scored and expressed as per μm length of dendrite. Three dendrites from each neuron was randomly selected and quantified in a double-blinded manner. For each experimental condition, twenty to thirty neurons were analyzed from 3 independent experiments. Data was presented as mean±SEM.

RNA Extraction, cDNA Synthesis, and Real-Time Quantitative PCR

Cortical neurons of 7-8DIV were treated with Adelostemma gracillimum refined fraction at various time intervals. Cells were washed in D-PBS (DEPC treated) and total RNA was extracted using RNA Shredder kit followed by RNeasy Mini kit (Invitrogen) according to the manufacturer's protocol. The quality of RNA was then visualized by formaldehyde denaturing gel electrophoresis. Total RNA was reverse-transcribed into single-stranded cDNA using SuperScript II Reverse Transcriptase (Invitrogen) with oligo-dT primers. Real-time Quantitative PCR was performed using Power SYBR Green PCR Master Mix on the 7500Fast Real-Time PCR System (Applied Biosystems). Thermal cycling was initiated with a 10-min denaturation step at 95° C., followed by 40 cycles of 95° C. for 30 sec, 60° C. for 1min and 72° C. for 30 sec. The final product was subjected to a Melt-curve detection at the end of the reaction. Regulation of gene expression was normalized against home gene, hypoxanthine phosphoribosyltransferase 1(HPRT1) and glyceraldehyde 3-phosphate dehydrogenase (GAPDH). Real-time PCR primers are as follows:

| BDNF Forward: | TTGAGCACGTGATCGAAGAG |
|---|---|
| BDNF Reverse: | CCAGCAGAAAGAGCAGAGGA |
| NT-3 Forward: | GGGGGATTGATGACAAACAC |
| NT-3 Reverse: | ACAAGGCACACACACAGGAA |
| Bcl-2 Forward: | ATAACCGGGAGATCGTGATG |
| Bcl-2 Reverse: | CAGGCTGGAAGGAGAAGATG |

-continued

```
c-fos Forward:    GGAGCCGGTCAAGAACATTA
c-fos Reverse:    TGCTGCATAGAAGGAACCAG
HPRT1 Forward:    TGACACTGGTAAAACAATGCA
HPRT1 Reverse:    GGTCCTTTTCACCAGCAAGCT
GAPDH Forward:    TGCACCACCAACTGCTTAGC
GAPDH Reverse:    GGCATGGACTGTGGTCATGAG
```

CREB Promoter Assay

Freshly isolated embryonic cortical neurons were transfected with a luciferase reporter gene (Cre-Luc) linked to CREB activation following the ACM lipofectamine method using Lipofectamine 2000, a cationic liposome based reagent (Invitrogen). The transfected cells were then seeded onto PDL-coated 48 well plates (NUNC) at a density of $1.3 \times 10^5$ cells per well and cultured for 7-12 days (7-12DIV) in Neurobasal medium with B27 supplement. Transfection was performed using 1 µL Lipofectamine 2000 and 0.4 µg DNA per well. Neurons were then treated with test samples for time periods of 6 hours. After treatment, the cells were washed with ice-cold DPBS and 100 µL of 1× luciferase lysis buffer (Promega) was added. The plates were placed in −20° C. to freeze the cells, after which they were thawed to facilitate lysis. The lysates were transferred onto white bottom plates and assayed for renilla luciferase using the luciferase assay kit (Promega). Increased CREB activation in the neurons leads to an enhanced luciferase production and this was quantified using a Promega GloMax™ 96 microplate luminometer. Data was compared to a DMSO vehicle control and represented in mean±SEM. The student t-test was used for statistical analysis. BDNF and rolipram were used as positive controls.

Morris Water Maze 6-8 week old (young) or 18-month old (aged) outbred male I.C.R. mice were housed five per cage in a climate controlled animal room (23-25° C.) under 12 hours light/dark cycling. The animals were allowed access to water and food ad lib. The mice used for the experiment were brought to particular laboratory conditions for three days before the test sessions, and all experiments were conducted between 14:00 and 18:00. The mice were assigned into one of three groups: group 1, young mice administered with vehicle control; group 2, aged mice administered with vehicle control; or group 3, aged mice administered with AG-0 (30 mg/kg). AG-0 was dissolved in physiological saline before the experiments each day. Oral administrations (p.o.) of AG-0 was initiated at the first day of the task and administered according to a volume of 10 mg/kg body weight. The compound was administered 45 minutes prior to the swimming tasks and performed daily for 5-6 consecutive days until the end of the task.

Each mouse was subjected to 4 trials per day. A trial began when a mouse held facing the pool wall was immersed in the water. The mouse was then allowed 60 seconds to search for a hidden platform. If the mouse failed to escape (locate the platform) within this time period, it was guided and placed on the platform. Regardless of whether the mouse found the platform or not, it remained there for 20 seconds. There was a 45-min recovery period between trials. The 4 trials were initiated from the 2 points (north and west) located farthest from the platform. Because both the escape latency and swimming distance of mice in the behavioral experiment showed similar group differences, only the escape latency (the time taken to locate the platform) was used to evaluate the memory performance in the test mice. Two-way ANOVA with repeated measures was used to analyze latency values and calculate the mean latency periods for each mouse. Data was expressed as mean±SEM using 2-way ANOVA.

Forced Swim Test

Outbred male I.C.R. mice of 5 weeks old weighing 22-26 g were used. The mice had free access to food (rodent chow #2053, 5 g/mouse/day) and water. The cage floors were covered with wood shavings and the mice were handled once per week while the cages were cleaned. Mice were randomly assigned into 4 groups: group 1, vehicle control (p.o.); group 2, AG-0 of 30 mg/kg (p.o); group 3, AG-0 of 100 mg/kg (p.o.); or group 4, imipramine of 15 mg/kg (i.p.). The number of mice per group was ~10. To facilitate adaptation to novel surroundings, the mice were transported to the test area from the core animal facility at least one week prior to testing. All experimental sessions were conducted in the morning between 9:00 am to 12:00 pm. AG-0 and imipramine were administered once per day for 6 days before inducing despair.

A Pyrex cylinder of 30 cm in height and 11.5 cm in diameter was filled with water (10 cm) to a level such that the mice would not be able to touch the bottom. On day one, a mouse was placed into the cylinder from which it could not escape, for 15 minutes, to induce despair. After 24 hours, it was placed into the cylinder for 6 min, and the process was monitored or recorded using Etho-Vision® XT Mobility detection (Noldus software). The duration the mouse ceased to struggle was measured and calculated during the last 4-min within the 6-min time frame.

Open Field Test

Outbred male I.C.R. mice of 5 weeks old weighing 22-26 g were used. The mice had free access to food (rodent chow #2053, 5 g/mouse/day) and water. The cage floors were covered with wood shavings and the mice were handled once per week while the cages were cleaned. Mice were randomly assigned into 4 groups: group 1, vehicle control (p.o.); group 2, AG-0 at 30 mg/kg (p.o); group 3, AG-0 at 100 mg/kg (p.o.); or group 4, imipramine at 15 mg/kg (i.p.). The number of mice per group was ~10. To facilitate adaptation to novel surroundings, mice were transported to the test area from the core animal facility at least one week prior to testing. All experimental sessions were conducted in the morning between 9:00 am to 12:00 pm. AG-0 and imipramine were given once per day for 6 days before testing the locomotor activity of the mice.

Mice were placed in a field of size 50 cm×50 cm×40 cm for 40 minutes for habituation and then test samples (last dosing) were administered. 45 minutes later, the mice were placed into the field and the distance they traveled within a 30-min time frame was recorded using Etho-Vision® XT Mobility detection (Noldus software). Testing was carried out in a temperature, noise and light-controlled room. Before each trial, the field was cleaned with 70% ethanol and wiped with wet cotton to prevent possible bias from odor clues left by previous mice.

Frings Audiogenic Seizure-Susceptible Mouse Model

The Frings mice were identified by the Frings group in the mid 50's. It is an inbred strain generated from a spontaneous mutation on a Swiss Albino background. The Frings mouse strain is superior to the conventional DRA/2J strain regarding seizure phenotype as its susceptibility to audiogenic seizure is maintained to adulthood (Shradski et al., 1998, *Genomics* 49, 188-192).

Treated mice (18-25 g) were placed individually in a round plastic chamber (14.5 cm in diameter; 30 cm in height), and exposed to 110-dB, 11-KHz sound for 20 sec. Seizure was scored when a full hindlimb tonic-extension was elicited, where those not displaying hindlimb tonic-extension were categorized as protected. The severity of the seizure was quantified according to a scoring scale reported in White et al., 1992, Epilepsy Res 12:217-226L: No response, 0; wild running for <10 s, 1; wild running >10 s, 2; clonic seizure, 3; forelimb extension/hindlimb flexion, 4; and forelimb and hindlimb extension, 5.

The rotorod test was used to evaluate possible motor impairment elicited by the treatment. Test subjects were trained to walk continuously on a rotating rod (1 inch in diameter, 6 rpm) for 2 min. During testing, animals were given 3 opportunities to continuously remain on the drum for 1 min. Neurological impairment was considered by the inability of the test subject to remain on the rotating rod for 1 min in a single trial. The dose amount of AG-0 required to elicit an anti-convulsant effect (ED50) in 50% of the test subjects and its associated 95% confidence limits was calculated according to the method of Litchfield and Wilcoxon, 1949 (*J. Pharmacol. Exp. Ther.* 96, 99-105), using a commercial computer program (PHARM/PCS; MicroComputer Specialists).

CRE-Dependent Transcription Assay

Freshly isolated embryonic cortical neurons were transfected with a luciferase reporter gene (Cre-Luc) linked to CREB activation following the ACM lipofectamine method using Lipofectamine 2000, a cationic liposome based reagent (Invitrogen). The transfected cells were then seeded onto PDL-coated 48 well plates (NUNC) at a density of $1.3 \times 10^5$ cells per well and cultured for 7-12 days (7-12DIV) in Neurobasal medium with B27 supplement. Transfection was performed using 1 µL Lipofectamine 2000 and 0.4 µg DNA per well. Neurons were then treated with test samples for time periods of 6 hours. After treatment, the cells were washed with ice-cold DPBS and 100 µL of 1× luciferase lysis buffer (Promega) was added. The plates were placed in $-20°$ C. to freeze the cells, after which they were thawed to facilitate lysis. The lysates were transferred onto white bottom plates and assayed for renilla luciferase using the luciferase assay kit (Promega). Increased CREB activation in the neurons leads to an enhanced luciferase production and this was quantified using a Promega GloMax™ 96 microplate luminometer. Data was compared to a DMSO vehicle control and represented in mean±SEM. The student t-test was used for statistical analysis. BDNF and rolipram were used as positive controls.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound of formula Ia:

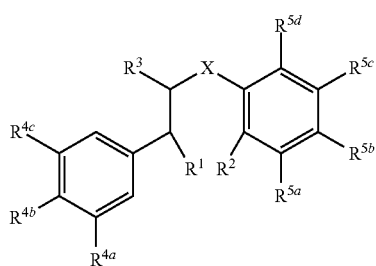

wherein

X is a bond or —O—;

$R^1$ is OH;

$R^2$ is selected from the group consisting of H and OH;

alternatively $R^1$ and $R^2$ are combined to form —O—;

$R^3$ is selected from the group consisting of $C_{1-6}$ alkyl and $C_{1-6}$ alkyl-OH;

each of $R^{4a}$, $R^{4b}$ and $R^{4c}$ is independently selected from the group consisting of H, OH, $C_{1-6}$ alkyl, and $C_{1-6}$ alkoxy;

each of $R^{5a}$, $R^{5b}$, $R^{5c}$ and $R^{5d}$ is independently selected from the group consisting of H, OH, $C_{1-6}$ alkyl, $C_{1-6}$ alkoxy, C(O)—H, $C_{2-6}$ alkenyl optionally substituted with $C_{1-6}$ alkoxy, and —C(O)—$C_{1-6}$ alkyl;

such that when X is —O— and $R^1$ is OH, then $R^3$ is $C_{1-6}$ alkyl, $R^{4a}$ and $R^{5d}$ are each independently selected from the group consisting of OH and $C_{1-6}$ alkoxy, $R^{4b}$ is OH, $R^{4c}$ is selected from the group consisting of H, OH and $C_{1-6}$ alkoxy, $R^{5a}$ and $R^{5c}$ are each H, and $R^{5b}$ is $C_{2-6}$ alkenyl;

such that when X is —O—, and $R^1$ and $R^2$ are combined to form —O—, then $R^3$ is $C_{1-6}$ alkyl, $R^{4a}$ is $C_{1-6}$ alkoxy, $R^{4b}$ is OH, $R^{4c}$, $R^{5a}$, $R^{5c}$ and $R^{5d}$ are each H, and $R^{5b}$ is $C_{2-6}$ alkenyl;

such that when X is a bond, and $R^1$ is OH, then $R^2$, $R^{4b}$, $R^{5b}$ and $R^{5c}$ are each H, $R^3$ is OH, $R^{4a}$ and $R^{5a}$ are each $C_{1-6}$ alkyl, and $R^{4c}$ and $R^{5d}$ are each $C_{1-6}$ alkoxy;

such that when X is a bond and $R^1$ and $R^2$ are combined to form —O—, then $R^3$ is selected from the group consisting of $C_{1-6}$ alkyl and $C_{1-6}$ alkyl-OH, $R^{4a}$ and $R^{5a}$ are each $C_{1-6}$ alkoxy, $R^{4b}$ is OH, $R^{4c}$ is selected from the group consisting of H, OH and $C_{1-6}$ alkoxy, $R^{5b}$ is H, $R^{5c}$ is selected from the group consisting of H, C(O)—H, and $C_{2-6}$ alkenyl substituted with $C_{1-6}$ alkoxy, and $R^{5d}$ is selected from the group consisting of H and C(O)—$C_{1-6}$ alkyl, wherein when $R^3$ is $C_{1-6}$ alkyl, then $R^{5d}$ is —C(O)—$C_{1-6}$ alkyl, and when $R^3$ is $C_{1-6}$ alkyl-OH, then $R^{5d}$ is H;

such that when X is —O—, $R^1$ and $R^2$ are each OH, $R^{5a}$ and $R^{5c}$ are each H, $R^3$ is Me, $R^{4a}$ and $R^{5d}$ are both OMe, $R^{4b}$ is OH, and $R^{5b}$ is $C_3$ alkenyl, then $R^{4c}$ is selected from the group consisting of OH and $C_{1-6}$ alkoxyl; and such that when X is —O—, $R^1$ is OH, $R^2$, $R^{5a}$, and $R^{5c}$ are each H, $R^3$ is Me, $R^{4a}$ and $R^{5d}$ are both OMe, $R^{4b}$ is OH, and $R^{5b}$ is $C_3$ alkenyl, then $R^{4c}$ is selected from the group consisting of OH and $C_{1-6}$ alkyl;

and salts and isomers thereof.

2. The compound of claim 1, having formula Ib:

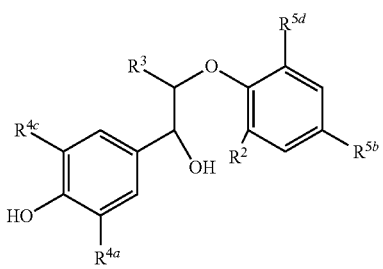

(Ib)

wherein $R^2$ is H;
$R^3$ is $C_{1-6}$ alkyl;
$R^{4a}$ and $R^{5d}$ are each independently selected from the group consisting of OH and $C_{1-6}$ alkoxy;
$R^{4c}$ is selected from the group consisting of H, OH and $C_{1-6}$ alkoxy; and
$R^{5b}$ is $C_{2-6}$ alkenyl;
such that, if $R^{4a}$ and $R^{5d}$ are both OMe, then $R^{4c}$ is selected from the group consisting of OH and $C_{1-6}$ alkyl.

3. The compound of claim 1, having formula Ic:

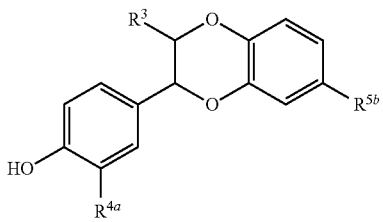

(Ic)

wherein $R^3$ is $C_{1-6}$ alkyl;
$R^{4a}$ is $C_{1-6}$ alkoxy; and
$R^{5b}$ is $C_{2-6}$ alkenyl.

4. The compound of claim 1, having formula Id:

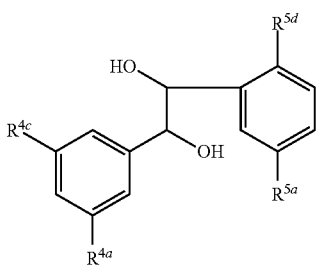

(Id)

wherein $R^{4a}$ and $R^{5a}$ are each $C_{1-6}$ alkyl; and
$R^{4c}$ and $R^{5d}$ are each $C_{1-6}$ alkoxy.

5. The compound of claim 1, having formula Ie:

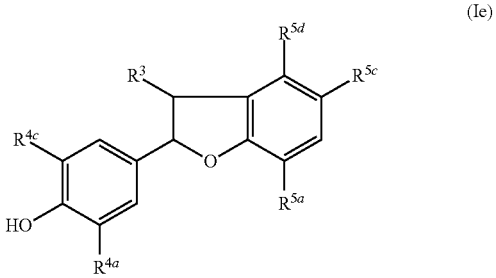

(Ie)

wherein $R^3$ is selected from the group consisting of $C_{1-6}$ alkyl and $C_{1-6}$ alkyl-OH;
$R^{4a}$ and $R^{5a}$ are each OH or $C_{1-6}$ alkoxy;
$R^{4c}$ is selected from the group consisting of H, OH and $C_{1-6}$ alkoxy;
$R^{5c}$ is selected from the group consisting of H, C(O)—H, and $C_{2-6}$ alkenyl substituted with $C_{1-6}$ alkoxy; and
$R^{5d}$ is selected from the group consisting of H and C(O)—$C_{1-6}$ alkyl;
wherein when $R^3$ is $C_{1-6}$ alkyl, then $R^{5d}$ is —C(O)—$C_{1-6}$ alkyl, and when $R^3$ is $C_{1-6}$ alkyl-OH, then $R^{5d}$ is H.

6. The compound of claim 1, selected from the group consisting of:

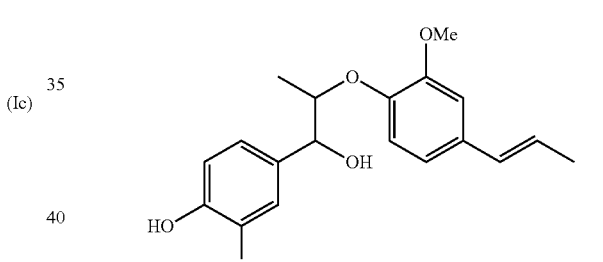

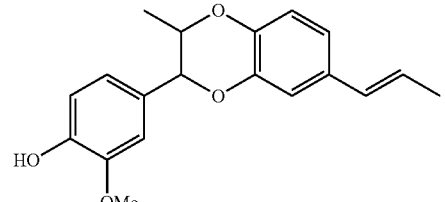

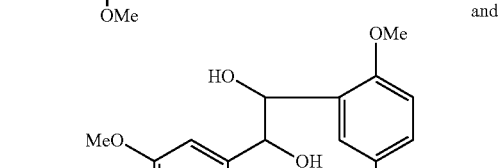

and

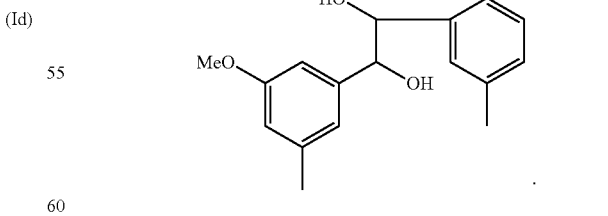

.

7. A pharmaceutical composition for treating a neurodegenerative disease or neuropathological condition in a subject, the composition comprising a compound of claim 1 and a pharmaceutically acceptable carrier or excipient.

8. A method of treating a neurodegenerative disease or neuropathological condition in a subject in need thereof, the method comprising administering to the subject a therapeutically effective amount of a compound of claim 1.

9. A method of inhibiting the activities of an NMDA receptor, the method comprising contacting the NMDA receptor with a compound of claim 1.

10. A method of inhibiting the activities of an amyloid-beta peptide, the method comprising contacting the amyloid-beta peptide with a compound of claim 1.

11. A method of treating depression in a subject, the method comprising administering to the subject a therapeutically effective amount of a compound of claim 1.

12. The method of claim 11, wherein the compound comprises GAG-C69.

13. A method of providing neuroprotection in a subject in need thereof, the method comprising administering to the subject a therapeutically effective amount of a compound of claim 1.

14. The method of claim 13, wherein the compound comprises GAG-C13, GAG-C14, GAG-C53, GAG-C63, GAG-C69, GAG-C73, GAG-C77, GAG-C78, GAG-C80, GAG-C122, GAG-C123, or GAG-C129.

* * * * *

SEQUENCE LISTING

```
<160> NUMBER OF SEQ ID NOS: 13

<210> SEQ ID NO 1
<211> LENGTH: 4
<212> TYPE: PRT
<213> ORGANISM: Artificial Sequence
<220> FEATURE:
<223> OTHER INFORMATION: synthetic caspase-3 cleavage substrate

<400> SEQUENCE: 1

Asp Glu Val Asp
 1

<210> SEQ ID NO 2
<211> LENGTH: 20
<212> TYPE: DNA
<213> ORGANISM: Artificial Sequence
<220> FEATURE:
<223> OTHER INFORMATION: synthetic real-time PCR primer BDNF Forward

<400> SEQUENCE: 2
ttgagcacgt gatcgaagag                                                    20

<210> SEQ ID NO 3
<211> LENGTH: 20
<212> TYPE: DNA
<213> ORGANISM: Artificial Sequence
<220> FEATURE:
<223> OTHER INFORMATION: synthetic real-time PCR primer BDNF Reverse

<400> SEQUENCE: 3
ccagcagaaa gagcagagga                                                    20

<210> SEQ ID NO 4
<211> LENGTH: 20
<212> TYPE: DNA
```

```
<213> ORGANISM: Artificial Sequence
<220> FEATURE:
<223> OTHER INFORMATION: synthetic real-time PCR primer NT-3 Forward

<400> SEQUENCE: 4
gggggattga tgacaaacac                                                   20

<210> SEQ ID NO 5
<211> LENGTH: 20
<212> TYPE: DNA
<213> ORGANISM: Artificial Sequence
<220> FEATURE:
<223> OTHER INFORMATION: synthetic real-time PCR primer NT-3 Reverse

<400> SEQUENCE: 5
acaaggcaca cacacaggaa                                                   20

<210> SEQ ID NO 6
<211> LENGTH: 20
<212> TYPE: DNA
<213> ORGANISM: Artificial Sequence
<220> FEATURE:
<223> OTHER INFORMATION: synthetic real-time PCR primer Bcl-2 Forward

<400> SEQUENCE: 6
ataaccggga gatcgtgatg                                                   20

<210> SEQ ID NO 7
<211> LENGTH: 20
<212> TYPE: DNA
<213> ORGANISM: Artificial Sequence
<220> FEATURE:
<223> OTHER INFORMATION: synthetic real-time PCR primer Bcl-2 Reverse

<400> SEQUENCE: 7
caggctggaa ggagaagatg                                                   20

<210> SEQ ID NO 8
<211> LENGTH: 20
<212> TYPE: DNA
<213> ORGANISM: Artificial Sequence
<220> FEATURE:
<223> OTHER INFORMATION: synthetic real-time PCR primer c-fos Forward

<400> SEQUENCE: 8
ggagccggtc aagaacatta                                                   20

<210> SEQ ID NO 9
<211> LENGTH: 20
<212> TYPE: DNA
<213> ORGANISM: Artificial Sequence
<220> FEATURE:
<223> OTHER INFORMATION: synthetic real-time PCR primer c-fos Reverse

<400> SEQUENCE: 9
tgctgcatag aaggaaccag                                                   20

<210> SEQ ID NO 10
<211> LENGTH: 21
<212> TYPE: DNA
<213> ORGANISM: Artificial Sequence
<220> FEATURE:
<223> OTHER INFORMATION: synthetic real-time PCR primer HPRT1 Forward

<400> SEQUENCE: 10
tgacactggt aaaacaatgc a                                                 21
```

```
<210> SEQ ID NO 11
<211> LENGTH: 21
<212> TYPE: DNA
<213> ORGANISM: Artificial Sequence
<220> FEATURE:
<223> OTHER INFORMATION: synthetic real-time PCR primer HPRT1 Reverse

<400> SEQUENCE: 11 ggtcctttc accagcaagc t                                                21

<210> SEQ ID NO 12
<211> LENGTH: 20
<212> TYPE: DNA
<213> ORGANISM: Artificial Sequence
<220> FEATURE:
<223> OTHER INFORMATION: synthetic real-time PCR primer GAPDH Forward

<400> SEQUENCE: 12
tgcaccacca actgcttagc                                                 20

<210> SEQ ID NO 13
<211> LENGTH: 21
<212> TYPE: DNA
<213> ORGANISM: Artificial Sequence
<220> FEATURE:
<223> OTHER INFORMATION: synthetic real-time PCR primer GAPDH Reverse

<400> SEQUENCE: 13
ggcatggact gtggtcatga g                                               21
```